United States Patent
Hatakeyama

(10) Patent No.: US 11,733,608 B2
(45) Date of Patent: Aug. 22, 2023

(54) RESIST COMPOSITION AND PATTERNING PROCESS

(71) Applicant: Shin-Etsu Chemical Co., Ltd., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 181 days.

(21) Appl. No.: 17/146,693

(22) Filed: Jan. 12, 2021

(65) Prior Publication Data

US 2021/0294211 A1    Sep. 23, 2021

(30) Foreign Application Priority Data

Feb. 14, 2020   (JP) .................................. 2020-023079

(51) Int. Cl.

| | | |
|---|---|---|
| *G03F 7/004* | (2006.01) | |
| *G03F 7/039* | (2006.01) | |
| *G03F 7/038* | (2006.01) | |
| *C07C 311/09* | (2006.01) | |
| *C07C 381/12* | (2006.01) | |
| *C07D 333/76* | (2006.01) | |
| *C08F 212/14* | (2006.01) | |
| *C07C 211/63* | (2006.01) | |
| *C07D 295/088* | (2006.01) | |
| *C07J 43/00* | (2006.01) | |
| *C08F 220/18* | (2006.01) | |
| *C07C 25/18* | (2006.01) | |

(52) U.S. Cl.
CPC ............ *G03F 7/0045* (2013.01); *C07C 25/18* (2013.01); *C07C 211/63* (2013.01); *C07C 311/09* (2013.01); *C07C 381/12* (2013.01); *C07D 295/088* (2013.01); *C07D 333/76* (2013.01); *C07J 43/003* (2013.01); *C08F 212/22* (2020.02); *C08F 212/24* (2020.02); *C08F 220/1802* (2020.02); *C08F 220/1806* (2020.02); *G03F 7/0382* (2013.01); *G03F 7/0392* (2013.01)

(58) Field of Classification Search
CPC .................. C08F 220/30; C08F 220/18; C08F 220/1807; C08F 220/1811; G03F 7/0045; G03F 7/0392; G03F 7/0395; G03F 7/0397; C07C 381/12; C07C 311/00; C07C 311/12; C07C 311/14; C07C 311/15; C07C 311/51

See application file for complete search history.

(56) References Cited

U.S. PATENT DOCUMENTS

| | | |
|---|---|---|
| 6,551,758 B2 | 4/2003 | Ohsawa et al. |
| 6,692,893 B2 | 2/2004 | Ohsawa et al. |
| 6,749,988 B2 | 6/2004 | Hatakeyama et al. |
| 6,916,593 B2 | 7/2005 | Hatakeyama et al. |
| 8,026,390 B2 | 9/2011 | Oh et al. |
| 8,148,044 B2 | 4/2012 | Yamaguchi et al. |
| 8,497,395 B2 | 7/2013 | Utsumi et al. |
| 9,250,518 B2 | 2/2016 | Hatakeyama et al. |
| 9,523,912 B2 | 12/2016 | Kataoka et al. |
| 9,897,914 B2* | 2/2018 | Hatakeyama .......... G03F 7/0395 |
| 10,054,853 B2 | 8/2018 | Fujiwara |
| 10,451,968 B2 | 10/2019 | Fujii |
| 11,269,253 B2* | 3/2022 | Hatakeyama .......... G03F 7/0397 |
| 2009/0274978 A1 | 11/2009 | Ohashi et al. |
| 2010/0233629 A1* | 9/2010 | Wada ................. C07D 295/033 430/286.1 |
| 2011/0008731 A1 | 1/2011 | Yamaguchi et al. |
| 2011/0269072 A1 | 11/2011 | Shibuya |
| 2013/0017377 A1 | 1/2013 | Kataoka et al. |
| 2013/0089819 A1 | 4/2013 | Kawaue et al. |
| 2015/0212417 A1 | 7/2015 | Hatakeyama et al. |
| 2016/0070167 A1 | 3/2016 | Kataoka et al. |
| 2017/0351177 A1 | 12/2017 | Hatakeyama et al. |
| 2017/0369616 A1 | 12/2017 | Hatakeyama et al. |
| 2019/0369491 A1* | 12/2019 | Hatakeyama .......... C07C 321/28 |

FOREIGN PATENT DOCUMENTS

| | | |
|---|---|---|
| CN | 102289149 A | 12/2011 |
| JP | 5-204157 A | 8/1993 |
| JP | 2001-194776 A | 7/2001 |
| JP | 2002-226470 A | 8/2002 |
| JP | 2002-363148 A | 12/2002 |
| JP | 2010-265226 A | 11/2010 |
| JP | 2011-252147 A | 12/2011 |
| JP | 2012-121838 A | 6/2012 |
| JP | 5572739 B2 | 8/2014 |
| JP | 2015-25789 A | 2/2015 |

(Continued)

OTHER PUBLICATIONS

Machine translation of JP2019211751 (no date).*

(Continued)

*Primary Examiner* — Amanda C. Walke
(74) *Attorney, Agent, or Firm* — WHDA, LLP

(57) ABSTRACT

A resist composition comprising a base polymer and a quencher containing an onium salt of iodized benzene ring-containing fluorosulfonamide offers a high sensitivity and minimal LWR or improved CDU, independent of whether it is of positive or negative tone.

(A)

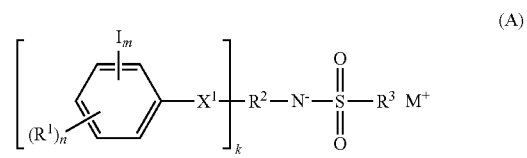

14 Claims, No Drawings

(56) References Cited

FOREIGN PATENT DOCUMENTS

| | | | | |
|---|---|---|---|---|
| JP | 2015-90382 | A | 5/2015 | |
| JP | 2015-161823 | A | 9/2015 | |
| JP | 2018-5224 | A | 1/2018 | |
| JP | 2019211751 | A | * 12/2019 | ........... C07C 311/51 |
| KR | 10-2013-0044239 | A | 5/2013 | |
| KR | 10-2017-0138355 | A | 12/2017 | |
| TW | 201009493 | A | 3/2010 | |
| TW | 201533528 | A | 9/2015 | |
| TW | 202003428 | A | 1/2020 | |
| WO | 2013/024777 | A1 | 2/2013 | |

OTHER PUBLICATIONS

Office Action dated Dec. 6, 2021, issued in counterpart TW Application No. 110104590. (8 pages).

Wang et al., "Photobase generator and photo decomposable quencher for high-resolution photoresist applications," SPIE vol. 7639, 2010, p. 76390W1-15. (15 pages).

Lio, "EUV Resists: What's Next?," SPIE vol. 9776, 2016, p. 97760V-1-14. (14 pages).

Yamamoto et al., "Polymer-Structure Dependence of Acid Generation in Chemically Amplified Extreme Ultraviolet Resists", Japanese Journal of Applied Physics, 2007, vol. 46, No. 7, pp. L142-L144. (3 pages).

Office Action dated Feb. 26, 2018, issued in TW Application No. 106121402 (counterpart to U.S. Appl. No. 16/426,673). (12 pages).

Non-Final Office Action dated May 7, 2020, issued in counterpart U.S. Appl. No. 16/130,271. (11 pages).

Non-Final Office Action dated Jun. 27, 2019, issued in counterpart U.S. Appl. No. 15/920,641. (10 pages).

Non-Final Office Action dated Aug. 9, 2018, issued in counterpart U.S. Appl. No. 15/623,561. (8 pages).

Office Action dated Nov. 24, 2020, issued in KR Application No. 10-2019-0063603 (counterpart to U.S. Appl. No. 16/426,673), with English translation. (10 pages).

Non-Final Action dated Jul. 20, 2021, issued in U.S. Appl. No. 16/426,673. (27 pages).

* cited by examiner

RESIST COMPOSITION AND PATTERNING PROCESS

CROSS-REFERENCE TO RELATED APPLICATION

This non-provisional application claims priority under 35 U.S.C. § 119(a) on Patent Application No. 2020-023079 filed in Japan on Feb. 14, 2020, the entire contents of which are hereby incorporated by reference.

TECHNICAL FIELD

This invention relates to a resist composition and a pattern forming process.

BACKGROUND ART

While a higher integration density, higher operating speed and lower power consumption of LSIs are demanded to comply with the expanding IoT market, the effort to reduce the pattern rule is in rapid progress. The wide-spreading logic device market drives forward the miniaturization technology. As the advanced miniaturization technology, microelectronic devices of 10-nm node are manufactured in a mass scale by the double, triple or quadro-patterning version of the immersion ArF lithography. The experimental mass-scale manufacture of 7-nm node devices by the next generation EUV lithography of wavelength 13.5 nm has started. The manufacture of 5-nm node devices as the full application of EUV lithography is on the verge of mass-scale production.

The EUV lithography enables to form line patterns to a line width of 20 nm or less when chemically amplified resist compositions are applied. Since the influence of image blur due to acid diffusion becomes more significant, the EUV lithography resist material needs more acid diffusion control than the ArF lithography resist material.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Addition of quenchers to these resist compositions is effective for the purpose of controlling the diffusion of the acid to unexposed region to improve the contrast. A number of amine quenchers were proposed as disclosed in Patent Document 1.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film. One means for enhancing the dissolution contrast is to reduce the concentration of amine with an increasing exposure dose. This may be achieved by applying a compound which loses the quencher function upon light exposure.

With respect to the acid labile group used in (meth) acrylate polymers for the ArF lithography resist material, deprotection reaction takes place when an acid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Further, since the sulfonium or iodonium salt capable of generating an α-non-fluorinated sulfonic acid, carboxylic acid or sulfonamide loses the quencher function through photo-decomposition, it functions as a photo-decomposable quencher (see Patent Document 2).

As the pattern feature size is reduced, the edge roughness (LWR) of line patterns or the critical dimension uniformity (CDU) of hole patterns is regarded significant. It is pointed out that LWR is affected by the segregation or agglomeration of a base polymer and acid generator and the diffusion of generated acid. There is a tendency that as the resist film becomes thinner, LWR becomes greater. A film thickness reduction to comply with the progress of miniaturization causes a degradation of LWR, which becomes a serious problem.

The EUV lithography resist material must meet high sensitivity, high resolution, low LWR and good CDU at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR or CDU. For EB which is high-energy radiation like EUV, there is a tradeoff relation between sensitivity and LWR or CDU.

The energy of EUV is extremely higher than that of ArF excimer laser. The number of photons available with EUV exposure is $\frac{1}{14}$ of the number by ArF exposure. The size of pattern features formed by the EUV lithography is less than half the size by the ArF lithography. Therefore, the EUV lithography is quite sensitive to a variation of photon number. A variation in number of photons in the radiation region of extremely short wavelength is shot noise as a physical phenomenon.

Attention is paid to stochastics. While it is impossible to eliminate the influence of shot noise, discussions are held how to reduce the influence. There is observed a phenomenon that under the influence of shot noise, values of CDU and LWR are increased and holes are blocked at a probability of one several millionth. The blockage of holes leads to electric conduction failure and non-operation of transistors, adversely affecting the performance of an overall device. As the means for reducing the influence of shot noise on the resist side, it is proposed to modify the resist film more absorptive so as to absorb more photons.

CITATION LIST

Patent Document 1: JP-A 2001-194776
Patent Document 2: JP-A 2012-121838 (U.S. Pat. No. 8,497,395)

DISCLOSURE OF INVENTION

For the acid-catalyzed chemically amplified resist, it is desired to develop a quencher capable of providing a high sensitivity and reducing LWR or CDU as well as a resist material which contributes to shot noise reduction.

An object of the invention is to provide a resist composition which exhibits a high sensitivity and a reduced LWR or improved CDU, independent of whether it is of positive tone or negative tone; and a pattern forming process using the same.

The inventor has found that using an onium salt of fluorosulfonamide having iodized benzene ring as the quencher, a resist material having a high sensitivity, reduced LWR, improved CDU, high contrast, improved resolution, and wide process margin is obtainable.

In one aspect, the invention provides a resist composition comprising a base polymer and a quencher, the quencher containing an onium salt having the formula (A).

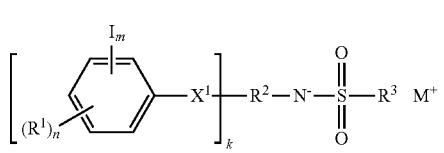
(A)

Herein m is an integer of 1 to 5, n is an integer of 0 to 4, m+n is from 1 to 5, k is 1 or 2.

$R^1$ is hydrogen, hydroxyl, optionally halogen-substituted $C_1$-$C_6$ saturated hydrocarbyl group, optionally halogen-substituted $C_1$-$C_6$ saturated hydrocarbyloxy group, optionally halogen-substituted $C_2$-$C_7$ saturated hydrocarbylcarbonyloxy group, optionally halogen-substituted $C_2$-$C_7$ saturated hydrocarbyloxycarbonyl group, optionally halogen-substituted $C_1$-$C_4$ saturated hydrocarbylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$, some or all of the hydrogen atoms in the saturated hydrocarbyl, saturated hydrocarbyloxy, saturated hydrocarbylcarbonyloxy, saturated hydrocarbyloxycarbonyl and saturated hydrocarbylsulfonyloxy groups may be substituted by halogen, $R^{1A}$ is hydrogen or a $C_1$-$C_6$ saturated hydrocarbyl group, $R^{1B}$ is a $C_1$-$C_6$ saturated hydrocarbyl, $C_2$-$C_8$ unsaturated aliphatic hydrocarbyl, $C_6$-$C_{14}$ aryl or $C_7$-$C_{15}$ aralkyl group.

$R^2$ is a $C_1$-$C_{10}$ (k+1)-valent hydrocarbon group.

$R^3$ is a $C_1$-$C_6$ fluorinated saturated hydrocarbyl group or $C_6$-$C_{10}$ fluorinated aryl group.

$X^1$ is a single bond, ether bond, carbonyl group, ester bond, amide bond, carbonate bond or $C_1$-$C_{20}$ hydrocarbylene group, the hydrocarbylene group may contain an ether bond, carbonyl moiety, ester bond, amide bond, sultone ring, lactam ring, carbonate bond, halogen, hydroxyl moiety or carboxyl moiety.

$M^+$ is a sulfonium cation having the formula (Aa), iodonium cation having the formula (Ab), or ammonium cation having the formula (Ac):

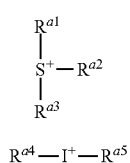
(Aa)

(Ab)
$R^{a4}$—$I^+$—$R^{a5}$

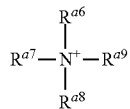
(Ac)

wherein $R^{a1}$ to $R^{a3}$ are each independently halogen or a $C_1$-$C_{20}$ hydrocarbyl group which may contain a heteroatom, $R^{a1}$ and $R^{a2}$ may bond together to form a ring with the sulfur atom to which they are attached, $R^{a4}$ and $R^{a5}$ are each independently halogen or a $C_1$-$C_{20}$ hydrocarbyl group which may contain a heteroatom, $R^{a6}$ to $R^{a9}$ are each independently hydrogen or a $C_1$-$C_{24}$ hydrocarbyl group which may contain at least one moiety selected from halogen, hydroxyl moiety, carboxyl moiety, ether bond, ester bond, thiol moiety, thioester bond, thionoester bond, dithioester bond, amino moiety, nitro moiety, sulfone moiety, and ferrocenyl moiety, $R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ each may bond together to form a spiro-ring with the nitrogen atom to which they are attached, $R^{a8}$ and $R^{a9}$, taken together, may form =C($R^{a10}$)($R^{a11}$), $R^{a10}$ and $R^{a11}$ are each independently hydrogen or a $C_1$-$C_{16}$ hydrocarbyl group, $R^{a6}$ and $R^{a10}$ may bond together to form a ring with the carbon and nitrogen atoms to which they are attached, the ring may contain a double bond, oxygen, sulfur or nitrogen.

Preferably, m is an integer of 2 to 4.

The resist composition may further comprise an acid generator capable of generating a sulfonic acid, imide acid or methide acid.

The resist composition may further comprising an organic solvent.

In a preferred embodiment, the base polymer comprises recurring units having the formula (a1) or recurring units having the formula (a2).

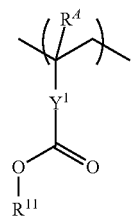
(a1)

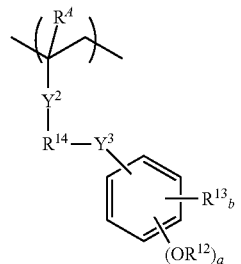
(a2)

Herein $R^A$ is each independently hydrogen or methyl, $Y^1$ is a single bond, phenylene group, naphthylene group, or $C_1$-$C_{12}$ linking group containing at least one moiety selected from ester bond and lactone ring, $Y^2$ is a single bond or ester bond, $Y^3$ is a single bond, ether bond or ester bond, $R^{11}$ and $R^{12}$ each are an acid labile group, $R^{13}$ is fluorine, trifluoromethyl, cyano or $C_1$-$C_6$ saturated hydrocarbyl group, $R^{14}$ is a single bond or $C_1$-$C_6$ alkanediyl group in which some carbon may be replaced by an ether bond or ester bond, a is 1 or 2, b is an integer of 0 to 4, and a+b is from 1 to 5.

In one preferred embodiment, the resist composition is a chemically amplified positive resist composition.

In another preferred embodiment, the base polymer is free of an acid labile group. The resist composition is often a chemically amplified negative resist composition.

In a preferred embodiment, the base polymer comprises recurring units of at least one type selected from recurring units having the formulae (f1) to (f3).

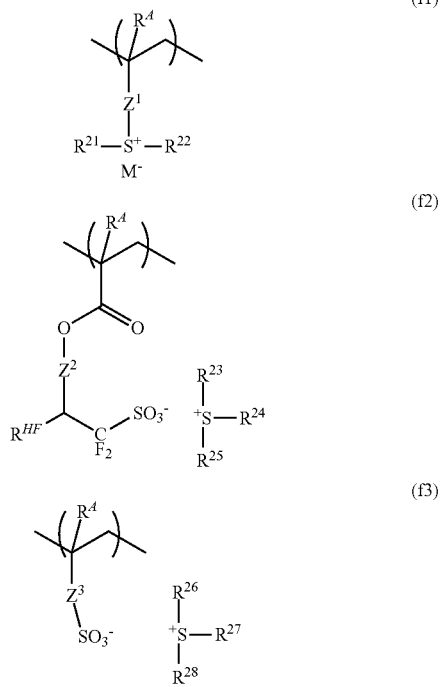

Herein $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, $Z^{21}$ is a $C_1$-$C_{12}$ saturated hydrocarbylene group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety. $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached. $R^{HF}$ is hydrogen or trifluoromethyl. $M^-$ is a non-nucleophilic counter ion.

The resist composition may further comprise a surfactant.

In another aspect, the invention provides a process for forming a pattern comprising the steps of applying the resist composition defined above onto a substrate to form a resist film thereon, exposing the resist film to high-energy radiation, and developing the exposed resist film in a developer.

Typically, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

A resist film containing an onium salt of sulfonamide having iodized benzene ring, represented by formula (A), has the advantage of high sensitivity because the sulfonamide having iodized benzene ring is fully absorptive to EB and EUV so that more secondary electrons are generated in the film upon light exposure. Since the bond distance between the anion and the cation of the onium salt is long owing to the steric hindrance of substituents on opposite sides of the amide bond, the inventive onium salt is liable to ion exchange with sulfonic acid as compared with the quencher in the form of carboxylic acid sulfonium salt. That is, the inventive onium salt has a higher quencher ability enough to provide a high contrast.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group. As used herein, the term "iodized" compound means an iodine-containing compound.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher, the quencher containing an onium salt of fluorosulfonamide having iodized benzene ring (referred to as iodized benzene ring-containing fluorosulfonamide, hereinafter). This onium salt is an acid generator capable of generating iodized benzene ring-containing sulfonamide or weak acid upon light exposure, while it also functions as a quencher because it has a strongly basic onium salt form. Since the iodized benzene ring-containing fluorosulfonamide does not possess a sufficient acidity to induce deprotection reaction of an acid labile group, it is recommended to separately add an acid generator capable of generating a strong acid such as sulfonic acid, imide acid or methide acid, as will be described later, in order to induce deprotection reaction of an acid labile group. Notably, the acid generator capable of generating sulfonic acid, imide acid or methide acid may be either of addition type which is added to the base polymer or of bound type which is bound in the base polymer.

When a resist composition containing the onium salt of iodized benzene ring-containing fluorosulfonamide in admixture with an acid generator capable of generating a perfluoroalkylsulfonic acid or superstrong acid is exposed to radiation, iodized benzene ring-containing fluorosulfonamide and perfluoroalkylsulfonic acid generate. Since the acid generator is not entirely decomposed, the undecomposed acid generator is present nearby. When the onium salt of iodized benzene ring-containing fluorosulfonamide co-exists with the perfluoroalkylsulfonic acid, first the perfluoroalkylsulfonic acid undergoes ion exchange with the onium salt of iodized benzene ring-containing fluorosulfonamide, whereby an onium salt of perfluoroalkylsulfonic acid is created and iodized benzene ring-containing fluorosulfonamide is released. This is because the salt of perfluoroalkylsulfonic acid having a high acid strength is more stable. In contrast, when an onium salt of perfluoroalkylsulfonic acid co-exists with iodized benzene ring-containing fluorosulfonamide, no ion exchange takes place. The ion exchange takes place not only with the perfluoroalkylsulfonic acid, but also similarly with arylsulfonic acid, alkylsulfonic acid, imide acid and methide acid having a higher acid strength than the iodized benzene ring-containing fluorosulfonamide.

The onium salt of iodized benzene ring-containing fluorosulfonamide is not only effective for suppressing acid diffusion, but is also highly absorptive to EUV so that it generates more secondary electrons, thereby providing the resist with a higher sensitivity and reducing shot noise. The onium salt of iodized benzene ring-containing fluorosulfonamide functions not only as a quencher for controlling acid diffusion, but also as a sensitizer.

For the LWR improving purpose, it is effective to prevent a polymer and/or acid generator from agglomeration as indicated above. Another factor to be taken into account for the LWR improving purpose is the dispersibility of a quencher. Even when the dispersibility of an acid generator in a resist film is improved, the uneven distribution of a quencher can cause a degradation of LWR. The introduction of halogen atoms into the quencher of sulfonium salt type efficiently enhances hydrophobicity and improves dispersibility. The introduction of bulky halogen atoms such as iodine is effective not only in the cation moiety, but also in the anion moiety of the sulfonium salt. The onium salt of iodized benzene ring-containing fluorosulfonamide according to the invention has iodine introduced in the anion moiety, whereby the dispersibility of the quencher within the resist film is enhanced and LWR is reduced.

The onium salt of iodized benzene ring-containing fluorosulfonamide exerts a LWR reducing effect, which may stand good either in positive and negative tone pattern formation by alkaline development or in negative tone pattern formation by organic solvent development.

Onium Salt of Iodized Benzene Ring-Containing Fluorosulfonamide

The resist composition contains an onium salt of iodized benzene ring-containing fluorosulfonamide, which has the formula (A).

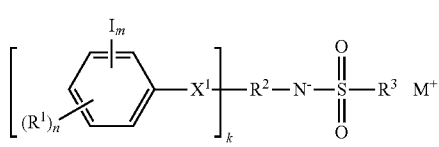

(A)

In formula (A), m is an integer of 1 to 5, n is an integer of 0 to 4, m+n is from 1 to 5, and k is 1 or 2. Preferably, m is an integer of 2 to 4, and n is 0 or 1.

In formula (A), $R^1$ is hydrogen, hydroxyl, optionally halogen-substituted $C_1$-$C_6$ saturated hydrocarbyl group, optionally halogen-substituted $C_1$-$C_6$ saturated hydrocarbyloxy group, optionally halogen-substituted $C_2$-$C_7$ saturated hydrocarbylcarbonyloxy group, optionally halogen-substituted $C_2$-$C_7$ saturated hydrocarbyloxycarbonyl group, optionally halogen-substituted $C_1$-$C_4$ saturated hydrocarbylsulfonyloxy group, fluorine, chlorine, bromine, amino, nitro, cyano, —$NR^{1A}$—$C(=O)$—$R^{1B}$, or $NR^{1A}$—$C(=O)$—$O$—$R^{1B}$. Some or all of the hydrogen atoms in the saturated hydrocarbyl, saturated hydrocarbyloxy, saturated hydrocarbylcarbonyloxy, saturated hydrocarbyloxycarbonyl and saturated hydrocarbylsulfonyloxy groups may be substituted by halogen. $R^{1A}$ is hydrogen or a $C_1$-$C_6$ saturated hydrocarbyl group. $R^{1B}$ is a $C_1$-$C_6$ saturated hydrocarbyl, $C_2$-$C_8$ unsaturated aliphatic hydrocarbyl, $C_6$-$C_{14}$ aryl or $C_7$-$C_{15}$ aralkyl group.

The $C_1$-$C_6$ saturated hydrocarbyl group may be straight, branched or cyclic, and examples thereof include $C_1$-$C_6$ alkyl groups such as methyl, ethyl, n-propyl, isopropyl, n-butyl, isobutyl, sec-butyl, tert-butyl, n-pentyl and n-hexyl, and $C_3$-$C_6$ cycloalkyl groups such as cyclopropyl, cyclobutyl, cyclopentyl and cyclohexyl. Examples of the saturated hydrocarbyl moiety in the $C_1$-$C_6$ saturated hydrocarbyloxy group, $C_2$-$C_7$ saturated hydrocarbylcarbonyloxy group and $C_2$-$C_7$ saturated hydrocarbyloxycarbonyl group are as exemplified above for the saturated hydrocarbyl group. Examples of the saturated hydrocarbyl moiety in the $C_1$-$C_4$ saturated hydrocarbylsulfonyloxy group are as exemplified above for the saturated hydrocarbyl group, but of 1 to 4 carbon atoms. Exemplary halogen atoms include fluorine, chlorine, bromine and iodine.

The $C_2$-$C_8$ unsaturated aliphatic hydrocarbyl group may be straight, branched or cyclic and examples thereof include $C_2$-$C_8$ alkenyl groups such as vinyl, 1-propenyl, and 2-propenyl. Suitable $C_6$-$C_{14}$ aryl groups include phenyl, naphthyl and fluorenyl. Suitable $C_7$-$C_{15}$ aralkyl groups include benzyl, phenethyl, naphthylmethyl, naphthylethyl, fluorenylmethyl and fluorenylethyl.

Among others, $R^1$ is preferably selected from fluorine, chlorine, bromine, hydroxyl, amino, optionally halogen-substituted $C_1$-$C_3$ saturated hydrocarbyl groups, optionally halogen-substituted $C_1$-$C_3$ saturated hydrocarbyloxy groups, optionally halogen-substituted $C_2$-$C_4$ saturated hydrocarbylcarbonyloxy groups, —$NR^{1A}$—$C(=O)$—$R^{1B}$, and —$NR^{1A}$—$C(=O)$—$O$—$R^{1B}$.

In formula (A), $R^2$ is a $C_1$-$C_{10}$ (k+1)-valent hydrocarbon group. The hydrocarbon group may be saturated or unsaturated and straight, branched or cyclic. Examples include $C_1$-$C_{10}$ alkanediyl groups such as methanediyl, ethane-1,1-diyl, ethane-1,2-diyl, propane-1,2-diyl, propane-1,3-diyl, propane-2,2-diyl, butane-1,2-diyl, butane-1,3-diyl, butane-1,4-diyl, butane-2,2-diyl, butane-2,3-diyl, 2-methylpropane-1,3-diyl, pentane-1,5-diyl, hexane-1,6-diyl, heptane-1,7-diyl, octane-1,8-diyl, nonane-1,9-diyl, and decane-1,10-diyl; $C_3$-$C_{10}$ saturated cyclic hydrocarbylene groups such as cyclopentanediyl, cyclohexanediyl, norbornanediyl, and adamantanediyl; $C_6$-$C_{10}$ arylene groups such as phenylene and naphthylene; hydrocarbylene groups obtained by combining the foregoing; and trivalent groups obtained by eliminating one hydrogen from the hydrocarbylene groups.

In formula (A), $R^3$ is a $C_1$-$C_6$ fluorinated saturated hydrocarbyl group or $C_6$-$C_{10}$ fluorinated aryl group. The $C_1$-$C_6$ fluorinated saturated hydrocarbyl group may be straight, branched or cyclic, and examples thereof include those exemplified above for the $C_1$-$C_6$ saturated hydrocarbyl group in which some or all hydrogen atoms are substituted by fluorine. Examples of the $C_6$-$C_{10}$ fluorinated aryl group include aryl groups such as phenyl and naphthyl in which some or all hydrogen atoms are substituted by fluorine; and groups obtained by combining the foregoing.

In formula (A), $X^1$ is a single bond, ether bond, carbonyl group, ester bond, amide bond, carbonate bond or $C_1$-$C_{20}$ hydrocarbylene group. The hydrocarbylene group may be saturated or unsaturated and straight, branched or cyclic. The hydrocarbylene group may contain an ether bond, carbonyl moiety, ester bond, amide bond, sultone ring, lactam ring, carbonate bond, halogen, hydroxyl moiety or carboxyl moiety.

In formula (A), M+ is a sulfonium cation having the formula (Aa), an iodonium cation having the formula (Ab), or an ammonium cation having the formula (Ac).

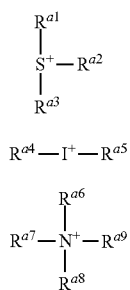

In formula (Aa), $R^{a1}$ to $R^{a3}$ are each independently halogen or a $C_1$-$C_{20}$ hydrocarbyl group which may contain a heteroatom. In formula (Ab), $R^{a4}$ and $R^{a5}$ are each independently halogen or a $C_1$-$C_{20}$ hydrocarbyl group which may contain a heteroatom.

Examples of the halogen represented by $R^{a1}$ to $R^{55}$ include fluorine, chlorine, bromine and iodine.

The $C_1$-$C_{20}$ hydrocarbyl group represented by $R^{a1}$ to $R^{a5}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ saturated cyclic hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl, and hexenyl; $C_2$-$C_{20}$ alkynyl groups such as ethynyl, propynyl and butynyl; $C_3$-$C_{20}$ unsaturated alicyclic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and combinations thereof. In the foregoing groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, ester bond, sulfonic ester bond, carbonate moiety, lactone ring, sultone ring, carboxylic anhydride or haloalkyl moiety.

$R^{a1}$ and $R^{a2}$ may bond together to form a ring with the sulfur atom to which they are attached. Preferred examples of the ring are shown by the following structure.

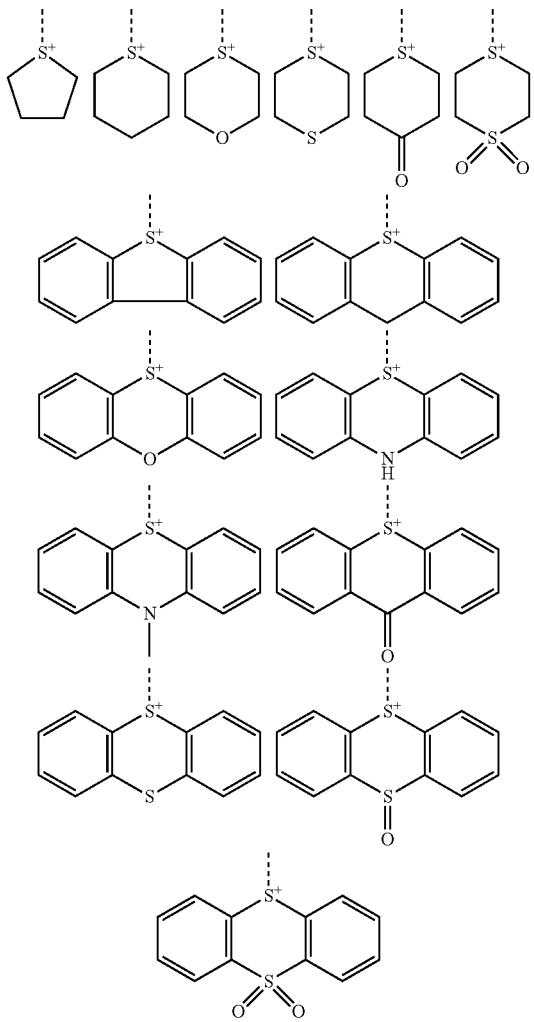

Herein the broken line designates an attachment to $R^{a3}$.

In formula (Ac), $R^{a6}$ to $R^{a9}$ are each independently hydrogen or a $C_1$-$C_{24}$ hydrocarbyl group. The hydrocarbyl group represented by $R^{a6}$ to $R^{a9}$ may contain at least one moiety selected from halogen, hydroxyl, carboxyl, ether bond, ester bond, thiol bond, thioester bond, thionoester bond, dithioester bond, amino, nitro, sulfone and ferrocenyl moiety. The hydrocarbyl group may be saturated or unsaturated and straight, branched or cyclic. Examples thereof include $C_1$-$C_{24}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{24}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{24}$ alkenyl groups such as vinyl, propenyl, butenyl, hexenyl; $C_2$-$C_{24}$ alkynyl groups such as ethynyl, propynyl, butynyl, 2-cyclohexylethynyl, 2-phenylethynyl; $C_3$-$C_{24}$ cyclic unsaturated aliphatic hydrocarbyl groups such as cyclohexenyl and norbornenyl; $C_6$-$C_{24}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl; $C_7$-$C_{24}$ aralkyl groups such as benzyl and phenethyl; and combinations thereof.

$R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ each may bond together to form a spiro-ring with the nitrogen atom to which they are attached, $R^{a8}$ and $R^{a9}$, taken together, may form $=C(R^{a10})(R^{a11})$. $R^{a10}$ and $R^{a11}$ are each independently hydrogen or a $C_1$-$C_{16}$ hydrocarbyl group. Examples of the hydrocarbyl group represented by $R^{a10}$ and $R^{a11}$ are as exemplified above for the hydrocarbyl groups represented by $R^{a6}$ to $R^{a9}$, but of 1 to 16 carbon atoms. $R^{a6}$ and $R^{a10}$ may bond together to form a ring with the carbon and nitrogen atoms to which they are attached, the ring may contain a double bond, oxygen, sulfur or nitrogen.

Examples of the anion in the onium salt having formula (A) are shown below, but not limited thereto.

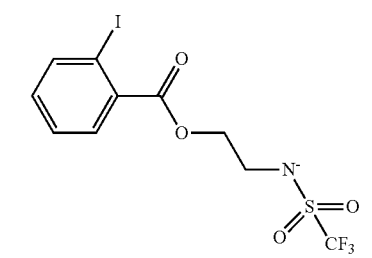

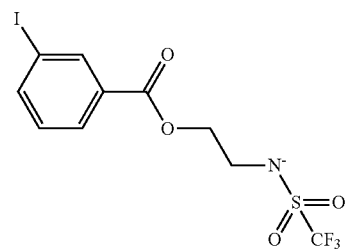

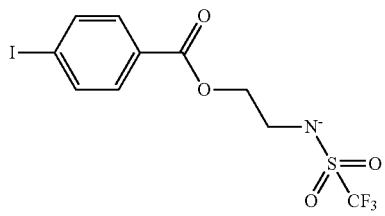

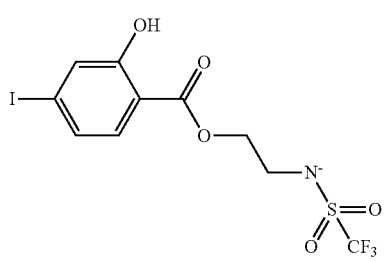

-continued

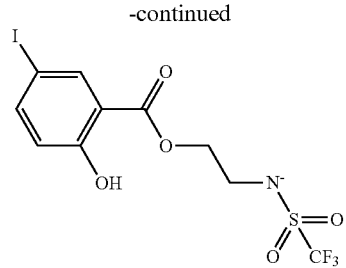

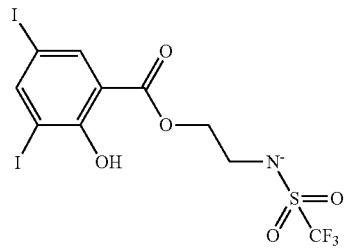

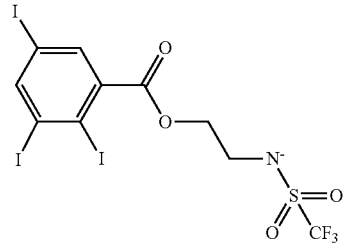

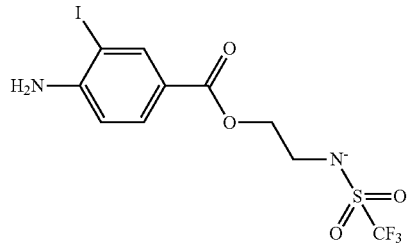

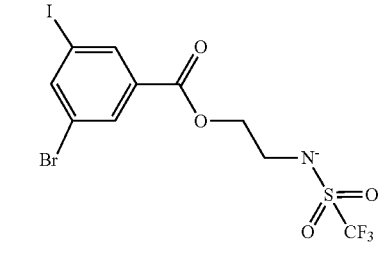

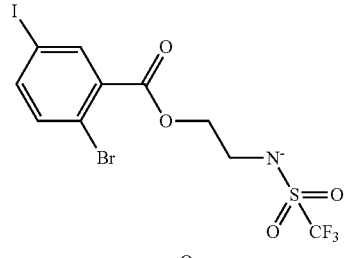

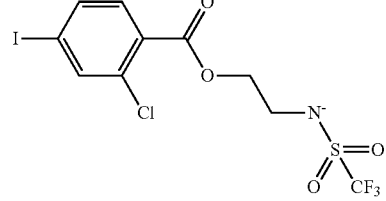

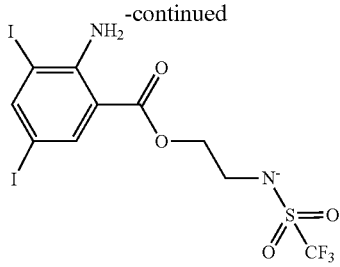
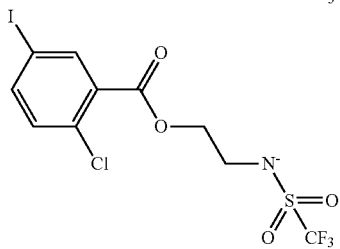
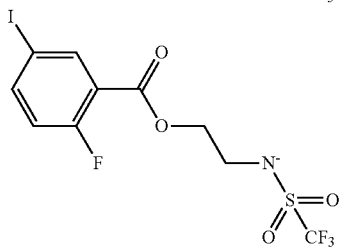
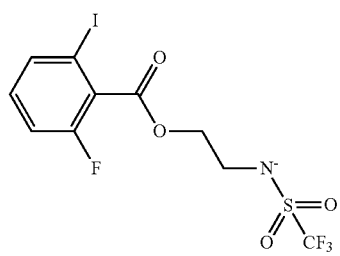
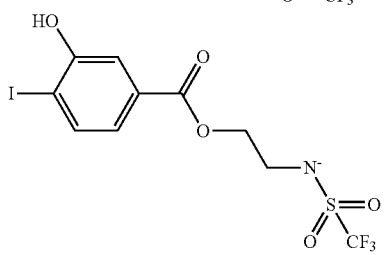
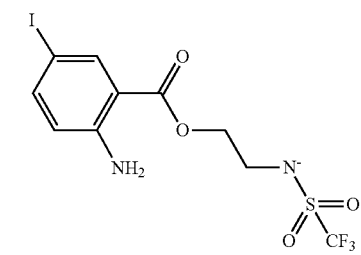
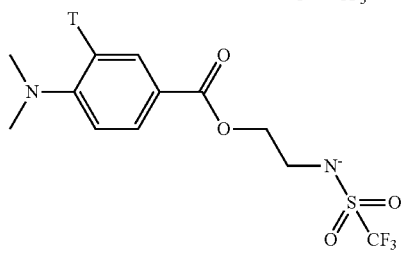
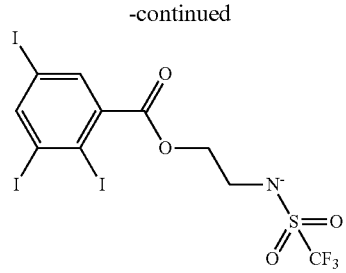
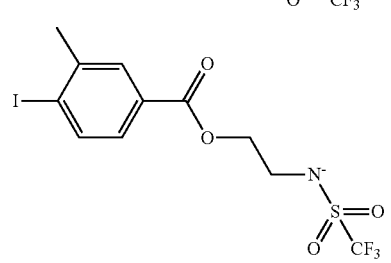
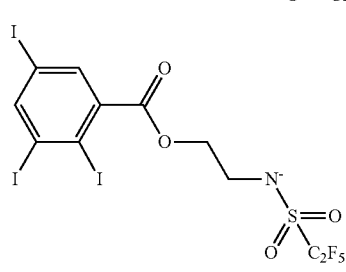
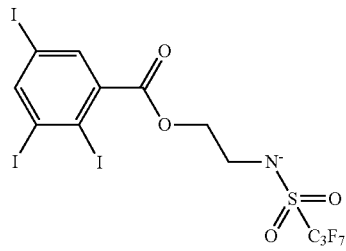
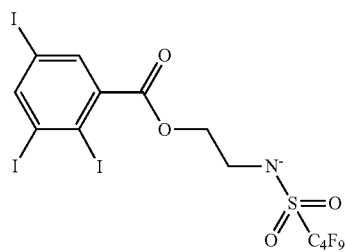
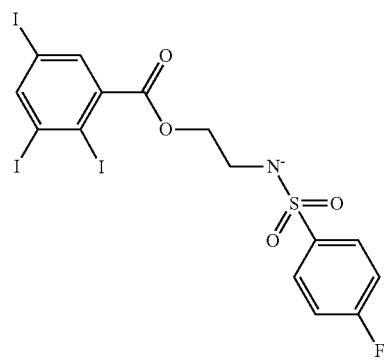

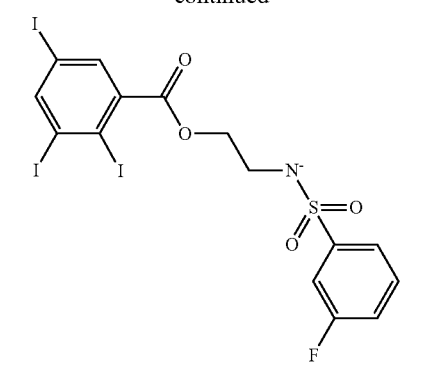
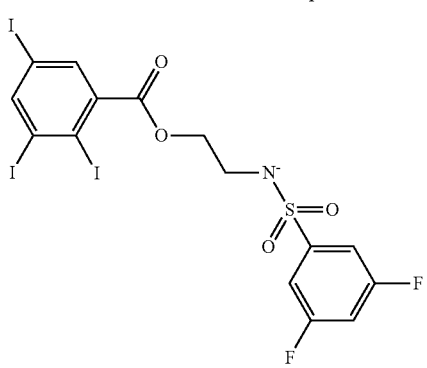
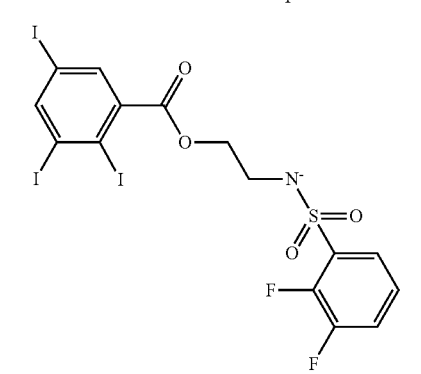
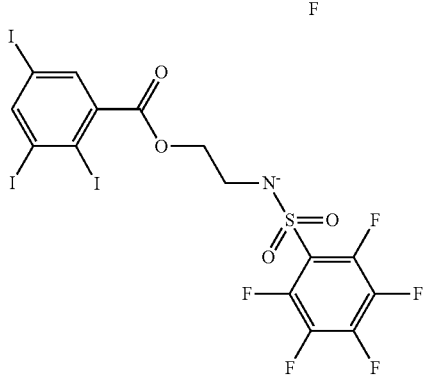
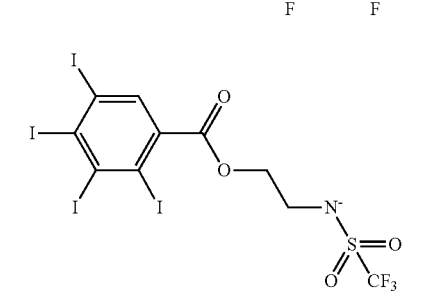
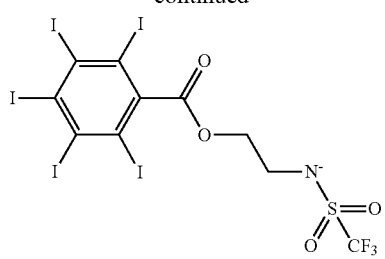
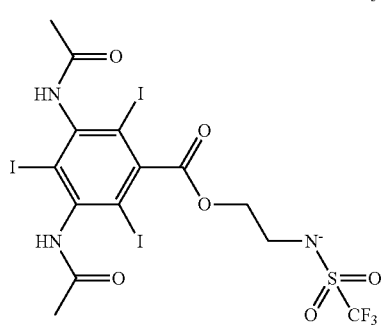
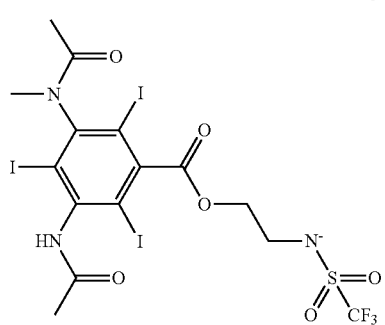
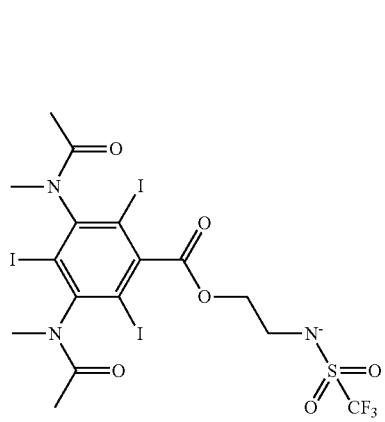
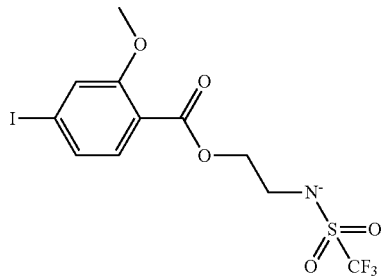

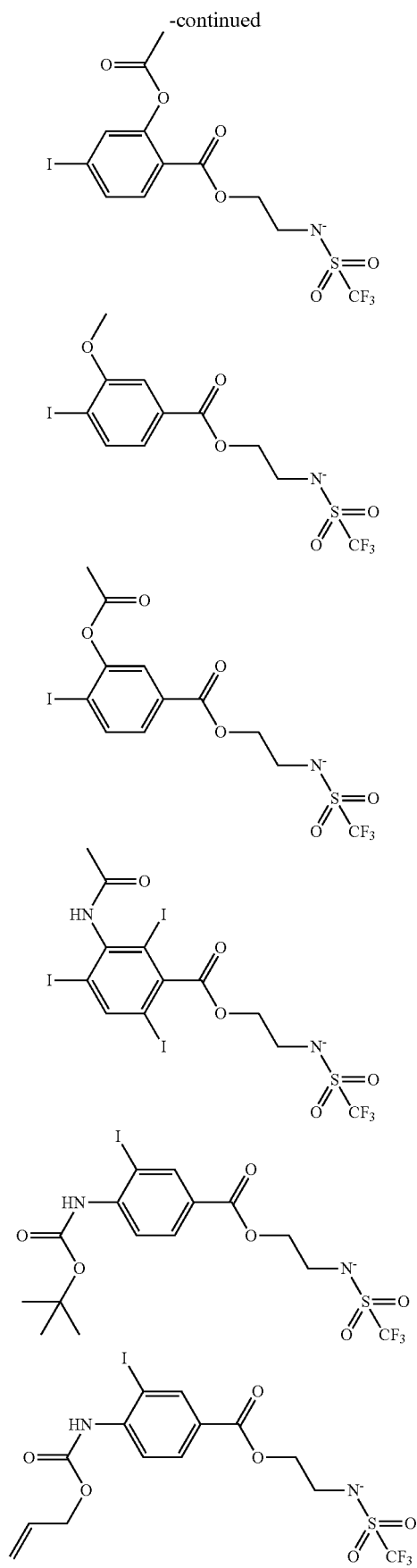
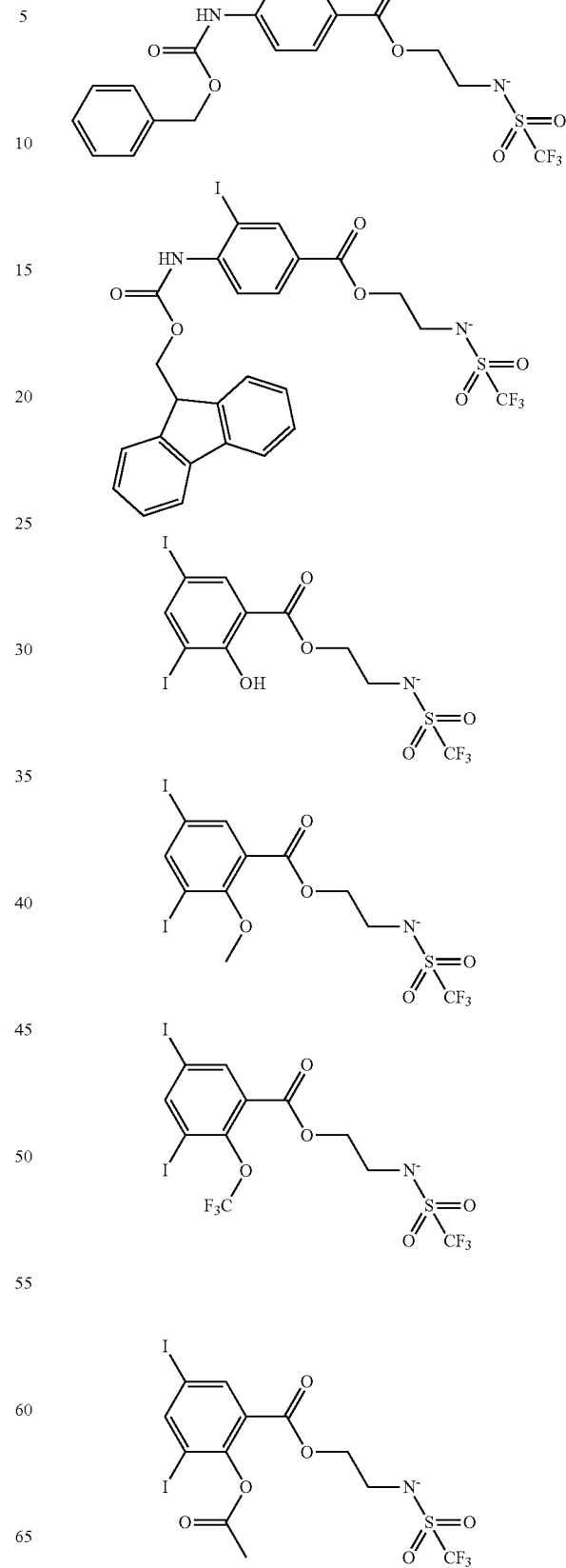

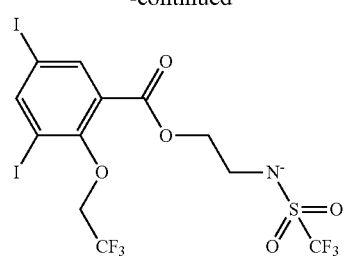
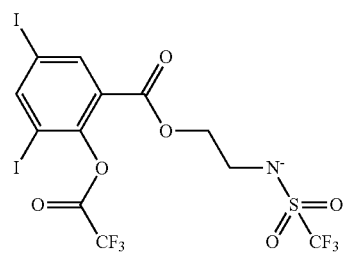
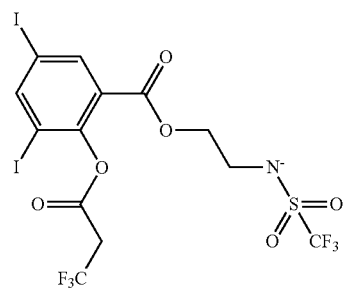
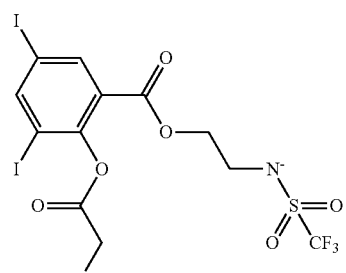
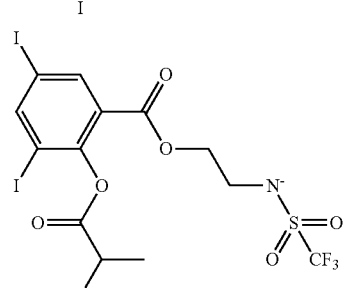
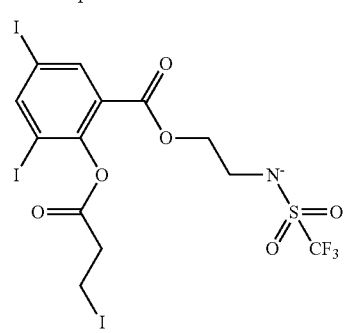
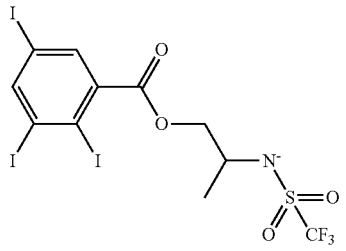
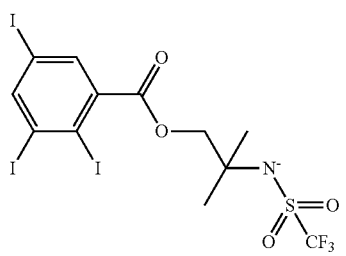
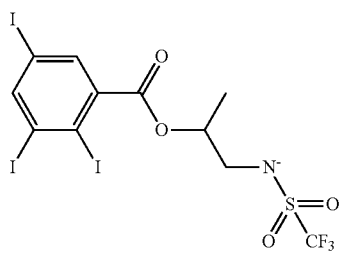
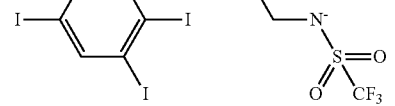
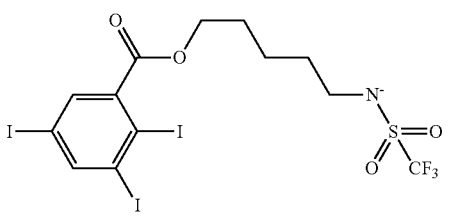
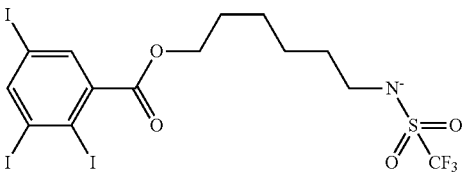
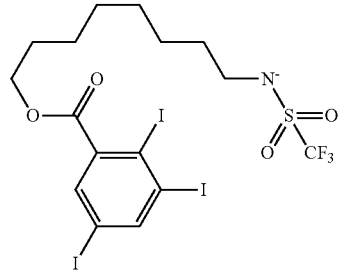

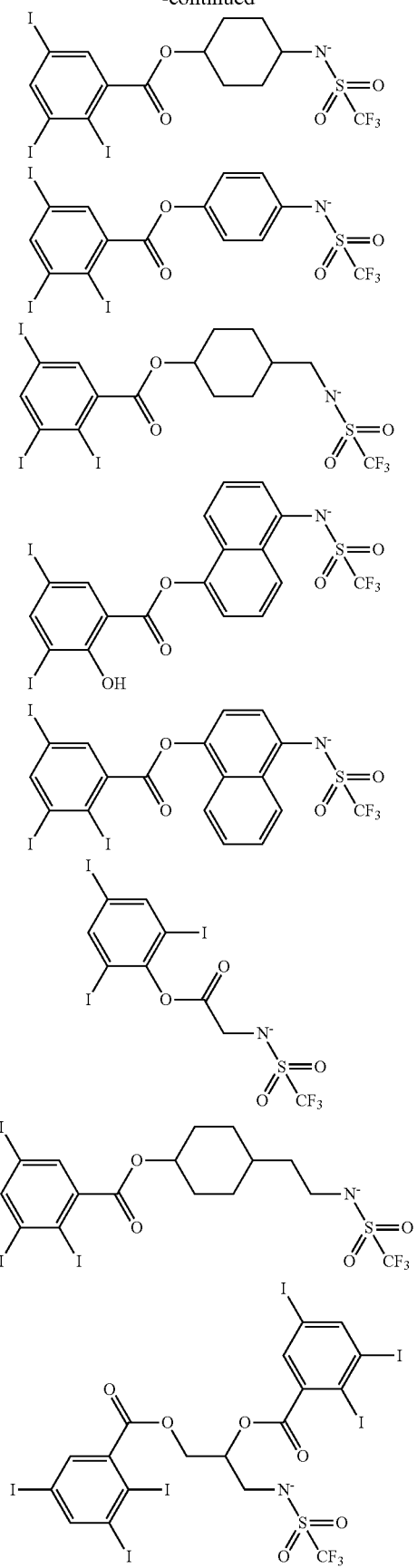
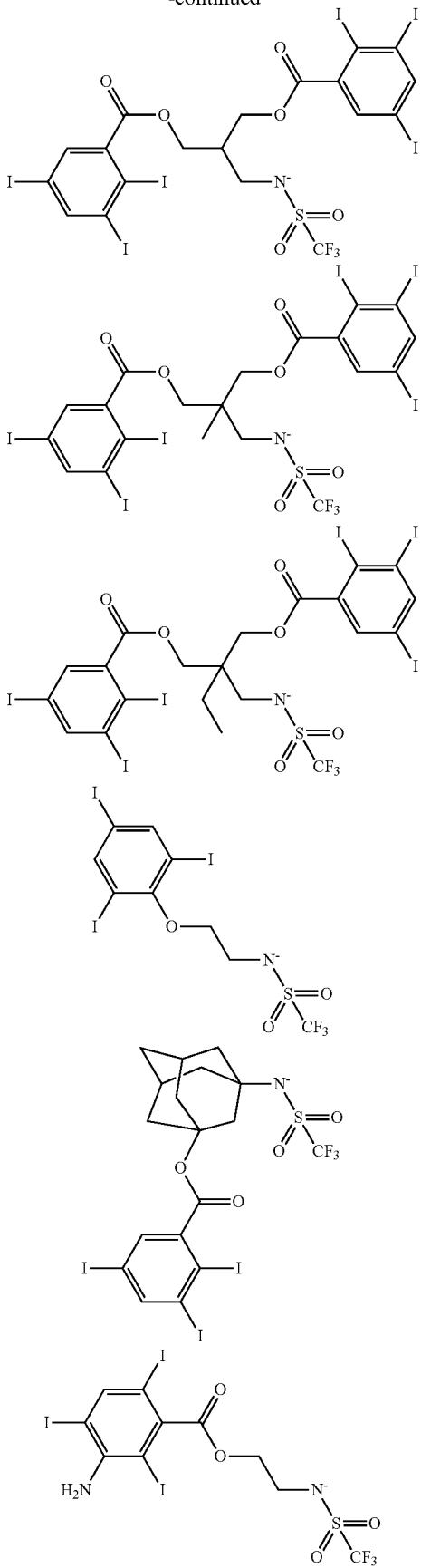

-continued
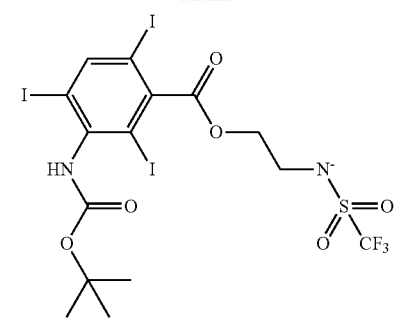
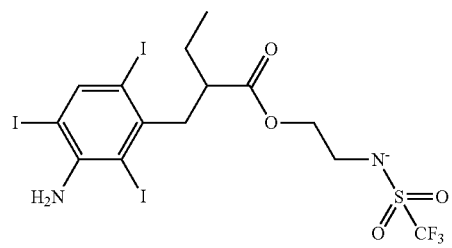
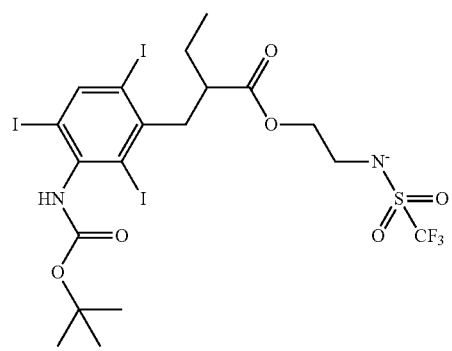
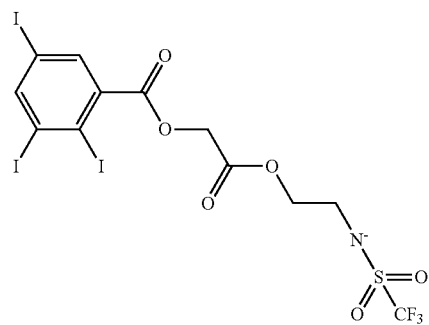
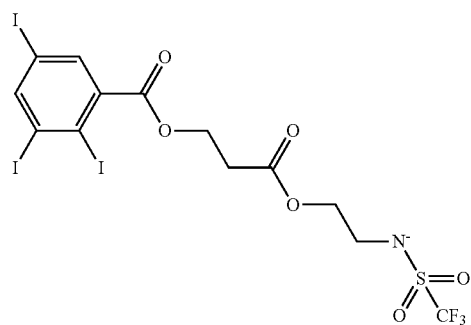
-continued
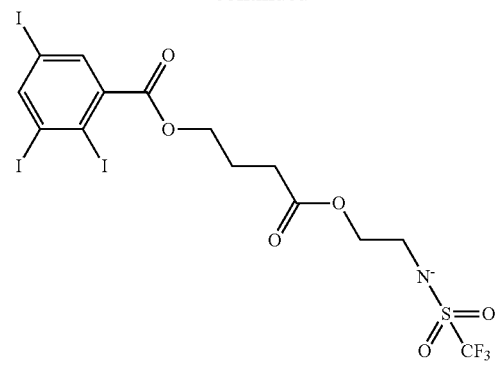
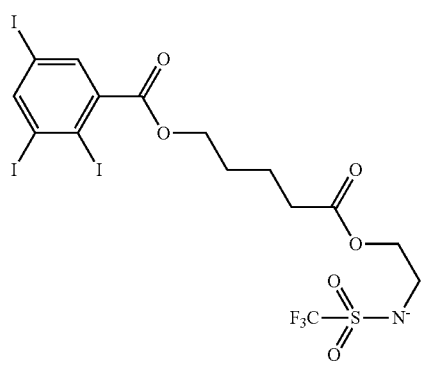
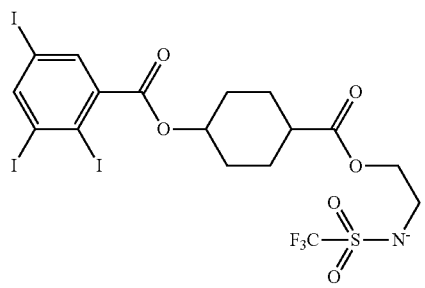
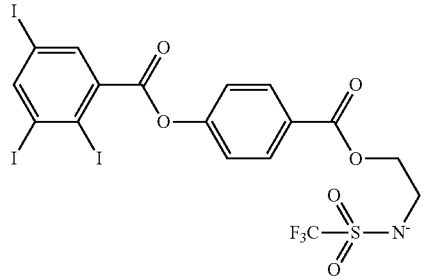
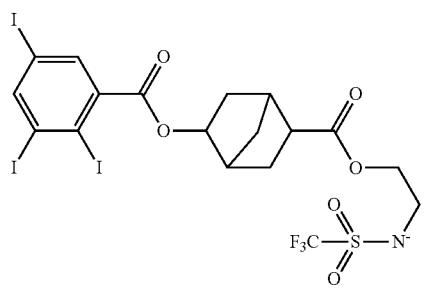

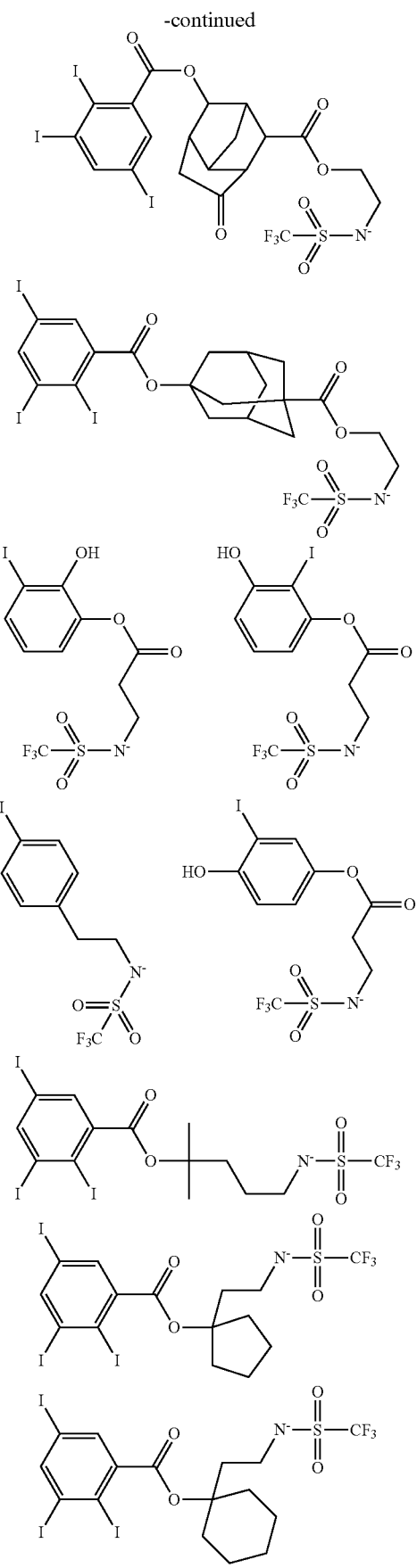
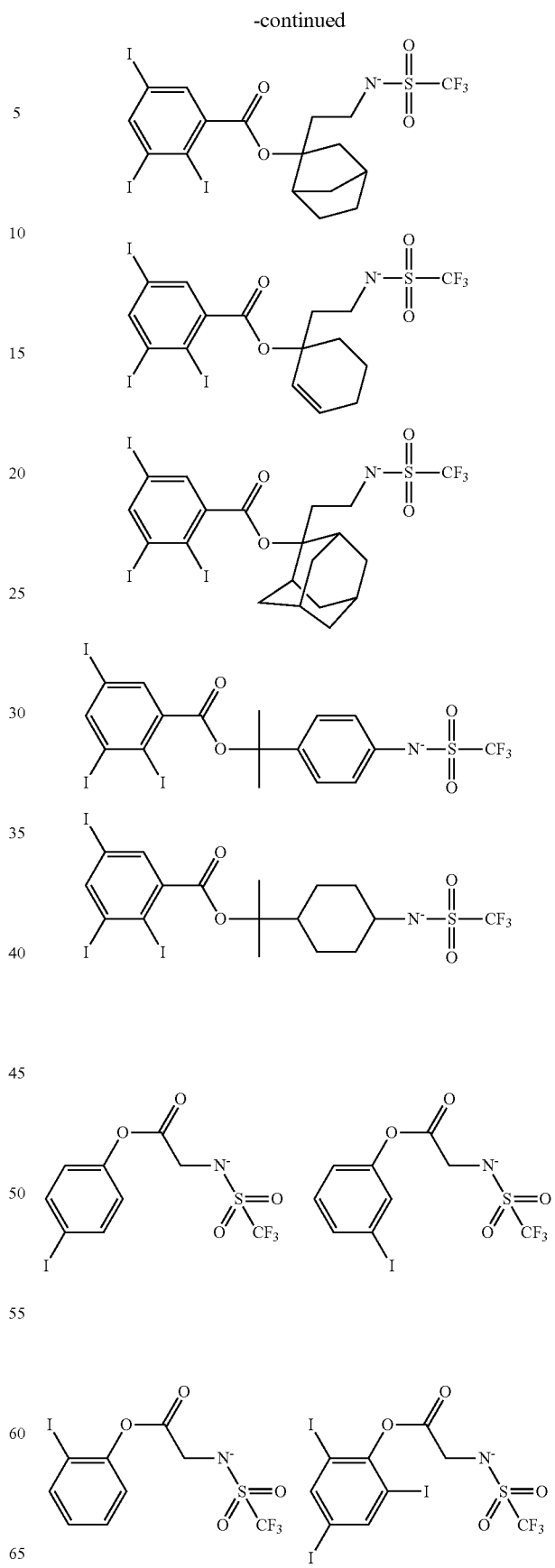

Examples of the sulfonium cation having formula (Aa) are shown below, but not limited thereto.
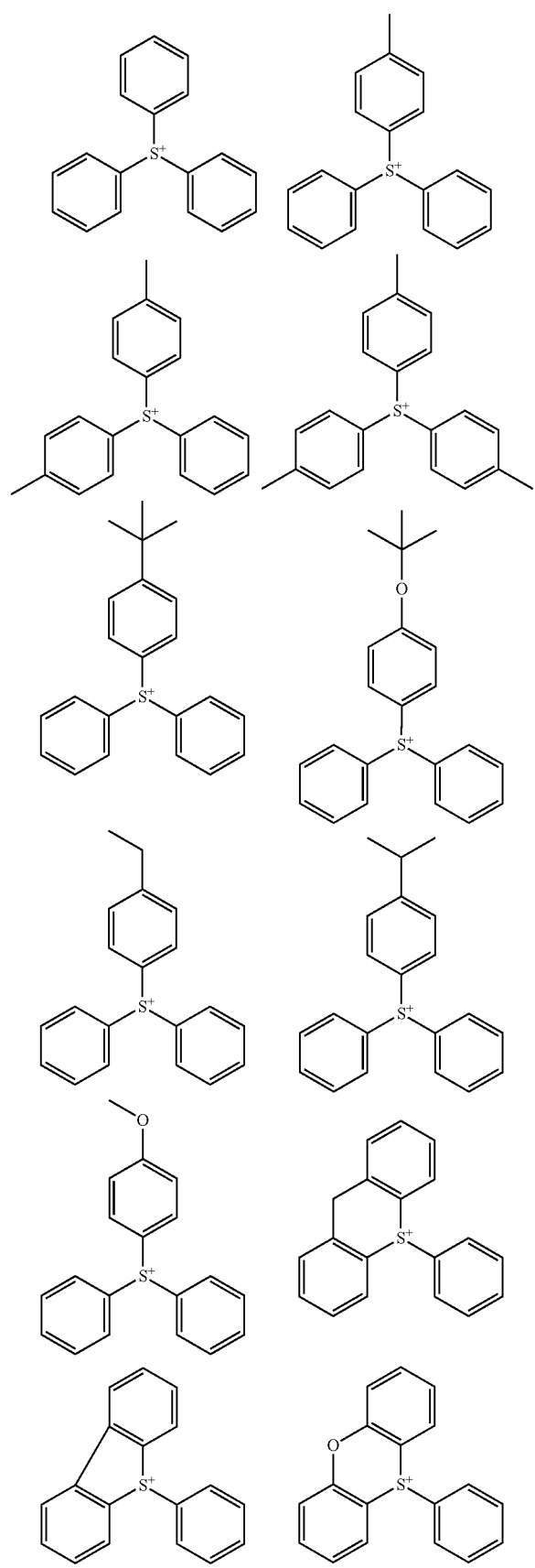
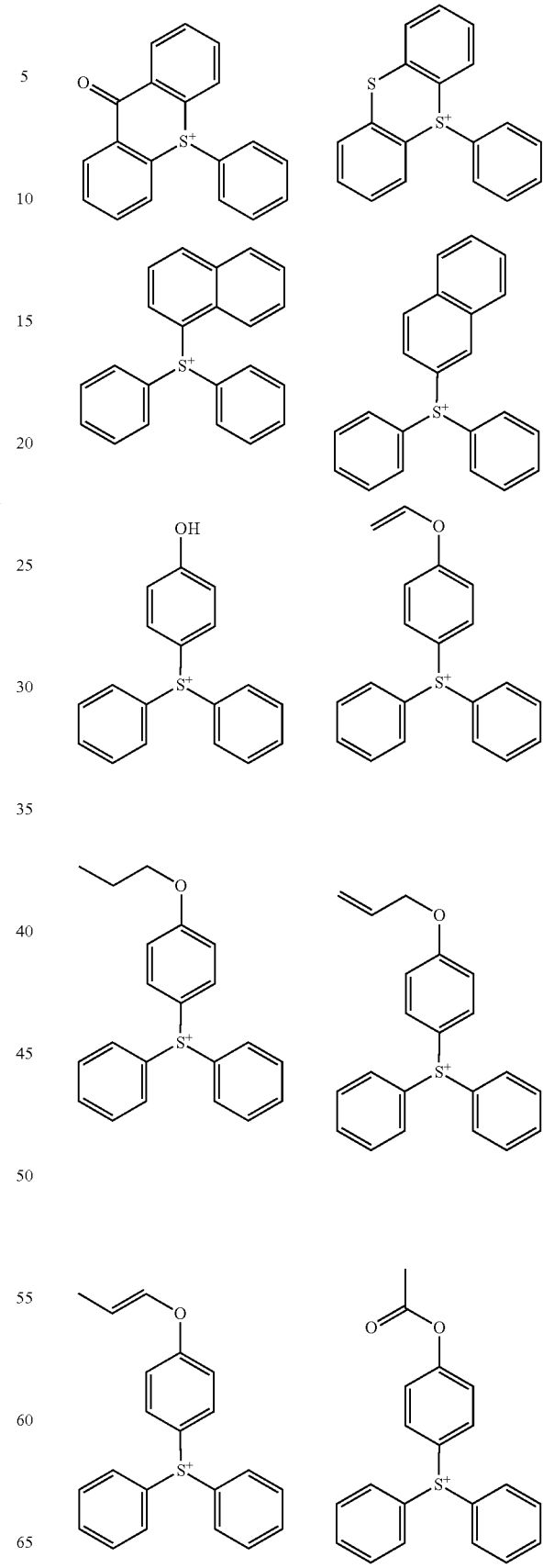

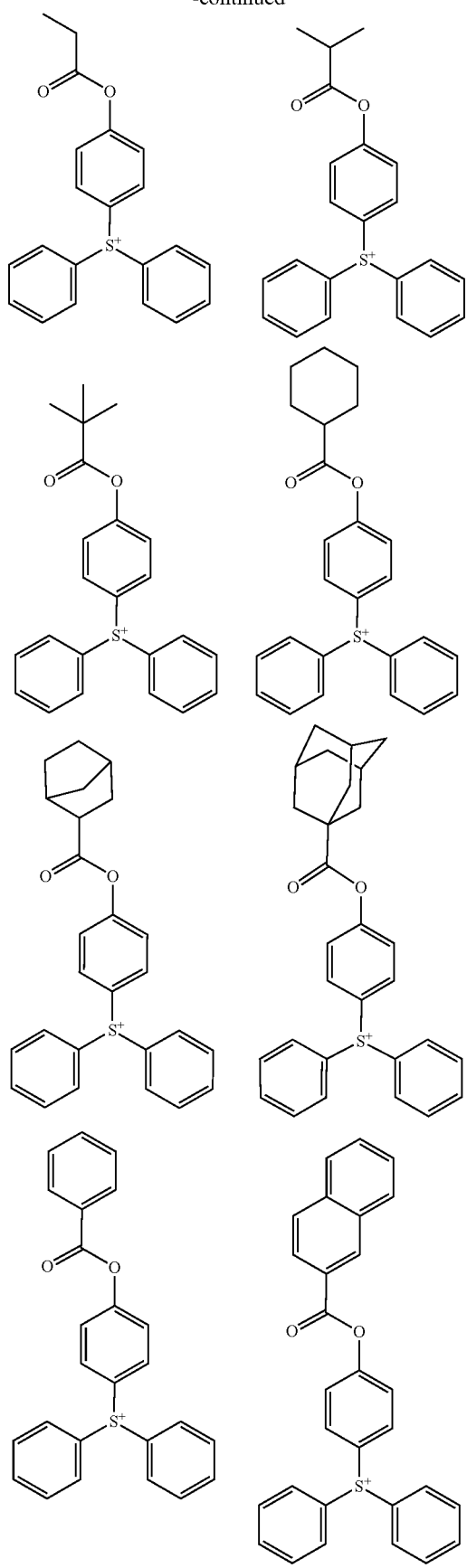
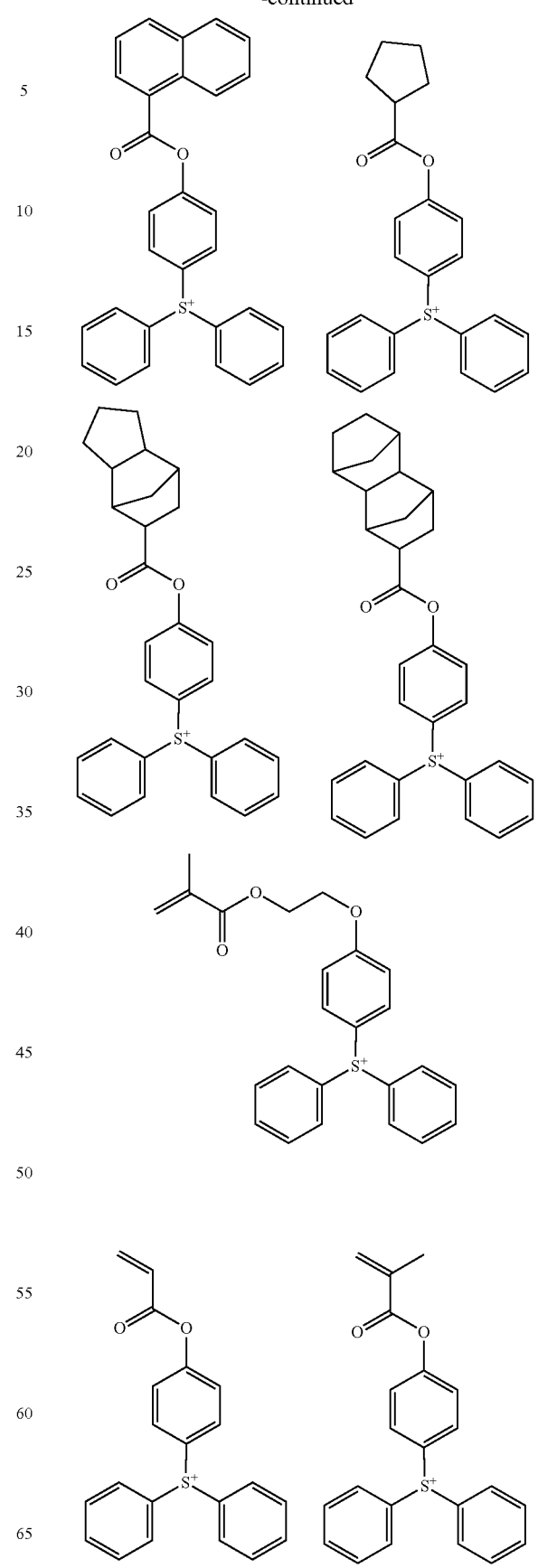

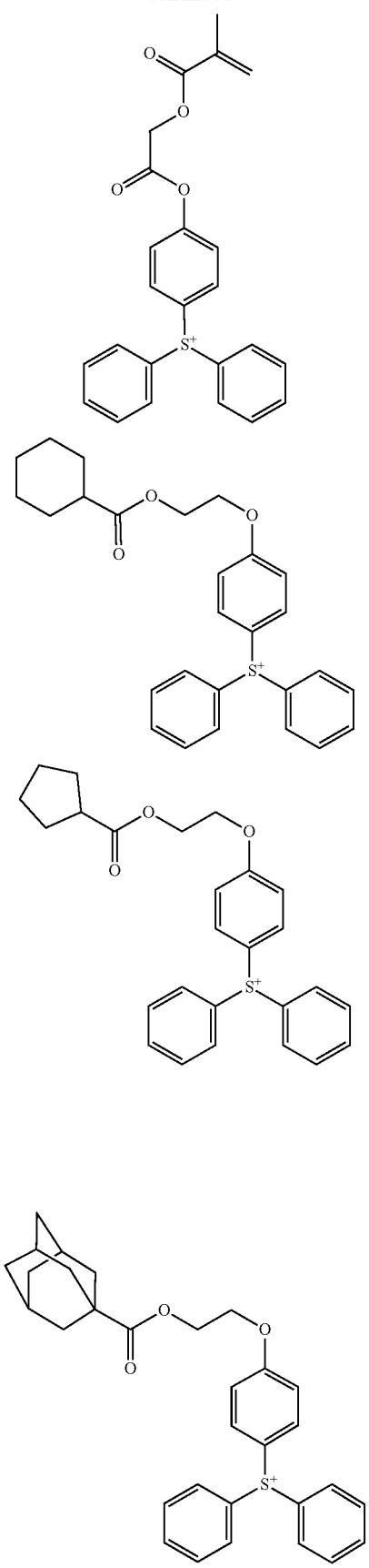
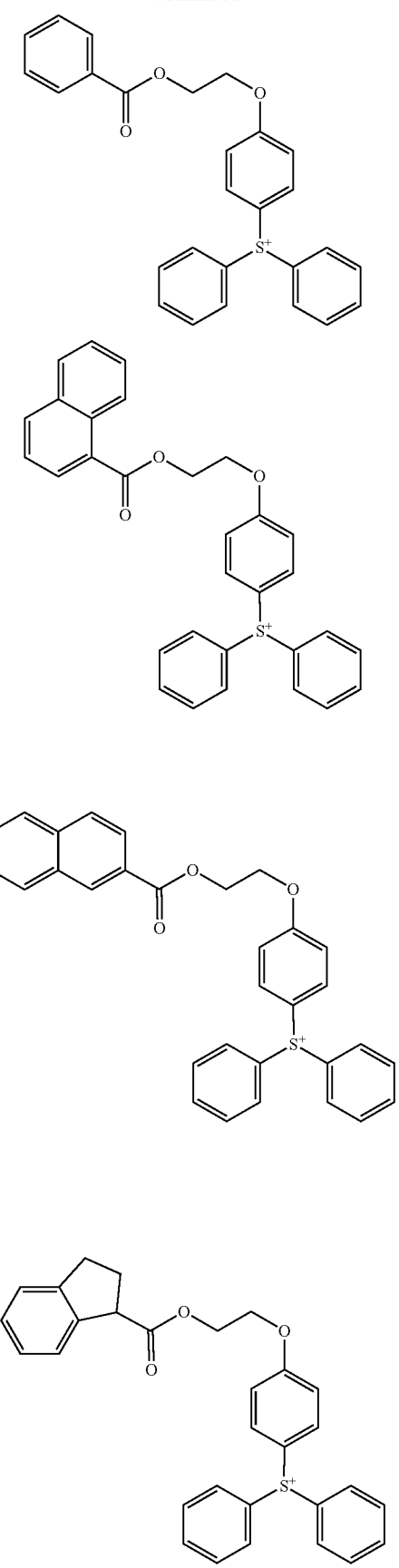

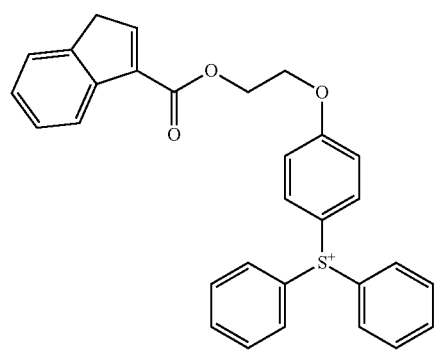
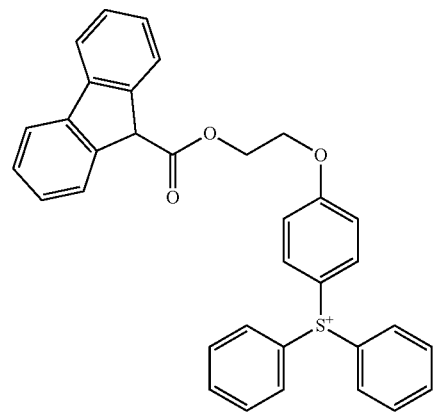
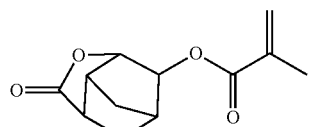
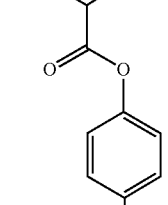
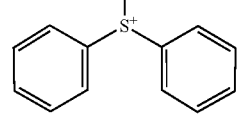
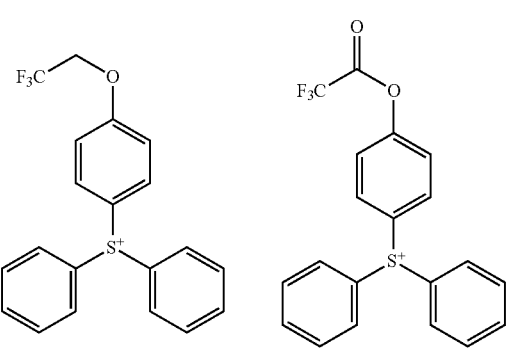
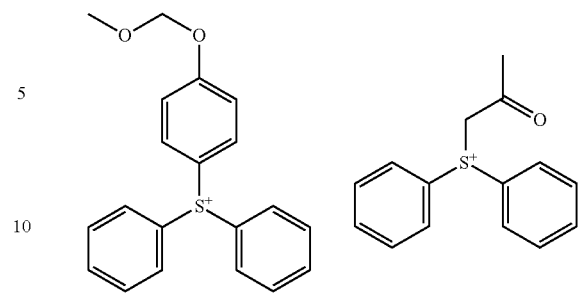
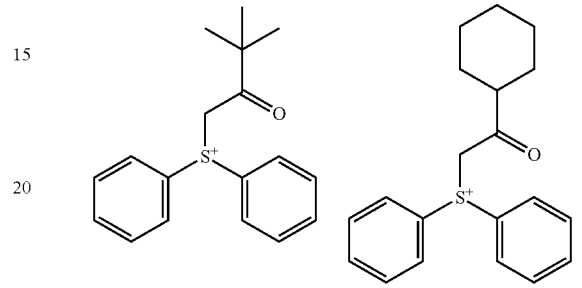
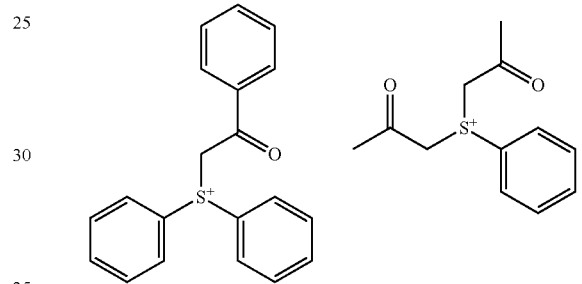
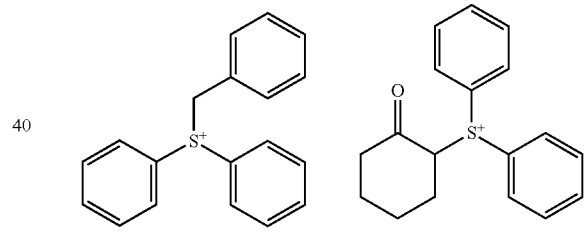
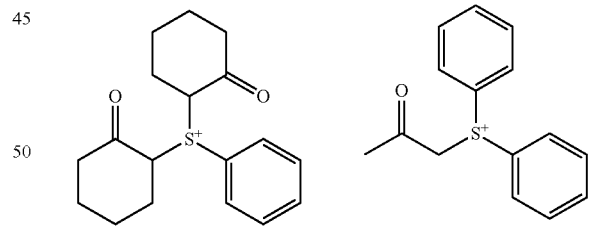
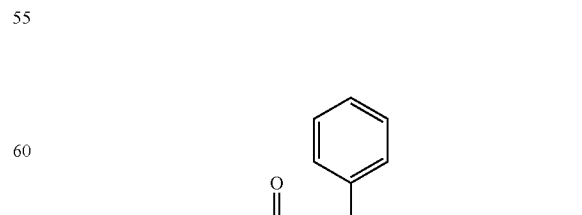

-continued
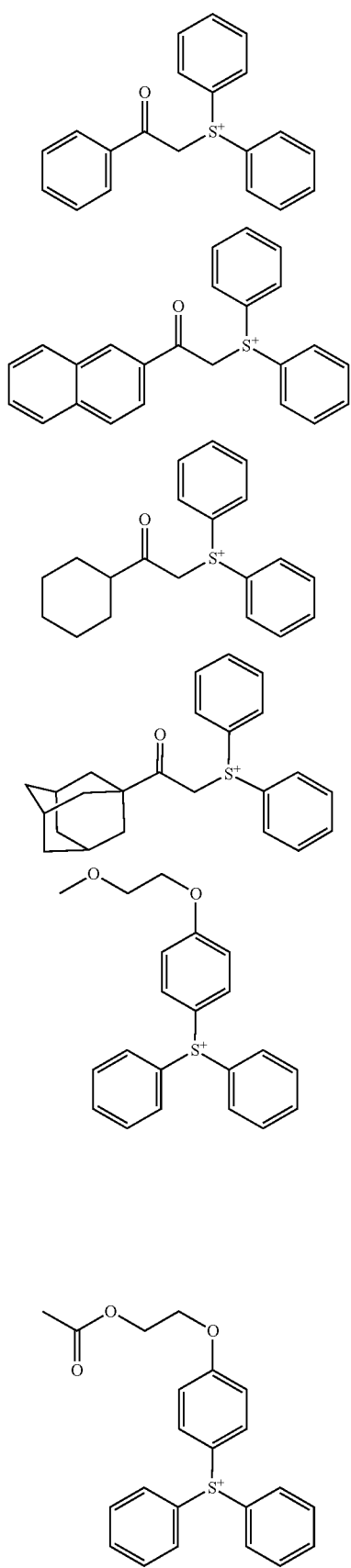
-continued
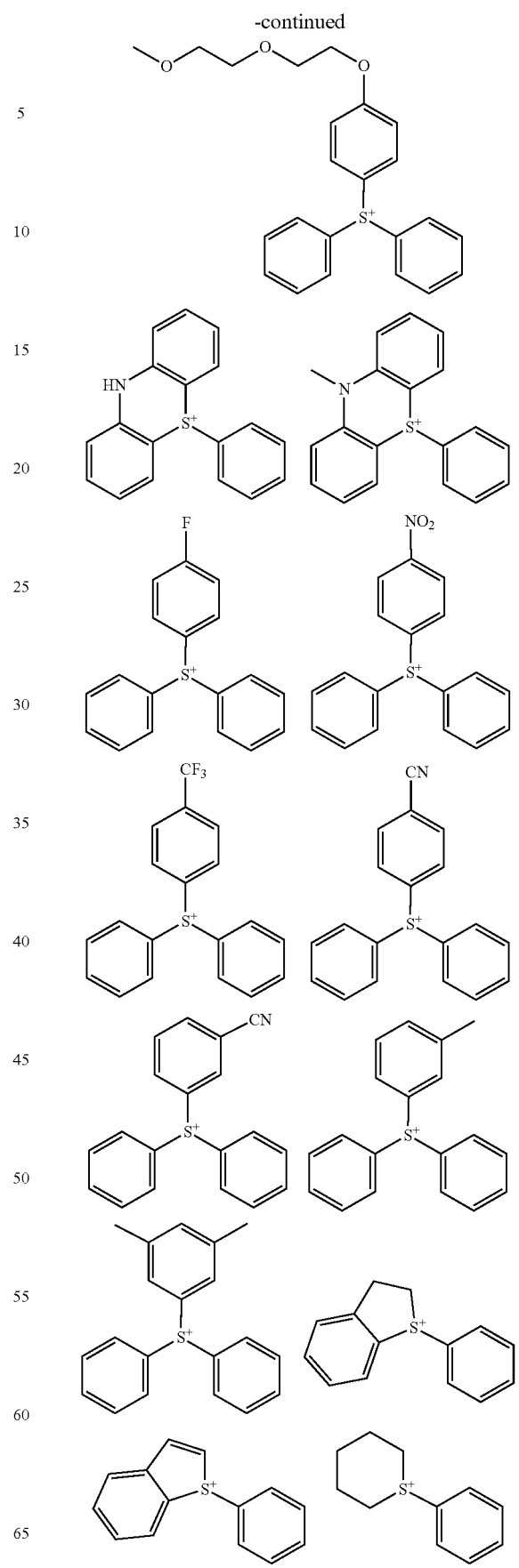

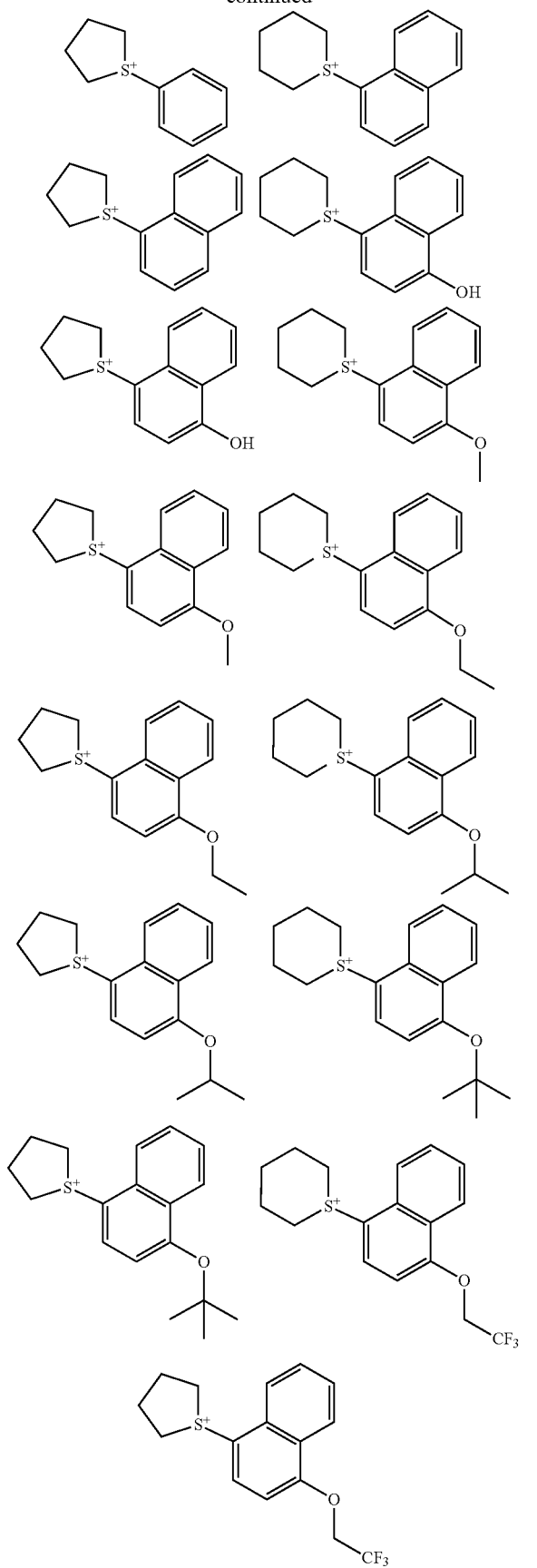
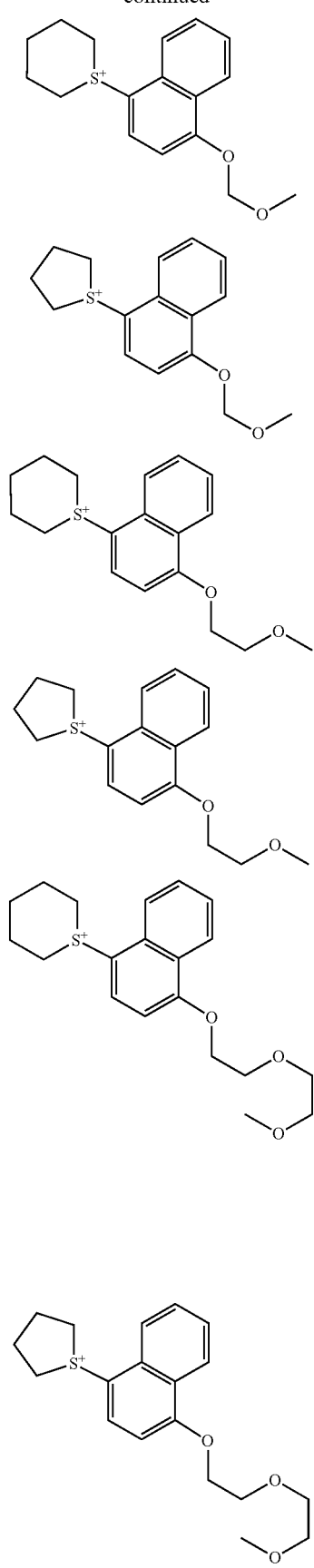

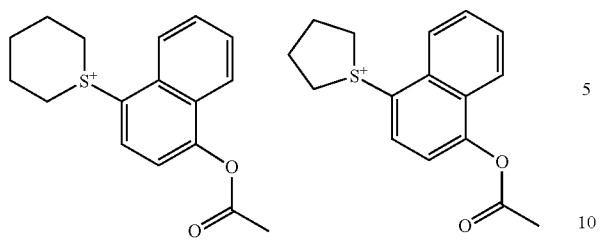
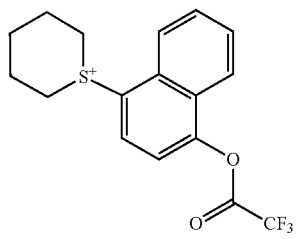
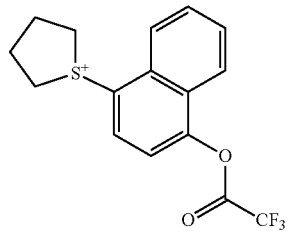
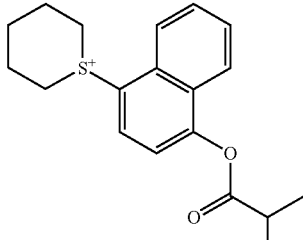
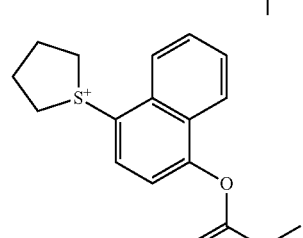
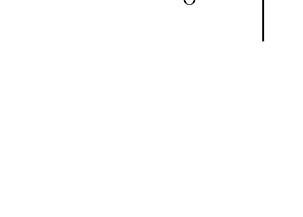
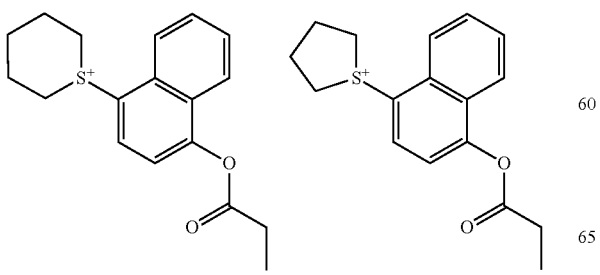
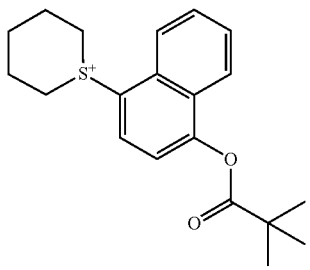
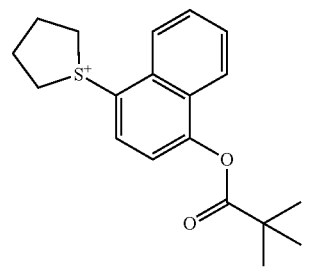
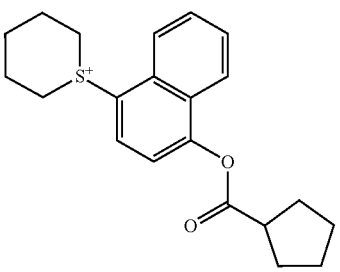
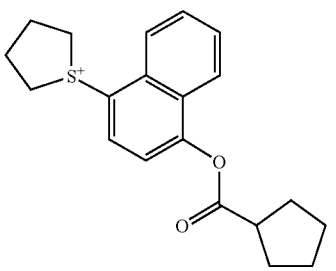
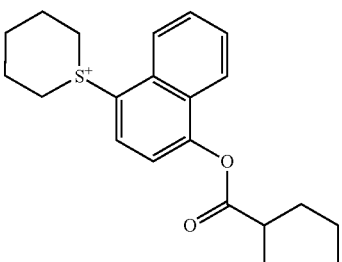
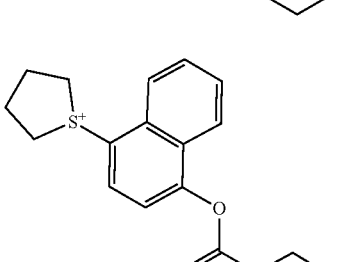

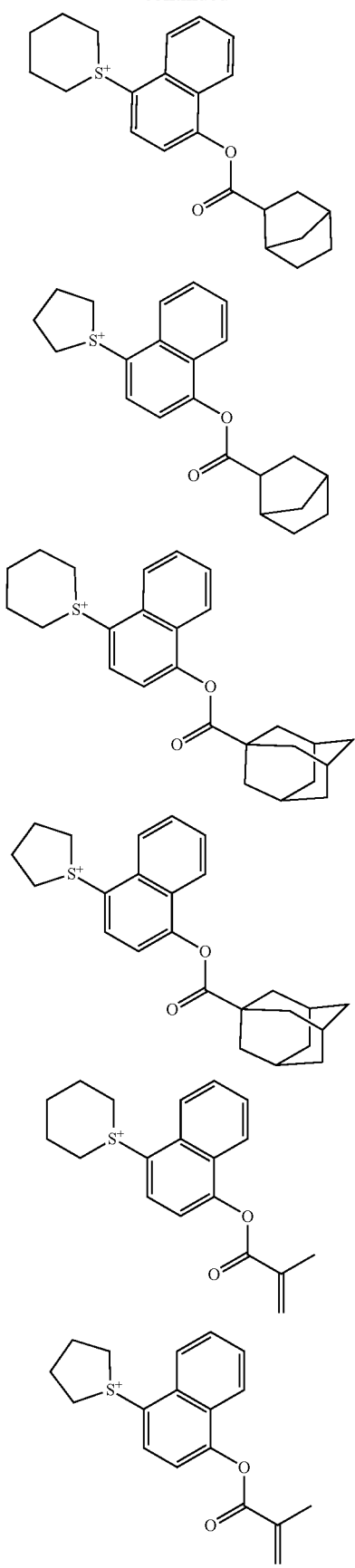
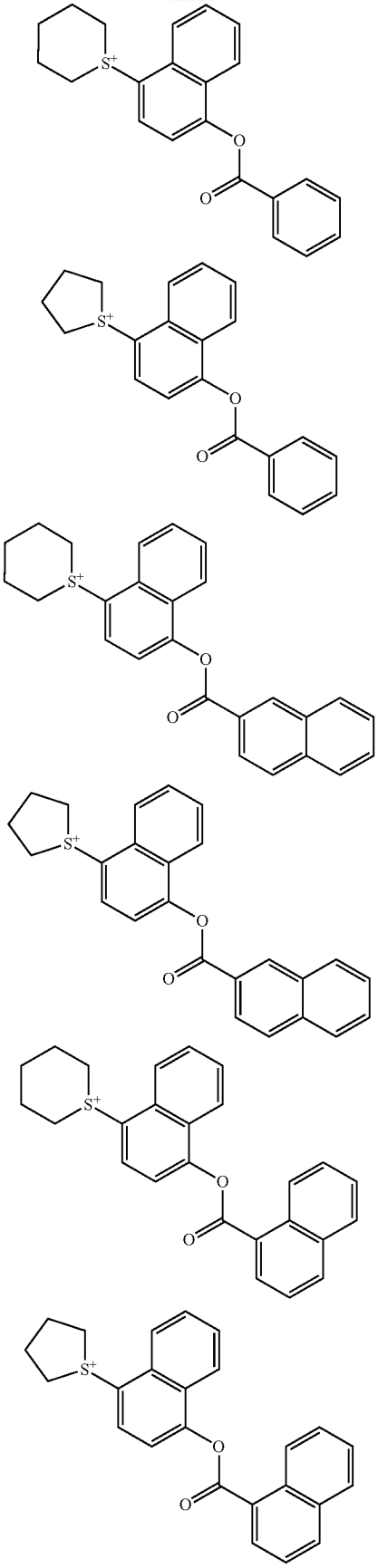

43
-continued
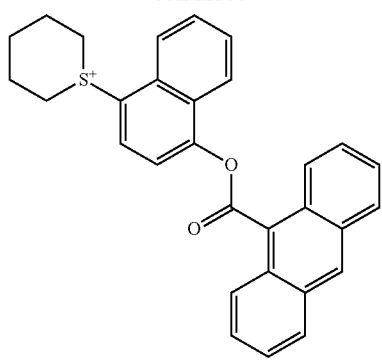
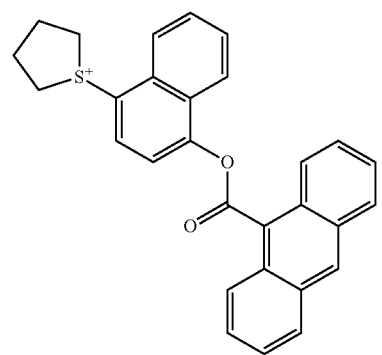
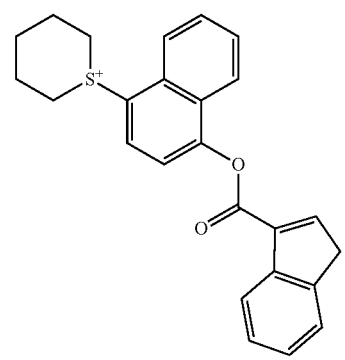
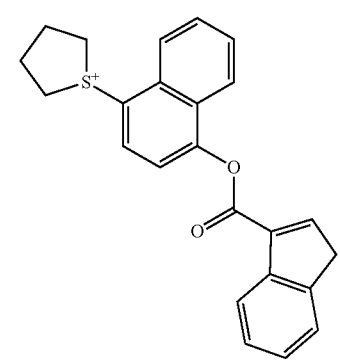
44
-continued
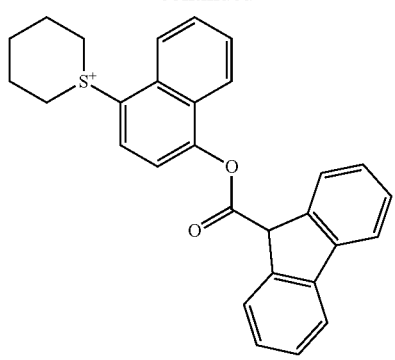
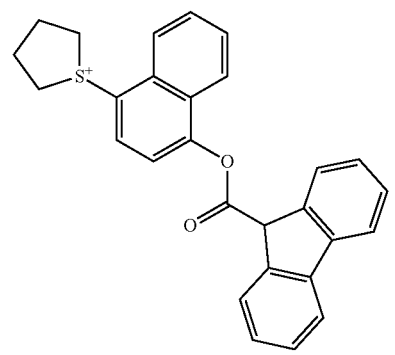
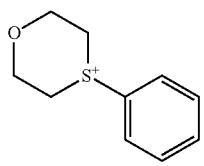 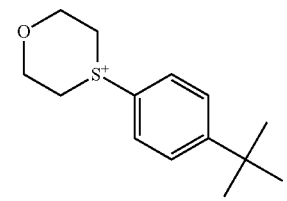
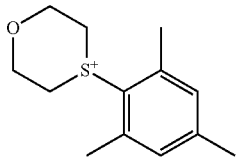 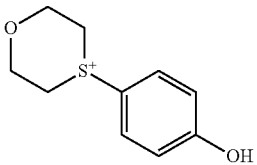
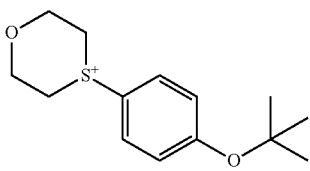
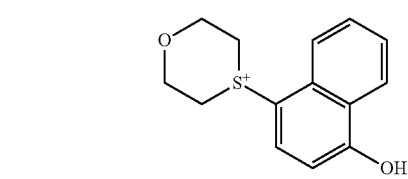
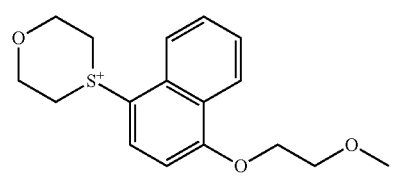

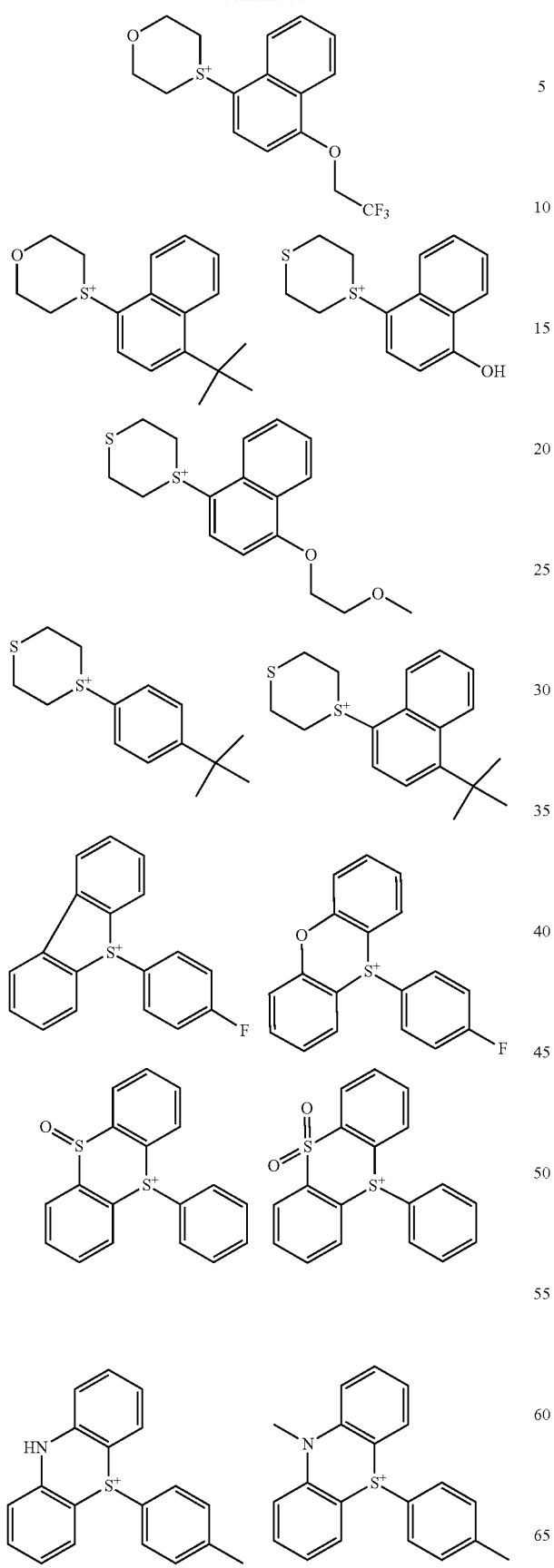
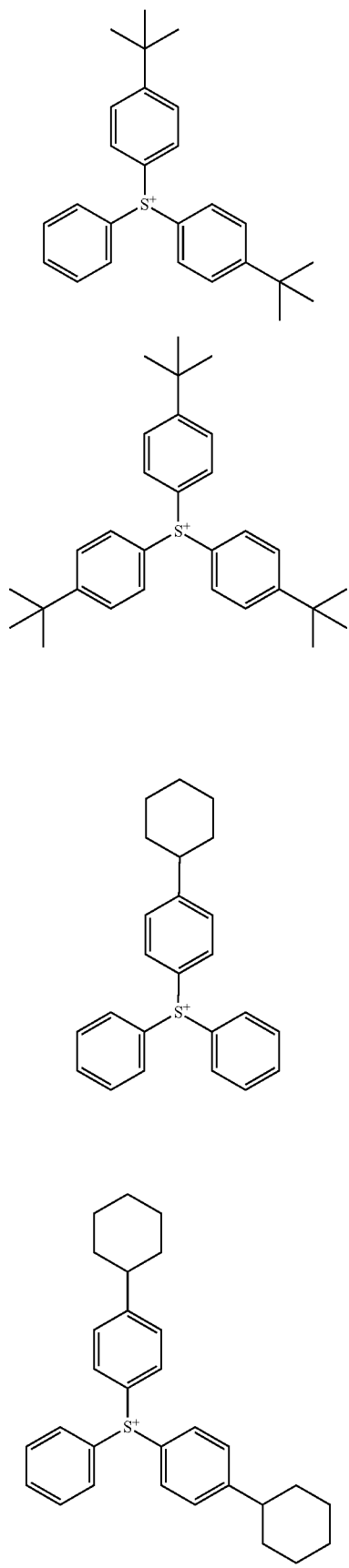

47
-continued
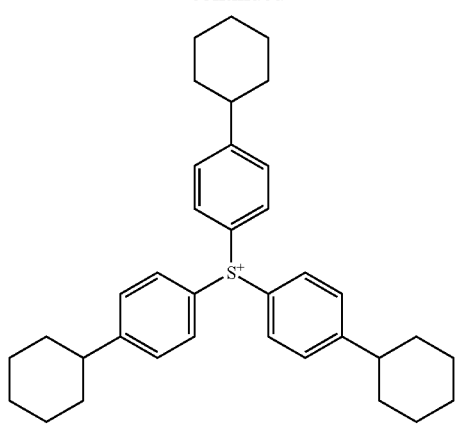
48
-continued
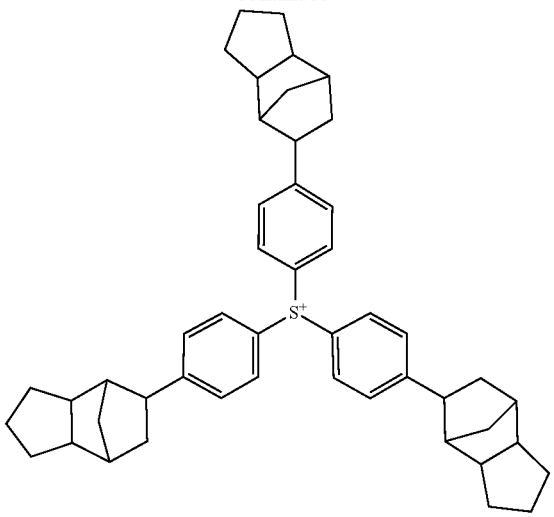
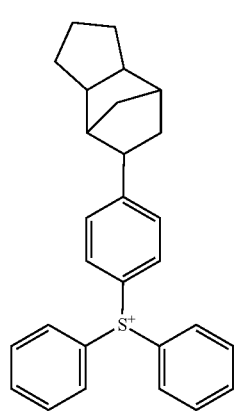
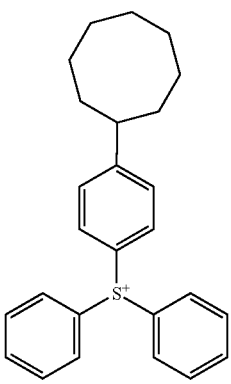
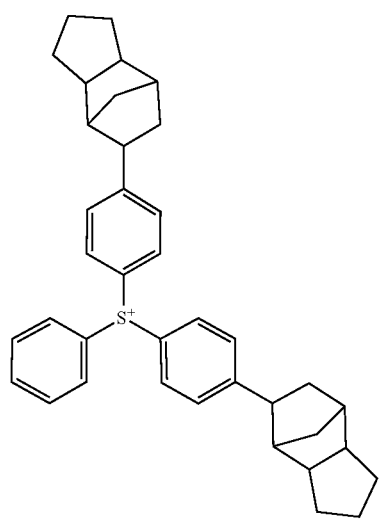
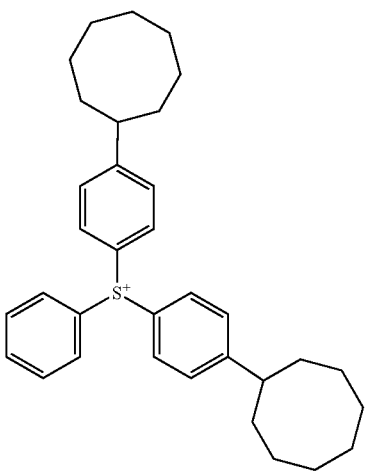

-continued
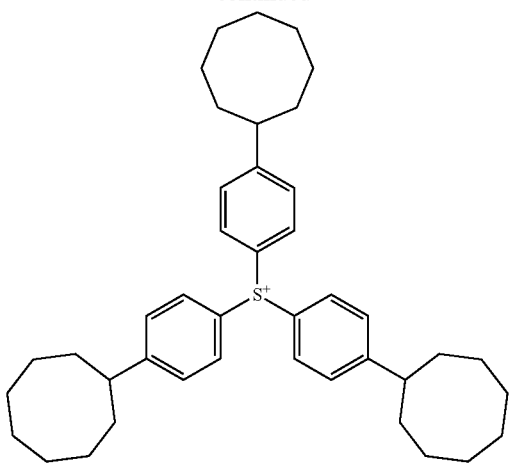
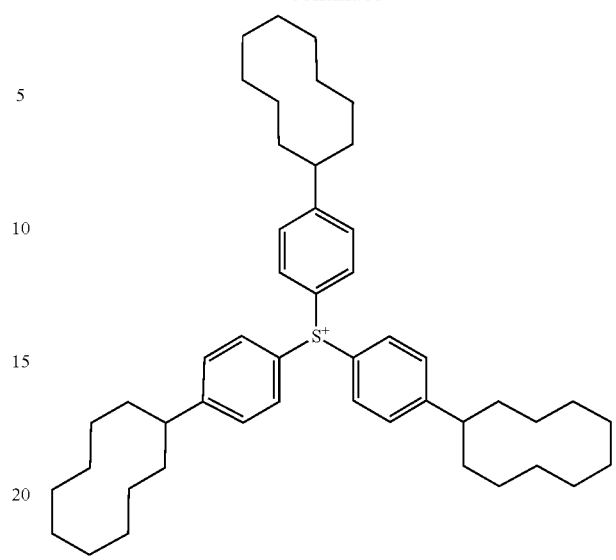
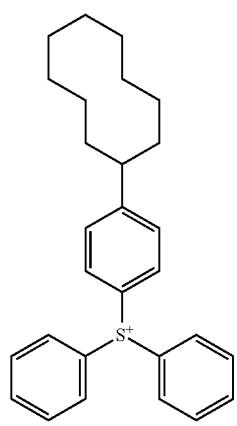
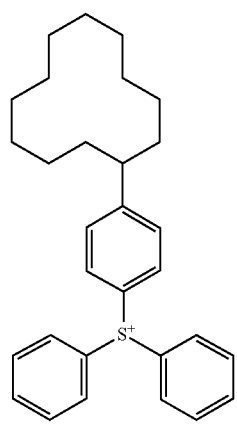
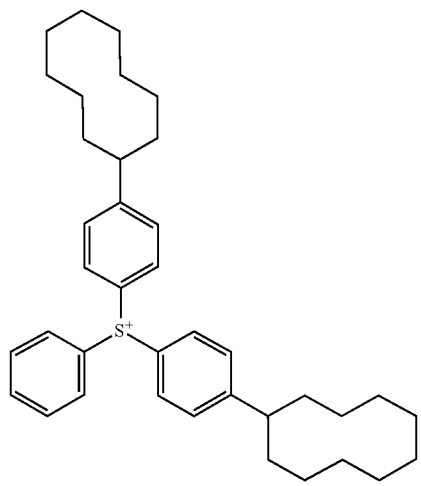
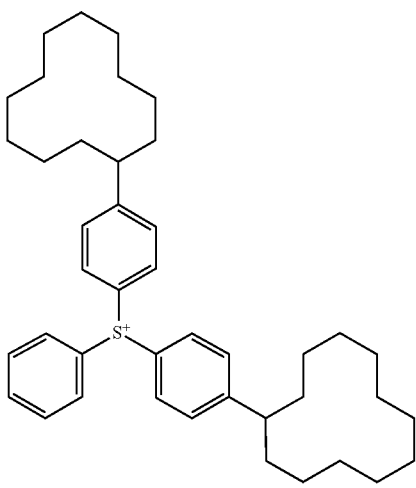

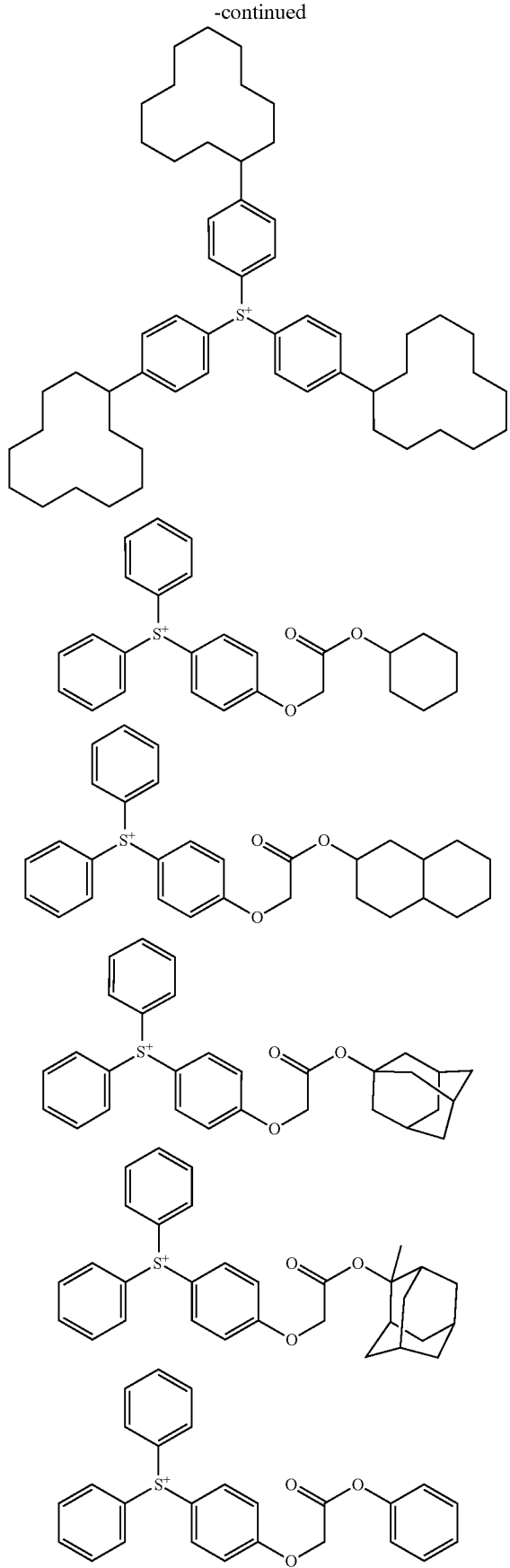
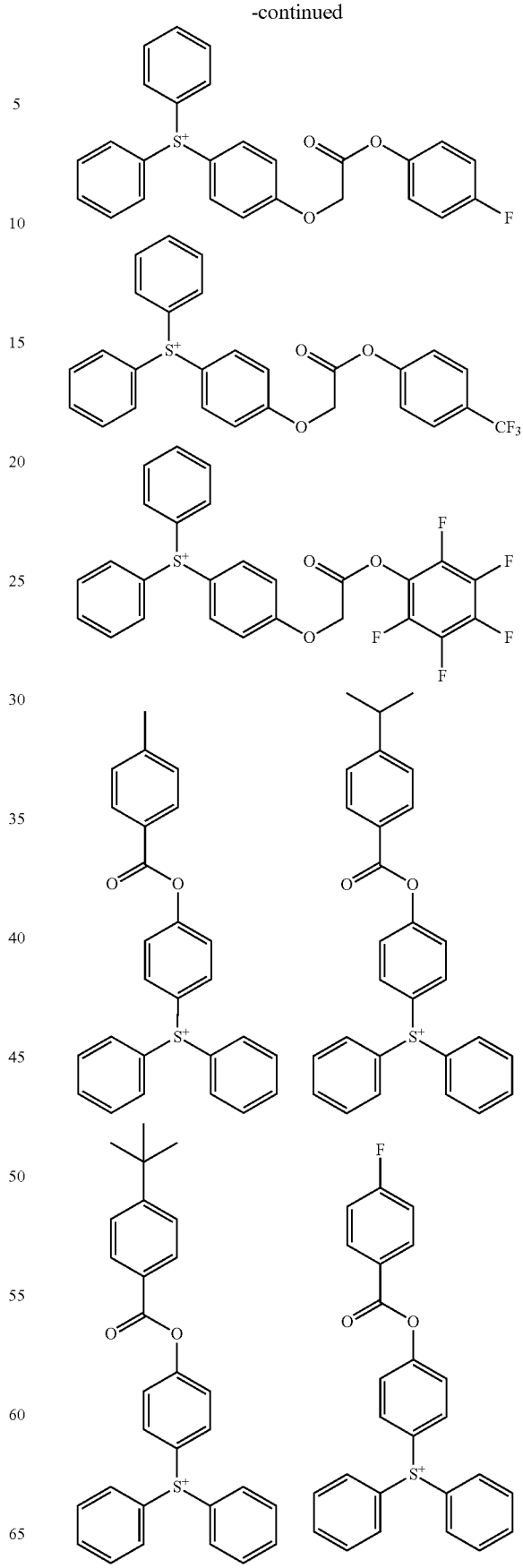

-continued
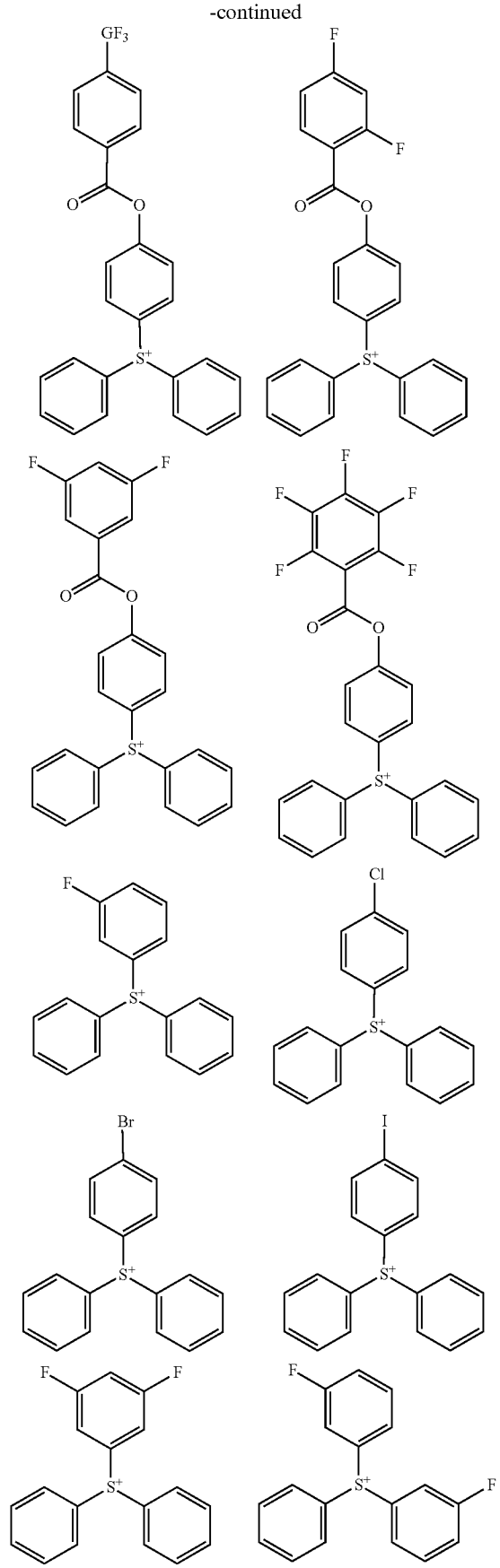
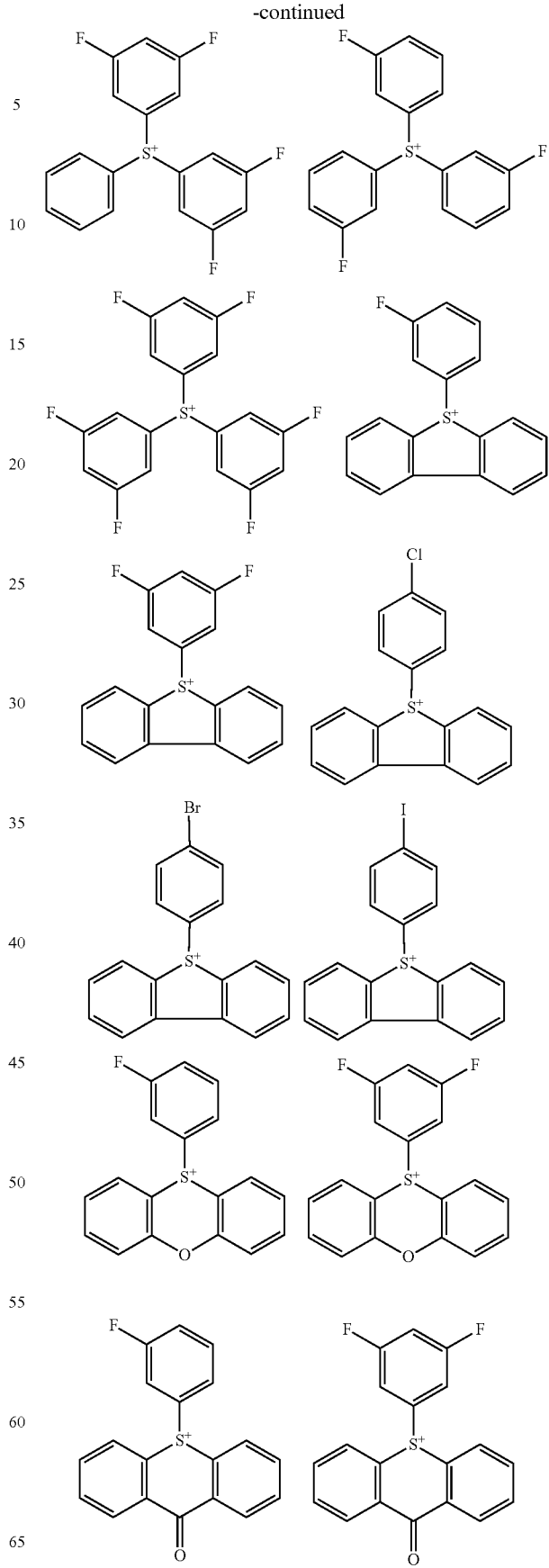

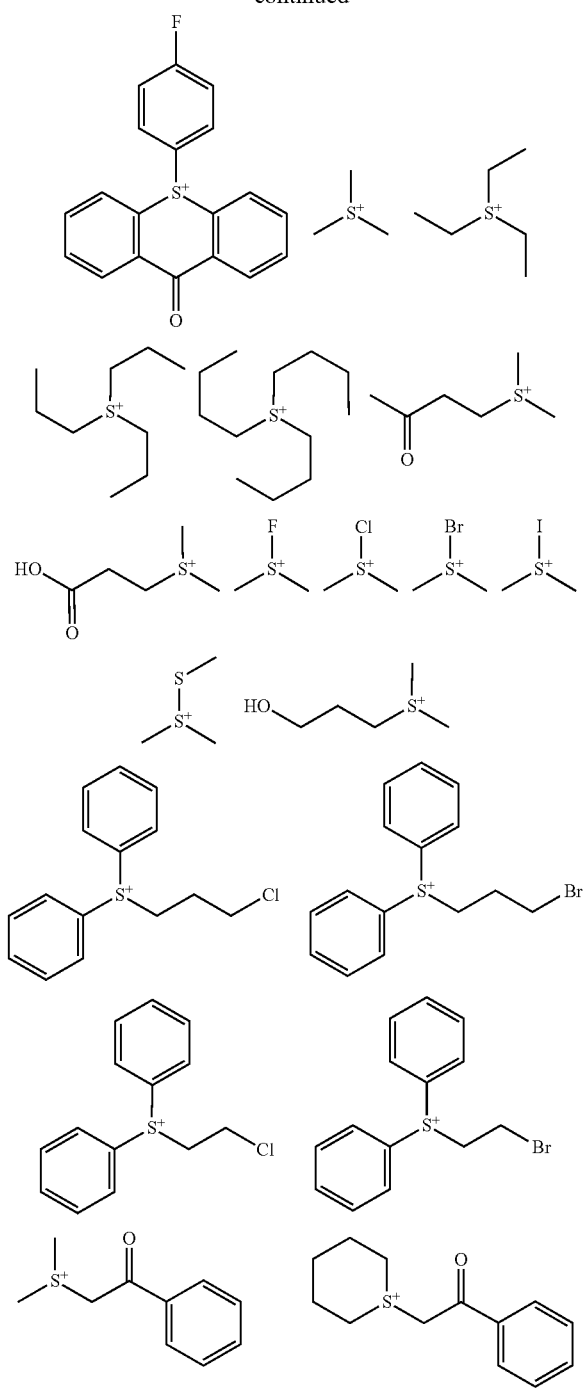
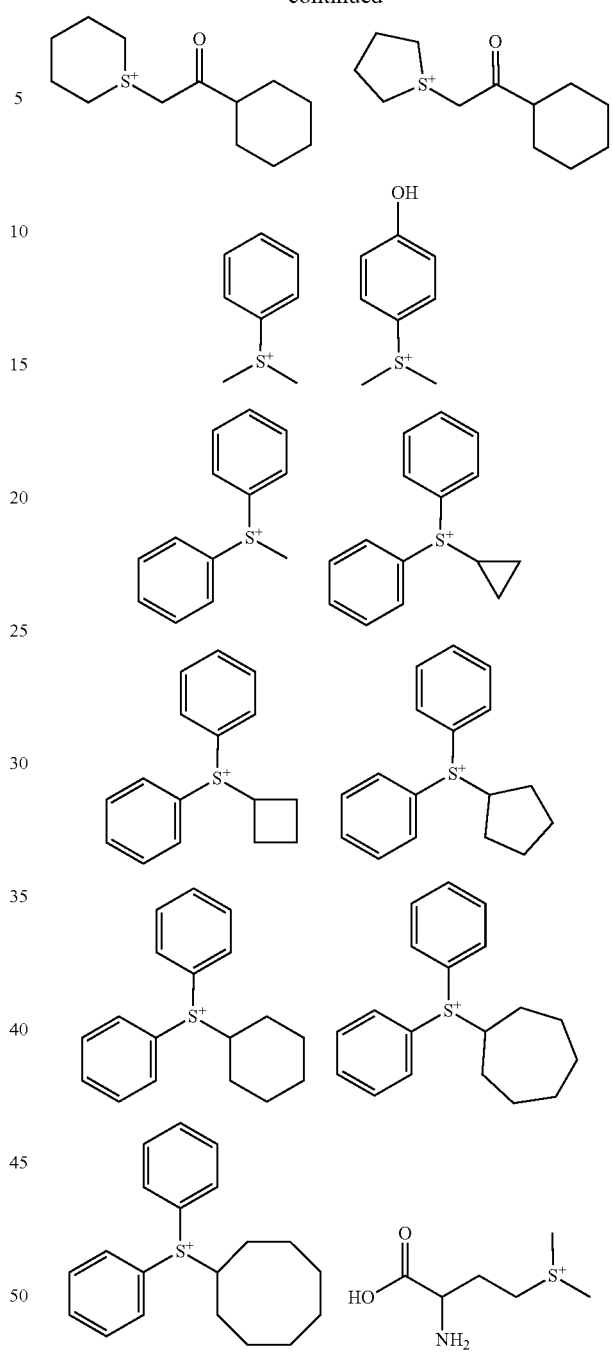
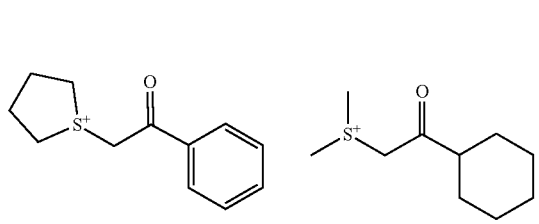
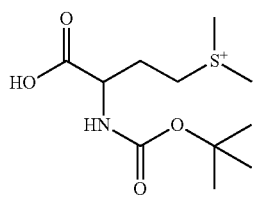

Examples of the iodonium cation having formula (Ab) are shown below, but not limited thereto.
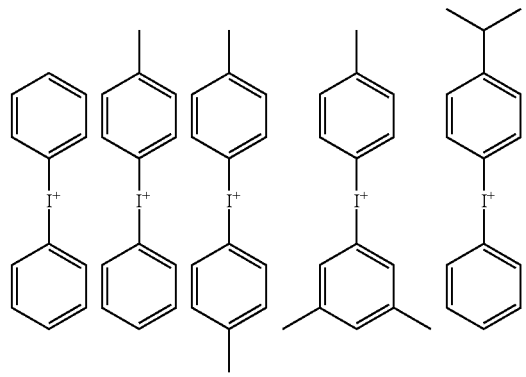
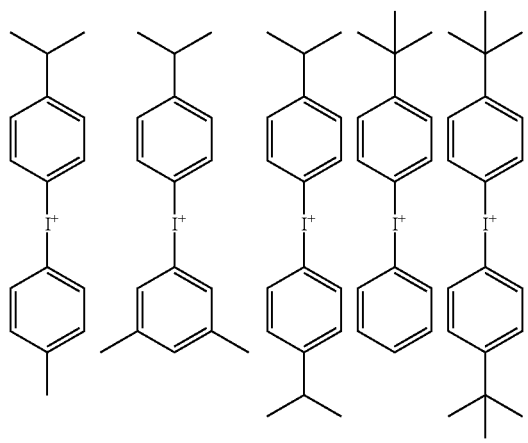
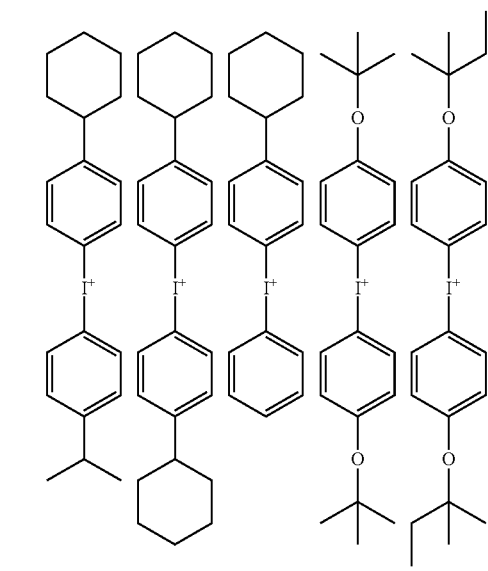
-continued
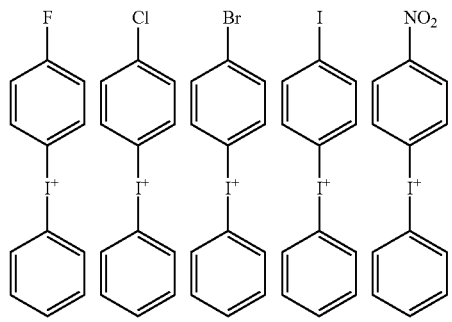
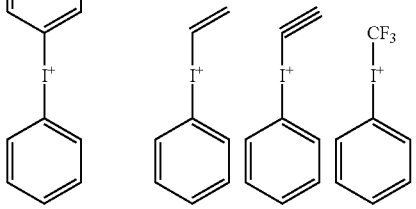
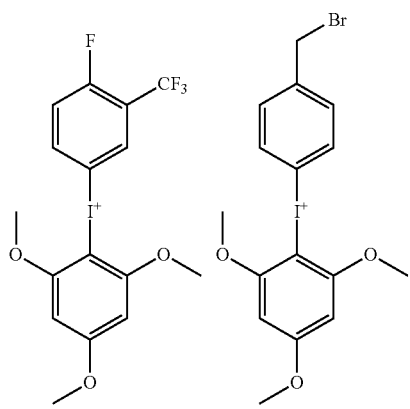
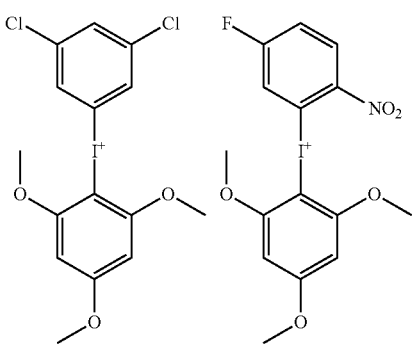

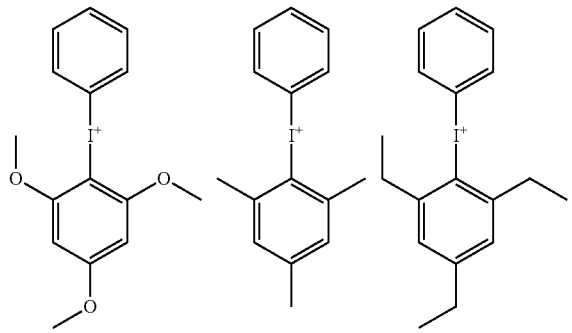
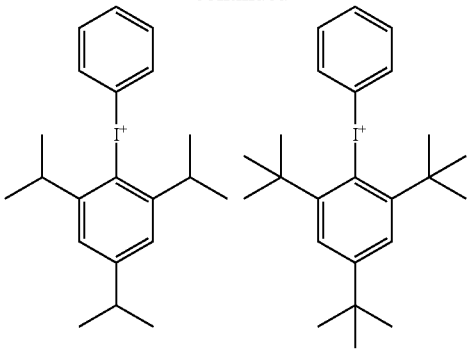 [SMILES: CC(C)c1cc(C(C)C)c([I+]c2ccccc2)c(C(C)C)c1 ; CC(C)(C)c1cc(C(C)(C)C)c([I+]c2ccccc2)c(C(C)(C)C)c1]
Examples of the ammonium cation having formula (Ac) are shown below, but not limited thereto.
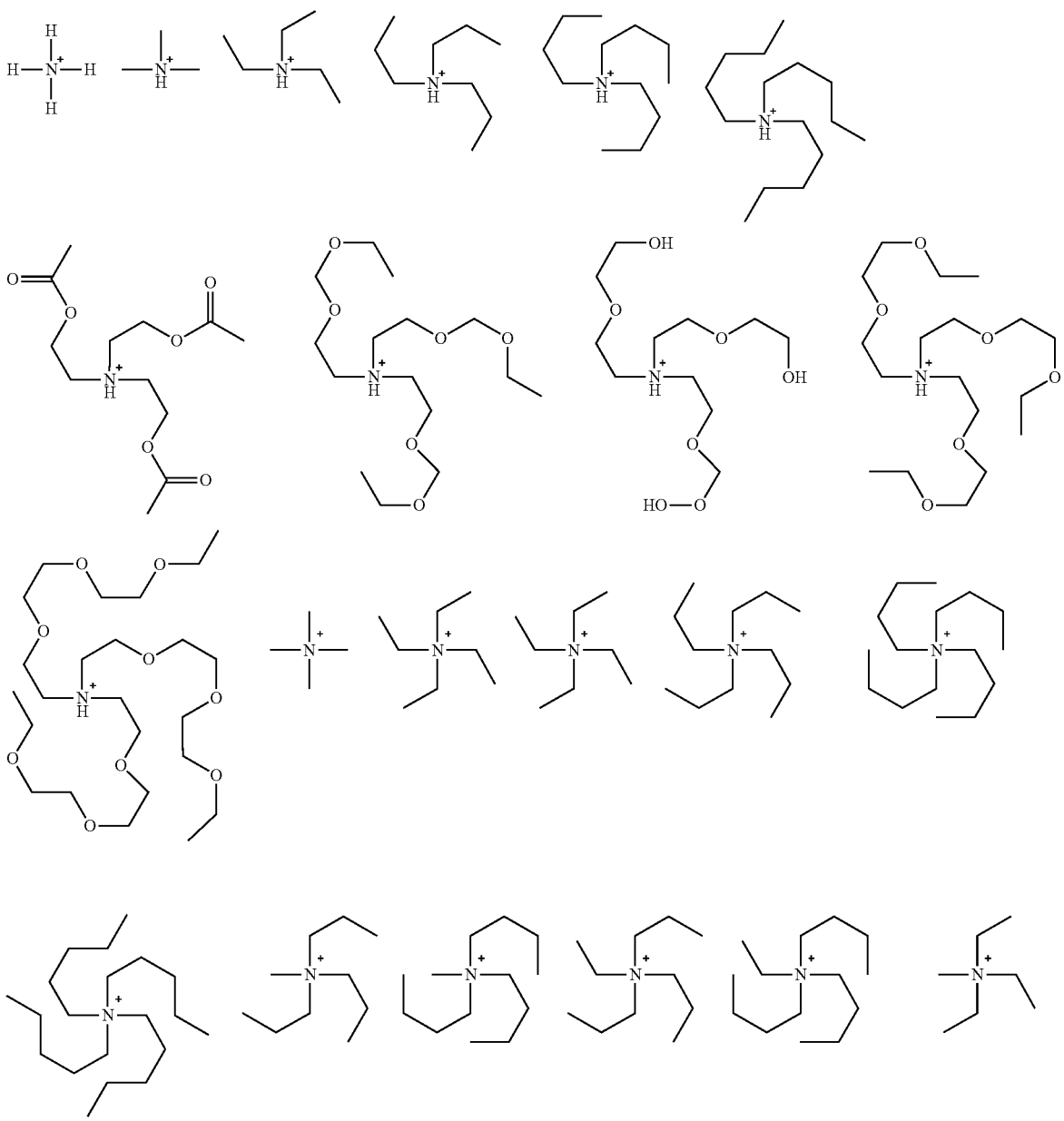

-continued
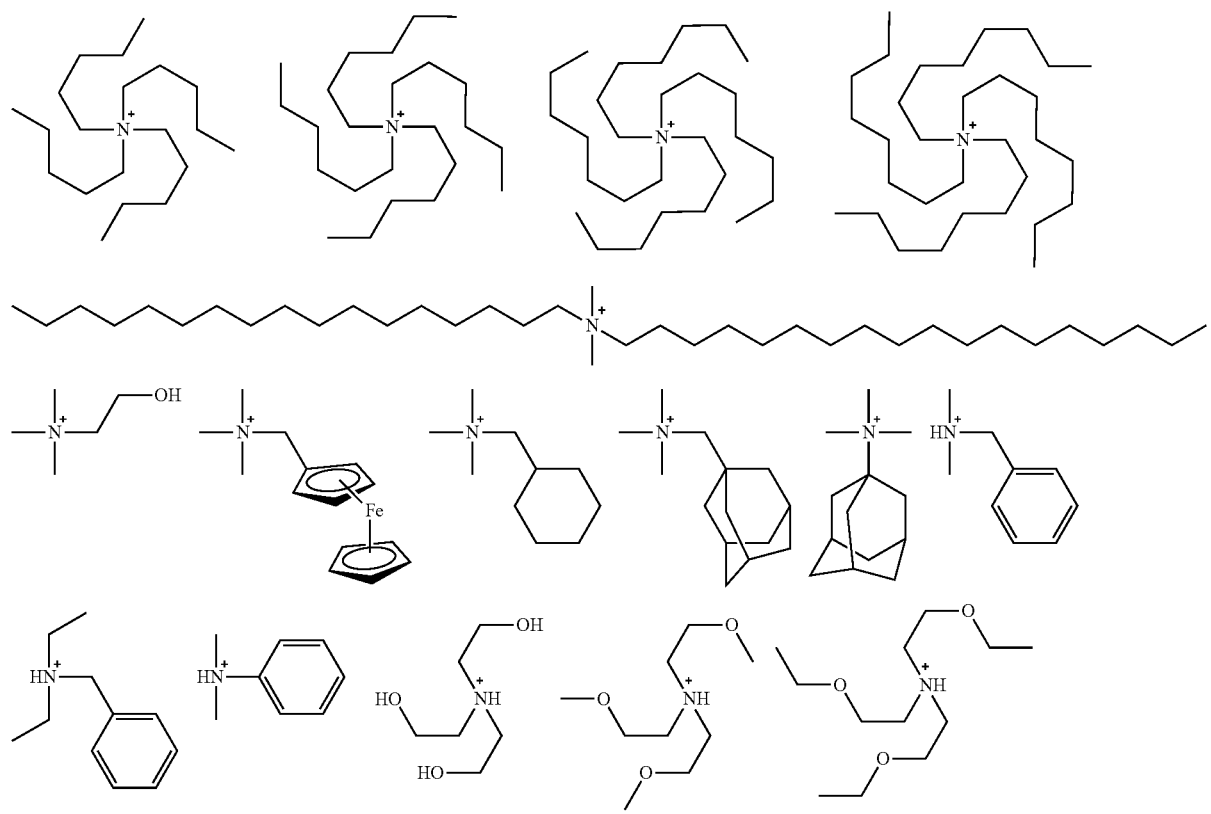
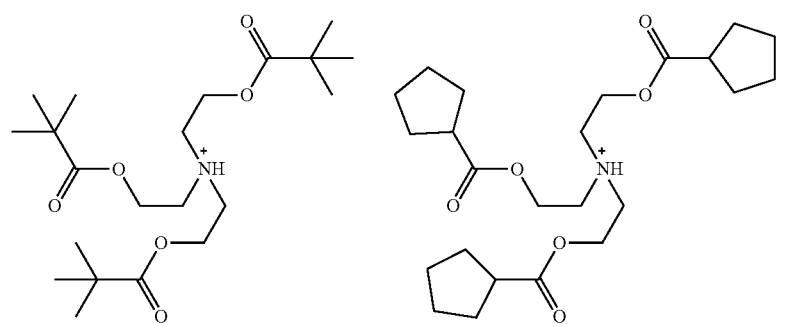
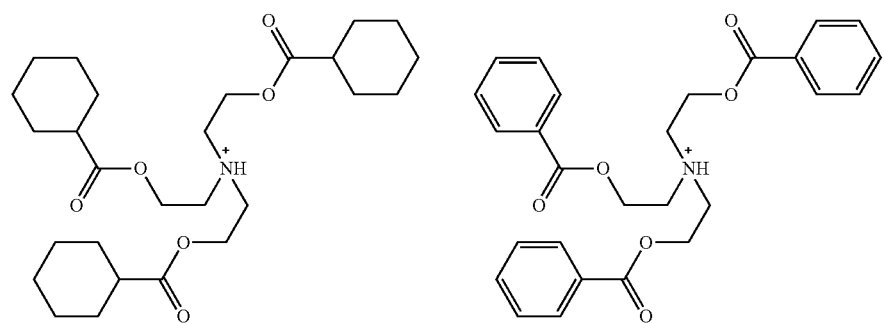

-continued
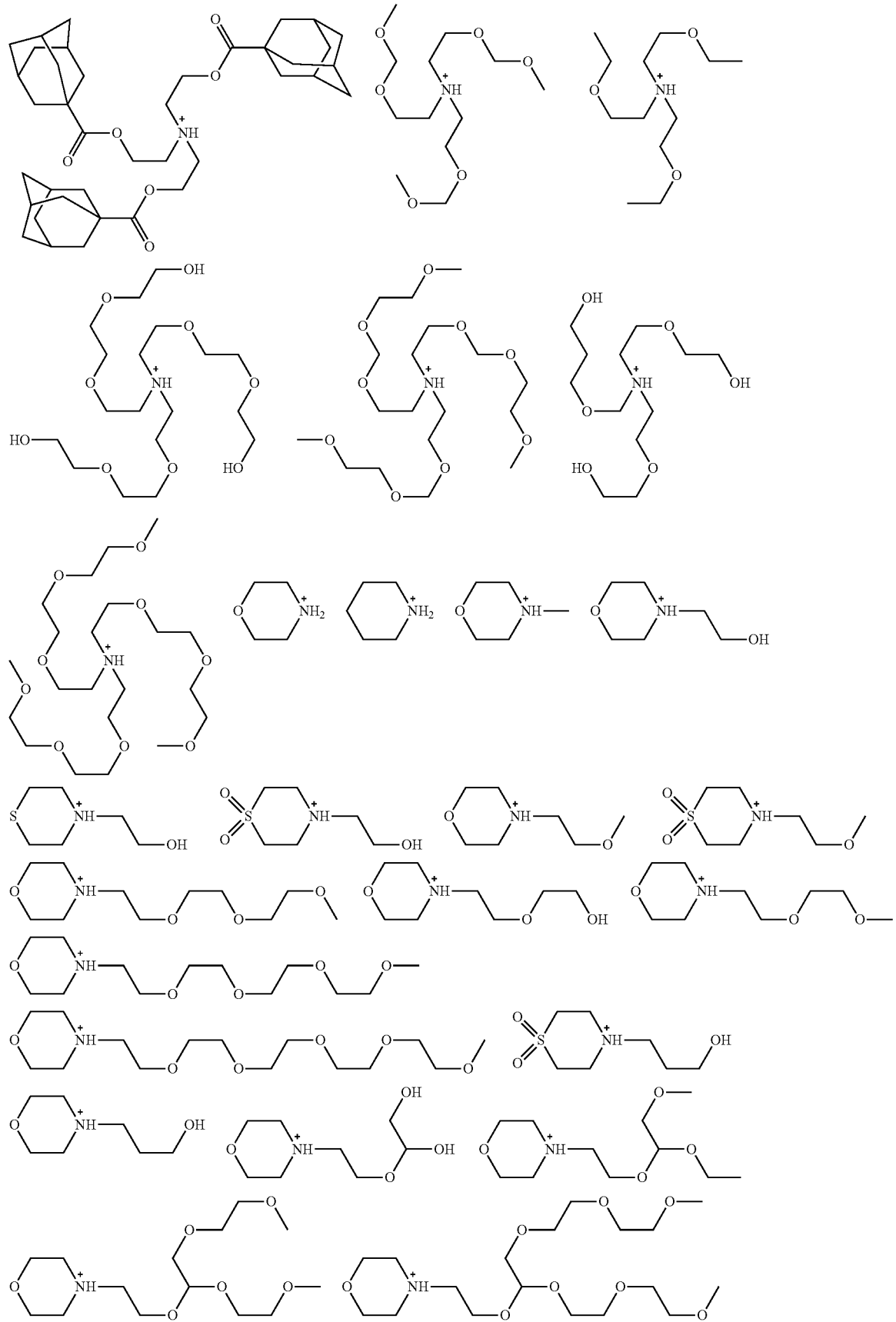

-continued
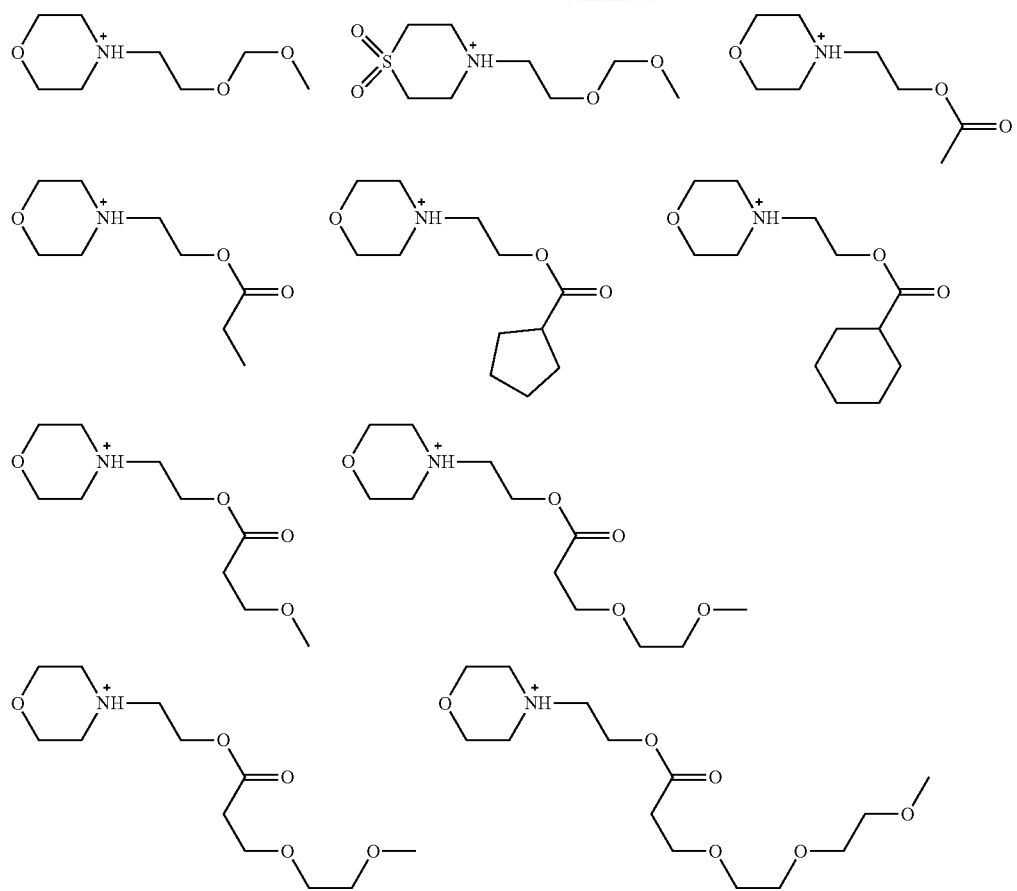
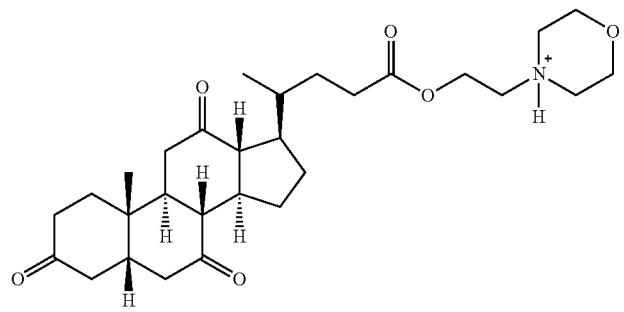
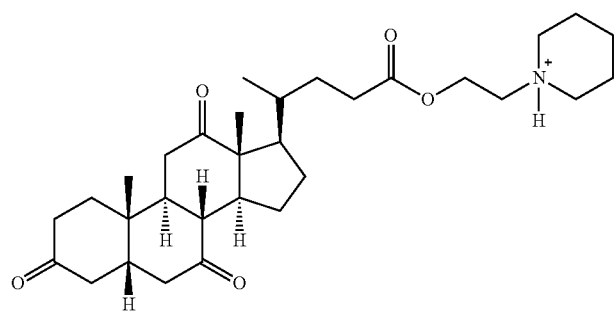

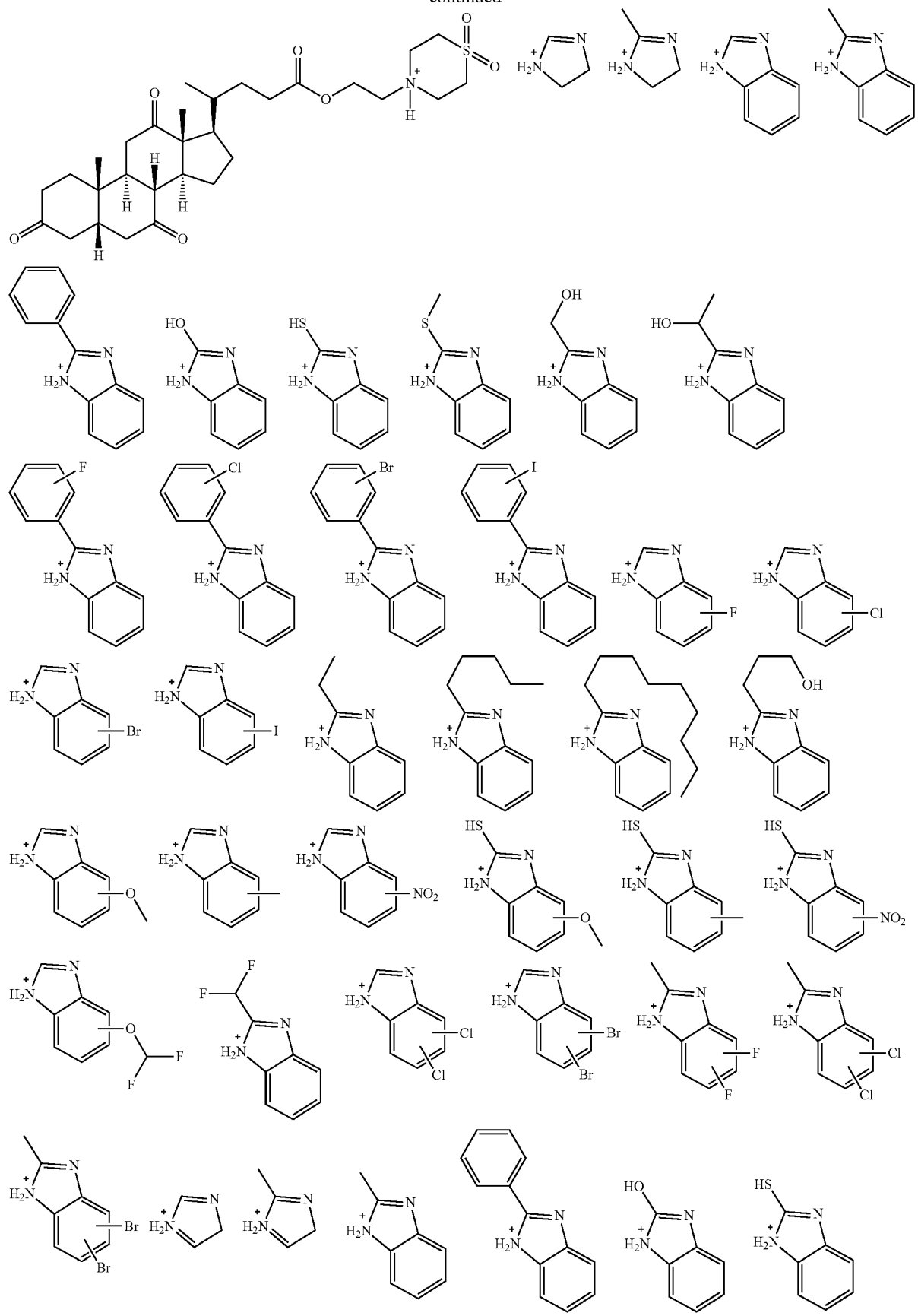

-continued
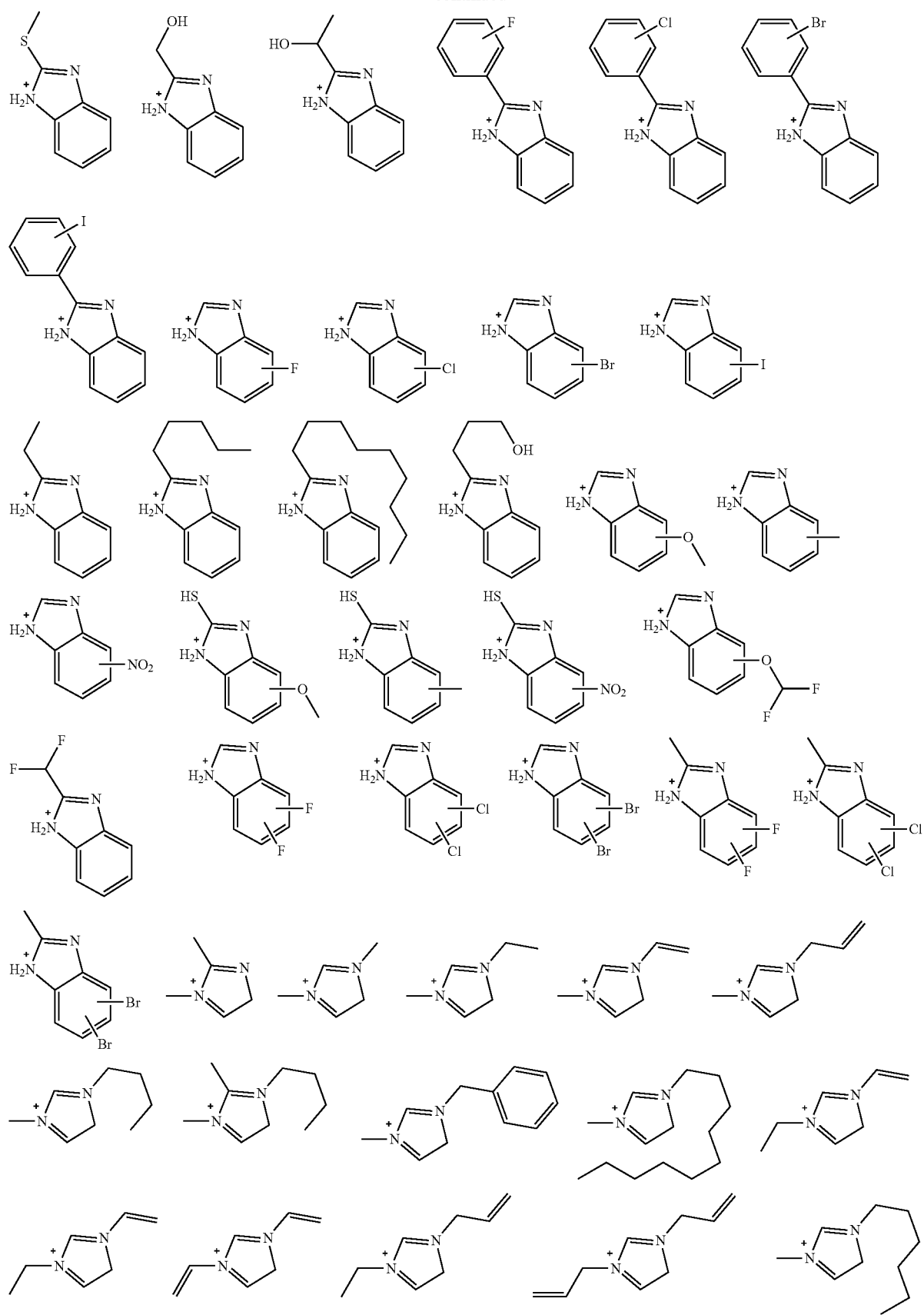

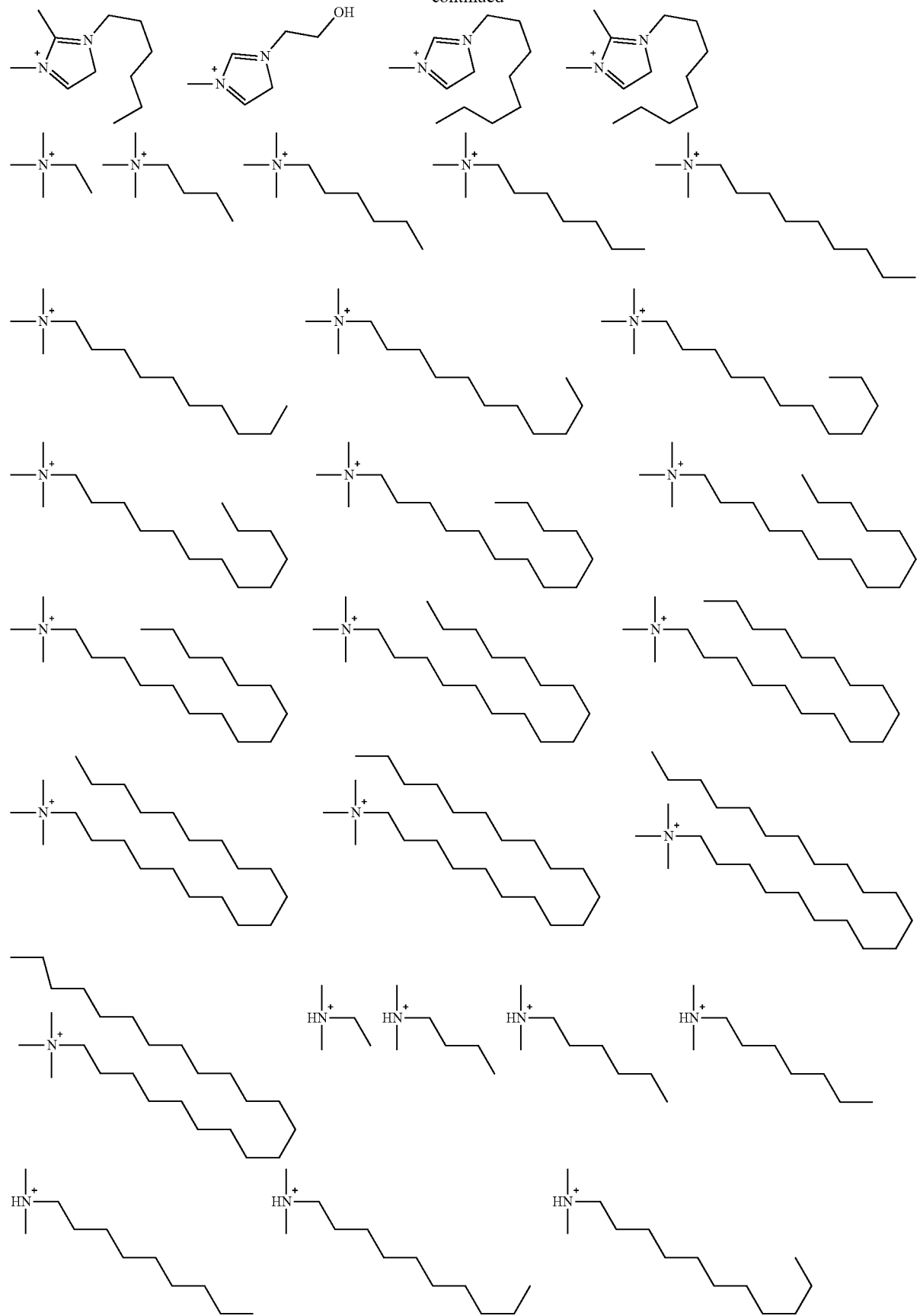

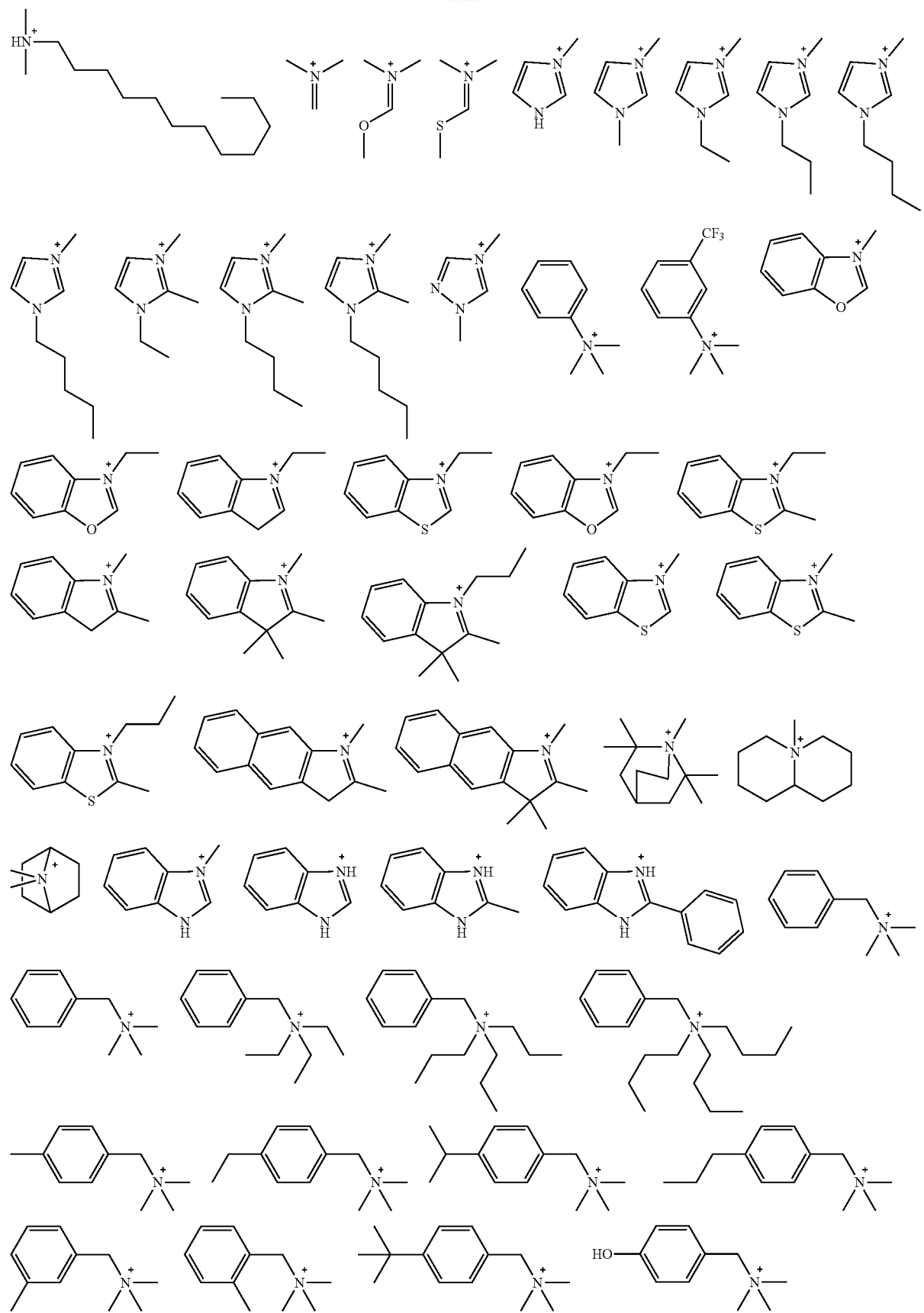

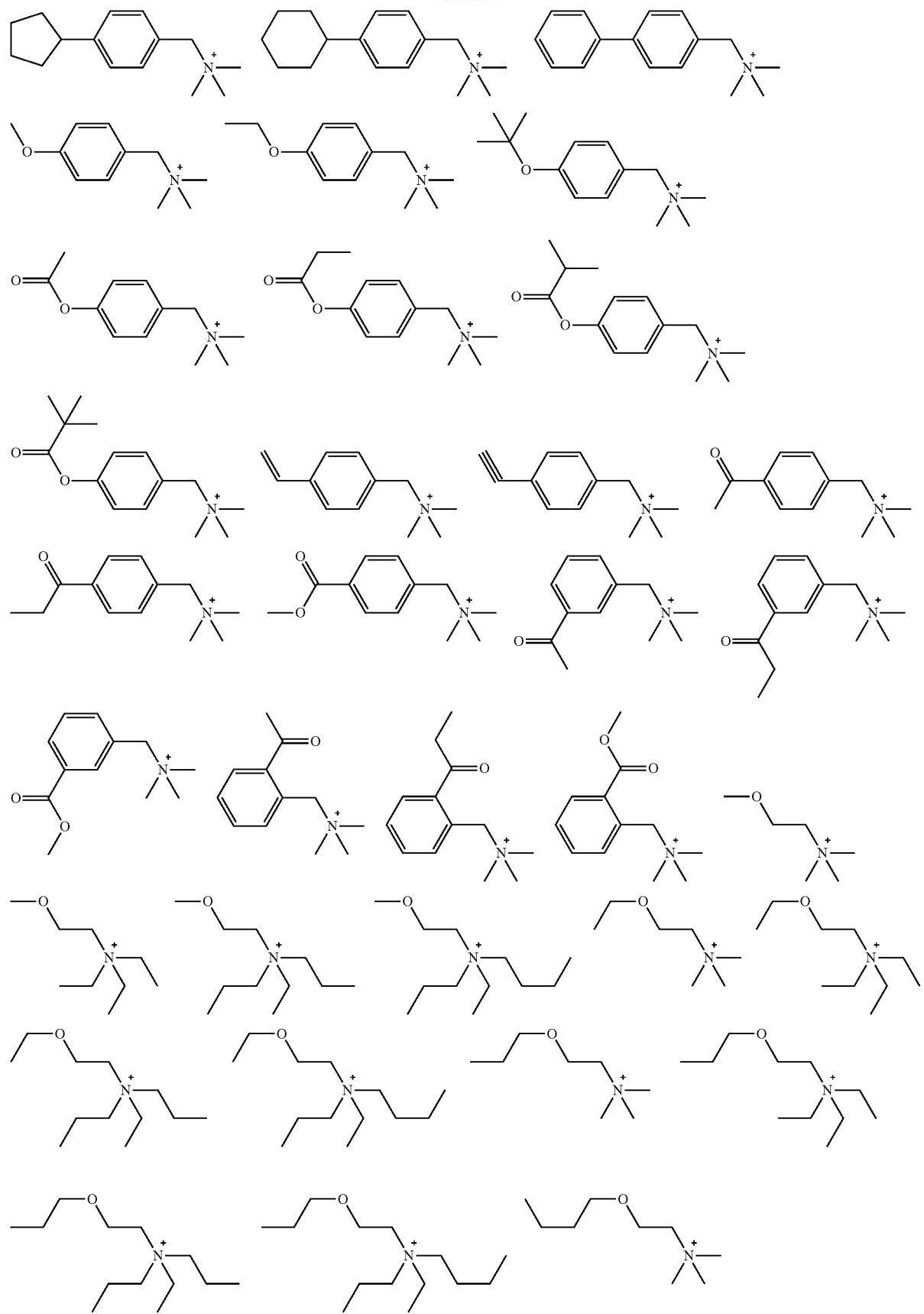

-continued
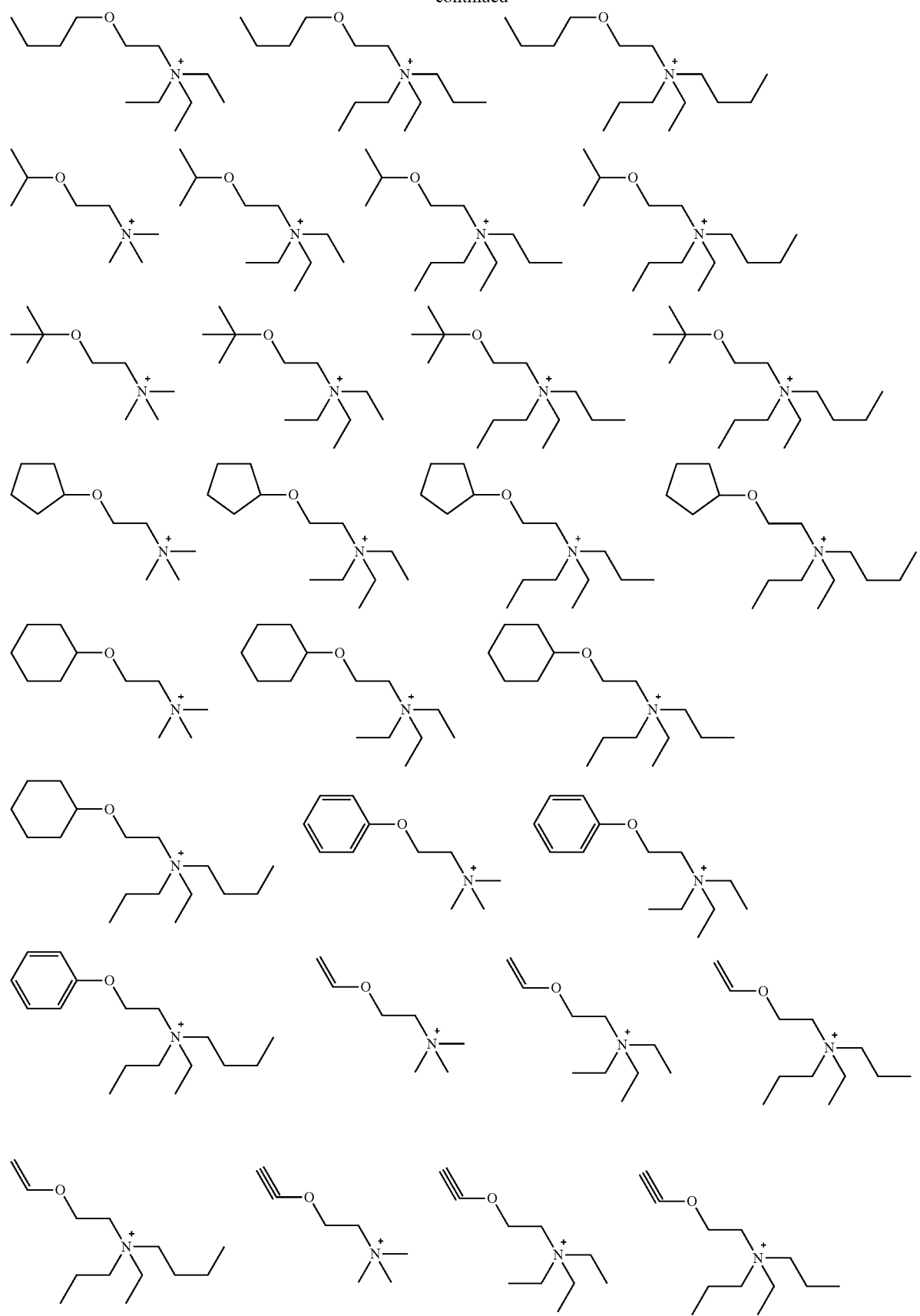

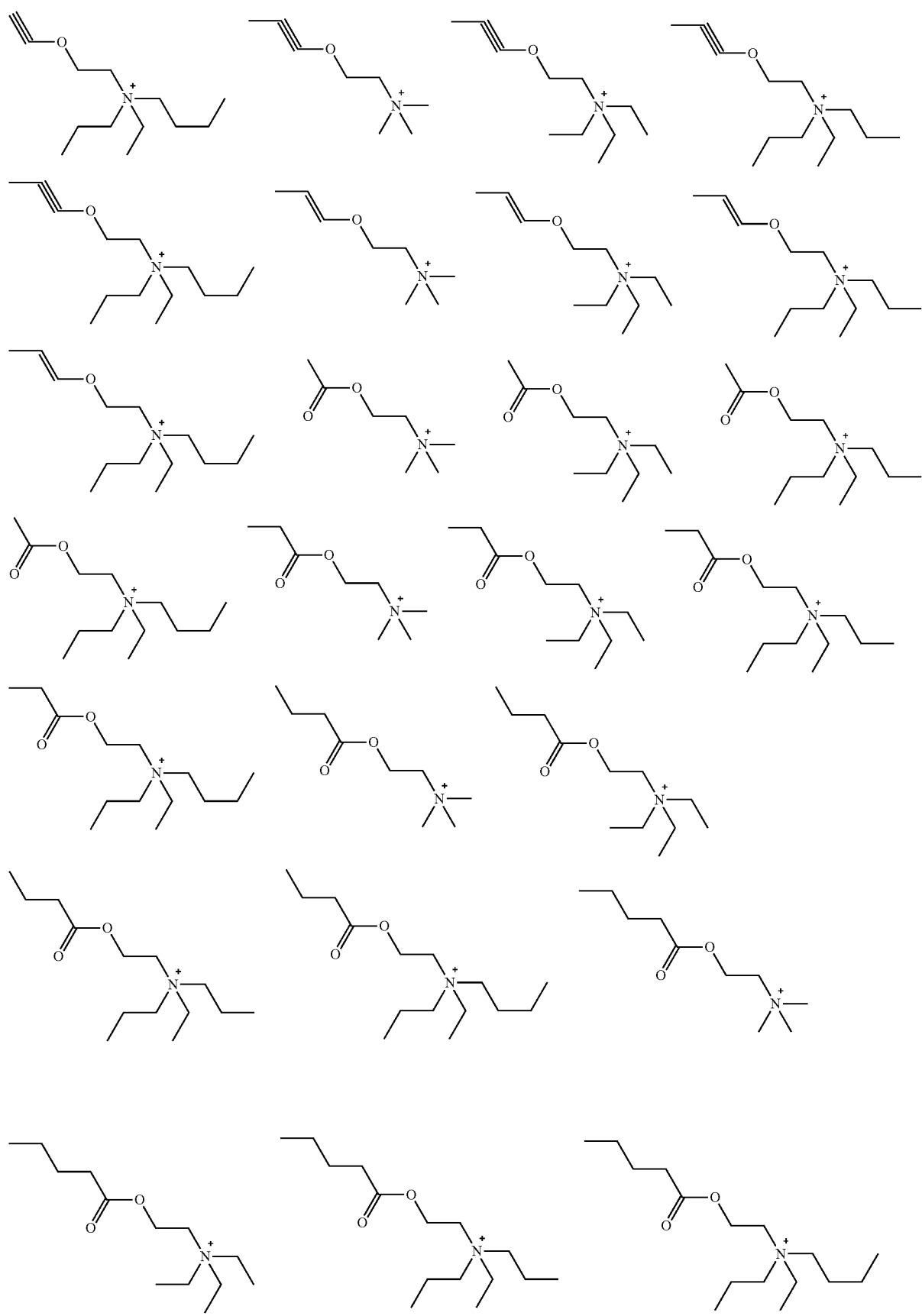

81 82
-continued
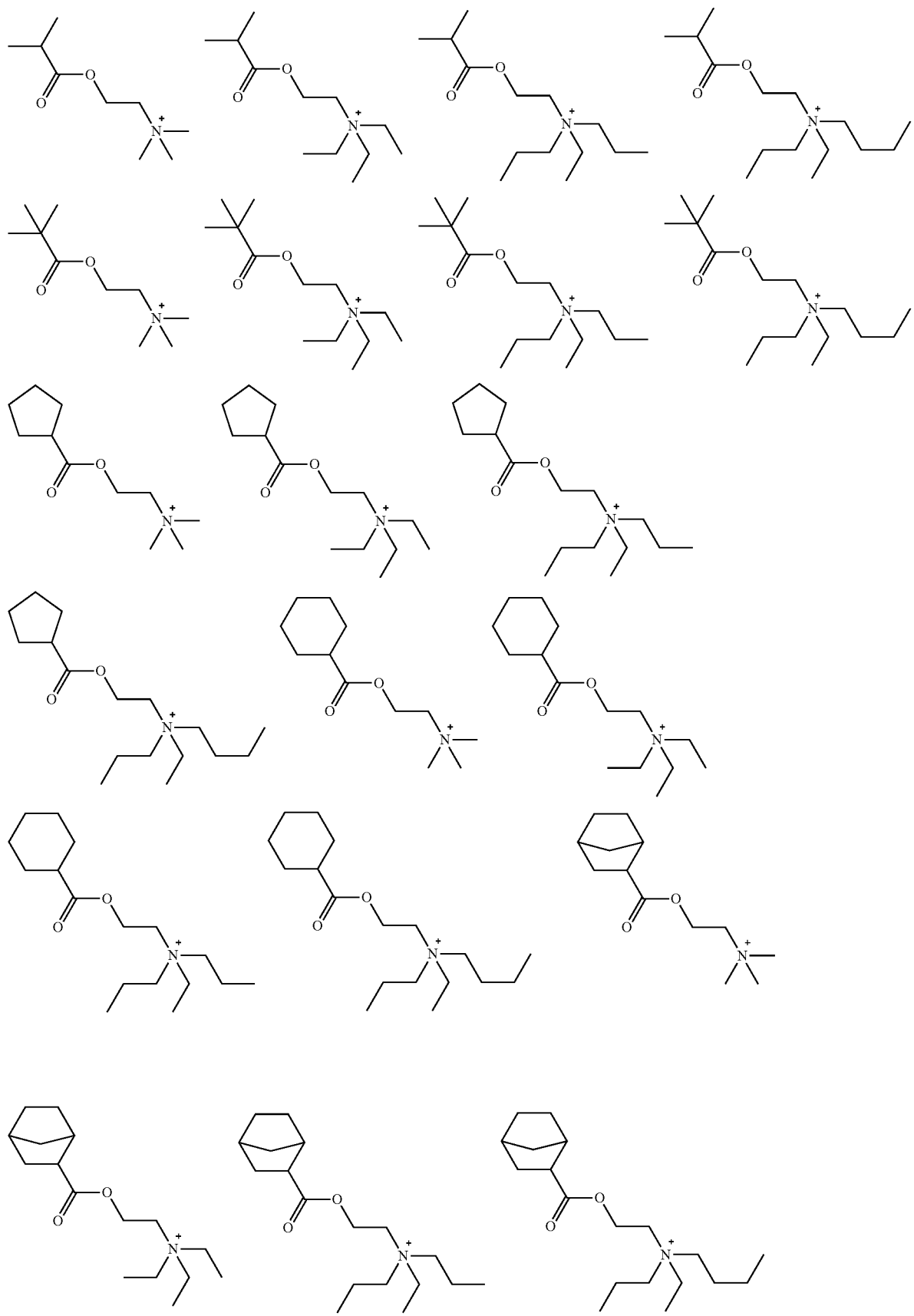

-continued
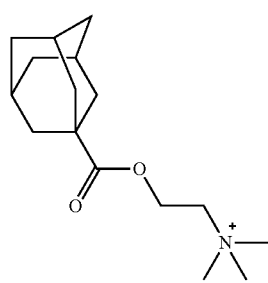
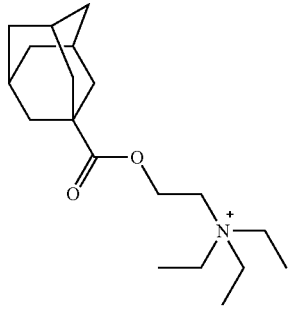
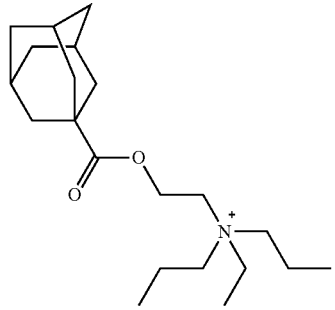
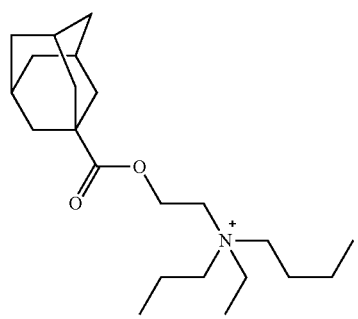
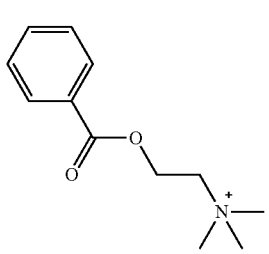
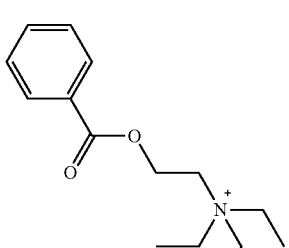
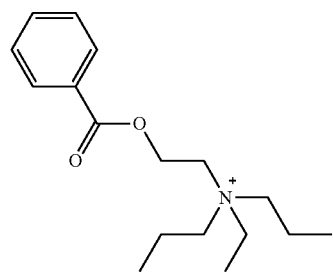
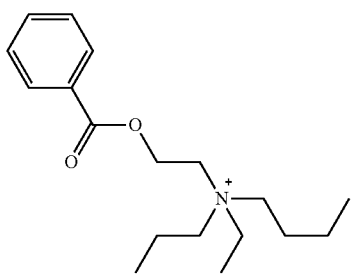
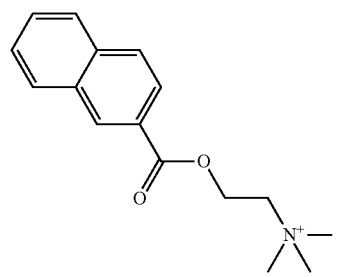
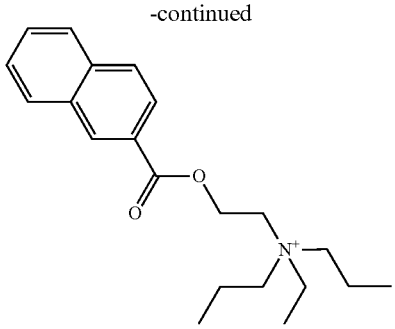
-continued
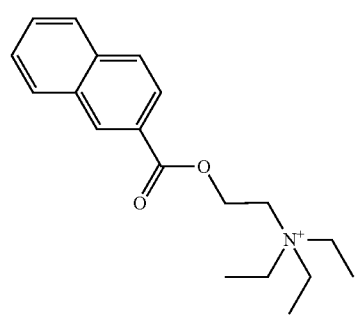
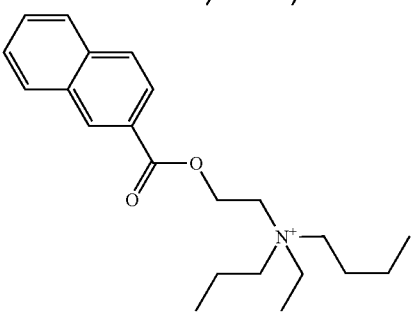

85
-continued
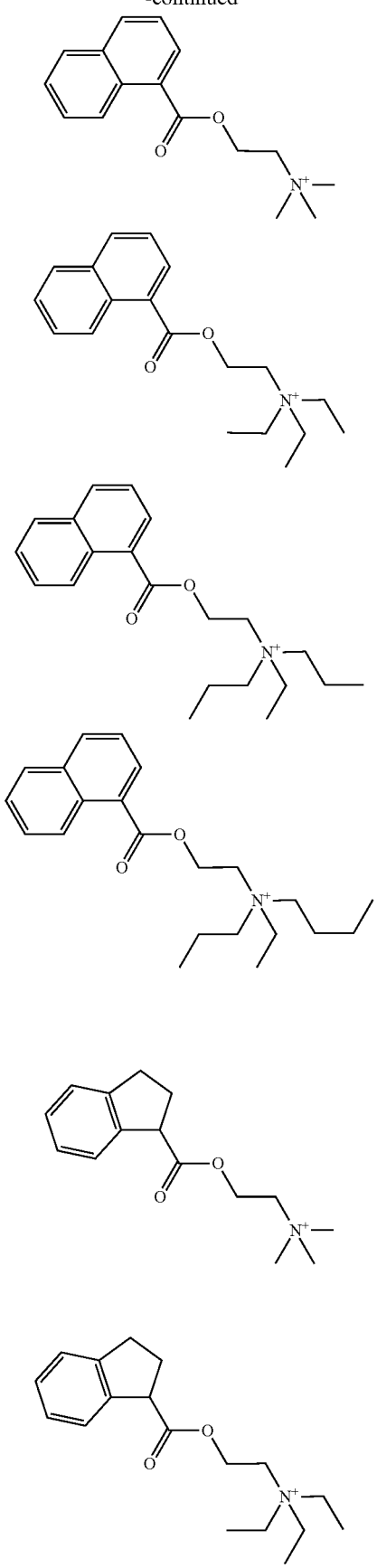
86
-continued
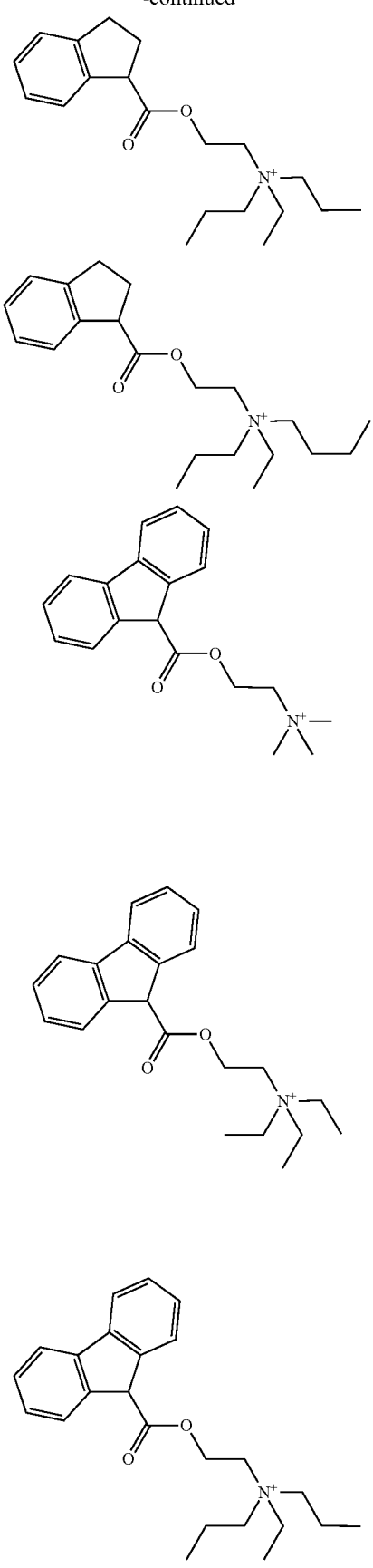

87
-continued
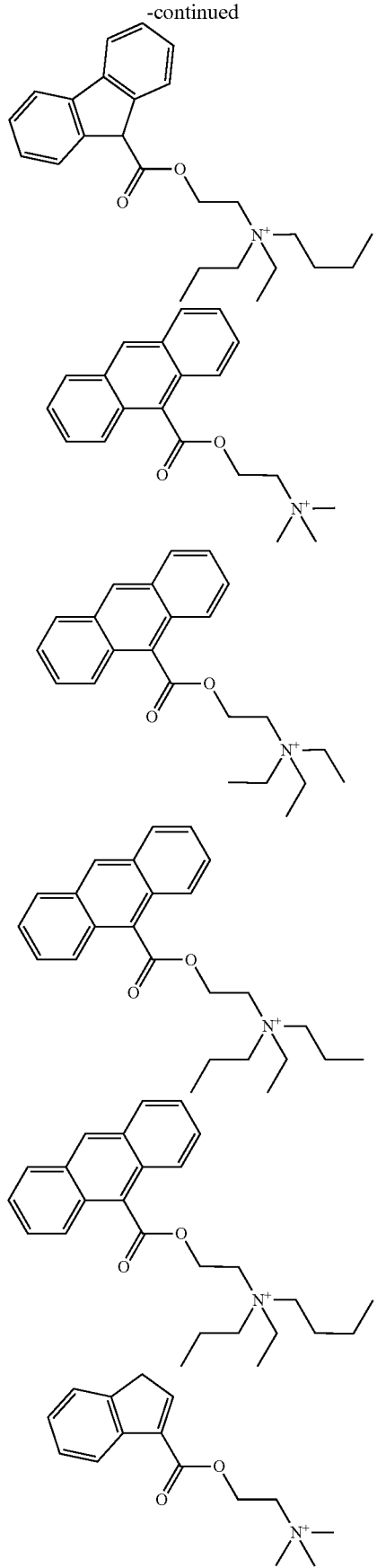
88
-continued
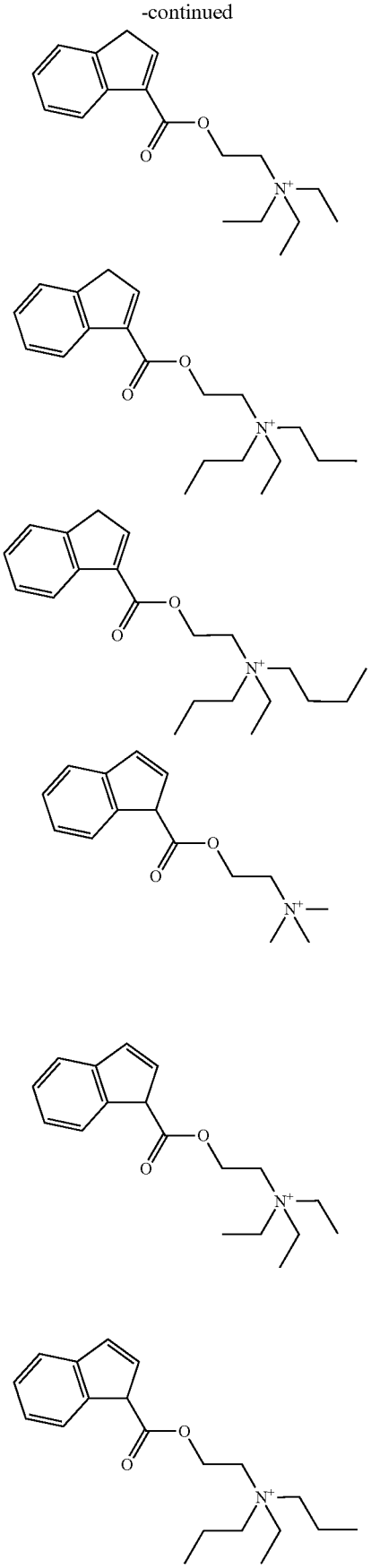

89
-continued
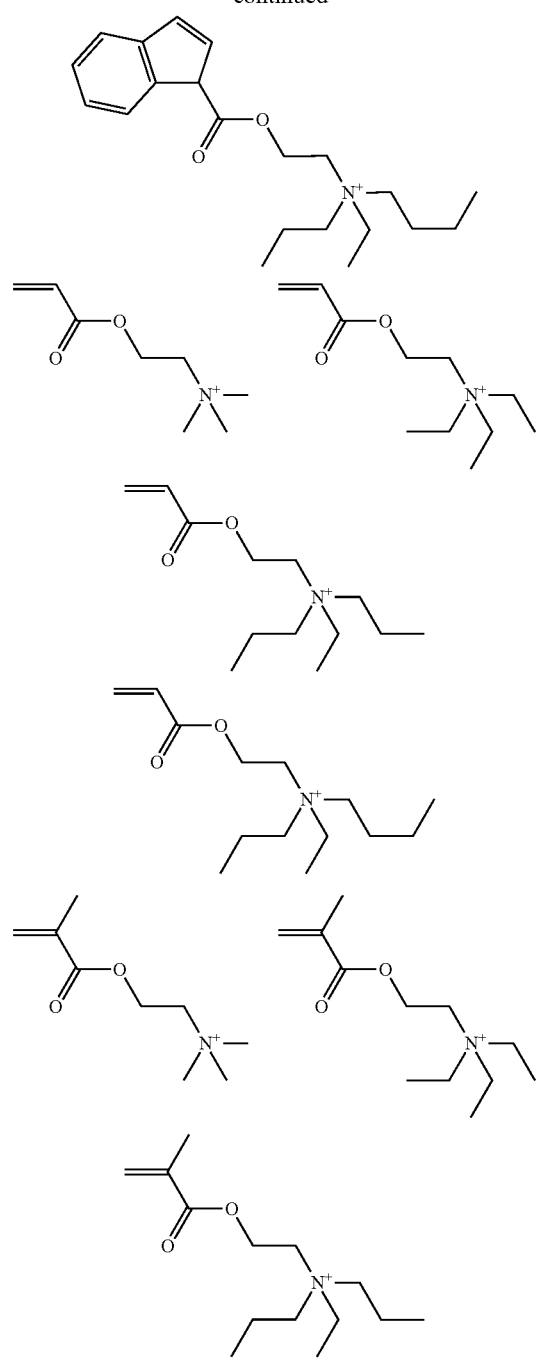
90
-continued
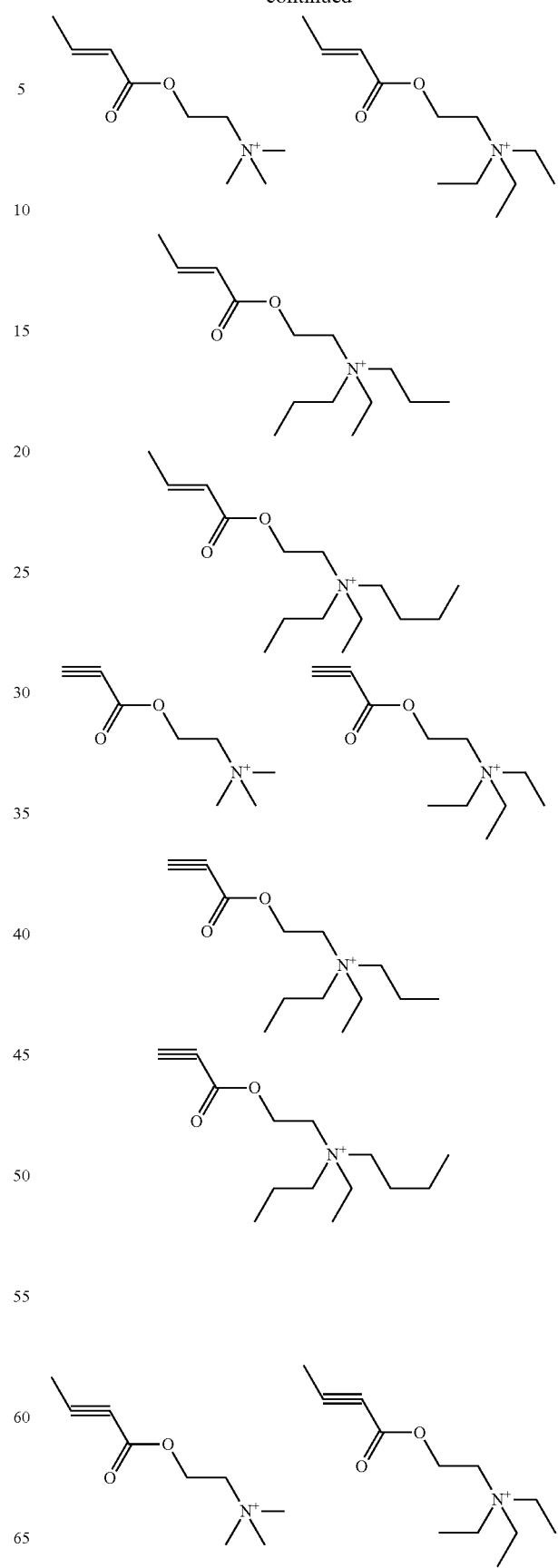

91
-continued
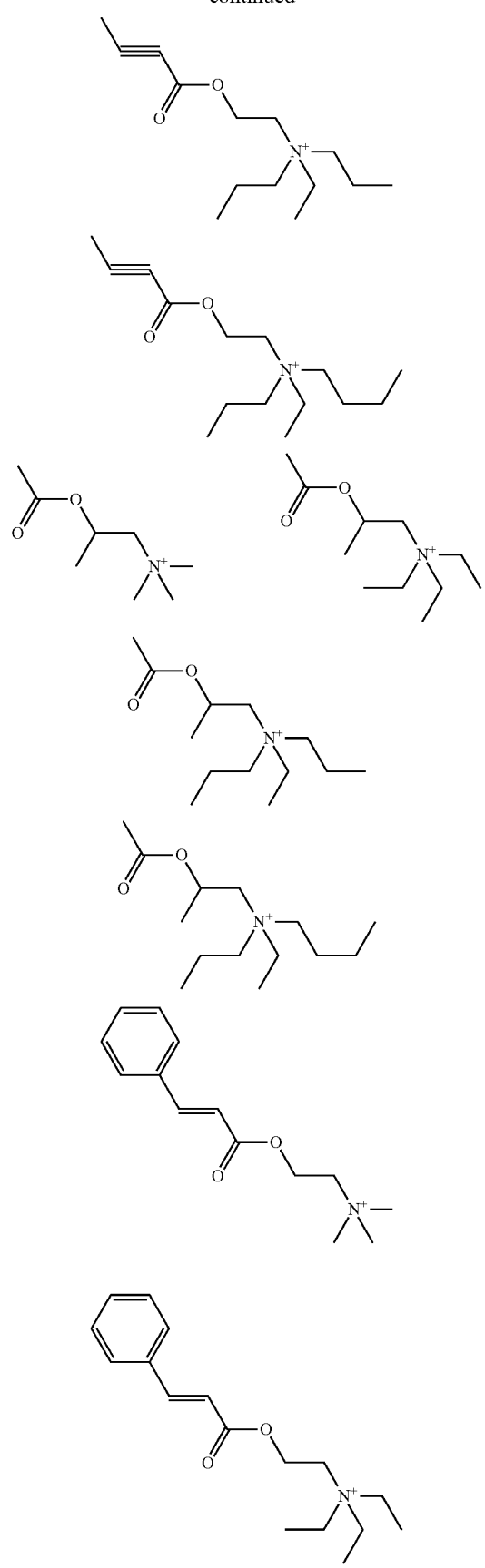
92
-continued
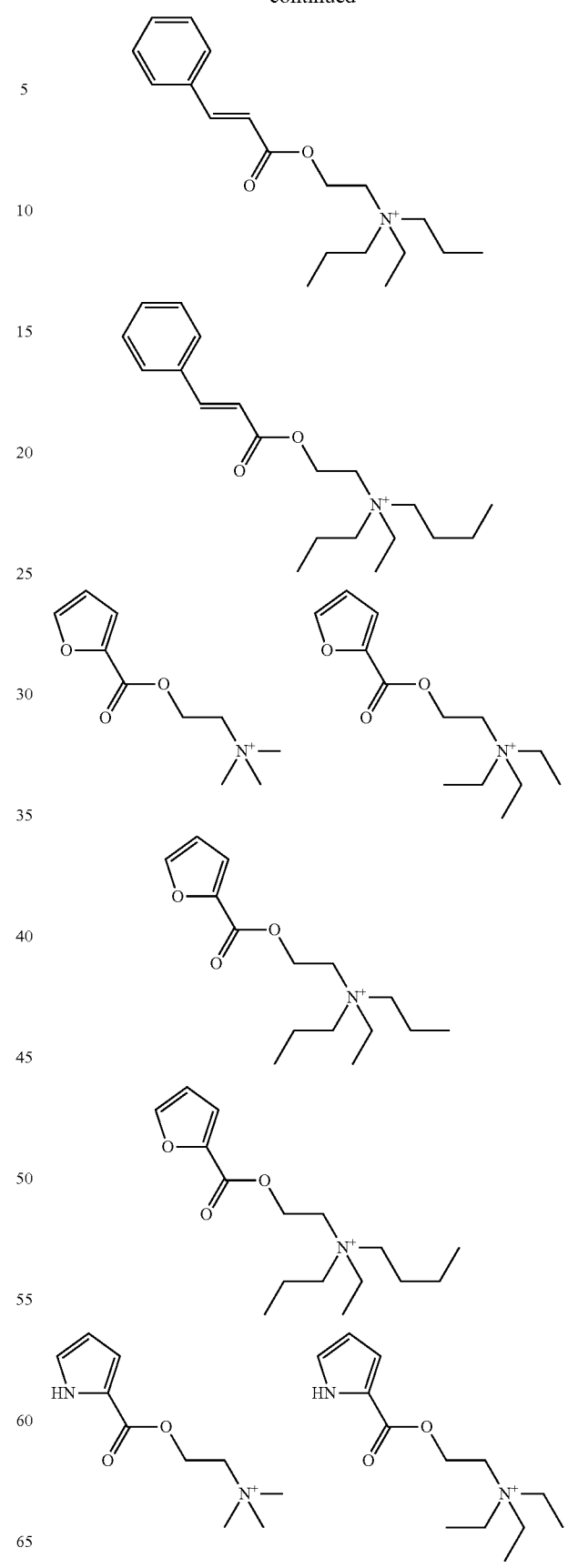

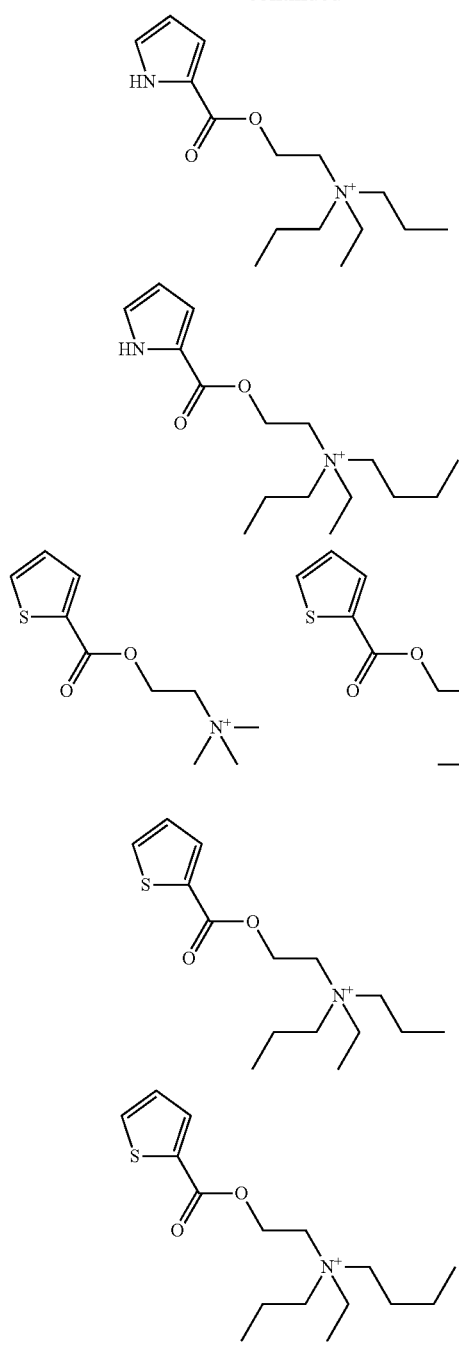
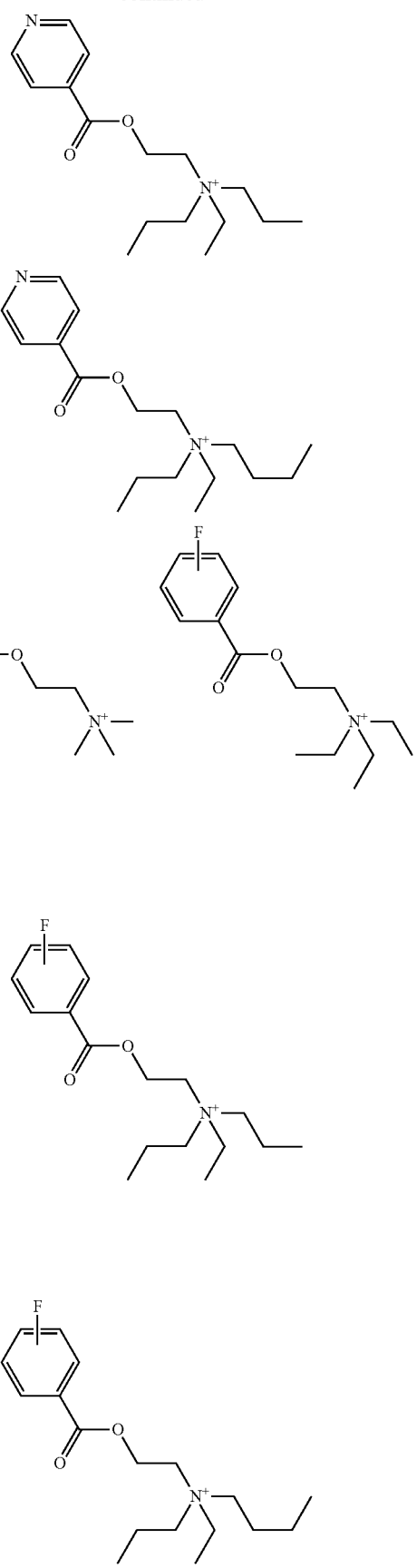

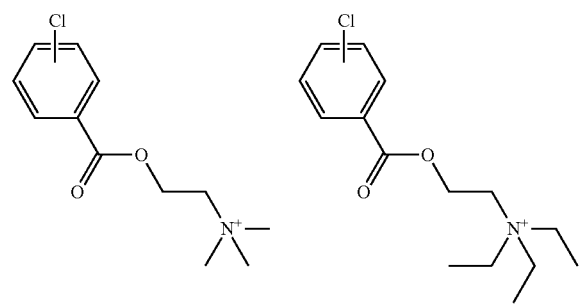
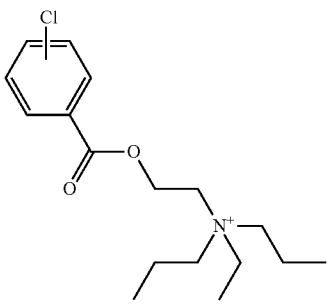
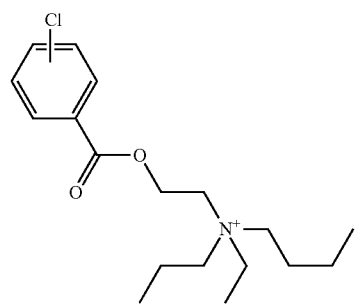
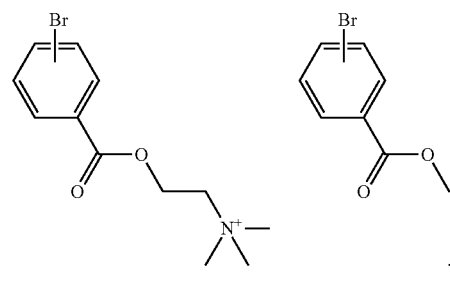
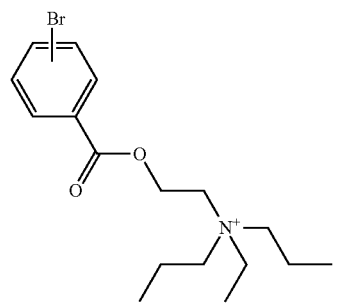
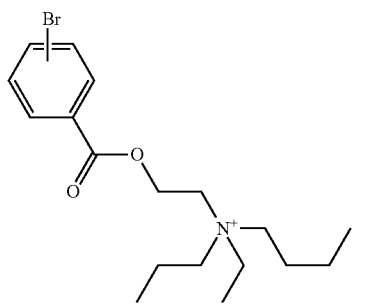
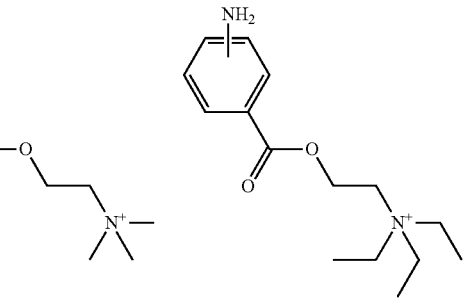
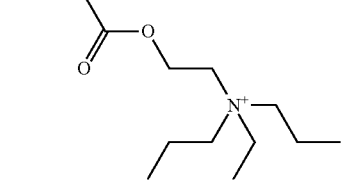
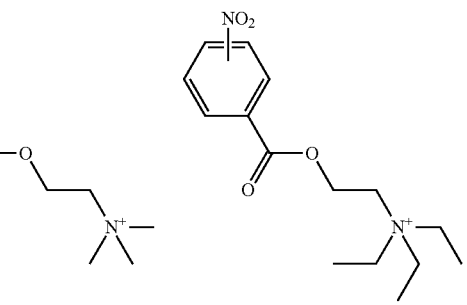

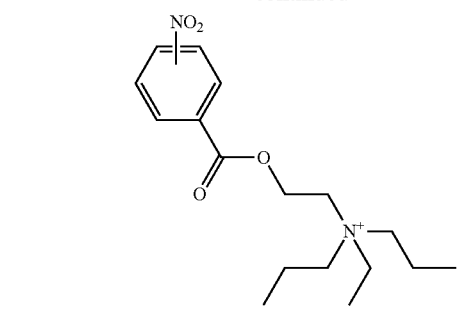
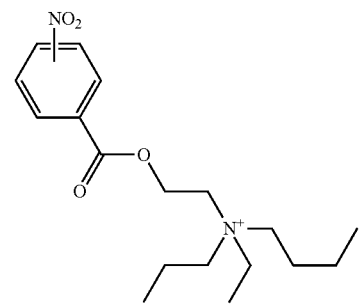
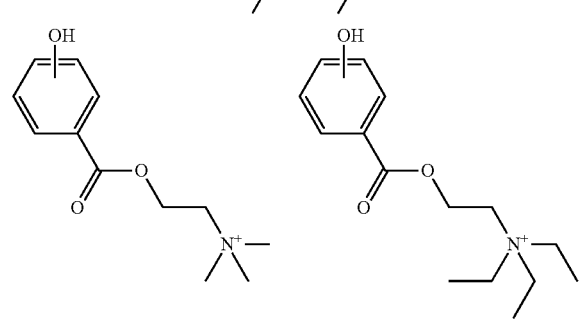
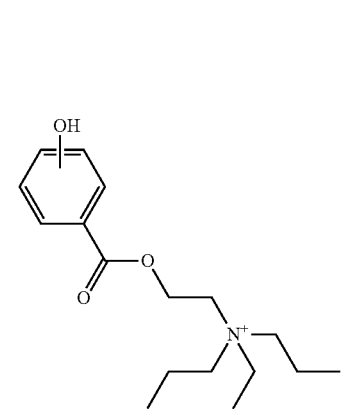
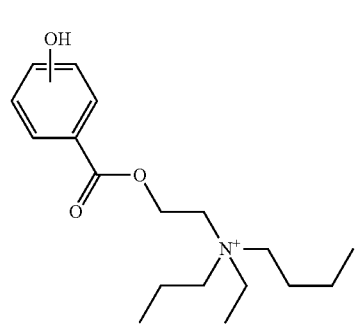
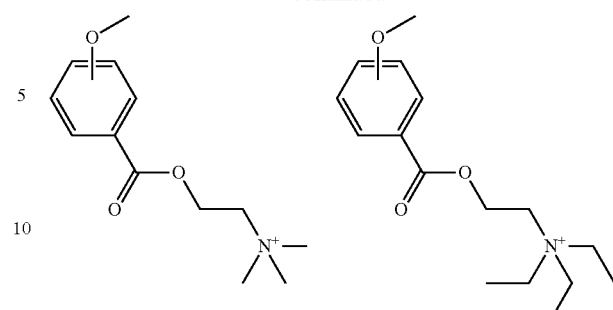
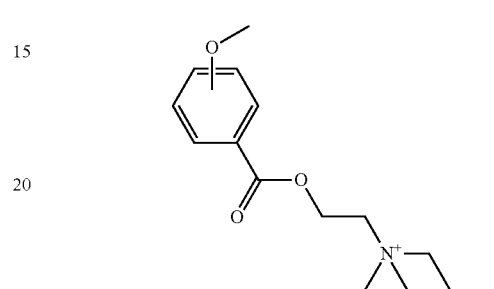
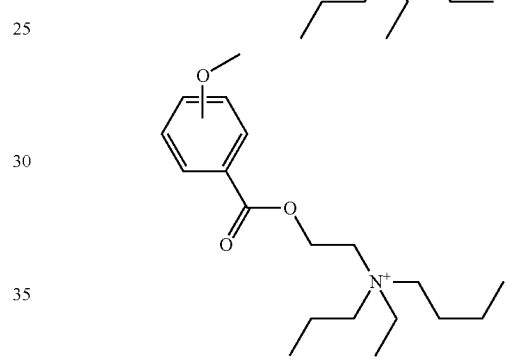
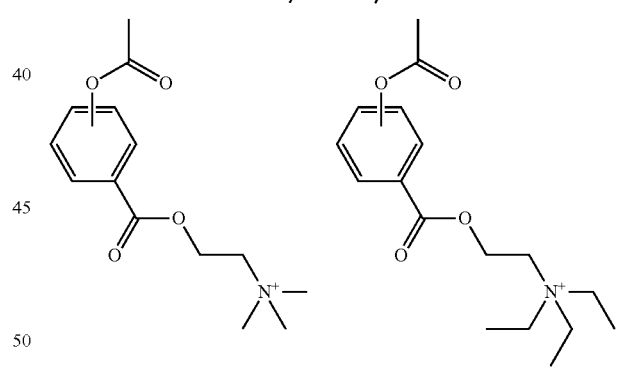
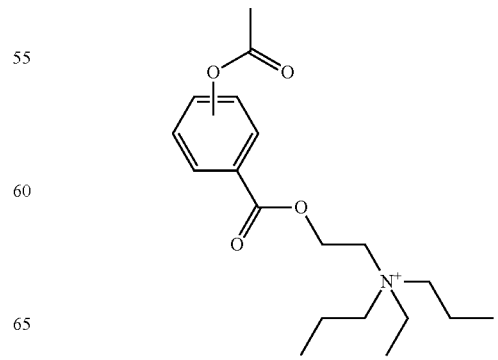

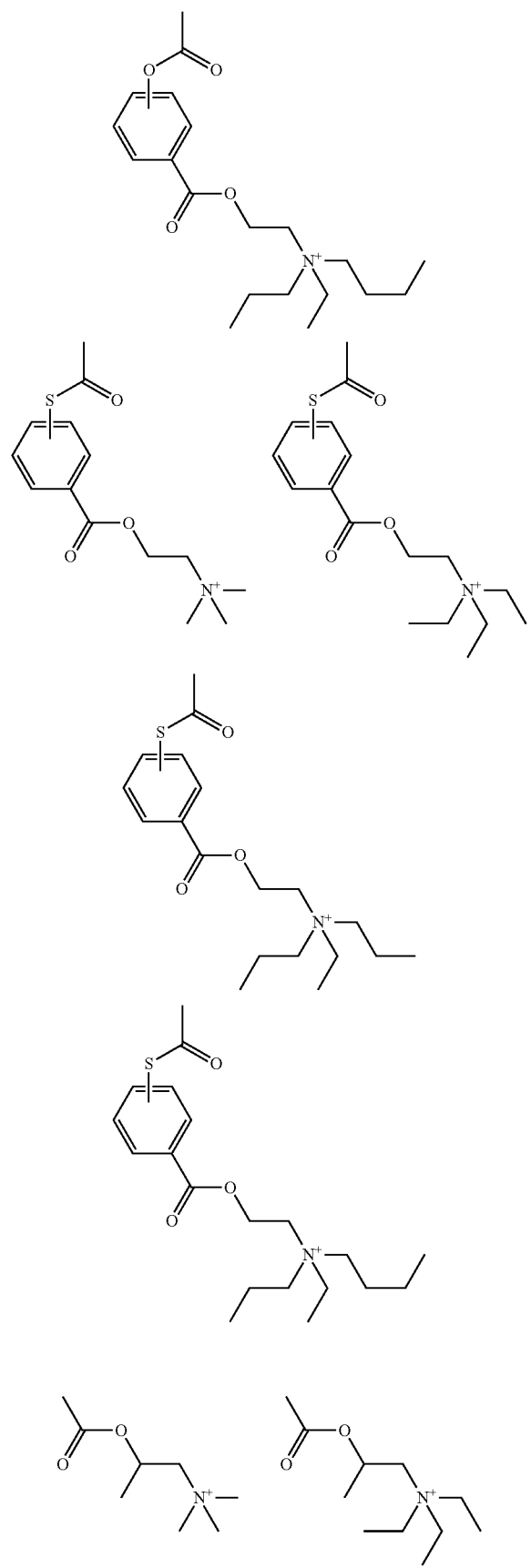

101
-continued
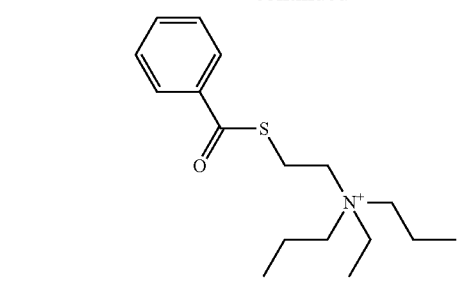
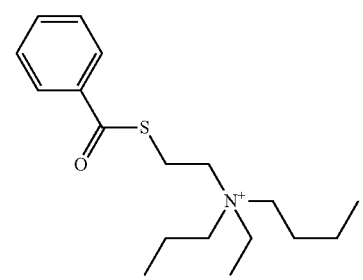
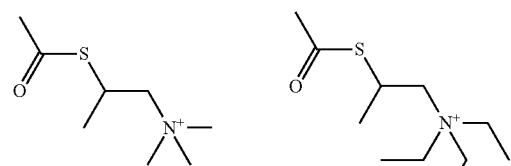
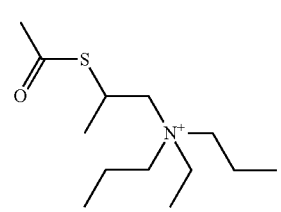 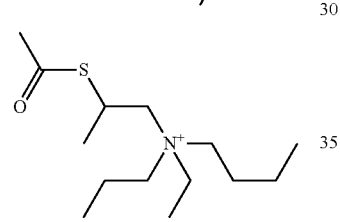
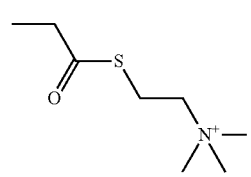
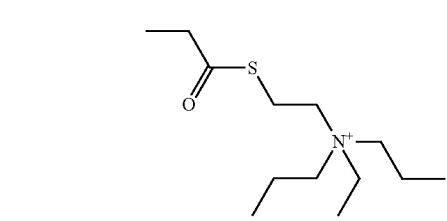
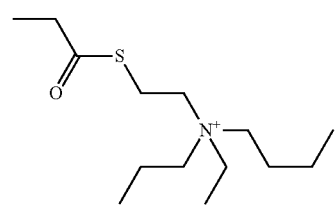
102
-continued
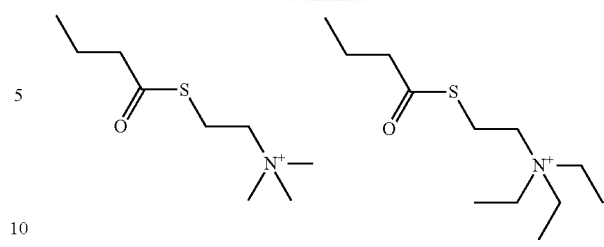
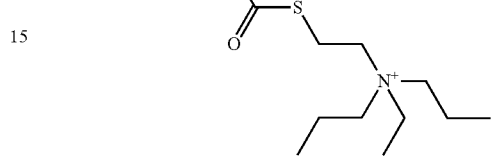
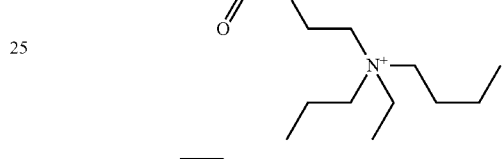
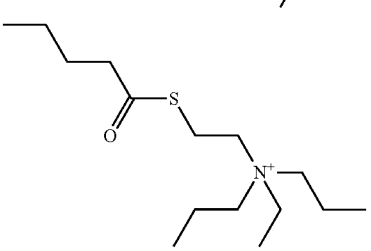
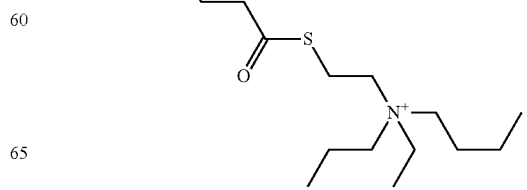

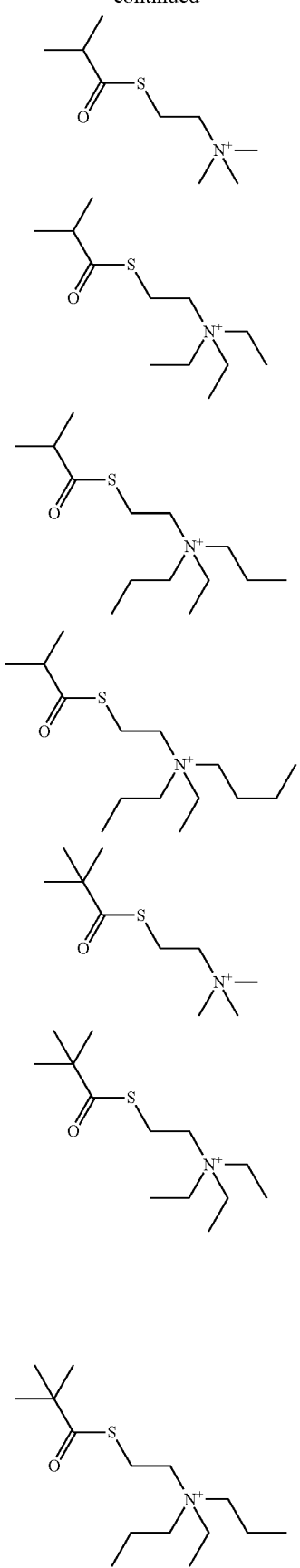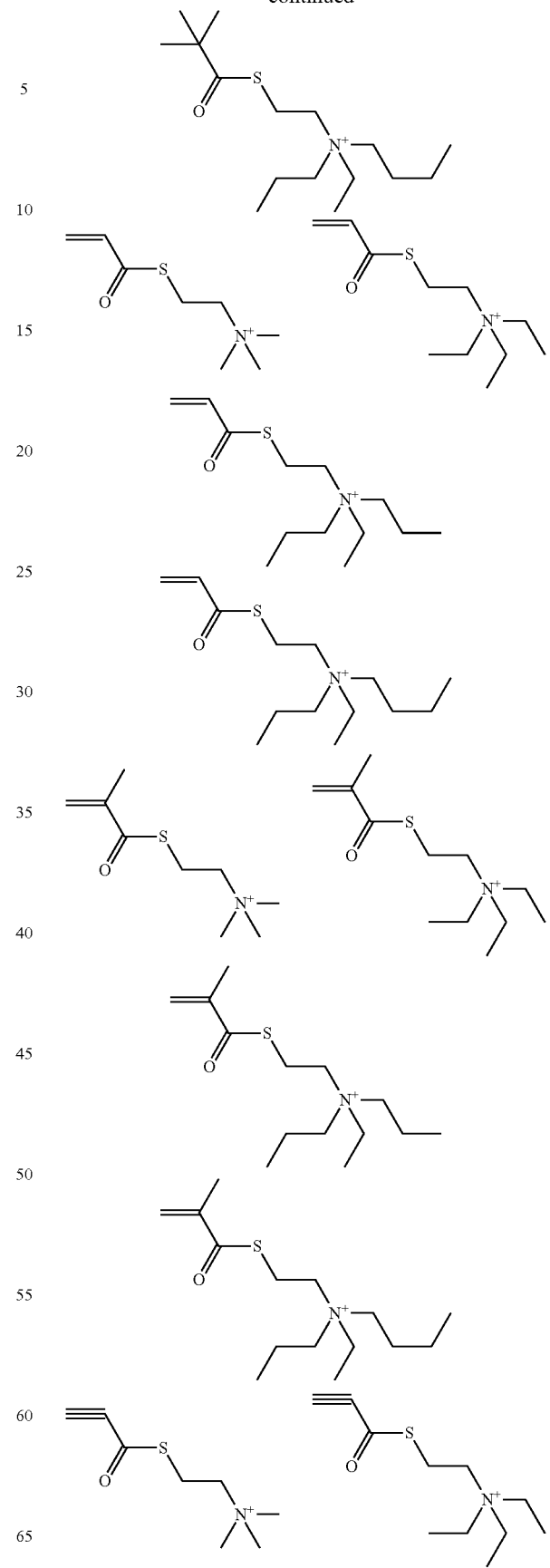

105
-continued
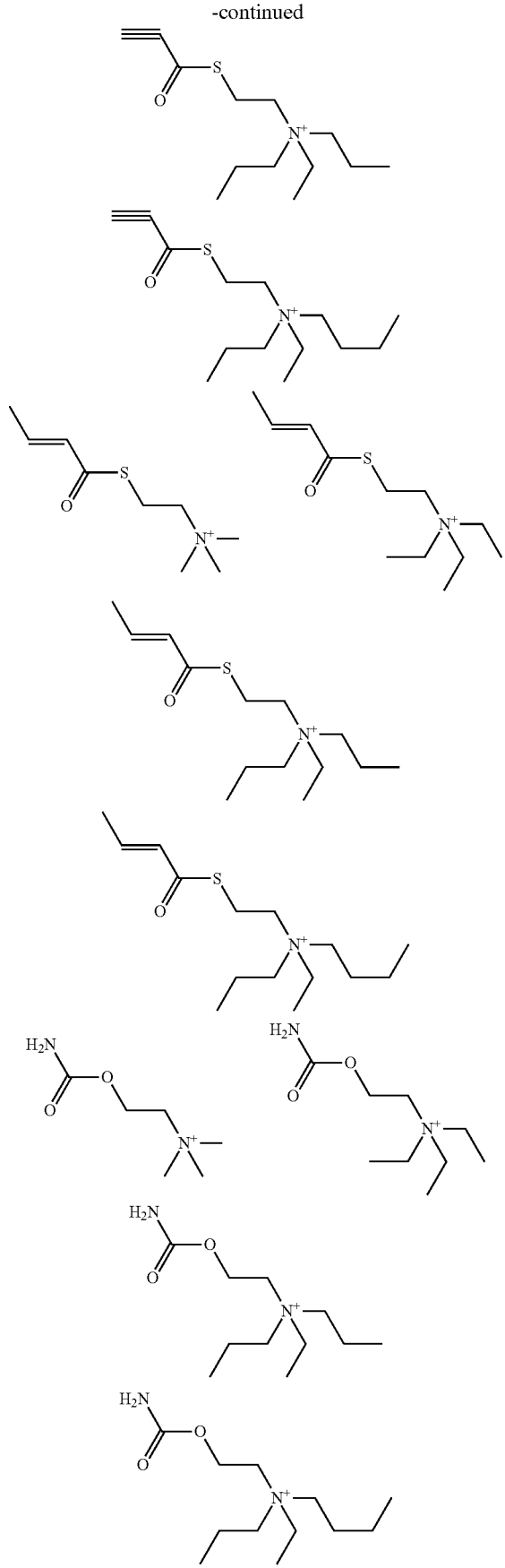
106
-continued
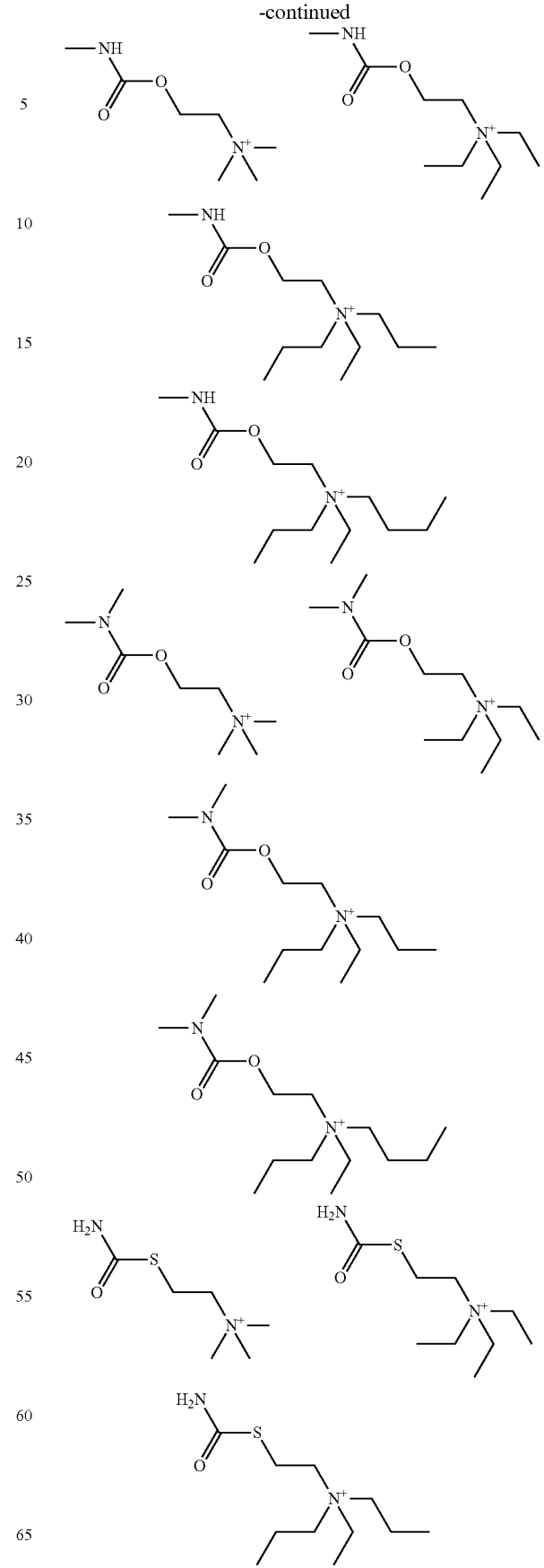

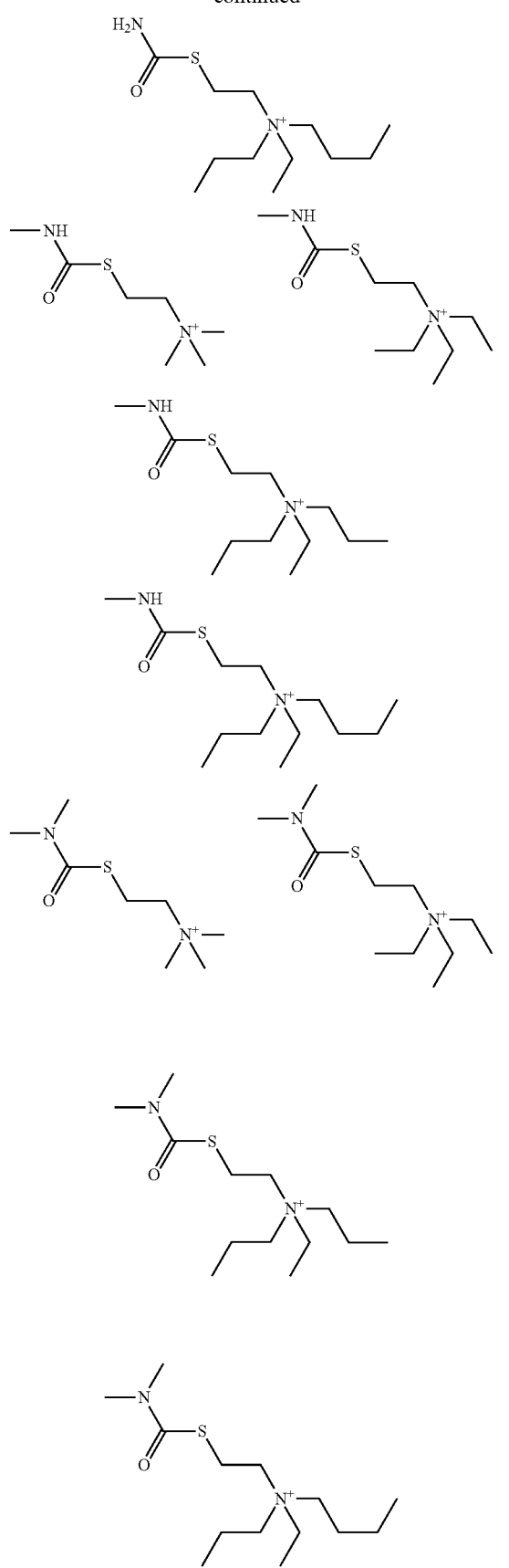
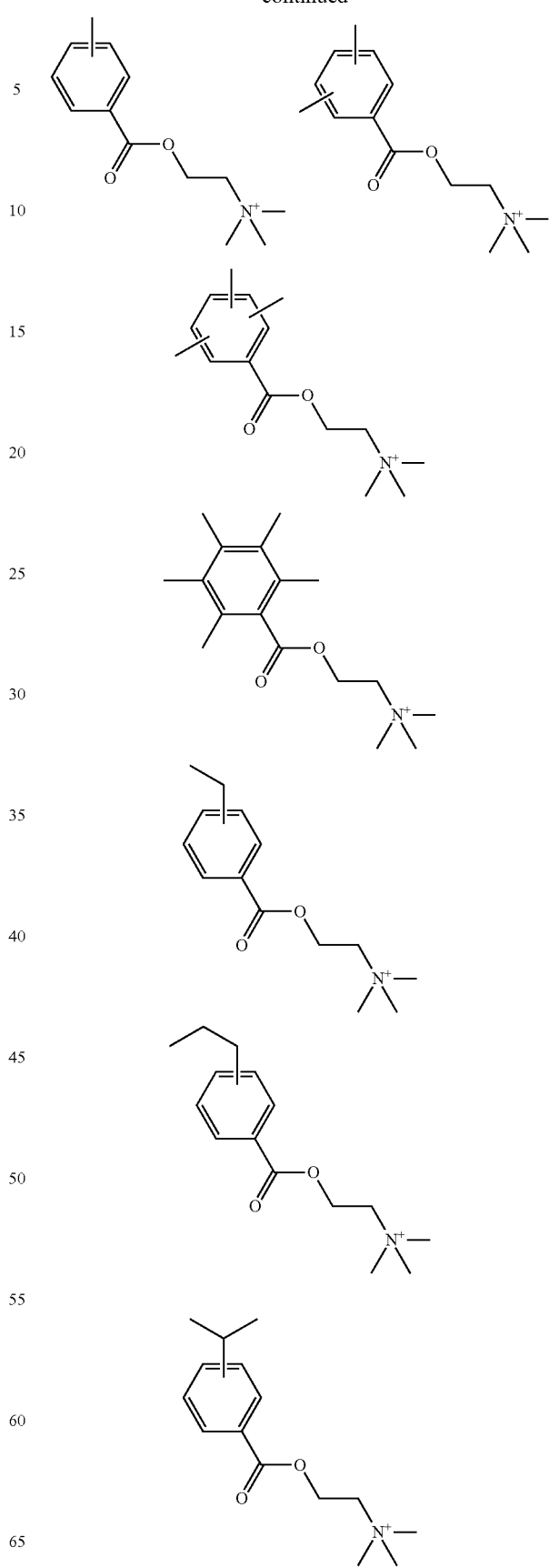

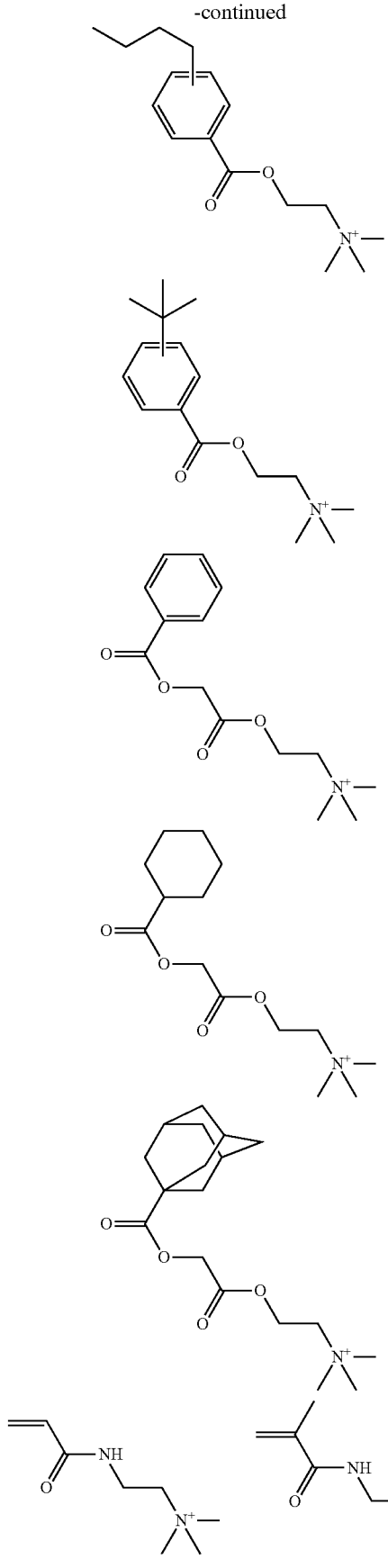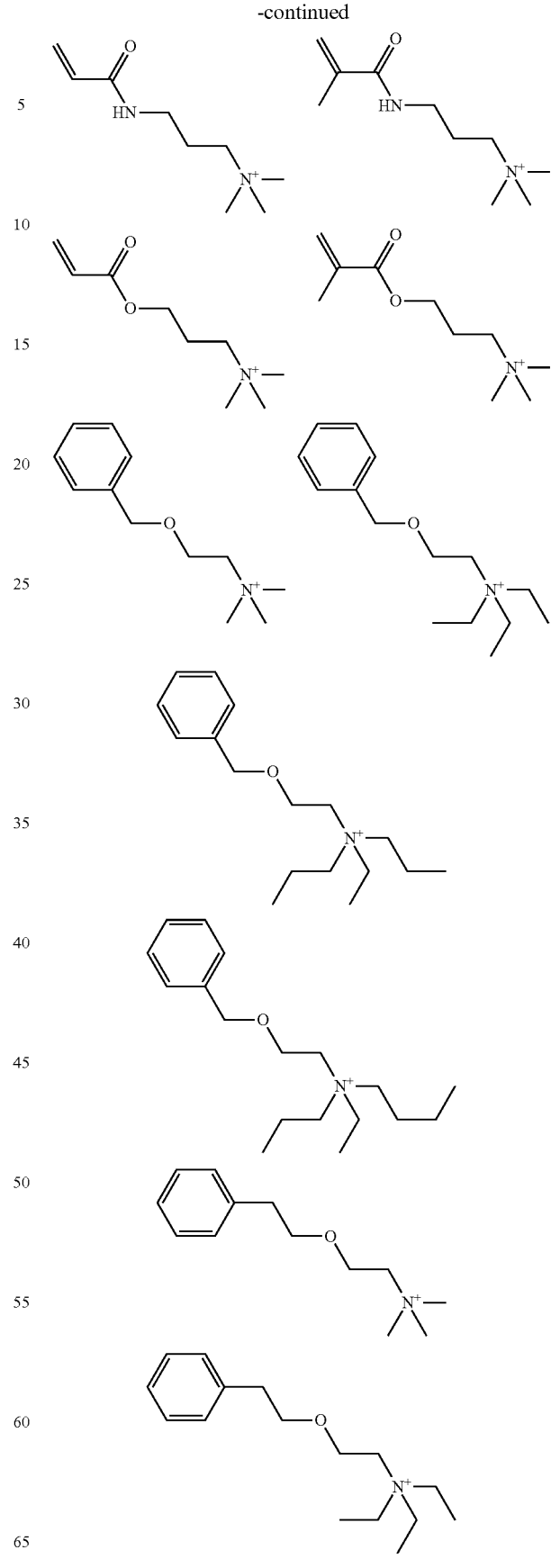

111
-continued
112
-continued
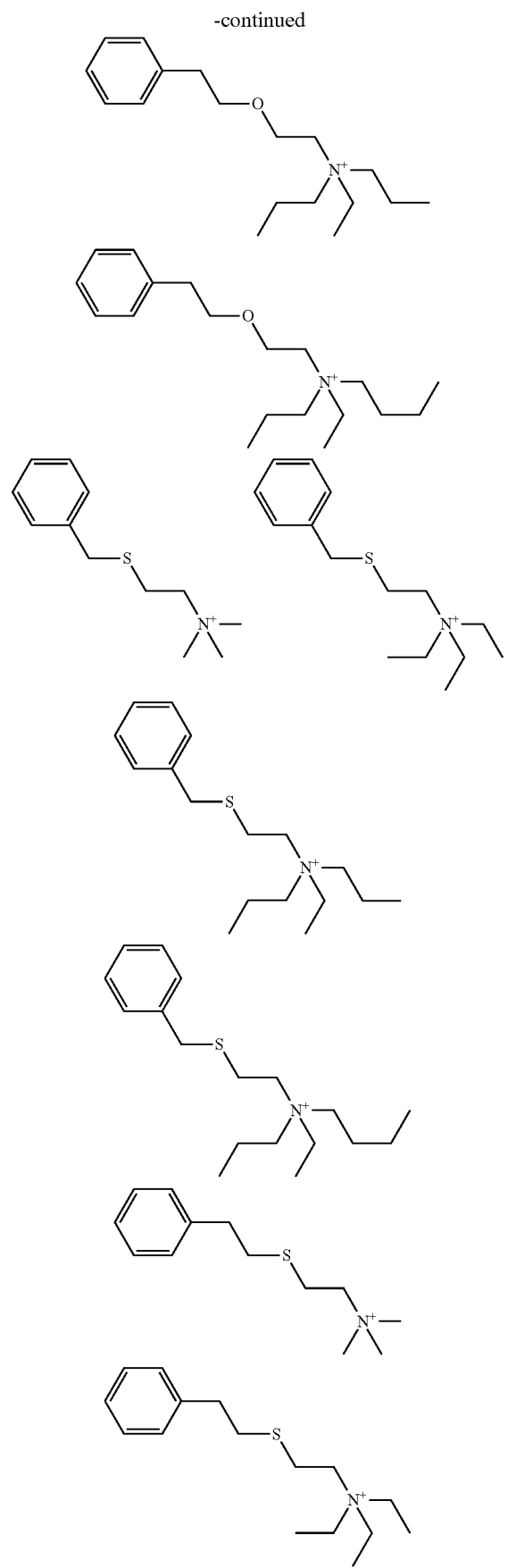
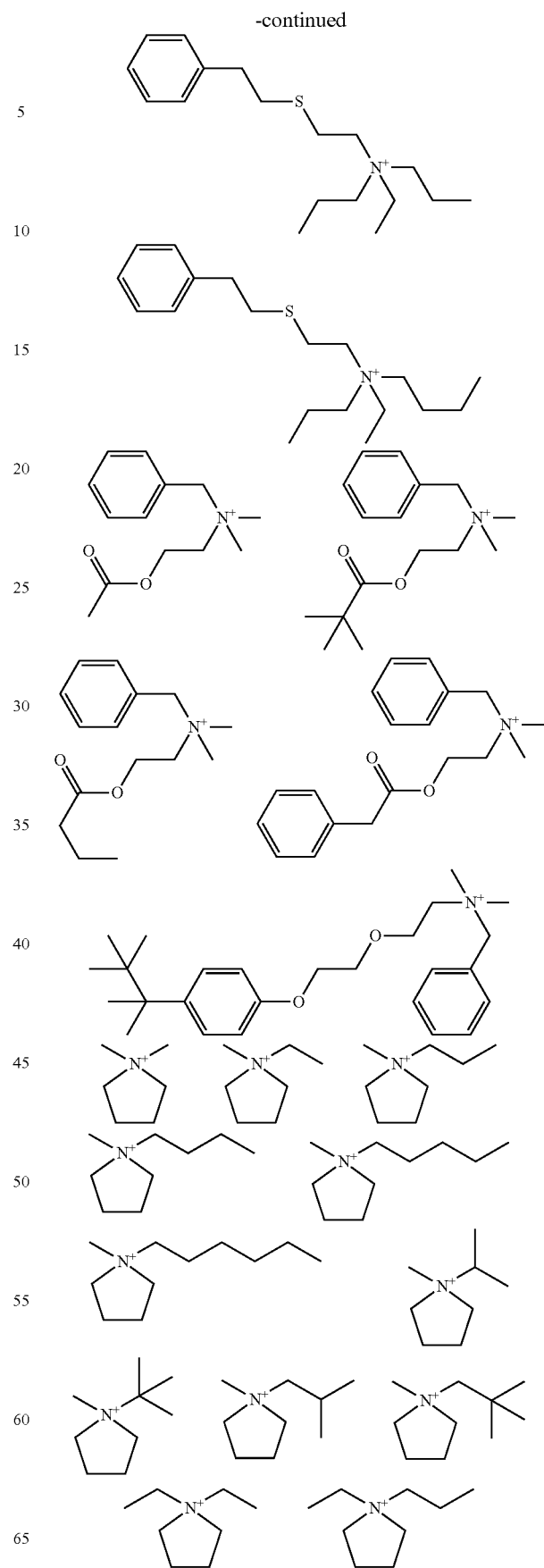

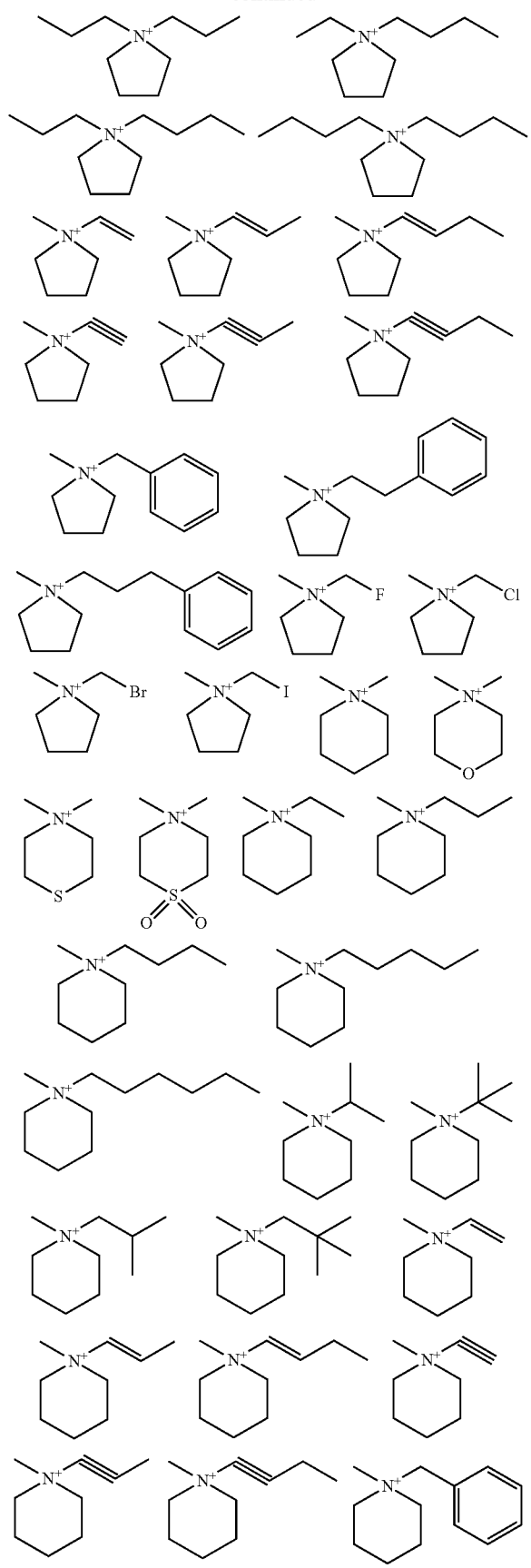

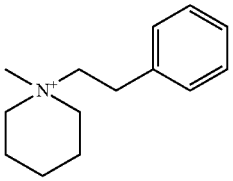
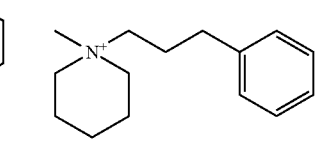

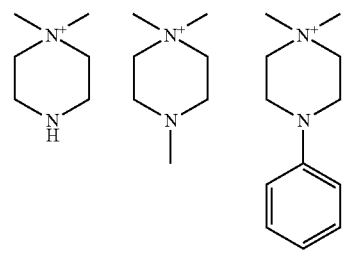

The onium salt having formula (A) may be synthesized, for example, by ion exchange with an onium salt of weaker acid than the iodized benzene ring-containing sulfonamide. Examples of the weaker acid than the iodized benzene ring-containing sulfonamide include hydrochloric acid and carbonic acid. When the onium salt is a sulfonium or iodonium salt, it may be synthesized by ion exchange between the iodized benzene ring-containing sulfonamide or a sodium or ammonium salt thereof and a sulfonium chloride or iodonium chloride. When the onium salt is a quaternary ammonium salt, it may be synthesized by neutralization reaction of the iodized benzene ring-containing sulfonamide with a quaternary ammonium hydroxide containing the desired cation. When the onium salt is a primary to tertiary ammonium salt, it may be synthesized by neutralization reaction of the iodized benzene ring-containing sulfonamide with a primary to tertiary amine providing the desired cation.

In the resist composition, the onium salt having formula (A) is preferably used in an amount of 0.001 to 50 parts, more preferably 0.01 to 20 parts by weight per 100 parts by weight of the base polymer, as viewed from sensitivity and acid diffusion suppressing effect.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

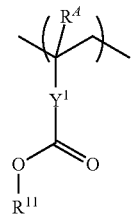

(a1)

-continued

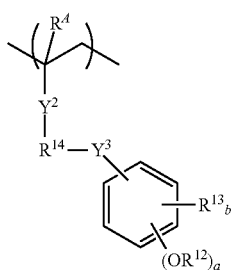
(a2)

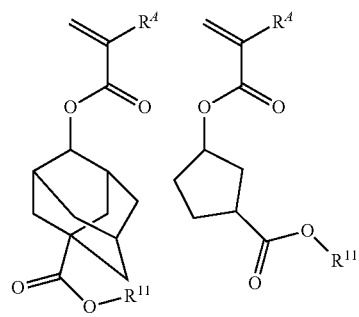

Herein $R^4$ is each independently hydrogen or methyl. $Y^1$ is a single bond, phenylene or naphthylene group, or $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ each are an acid labile group. $R^{13}$ is fluorine, trifluoromethyl, cyano or $C_1$-$C_6$ saturated hydrocarbyl group. $R^{14}$ is a single bond or $C_1$-$C_6$ alkanediyl group in which some carbon may be replaced by an ether bond or ester bond. The subscript "a" is 1 or 2, b is an integer of 0 to 4, and a+b is from 1 to 5.

Examples of the monomer from which the recurring units (a1) are derived are shown below, but not limited thereto. $R^4$ and $R^{11}$ are as defined above.

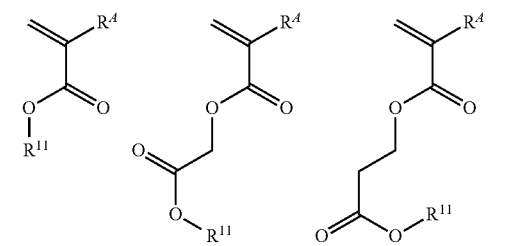

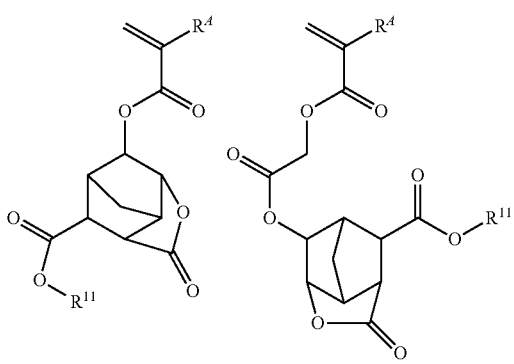

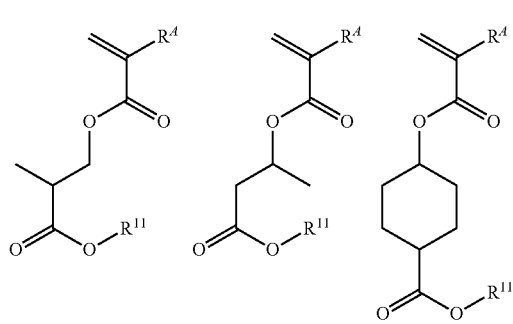

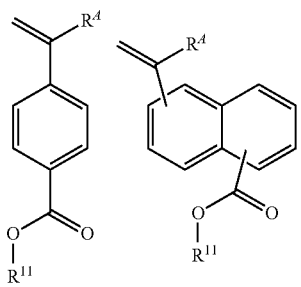

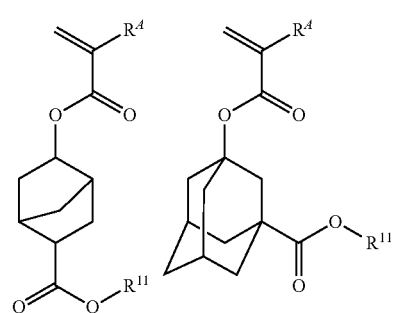

Examples of the monomer from which the recurring units (a2) are derived are shown below, but not limited thereto. $R^4$ and $R^{12}$ are as defined above.

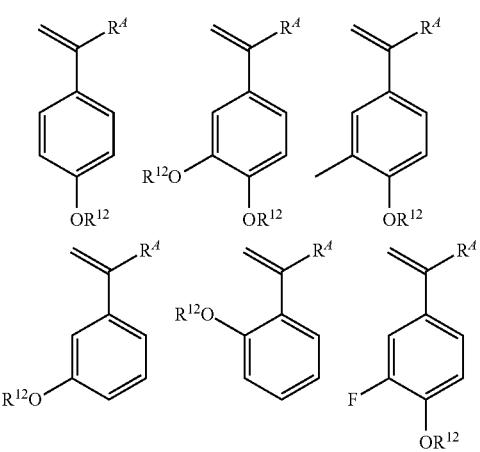

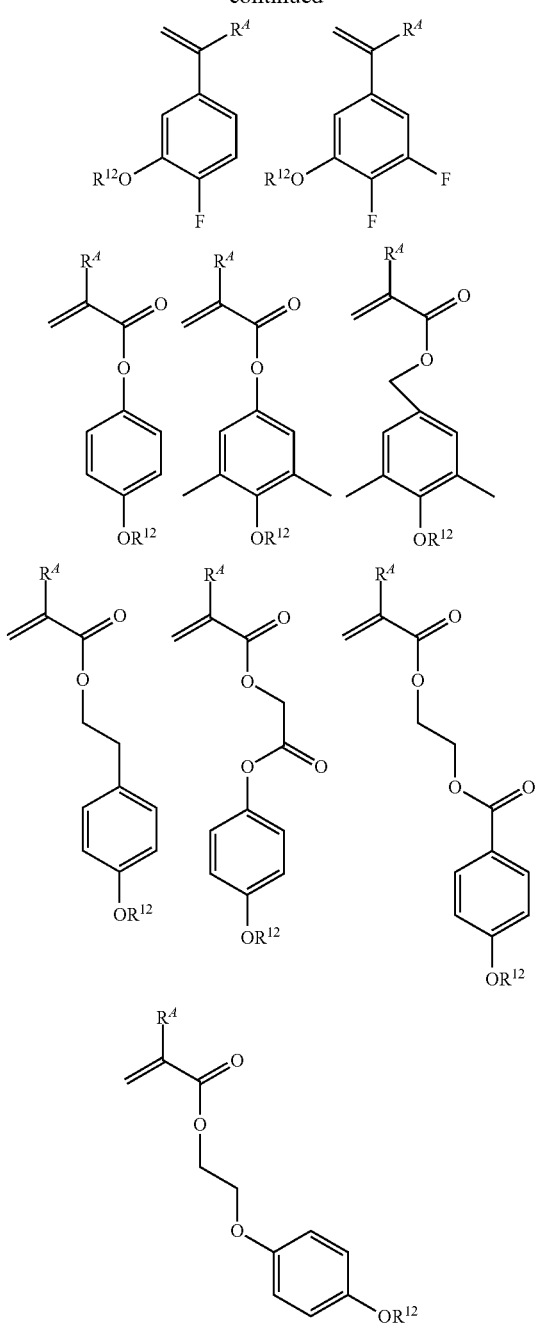

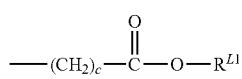

The acid labile groups represented by $R^{11}$ and $R^{12}$ may be selected from a variety of such groups, for example, those groups described in JP-A 2013-080033 (U.S. Pat. No. 8,574, 817) and JP-A 2013-083821 (U.S. Pat. No. 8,846,303).

Typical of the acid labile group are groups of the following formulae (AL-1) to (AL-3).

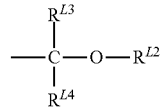

(AL-1)

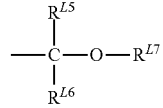

(AL-2)

(AL-3)

Herein the broken line designates a valence bond.

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached, the ring being preferably of 4 to 16 carbon atoms and especially alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached, the ring being preferably of 4 to 16 carbon atoms and especially alicyclic.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

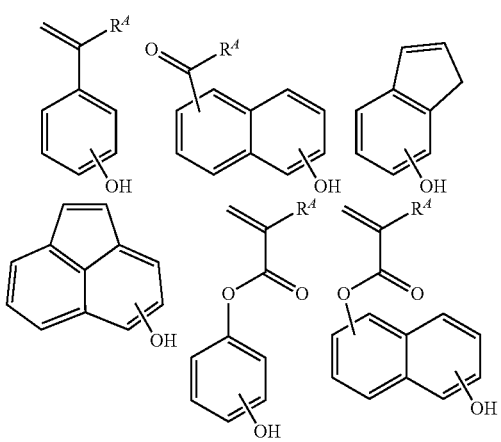

119
-continued

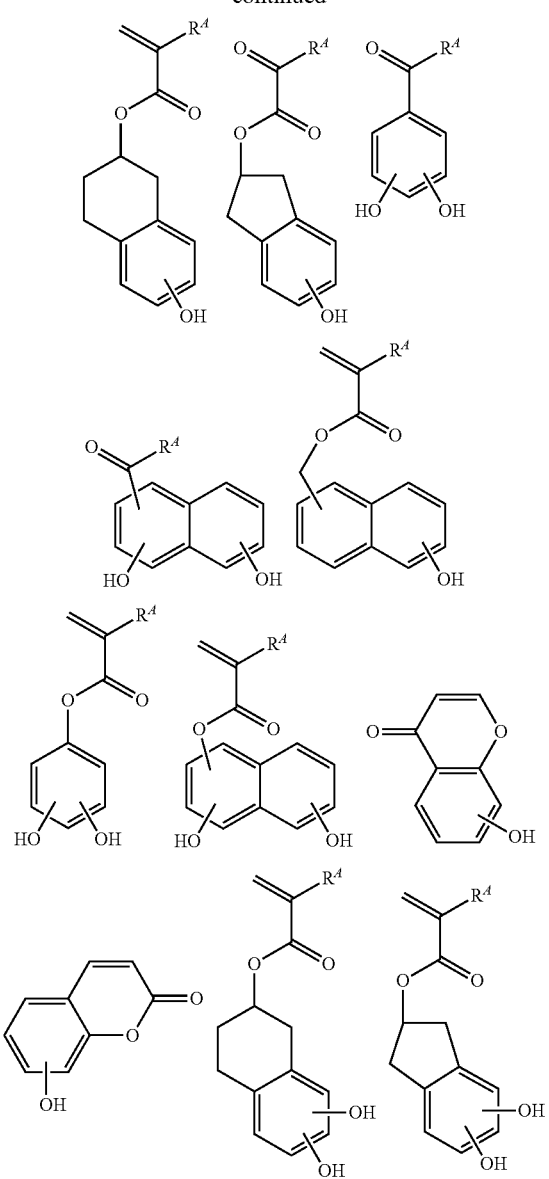

120
-continued

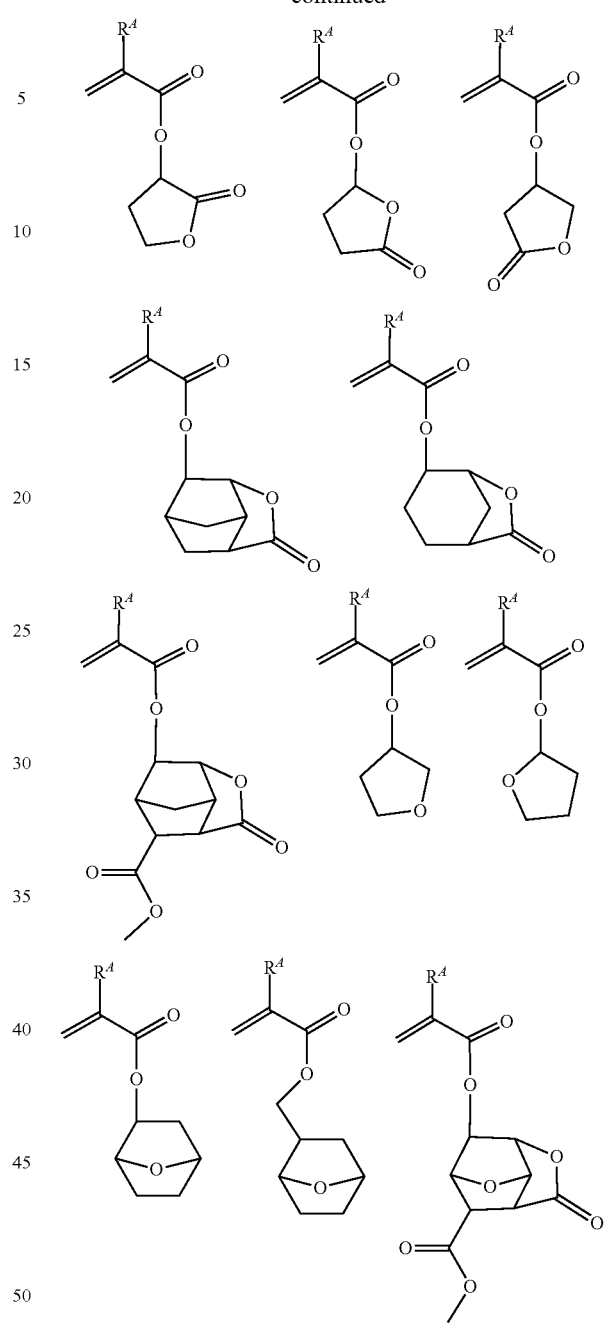

Further, recurring units (c) having another adhesive group selected from hydroxyl (other than the foregoing phenolic hydroxyl), carboxyl, lactone ring, ether bond, ester bond, carbonyl and cyano groups may also be incorporated in the base polymer. Examples of suitable monomers from which recurring units (c) are derived are given below, but not limited thereto. Herein $R^A$ is as defined above.

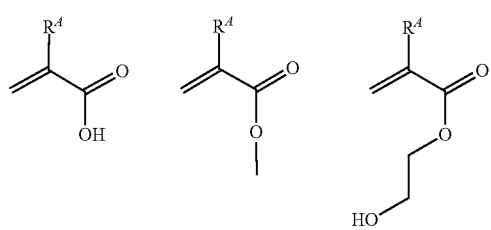

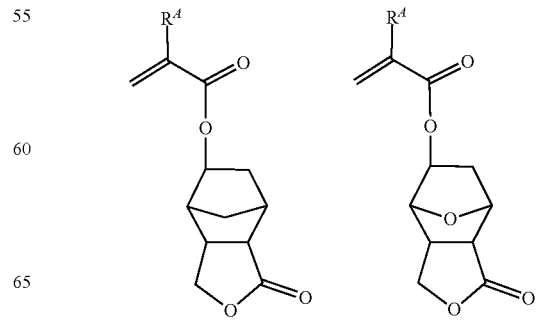

121
-continued
122
-continued
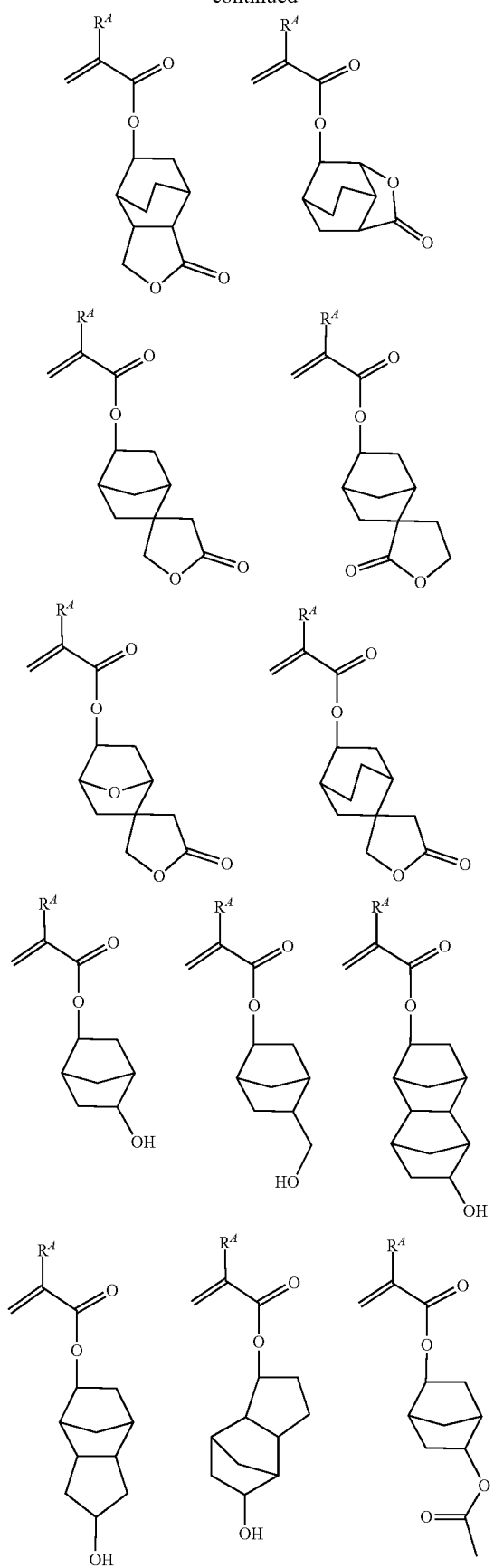
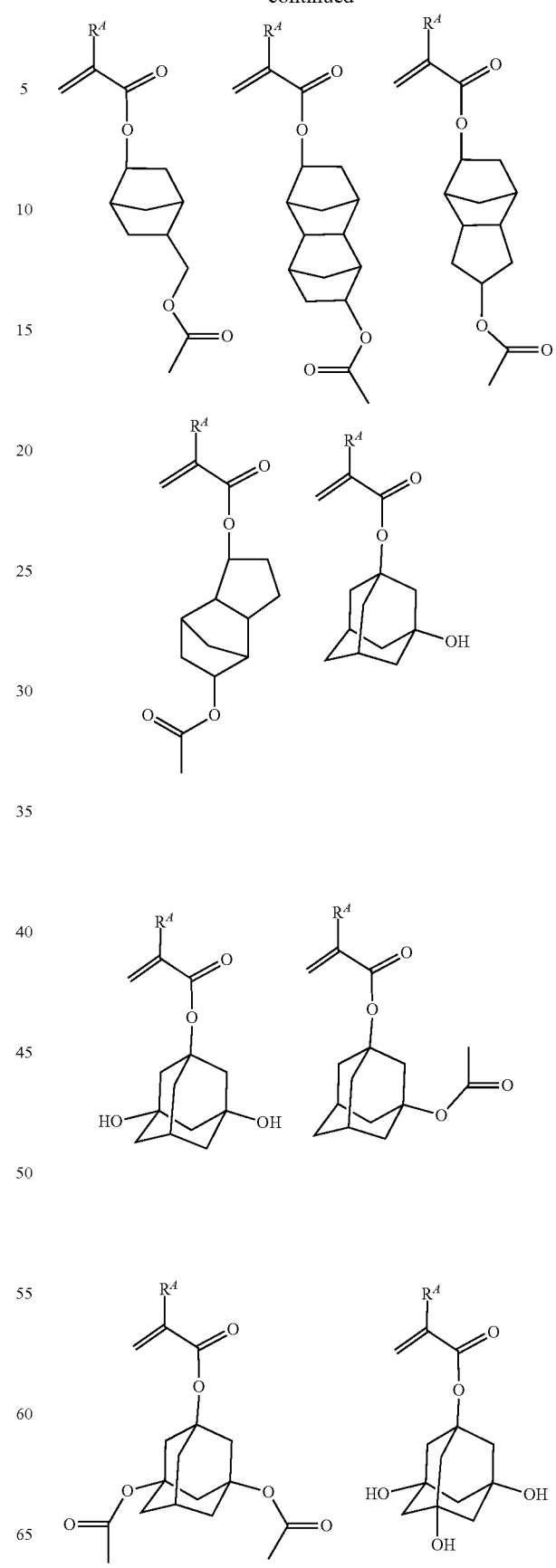

123
-continued
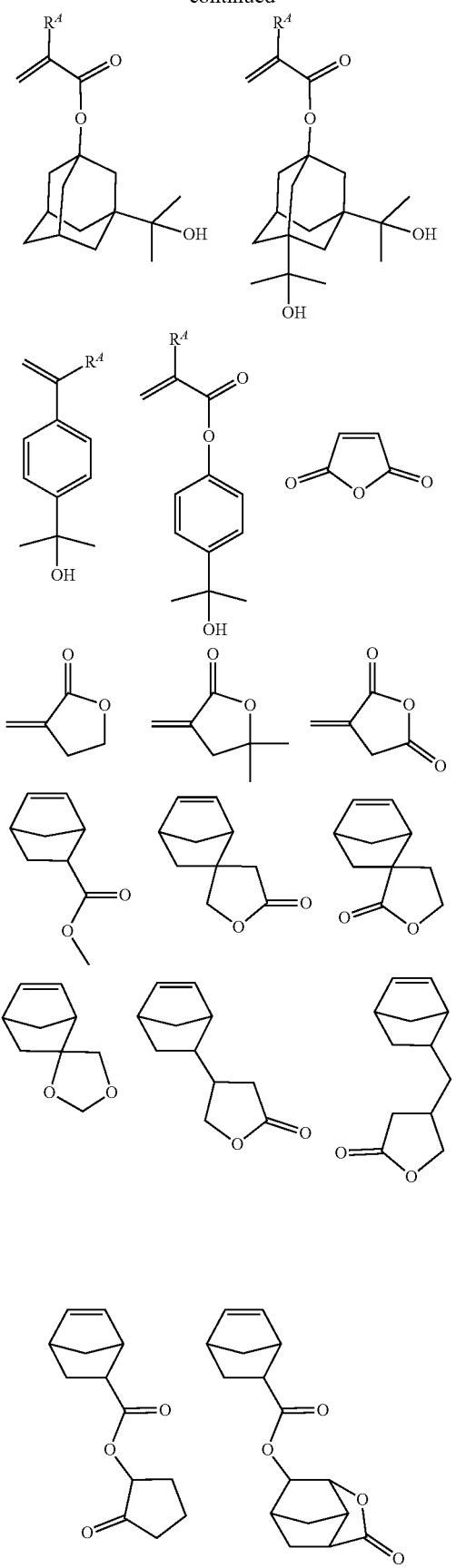
124
-continued
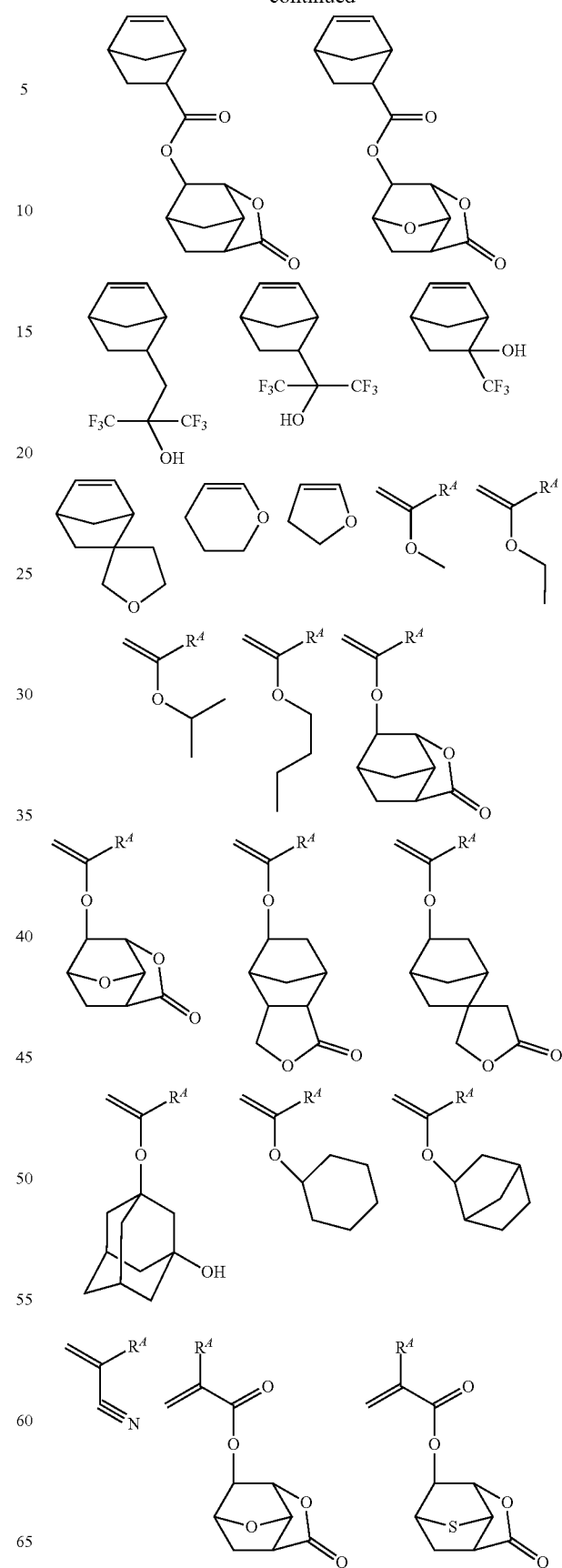

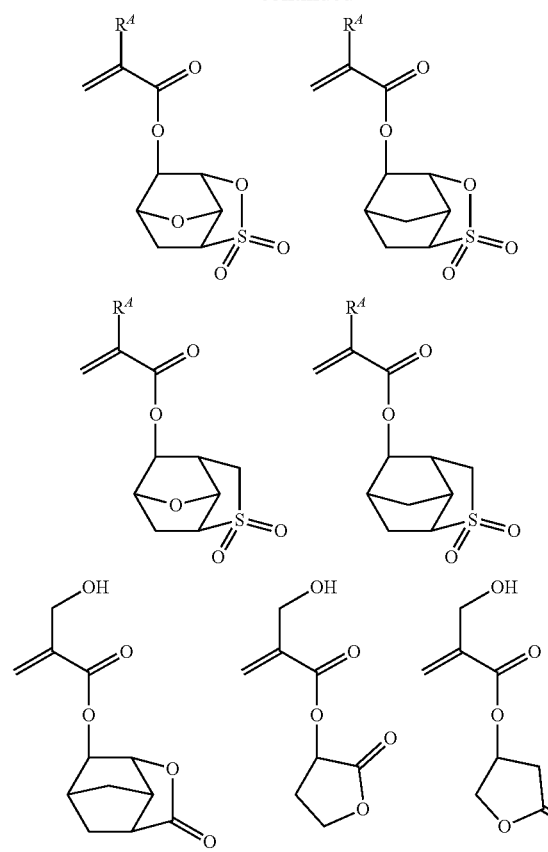
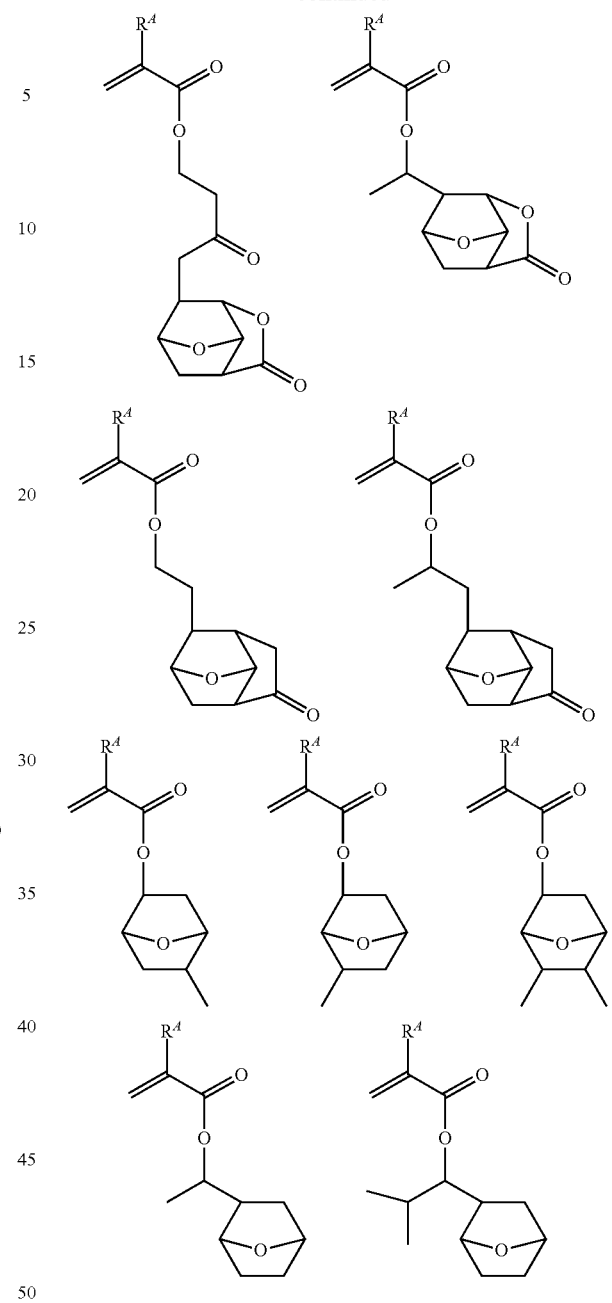
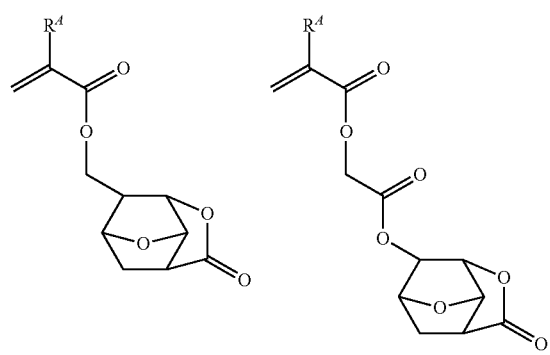

127
-continued
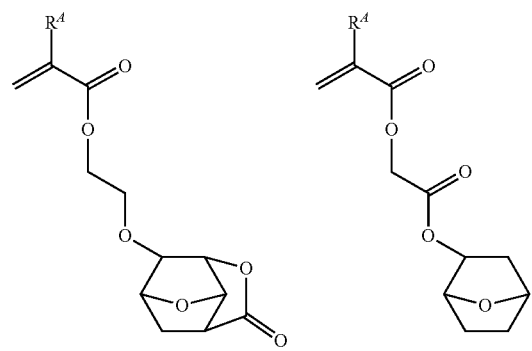
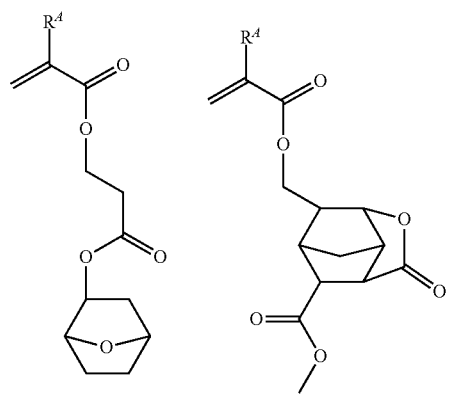
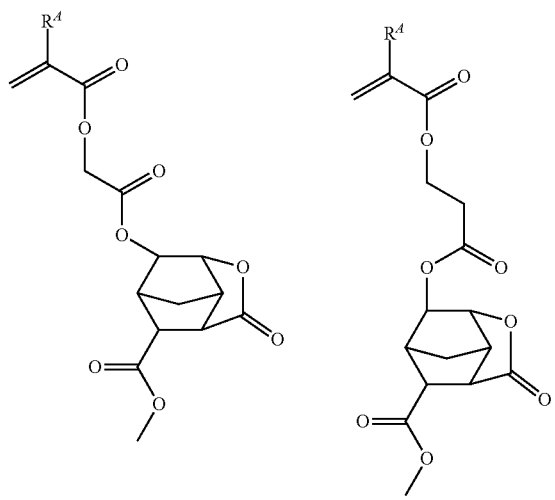
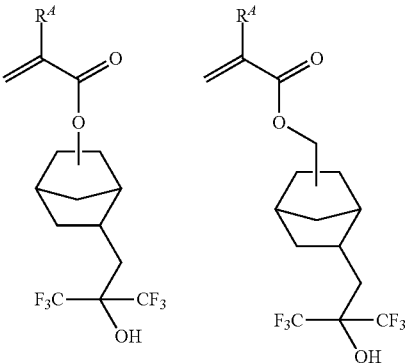
128
-continued
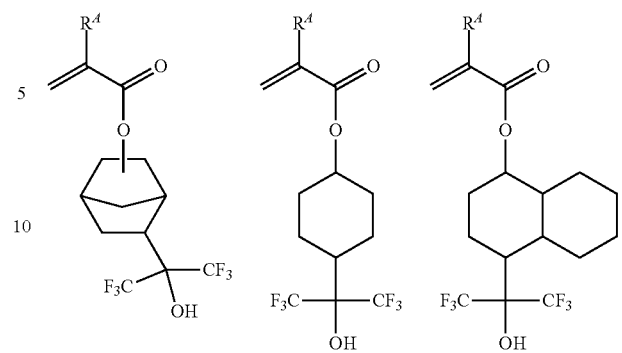
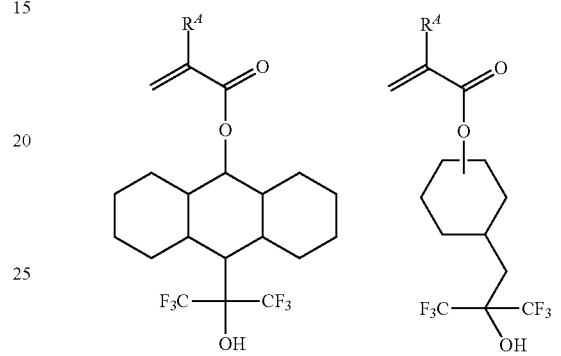
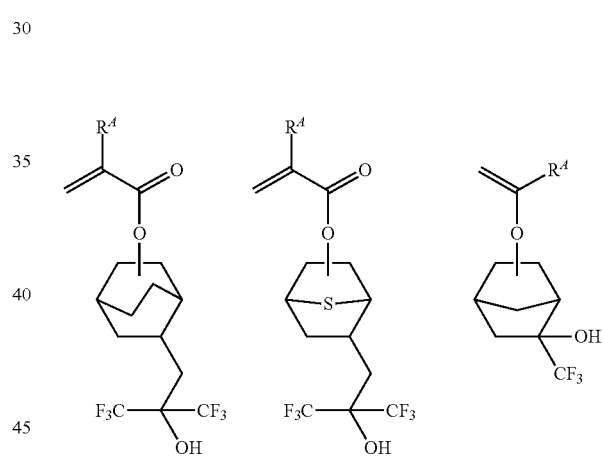
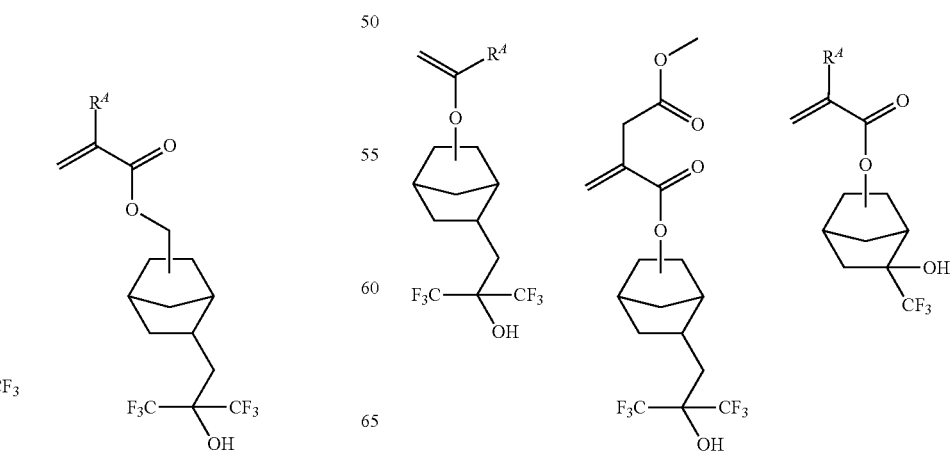

-continued
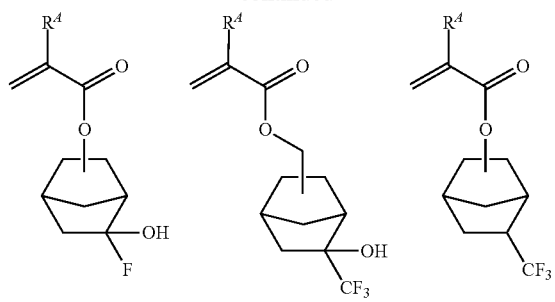
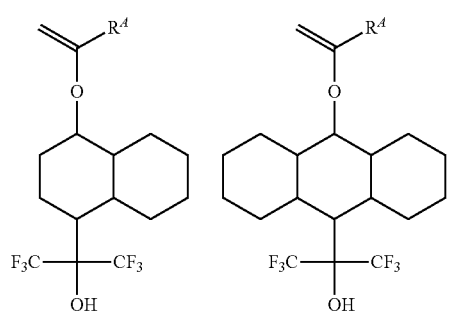
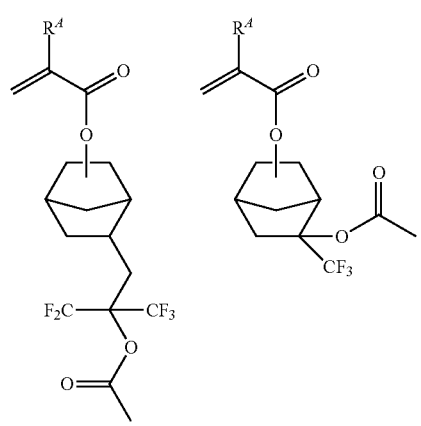
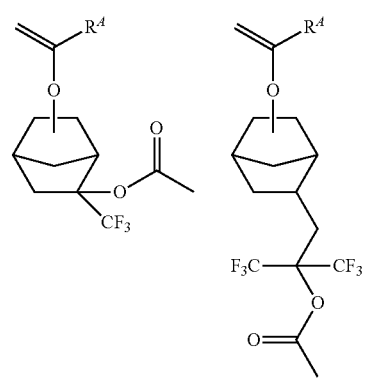
-continued
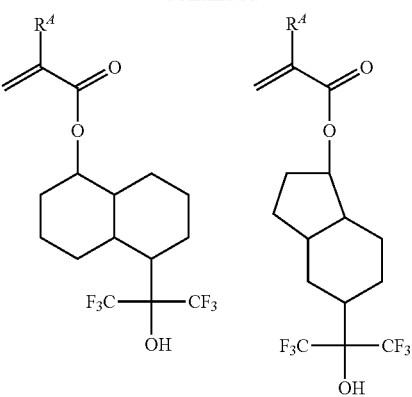
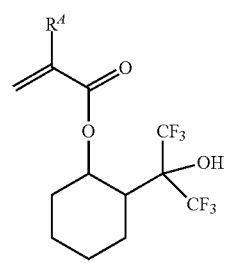
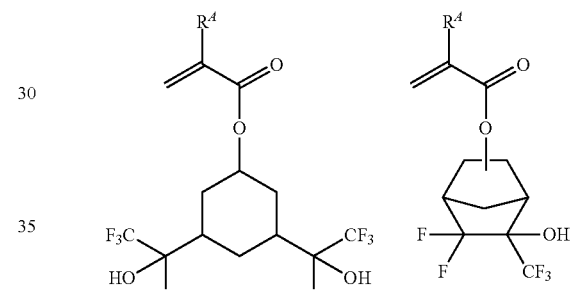
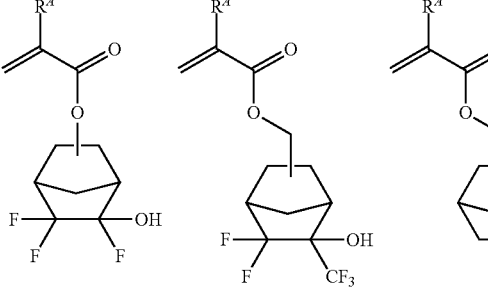
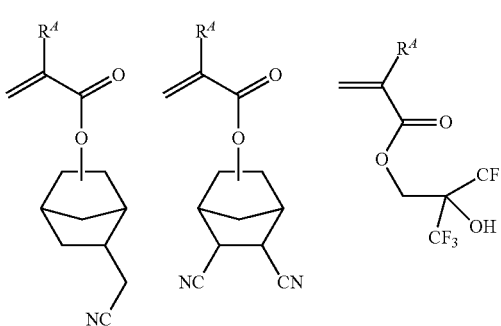

-continued
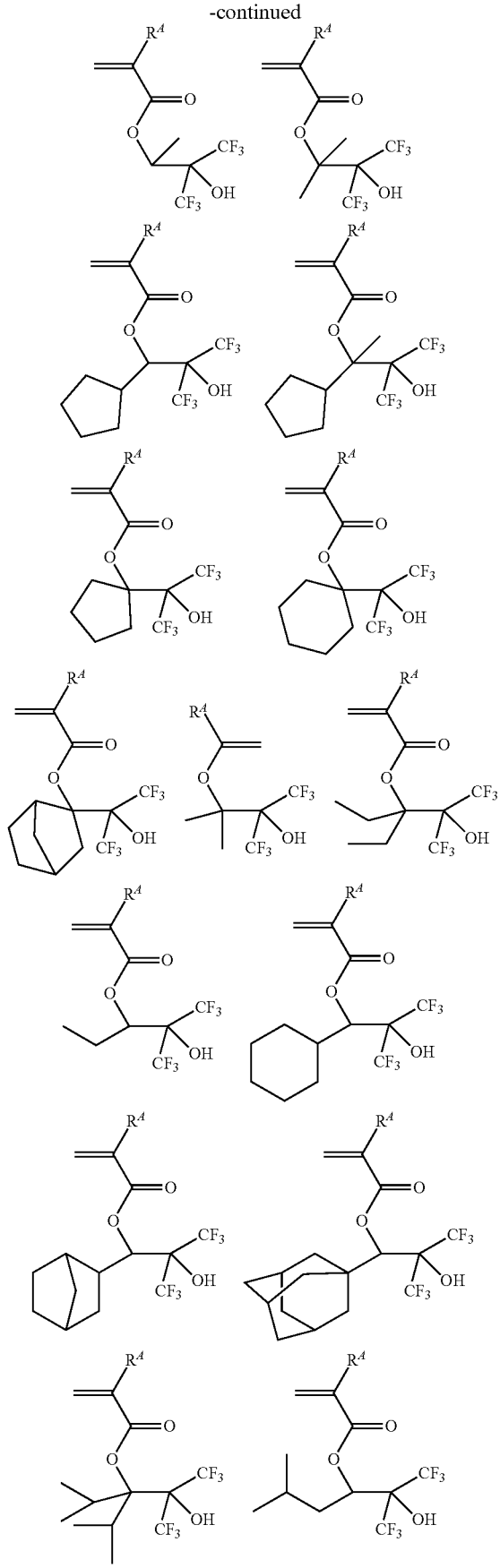
-continued
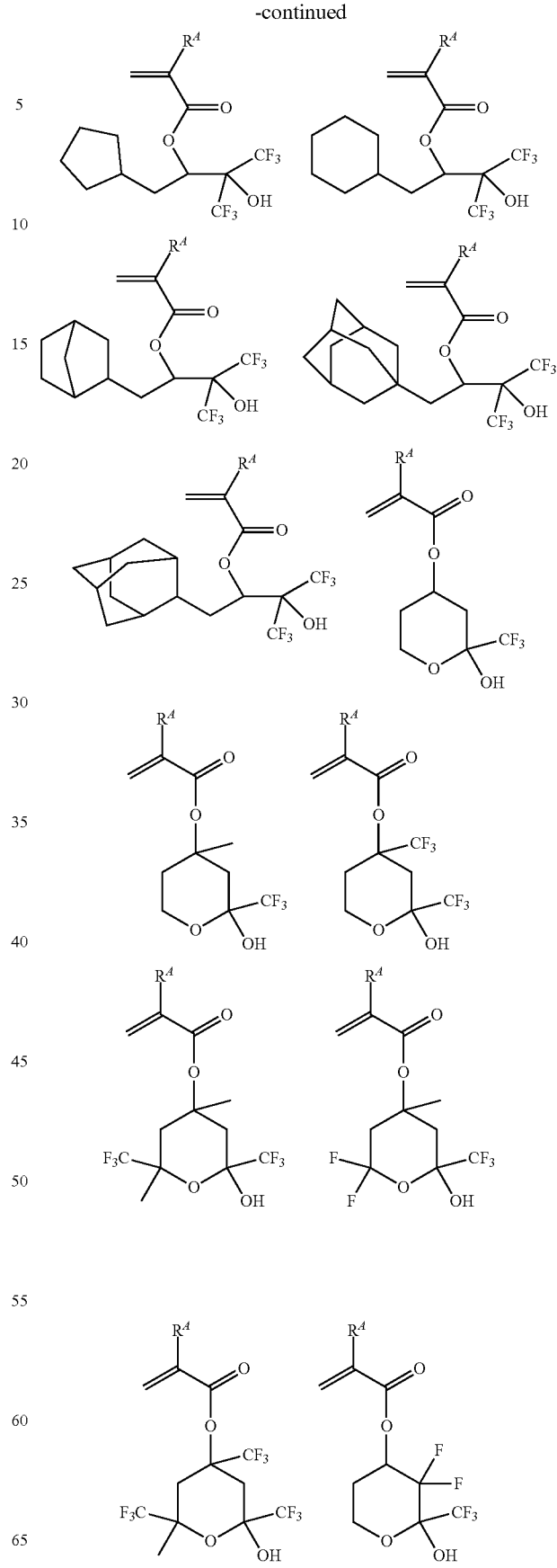

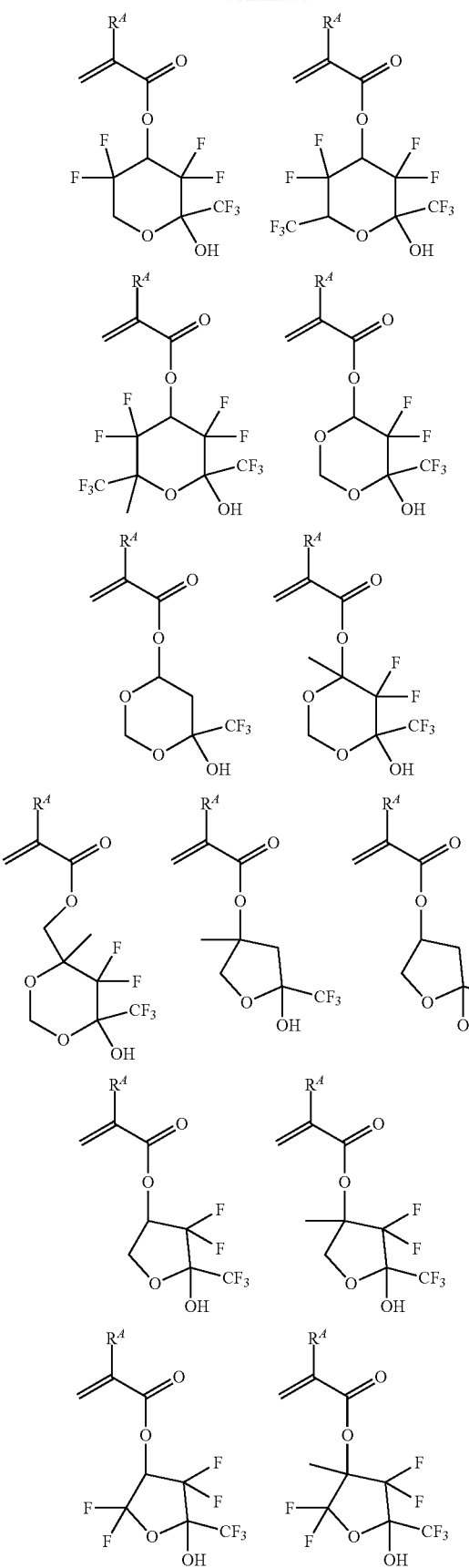
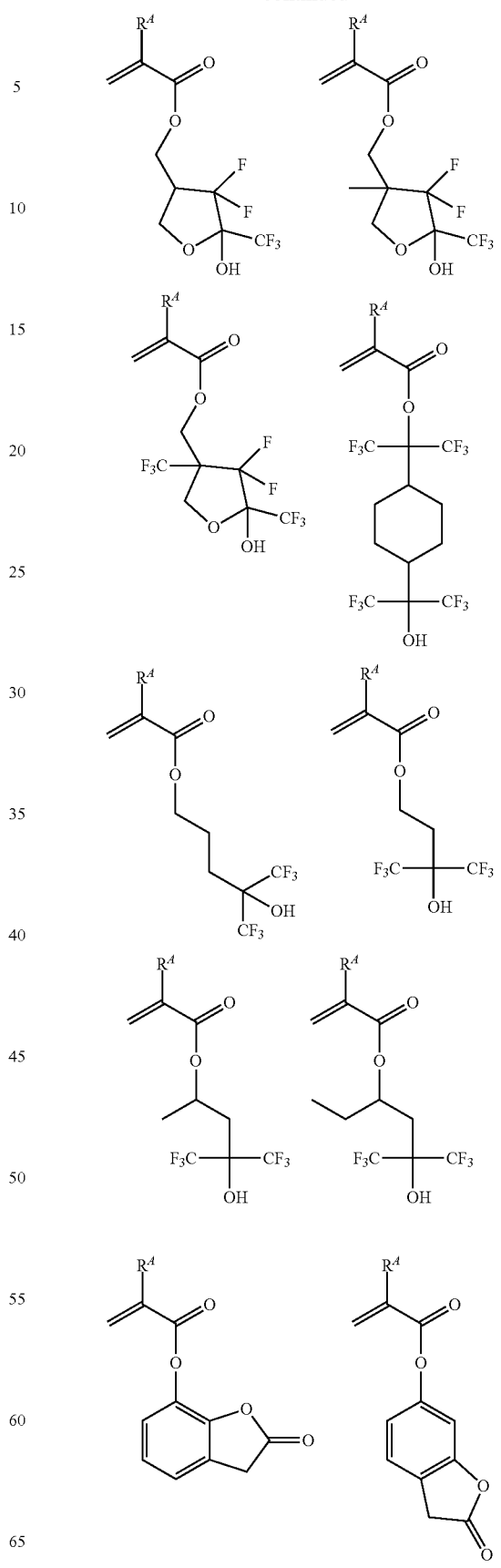

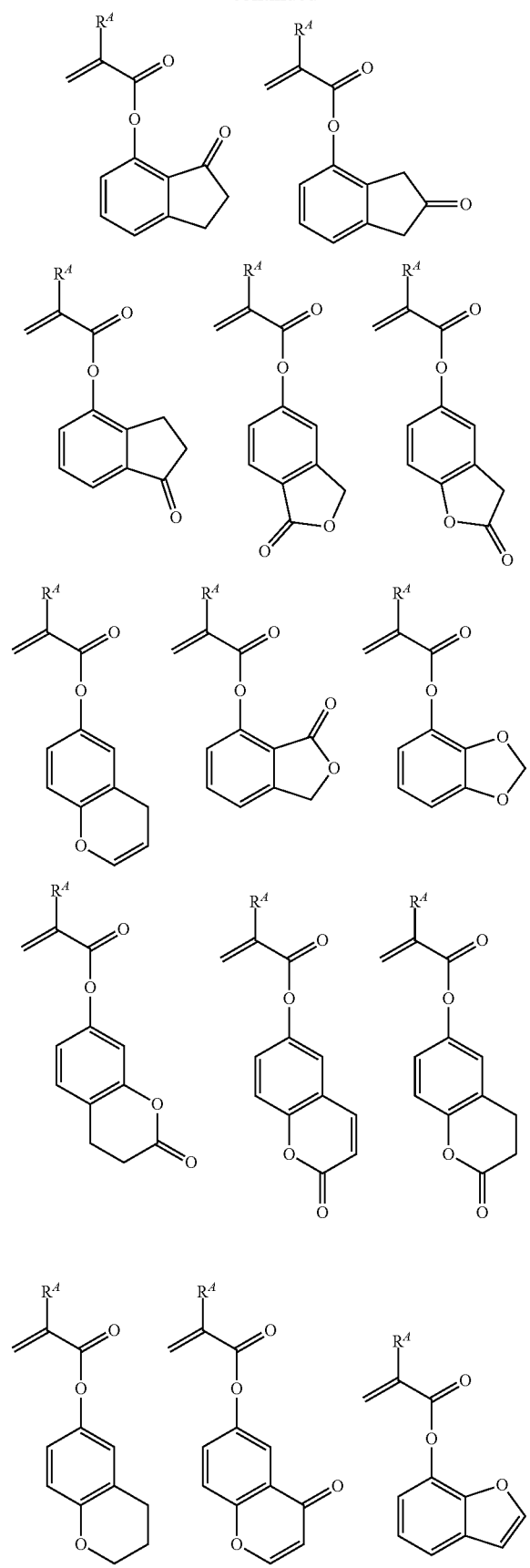
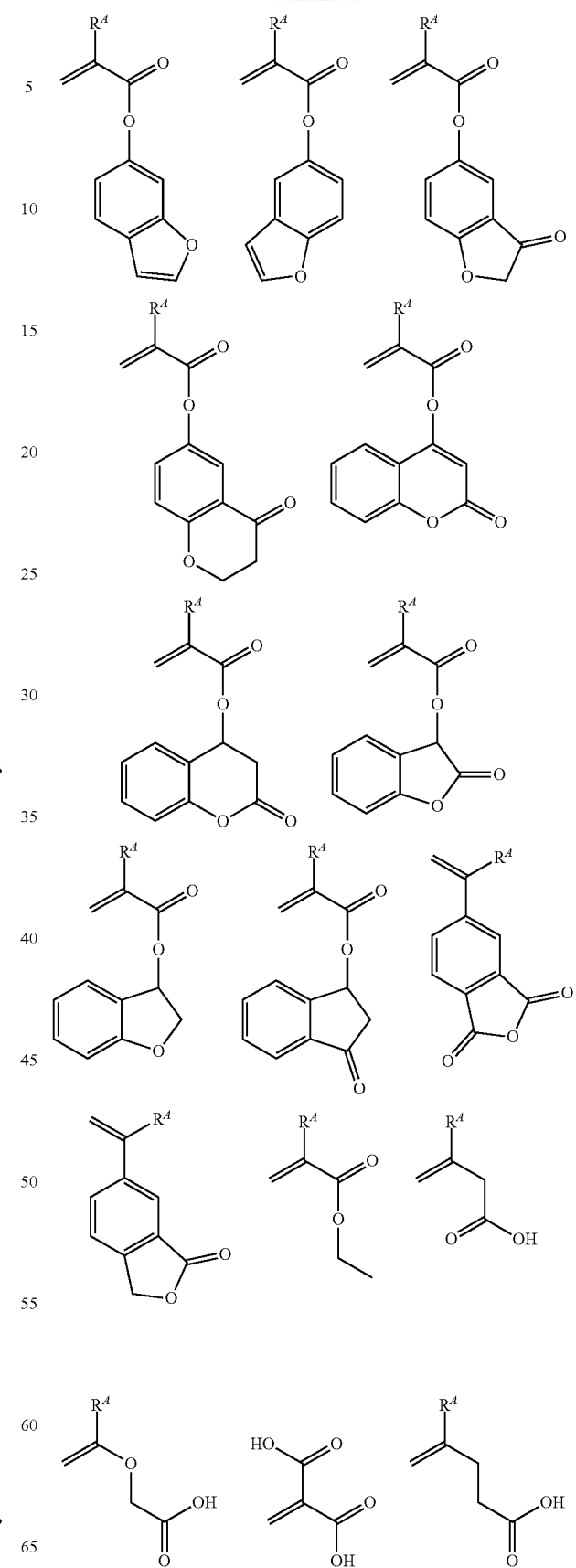

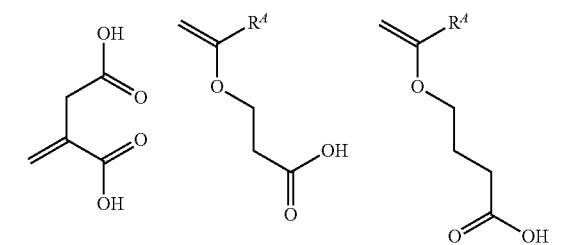
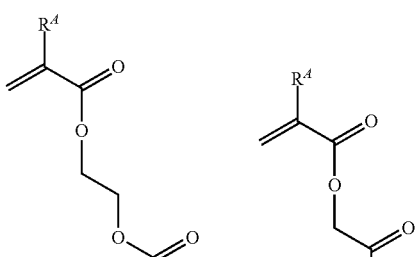
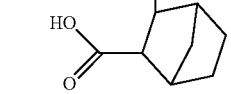
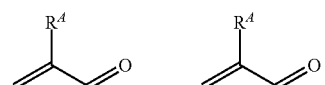
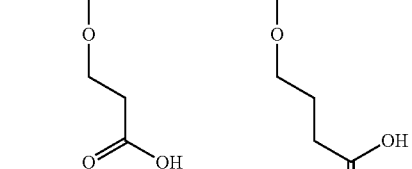
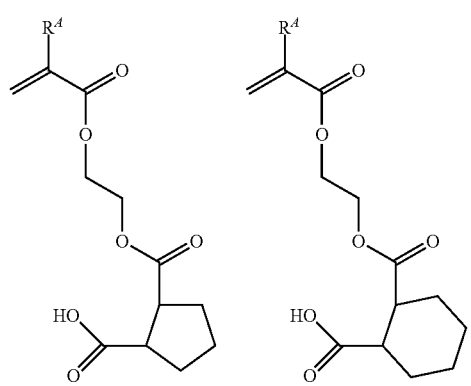
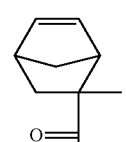
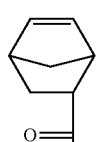
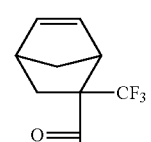
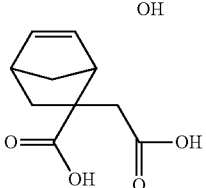
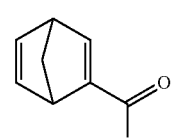
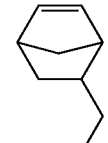
In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.
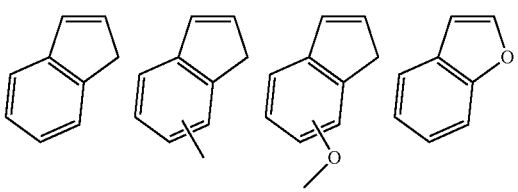
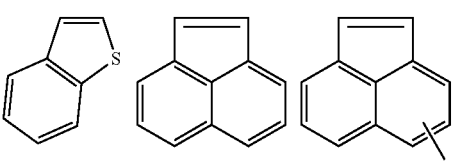

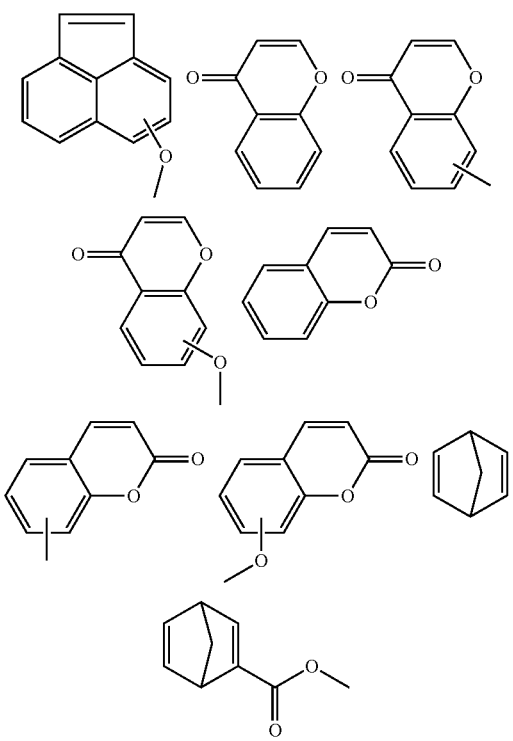

The base polymer may further comprise recurring units (e) derived from styrene, vinylnaphthalene, vinylanthracene, vinylpyrene, methyleneindene, vinylpyridine, and vinylcarbazole.

The base polymer may further comprise recurring units (f) derived from an onium salt having a polymerizable unsaturated bond. Preferred recurring units (f) include recurring units having formula (f1), recurring units having formula (f2) and recurring units having formula (f3). These units are simply referred to as recurring units (f1), (f2) and (f3), which may be used alone or in combination of two or more types.

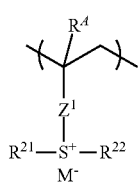 (f1)

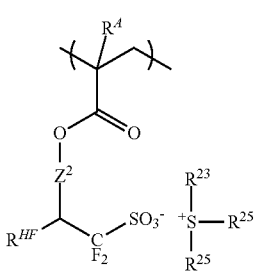 (f2)

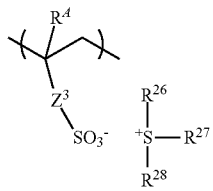 (f3)

In formulae (f1) to (f3), $R^A$ is as defined above. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—. $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—. $Z^{21}$ is a $C_1$-$C_{12}$ saturated hydrocarbylene group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—. $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety. Notably, the aliphatic hydrocarbylene group represented by $Z^{11}$ and $Z^{31}$ may be saturated or unsaturated and straight, branched or cyclic. The saturated hydrocarbylene group represented by $Z^{21}$ may be straight, branched or cyclic.

In formulae (f1) to (f3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl group represented by $R^{a1}$ to $R^{a3}$ in formula (Aa). A pair of $R^{23}$ and $R^{24}$ or $R^{26}$ and $R^{27}$ may bond together to form a ring with the sulfur atom to which they are attached. Examples of the ring are as exemplified above for the ring that $R^{a1}$ and $R^{a2}$ in formula (Aa), taken together, form with the sulfur atom to which they are attached.

In formula (f2), $R^{HF}$ is hydrogen or trifluoromethyl.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl substituted at β-position as represented by the formula (f1-2).

$$R^{31}-CF_2-SO_3^-$$ (f1-1)

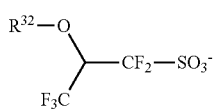
(f1-2)

In formula (f1-1), $R^{31}$ is hydrogen or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples thereof are as will be exemplified for the hydrocarbyl group $R^{111}$ in formula (1A').

In formula (f1-2), $R^{32}$ is hydrogen or a $C_1$-$C_{30}$ hydrocarbyl or $C_2$-$C_{30}$ hydrocarbylcarbonyl group, which may contain an ether bond, ester bond, carbonyl moiety or lactone ring. The hydrocarbyl group and the hydrocarbyl moiety in the hydrocarbylcarbonyl group may be saturated or unsaturated and straight, branched or cyclic. Examples thereof are as will be exemplified for the hydrocarbyl group $R^{111}$ in formula (1A').

Examples of the cation in the monomer from which recurring unit (f1) is derived are shown below, but not limited thereto. $R^A$ is as defined above.

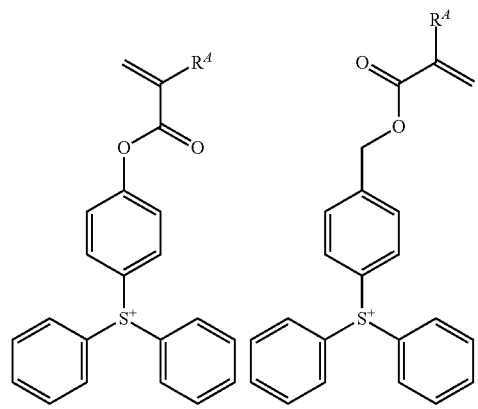

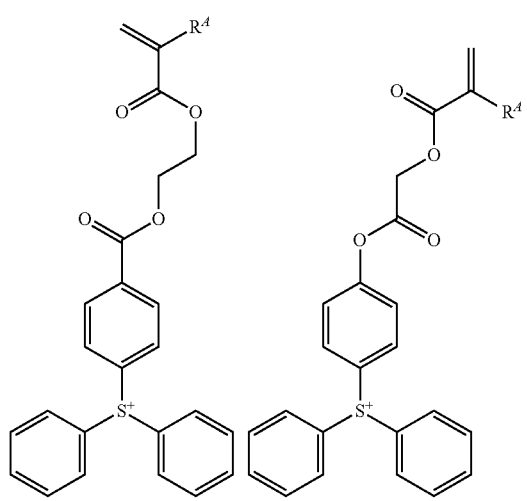

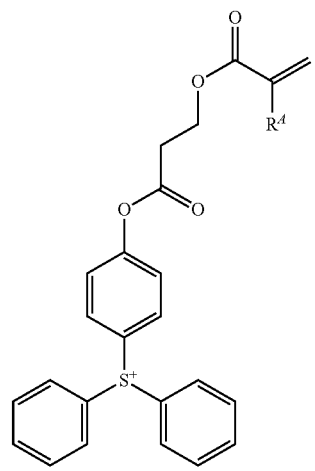

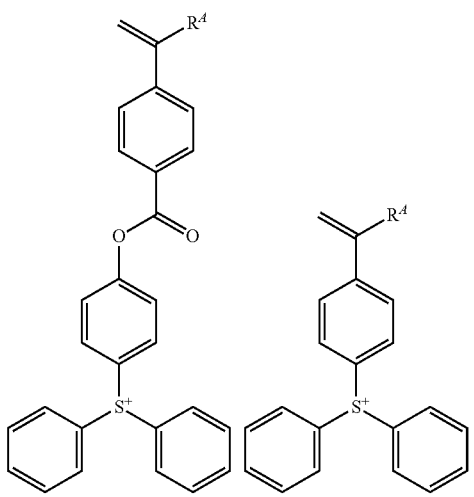

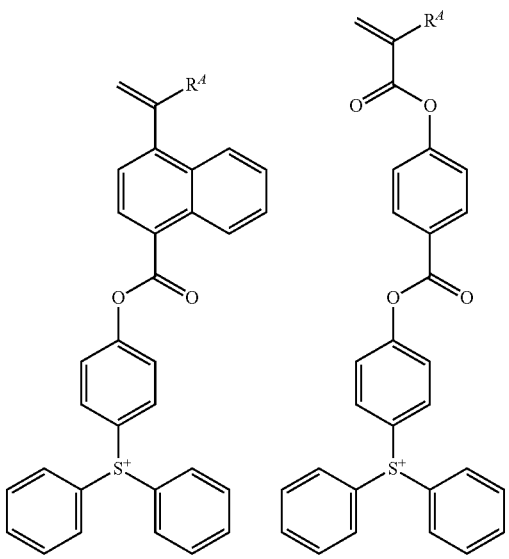

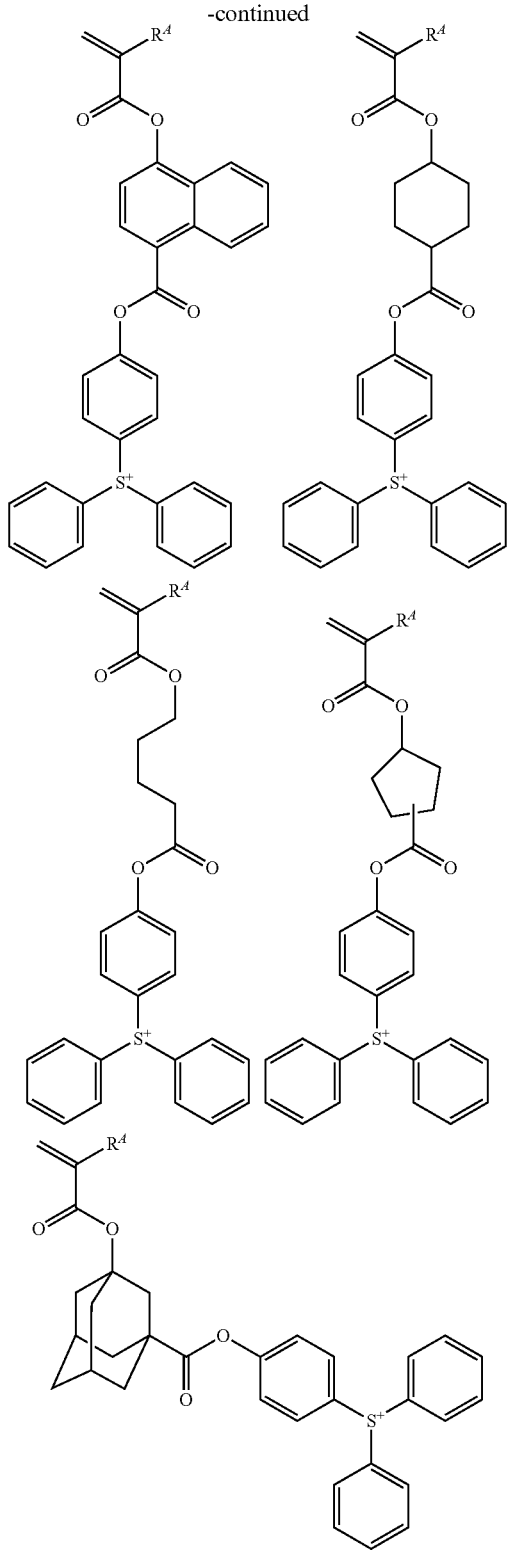
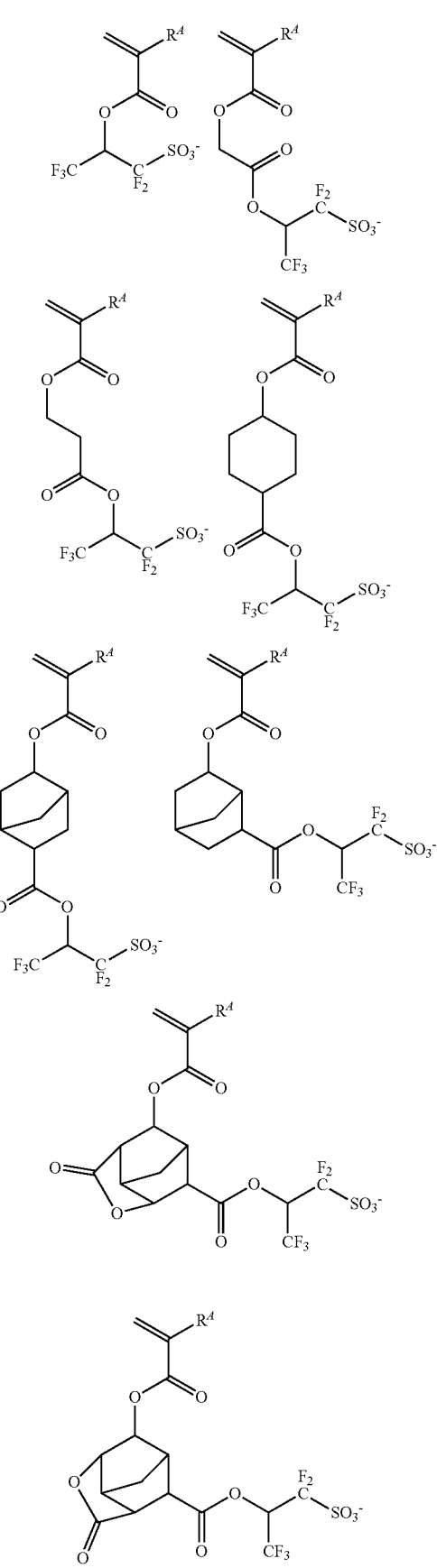
Examples of the cation in the monomer from which recurring unit (f2) or (f3) is derived are as exemplified above for the sulfonium cation having formula (Aa).
Examples of the anion in the monomer from which recurring unit (f2) is derived are shown below, but not limited thereto. $R^A$ is as defined above.

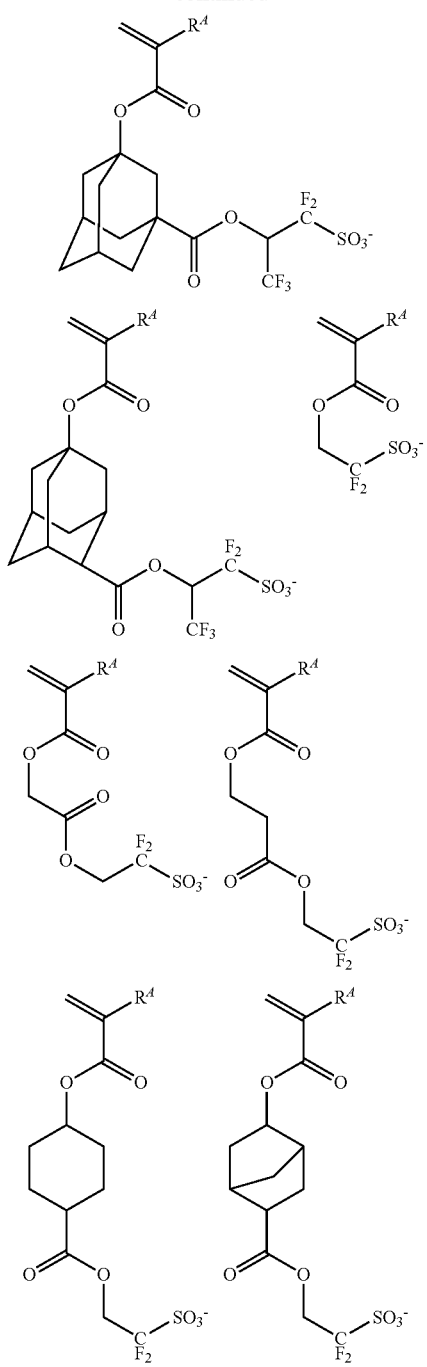
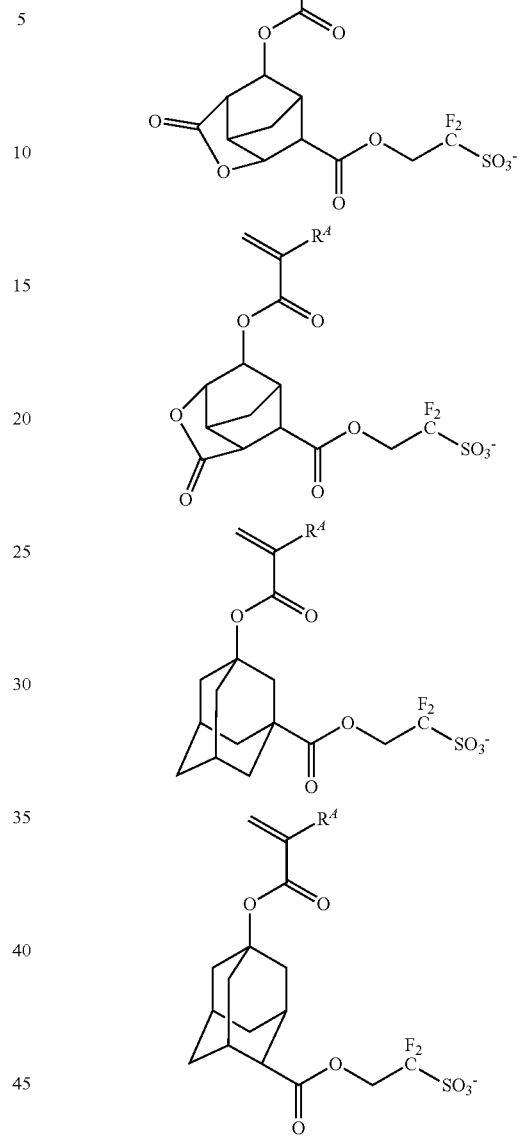
Examples of the anion in the monomer from which recurring unit (f3) is derived are shown below, but not limited thereto. $R^A$ is as defined above.
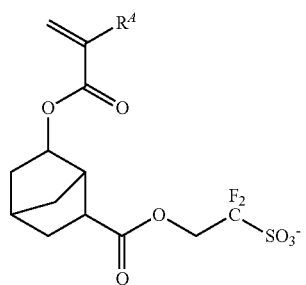
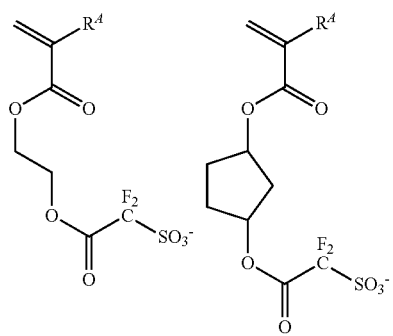

-continued

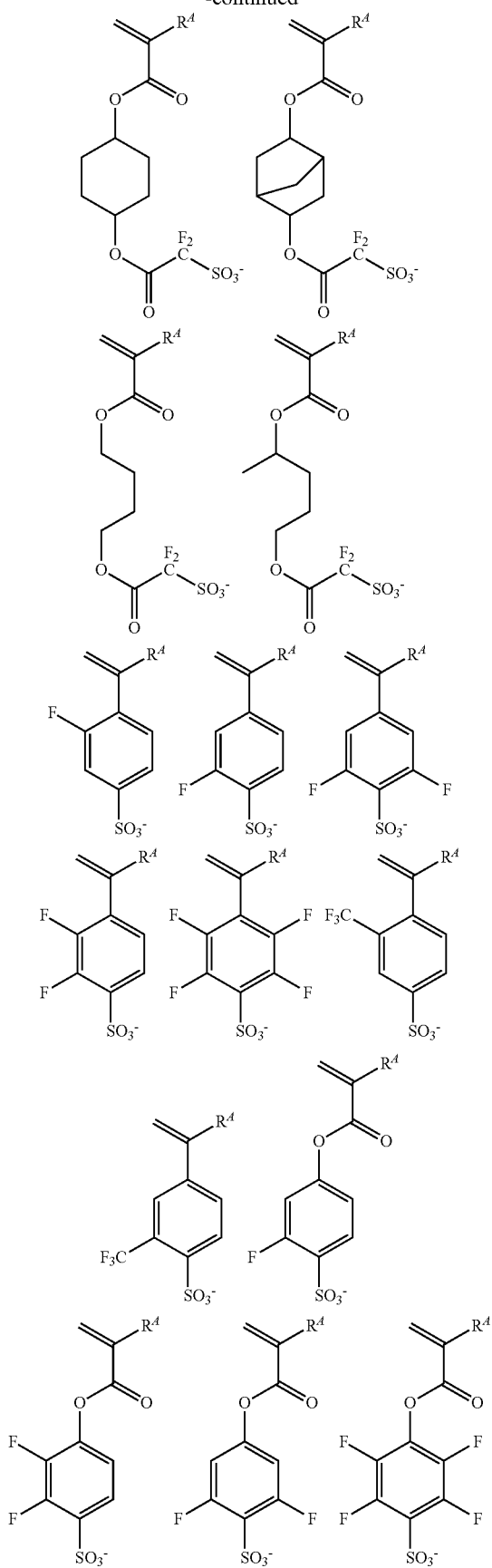

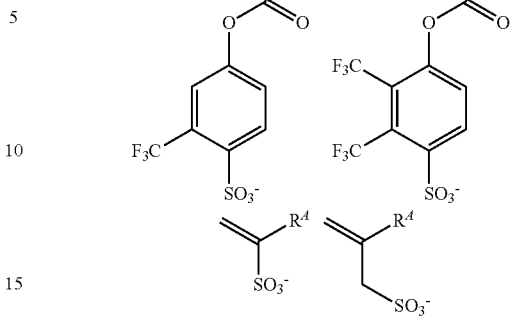

The attachment of an acid generator to the polymer main chain is effective in restraining acid diffusion, thereby preventing a reduction of resolution due to blur by acid diffusion. Also LWR is improved since the acid generator is uniformly distributed. Where a base polymer containing recurring units (f), i.e., polymer-bound acid generator is used, the addition of a separate acid generator may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \le a1 \le 1.0$, $0 \le a2 < 1.0$, $0 < a1+a2 < 1.0$, $0 \le b \le 0.9$, $0 \le c \le 0.9$, $0 \le d \le 0.8$, $0 \le e \le 0.8$, and $0 \le f \le 0.5$; more preferably $0 \le a1 \le 0.9$, $0 \le a2 \le 0.9$, $0.1 \le a1+a2 \le 0.9$, $0 \le b \le 0.8$, $0 \le c \le 0.8$, $0 \le d \le 0.7$, $0 \le e \le 0.7$, and $0 \le f \le 0.4$; and even more preferably $0 \le a1 \le 0.8$, $0 \le a2 \le 0.8$, $0.1 \le a1+a2 \le 0.8$, $0 \le b \le 0.75$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \le 1.0$, $0 \le c \le 0.9$, $0 \le d \le 0.8$, $0 \le e \le 0.8$, and $0 \le f \le 0.5$; more preferably $0.2 \le b \le 1.0$, $0 \le c \le 0.8$, $0 \le d \le 0.7$, $0 \le e \le 0.7$, and $0 \le f \le 0.4$; and even more preferably $0.3 \le b \le 1.0$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using THF solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable. The base polymer may contain a polymer different from the polymer defined above as long as the benefits of the invention are not impaired, although the absence of such an additional polymer is preferred.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the onium salt of formula (A) functions as a quencher and the inventive resist composition functions as a chemically amplified positive or negative resist composition. When the resist composition is formulated as a chemically amplified resist composition utilizing acid catalyzed reaction, it becomes quite useful because of a higher sensitivity and better resist properties. Where the base polymer is a polymer-bound acid generator, an acid generator of addition type may be omitted.

The acid generator is typically a compound (PAG) capable of generating a strong acid upon exposure to actinic ray or radiation. Although the PAG used herein may be any compound capable of generating a strong acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, salts having the formula (1) are also preferred.

In formula (1), $R^{101}$ to $R^{103}$ are each independently halogen or a $C_1$-$C_{20}$ hydrocarbyl group which may contain a heteroatom. Suitable halogen atoms include fluorine, chlorine, bromine and iodine. The hydrocarbyl group may be saturated or unsaturated and straight, branched or cyclic, and examples thereof include those exemplified above for the hydrocarbyl groups $R^{a1}$ to $R^{a3}$ in formula (Aa). Also, $R^{101}$ and $R^{102}$ may bond together to form a ring with the sulfur atom to which they are attached. Examples of the ring are as exemplified above for the ring that $R^{a1}$ and $R^{a2}$ in formula (Aa), taken together, form with the sulfur atom to which they are attached.

Examples of the cation in the sulfonium salt having formula (1) are as exemplified above for the sulfonium cation having formula (Aa).

In formula (1), $X^-$ is an anion selected from the following formulae (1A) to (1D).

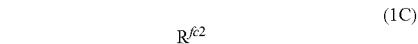

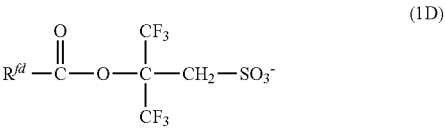

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic, and examples thereof are as will be exemplified for the hydrocarbyl group $R^{111}$ in formula (1A').

Of the anions of formula (1A), a structure having formula (1A') is preferred.

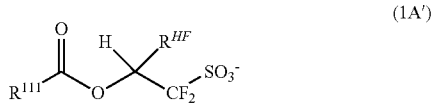

(1A')

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group may be saturated or unsaturated and straight, branched or cyclic. Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl; $C_7$-$C_{38}$ aralkyl groups such as benzyl and diphenylmethyl; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety.

Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are as exemplified for the anion having formula (1A) in JP-A 2018-197853 (US 20180335696).

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and the ring-forming pair is preferably a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are as exemplified for the anion having formula (1D) in JP-A 2018-197853 (US 20180335696).

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

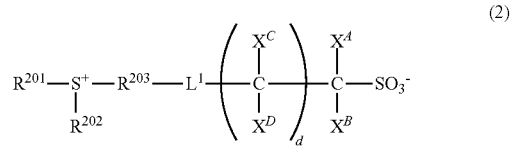

(2)

In formula (2), $R^{201}$ and $R^{202}$ are each independently halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{a1}$ and $R^{a2}$ in formula (Aa), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, and adamantyl; $C_6$-$C_{30}$ aryl groups such as phenyl, naphthyl and anthracenyl; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; arylene groups such as phenylene and naphthylene; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Of the heteroatoms, oxygen is preferred.

In formula (2), $L^1$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), d is an integer of 0 to 3.

Of the PAGs having formula (2), those having formula (2') are preferred.

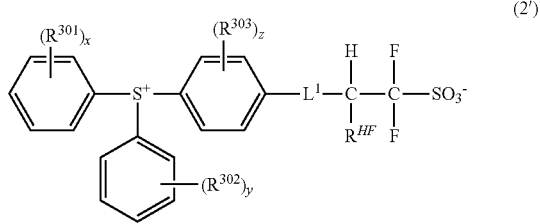

(2')

In formula (2'), $L^1$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

Also a sulfonium or iodonium salt having an anion containing an iodized or brominated aromatic ring may be used as the PAG. Suitable are sulfonium and iodonium salts having the formulae (3-1) and (3-2).

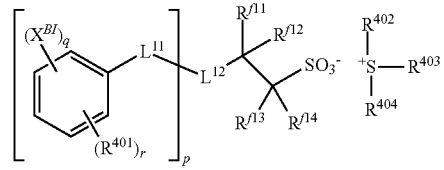

(3-1)

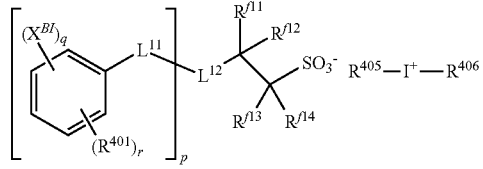

(3-2)

In formulae (3-1) and (3-2), p is an integer of 1 to 3, q is an integer of 1 to 5, and r is an integer of 0 to 3, and $1 \leq q+r \leq 5$. Preferably, q is 1, 2 or 3, more preferably 2 or 3, and r is 0, 1 or 2.

In formulae (3-1) and (3-2), $X^{BI}$ is iodine or bromine, and may be the same or different when p and/or q is 2 or more.

$L^{11}$ is a single bond, ether bond, ester bond, or a $C_1$-$C_6$ saturated hydrocarbylene group which may contain an ether bond or ester bond. The saturated hydrocarbylene group may be straight, branched or cyclic.

$L^{12}$ is a single bond or a $C_1$-$C_{20}$ divalent linking group when r is 1, and a $C_1$-$C_{20}$ tri- or tetravalent linking group which may contain oxygen, sulfur, nitrogen when r is 2 or 3.

$R^{401}$ is a hydroxyl group, carboxyl group, fluorine, chlorine, or a $C_1$-$C_{20}$ hydrocarbyl, $C_1$-$C_{20}$ hydrocarbyloxy, $C_2$-$C_{20}$ hydrocarbylcarbonyl, $C_2$-$C_{20}$ hydrocarbyloxycarbonyl, $C_2$-$C_{20}$ hydrocarbylcarbonyloxy or $C_1$-$C_{20}$ hydrocarbylsulfonyloxy group, which may contain fluorine, chlorine, bromine, hydroxyl, amino or ether bond, or —N($R^{401A}$)($R^{401B}$), —NR$^{401C}$—C(=O)—R$^{401D}$ or —NR$^{401C}$—C(=O)—O—R$^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain halogen, hydroxyl, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. $R^{401D}$ is a $C_1$-$C_{16}$ aliphatic hydrocarbyl group, $C_6$-$C_{12}$ aryl group or $C_7$-$C_{15}$ aralkyl group, which may contain halogen, hydroxyl, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. The aliphatic hydrocarbyl group may be saturated or unsaturated and straight, branched or cyclic. The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched or cyclic. Groups $R^{401}$ may be the same or different when p and/or r is 2 or more. Of these, $R^{401}$ is preferably hydroxyl, —NR$^{401C}$—C(=O)—R$^{401D}$, —NR$^{401C}$—C(=O)—O—R$^{401D}$, fluorine, chlorine, methyl or methoxy.

In formulae (3-1) and (3-2), $Rf^{11}$ to $Rf^{14}$ are each independently hydrogen, fluorine or trifluoromethyl, at least one of $Rf^{11}$ to $Rf^{14}$ is fluorine or trifluoromethyl, or $Rf^{11}$ and $Rf^{12}$, taken together, may form a carbonyl group. Preferably, both $Rf^{13}$ and $Rf^{14}$ are fluorine.

$R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof include those exemplified above for the hydrocarbyl groups $R^{a1}$ to $R^{a5}$ in formulae (Aa) and (Ab). In these groups, some or all of the hydrogen atoms may be substituted by hydroxyl, carboxyl, halogen, cyano, nitro, mercapto, sultone, sulfone, or sulfonium salt-containing moieties, and some carbon may be replaced by an ether bond, ester bond, carbonyl moiety, amide bond, carbonate moiety or sulfonic acid ester bond. $R^{402}$ and $R^{403}$ may bond together to form a ring with the sulfur atom to which they are attached. Exemplary rings are the same as described above for the ring that $R^{a1}$ and $R^{a2}$ in formula (Aa), taken together, form with the sulfur atom to which they are attached.

Examples of the cation in the sulfonium salt having formula (3-1) include those exemplified above as the sulfonium cation having formula (Aa). Examples of the cation in the iodonium salt having formula (3-2) include those exemplified above as the iodonium cation having formula (Ab).

Examples of the anion in the onium salts having formulae (3-1) and (3-2) are shown below, but not limited thereto. Herein $X^{BI}$ is as defined above.

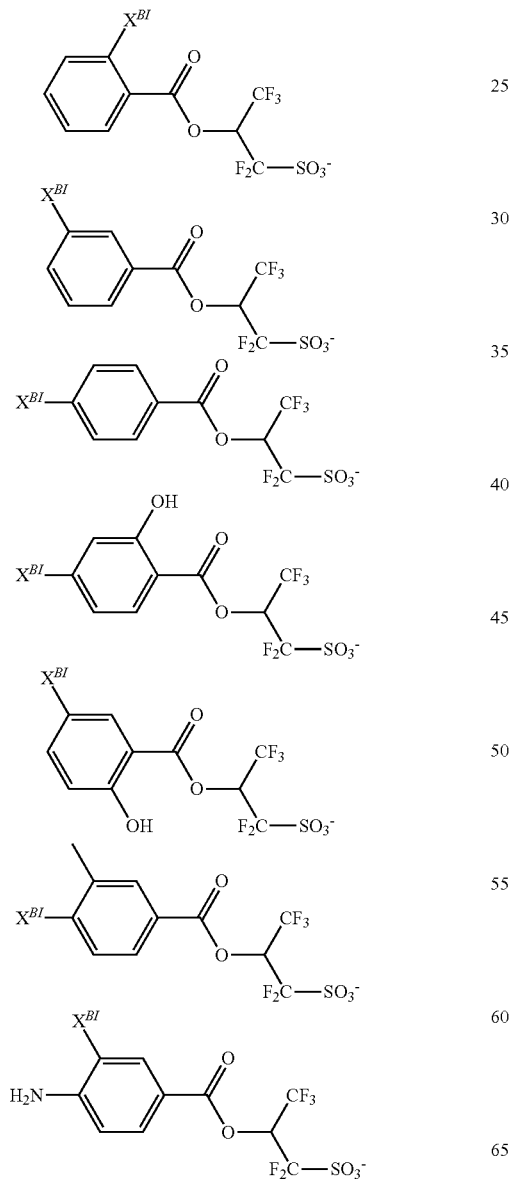
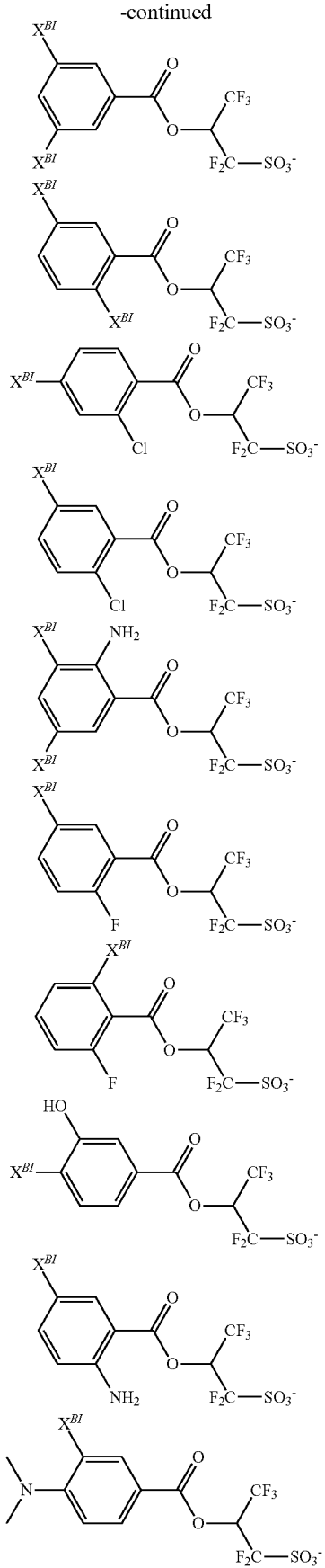

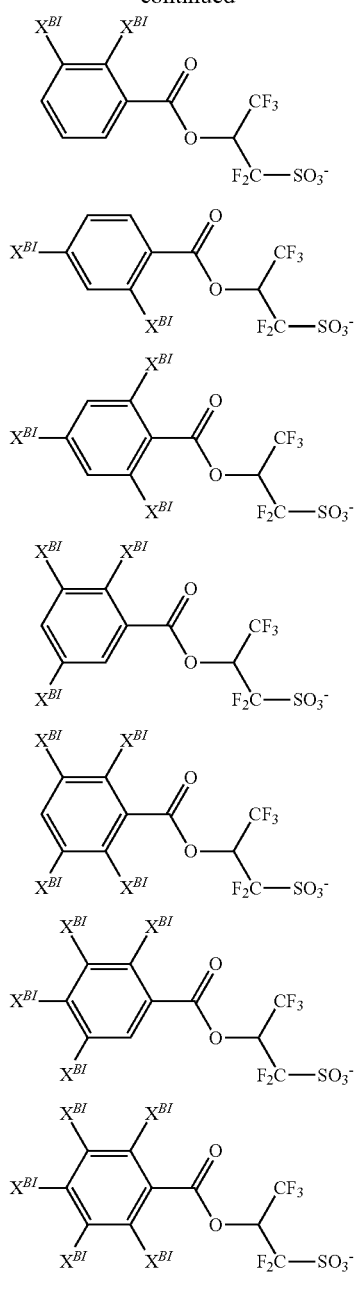
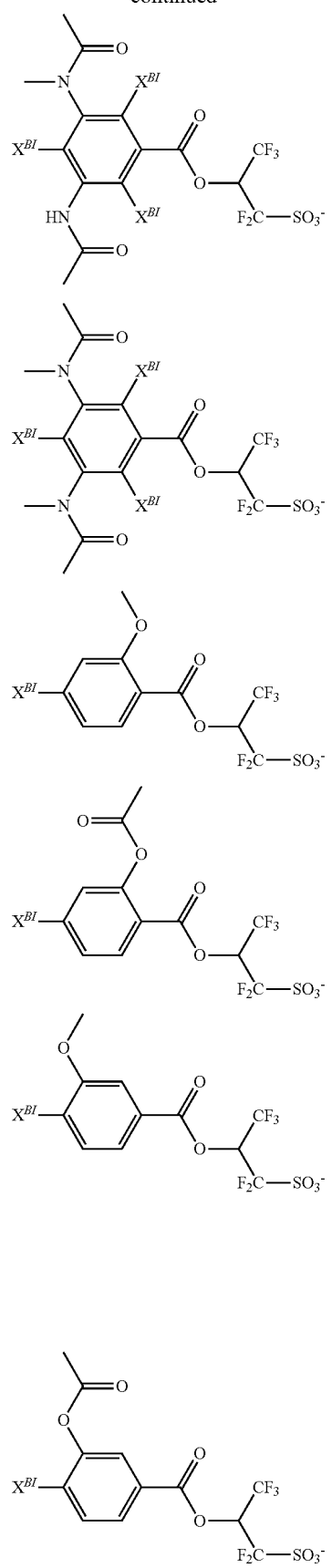

-continued
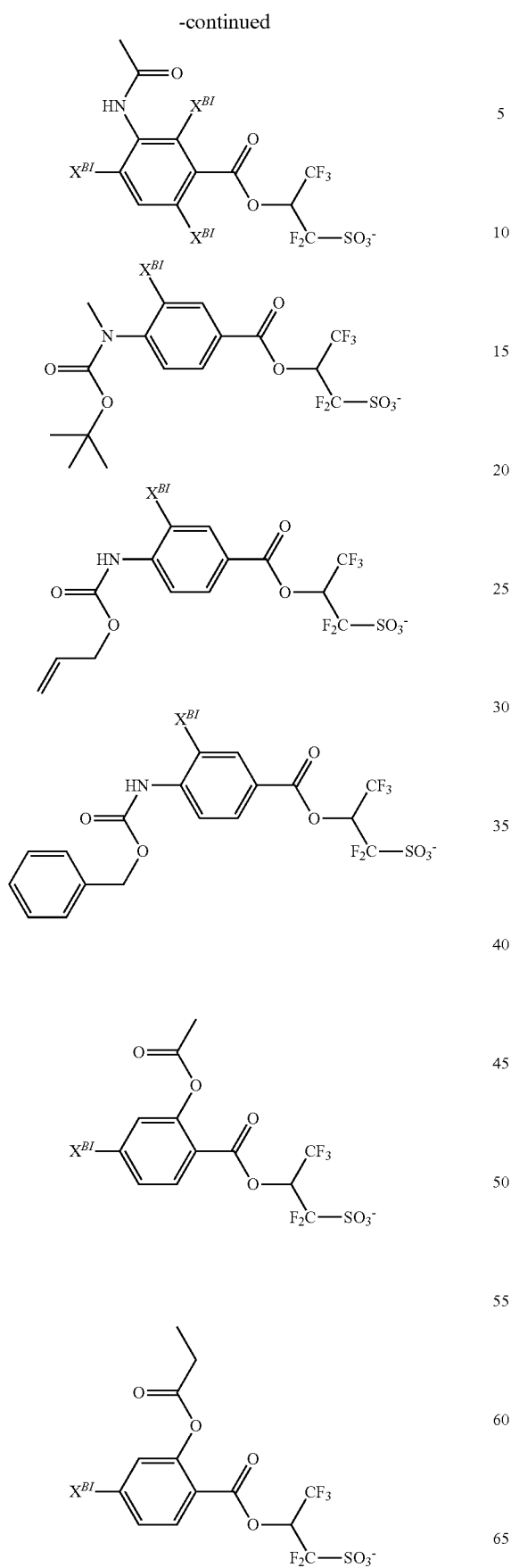
-continued
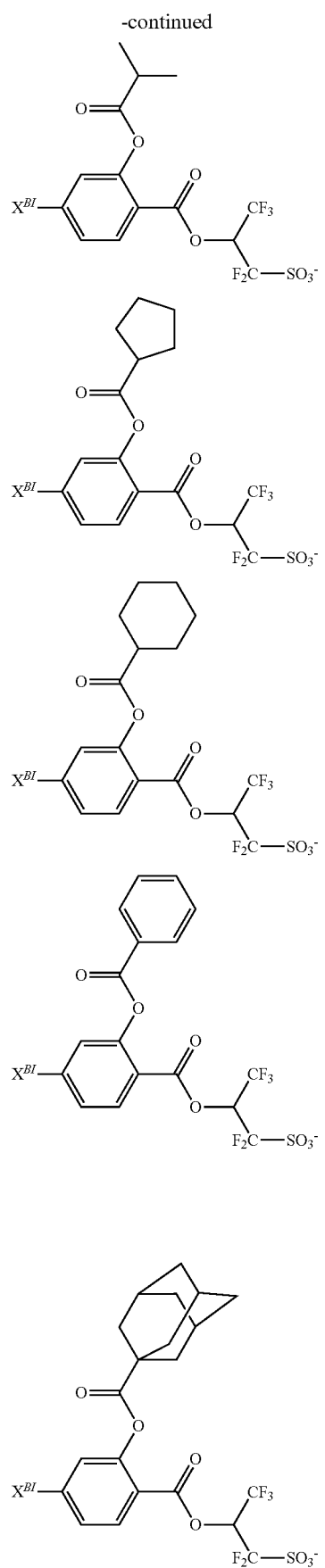

161
-continued
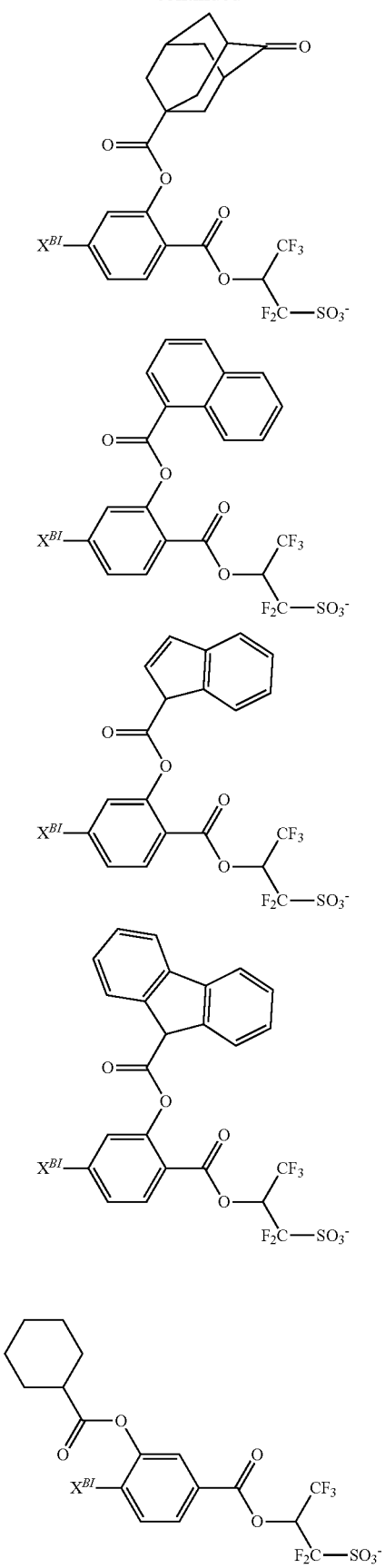
162
-continued
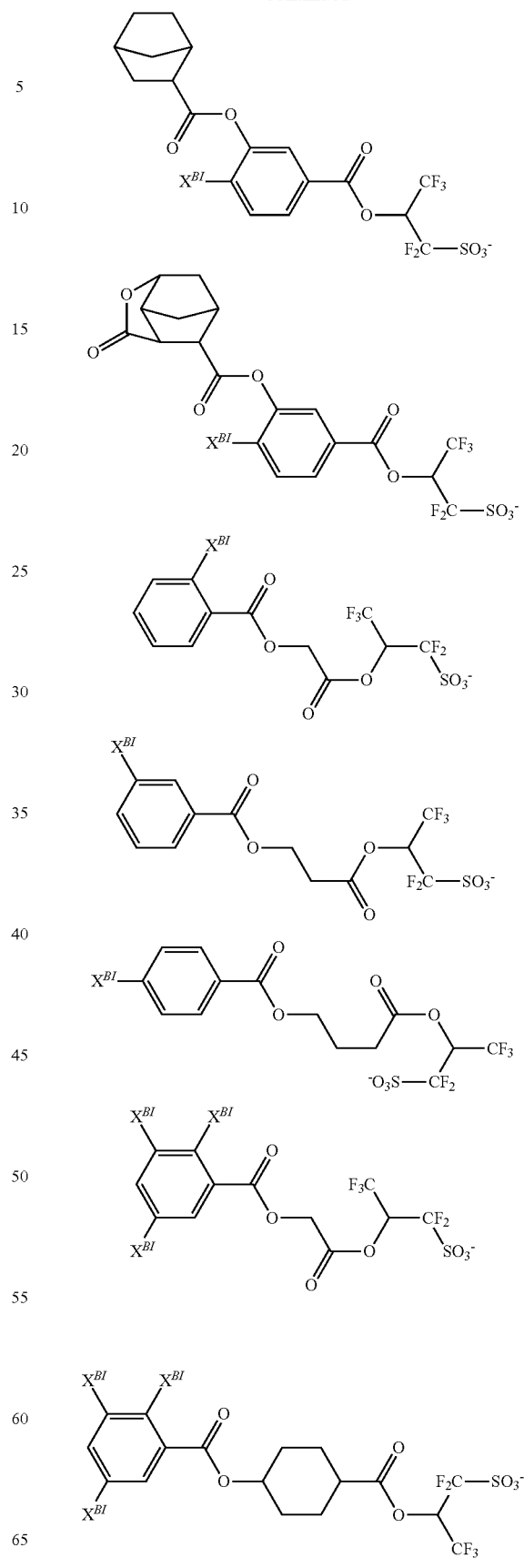

-continued
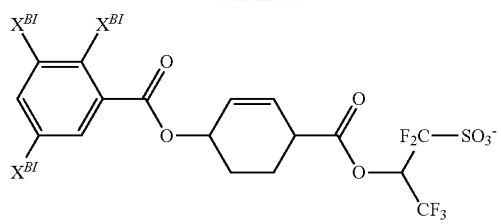
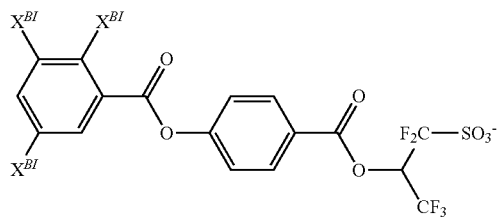
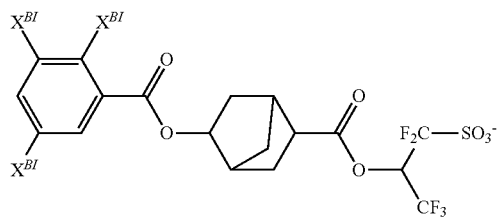
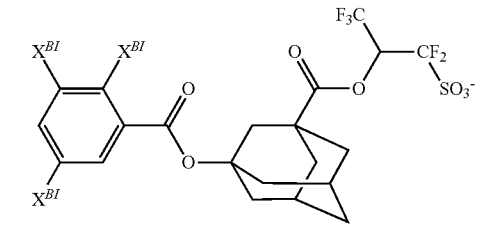
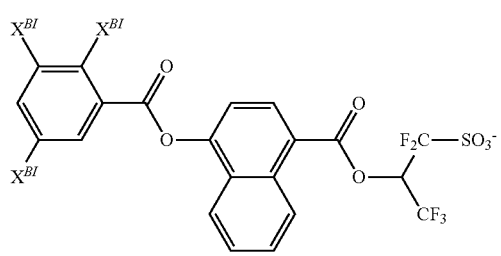
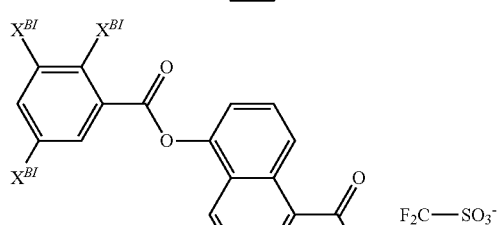
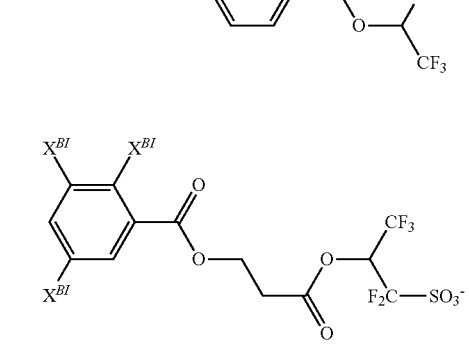
-continued
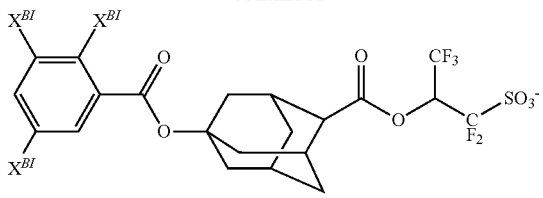
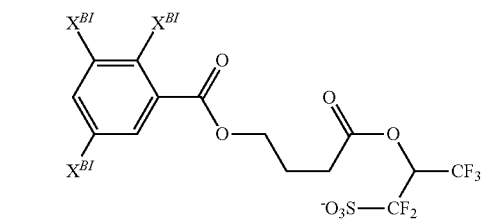
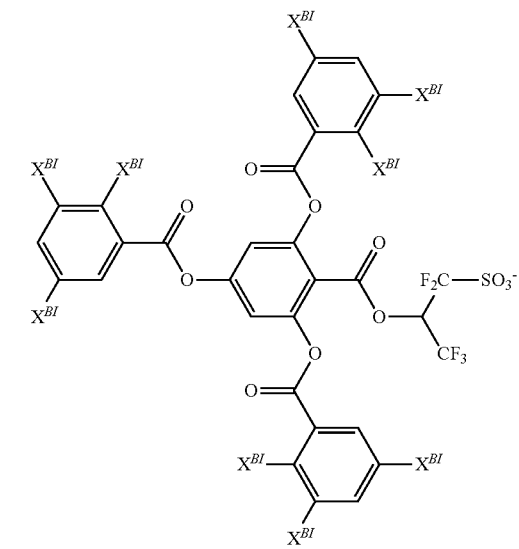
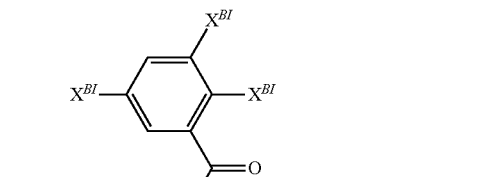
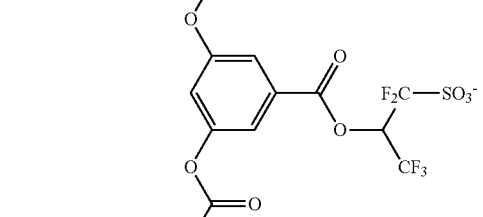
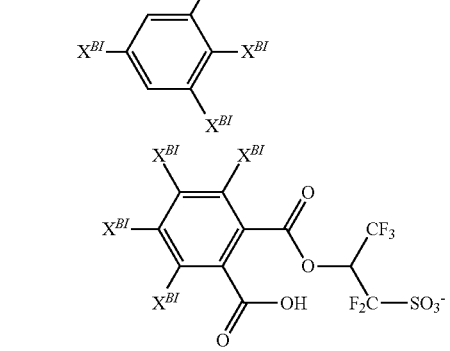

-continued
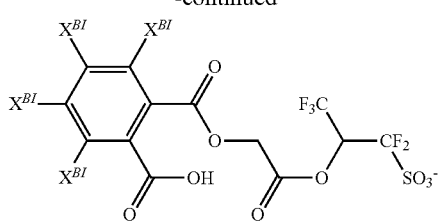
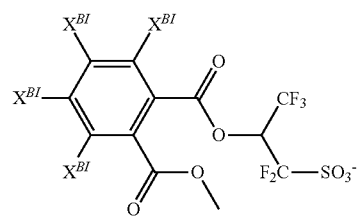
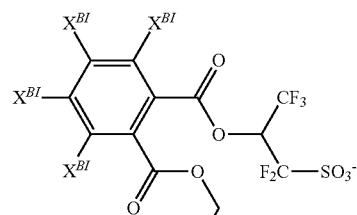
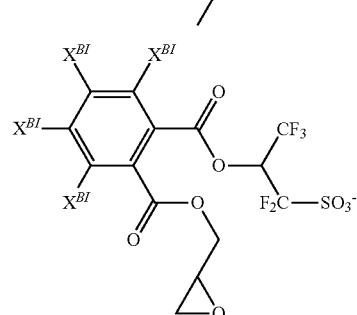
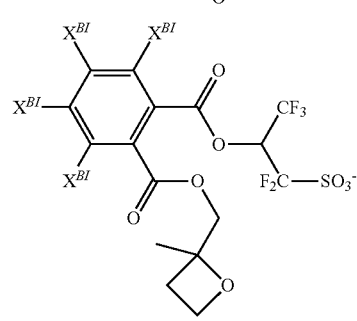
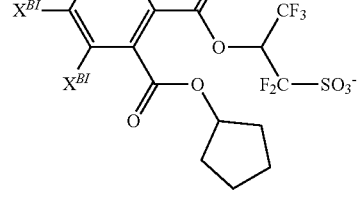
-continued
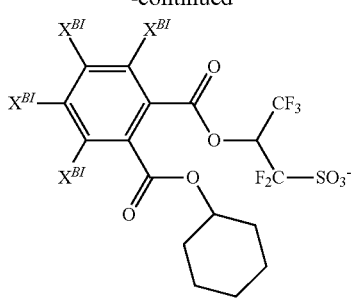
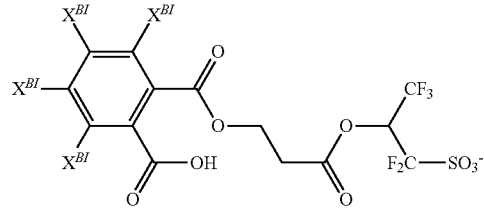
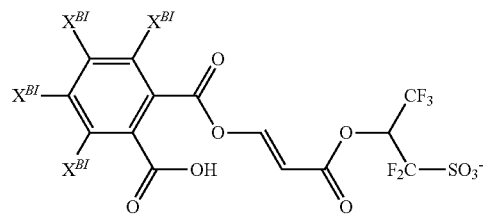
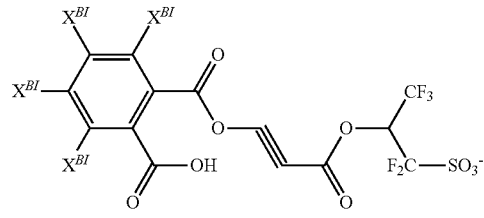
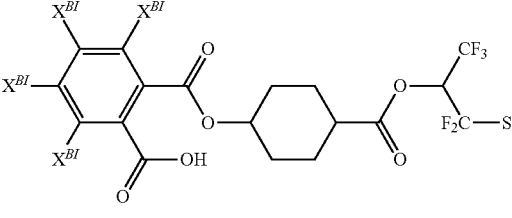
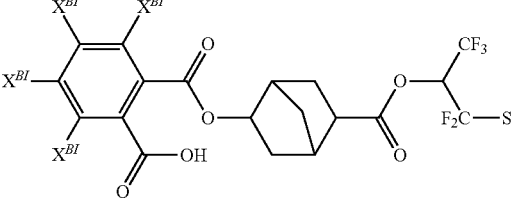
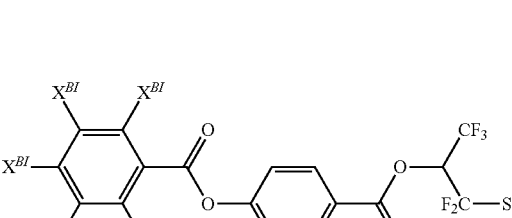

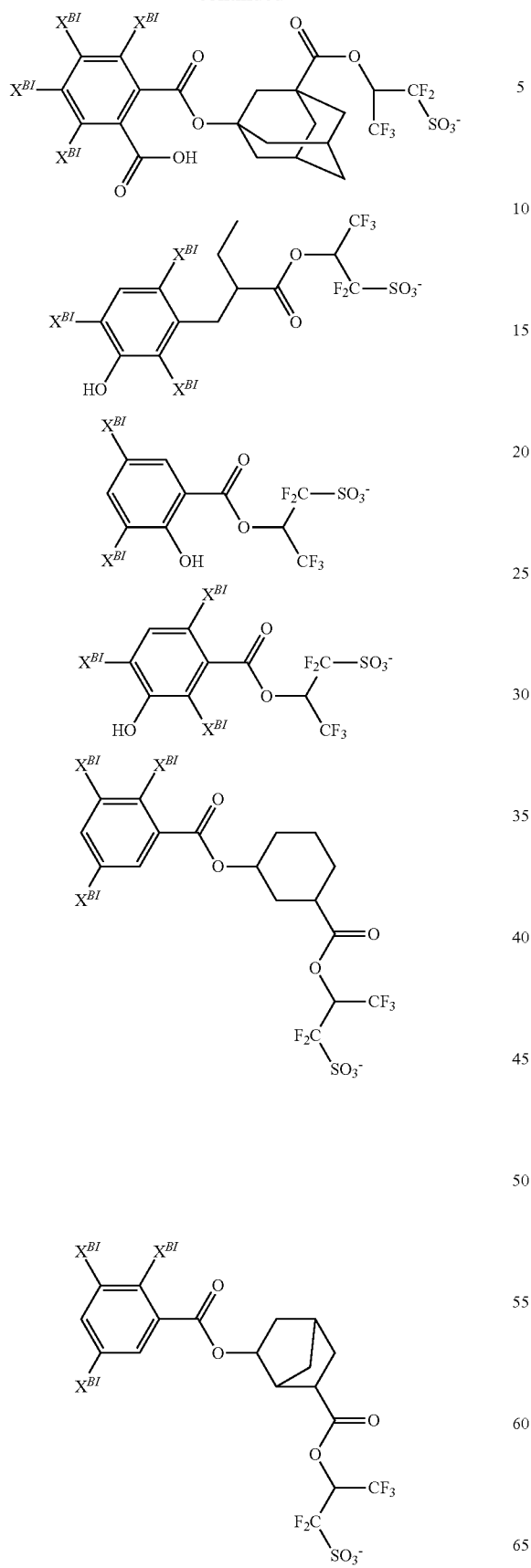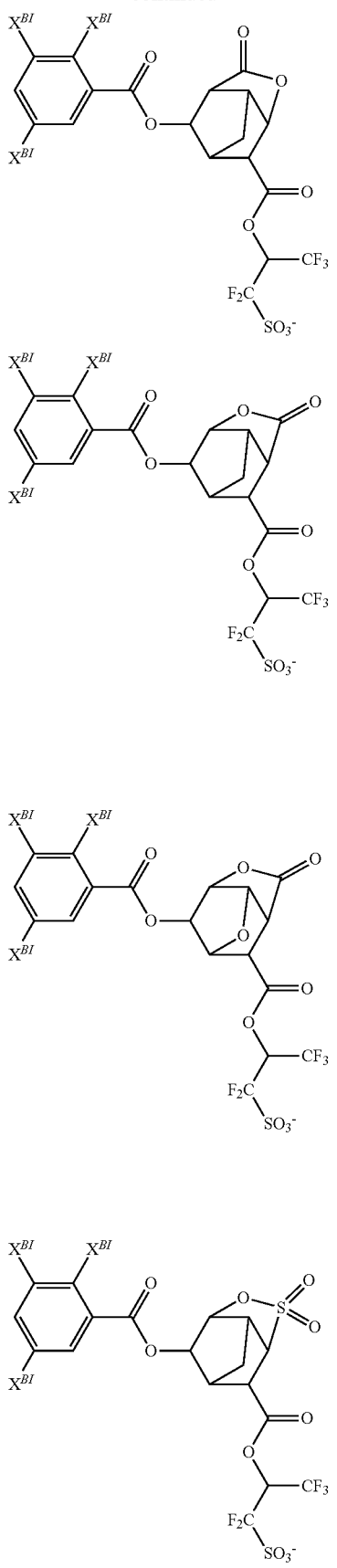

-continued
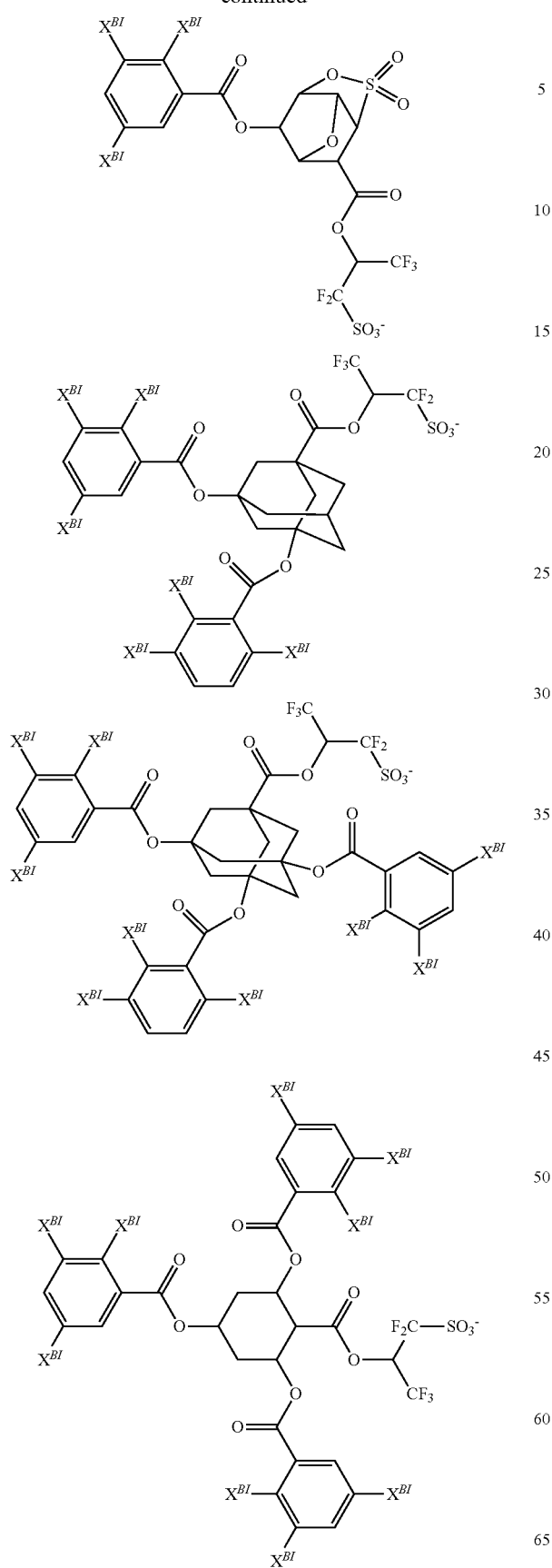
-continued
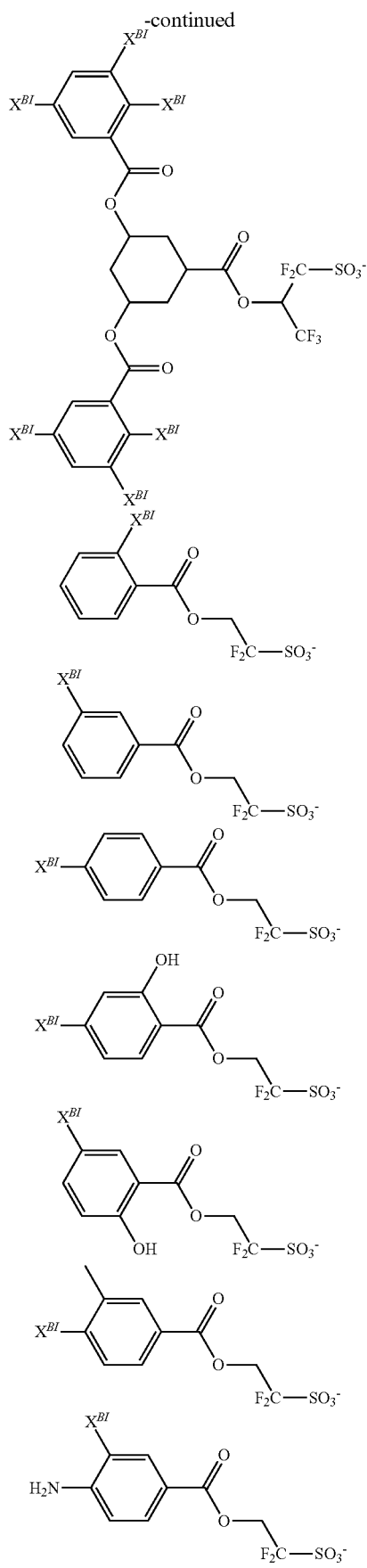

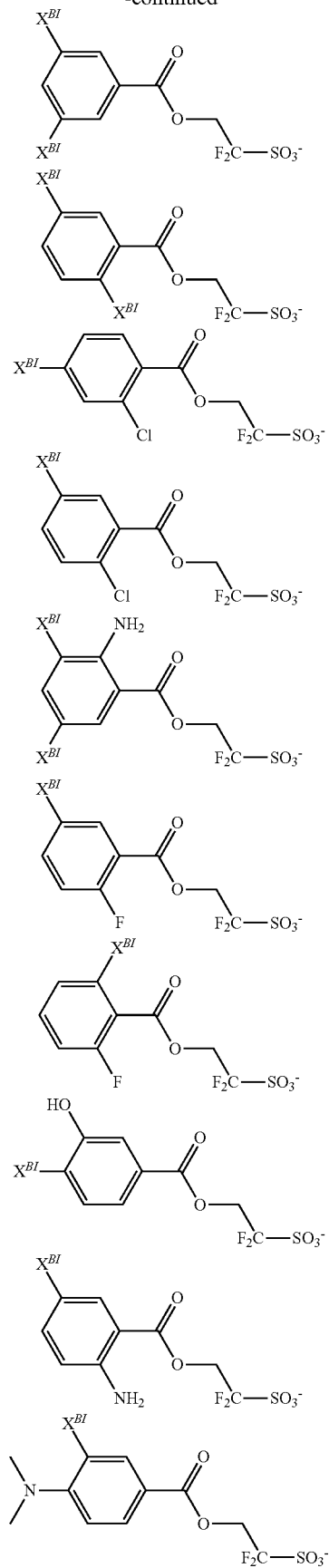
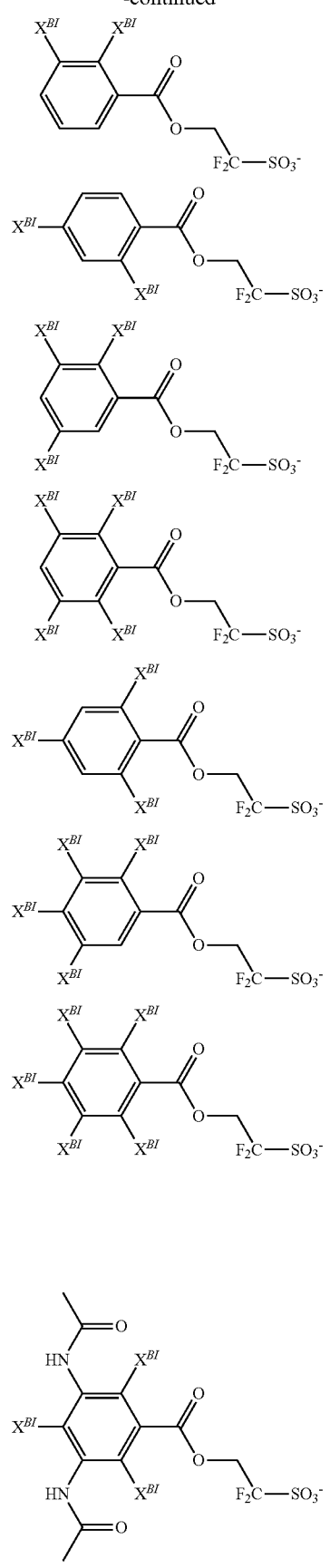

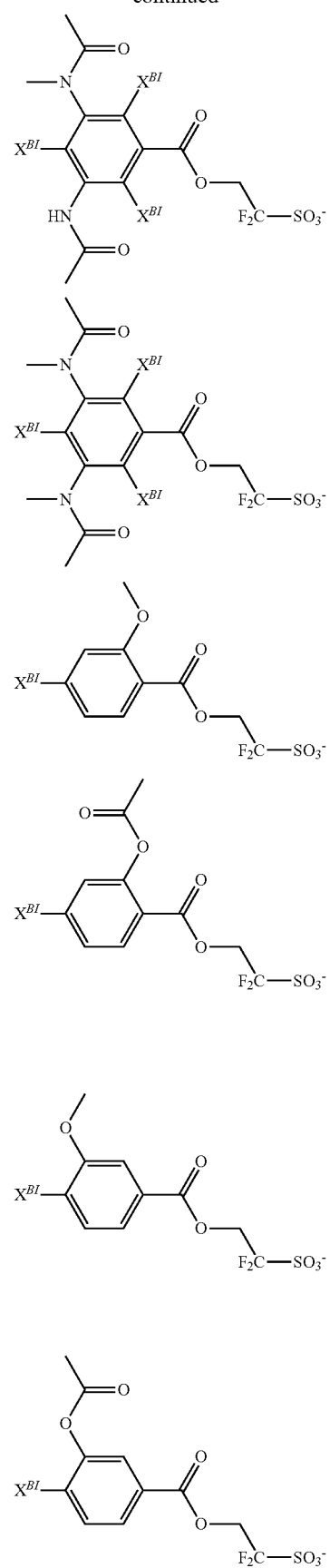
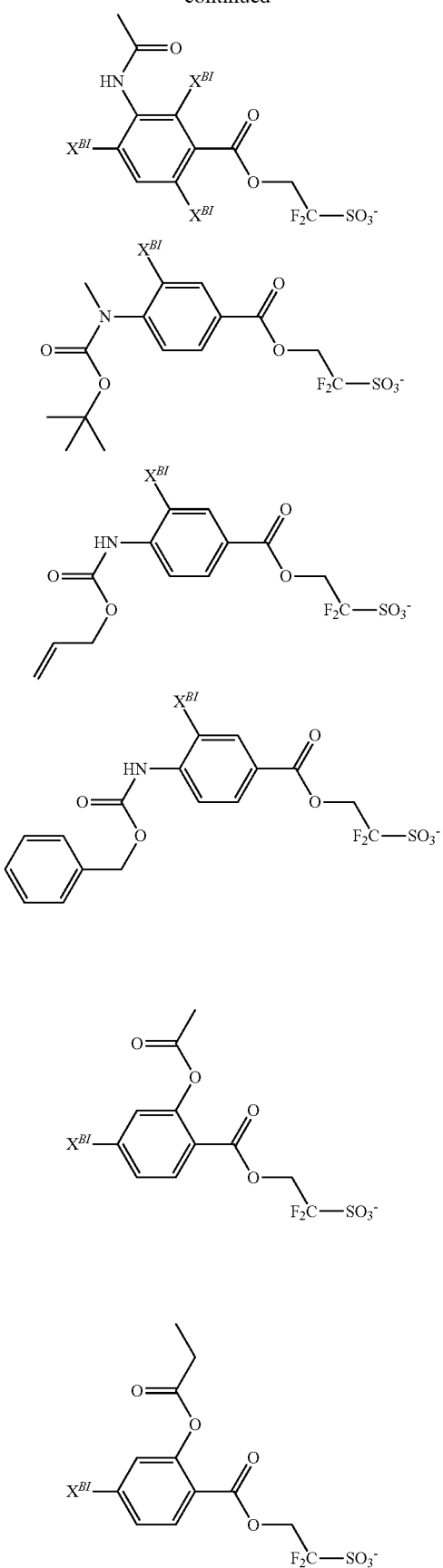

175
-continued
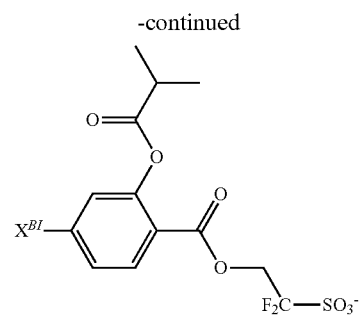
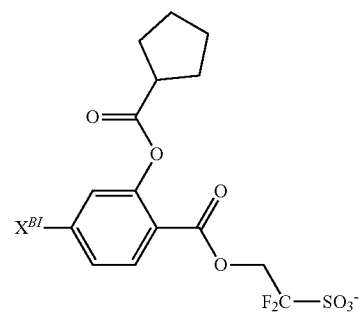
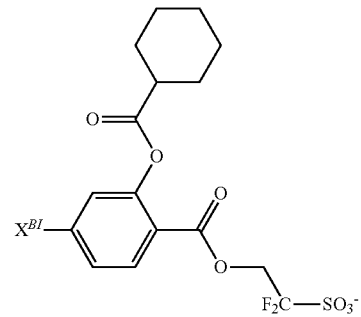
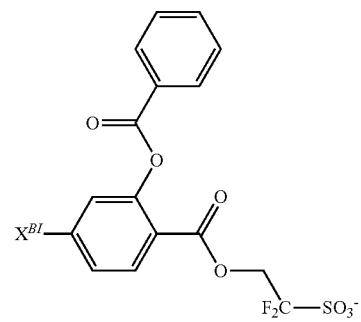
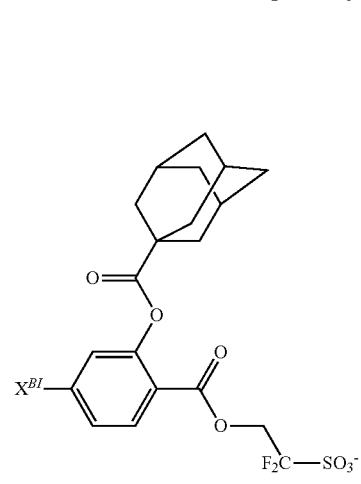
176
-continued
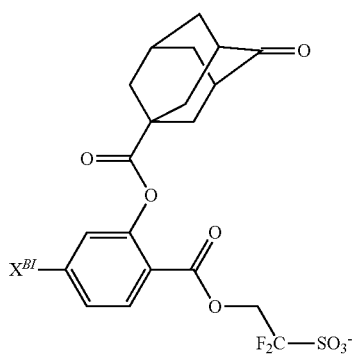
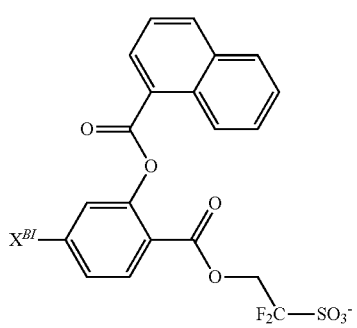
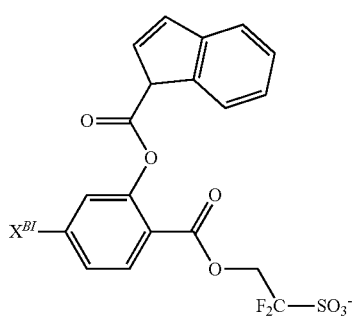
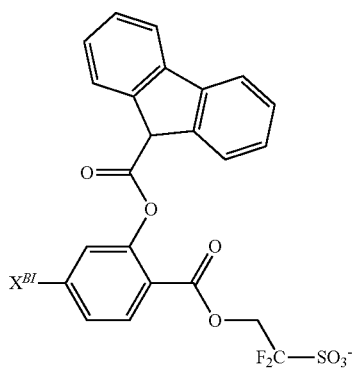
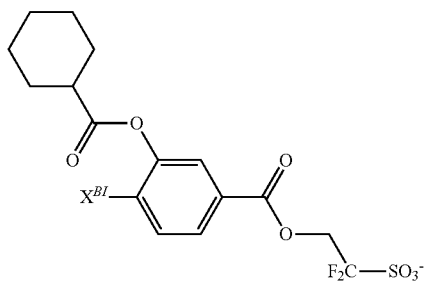

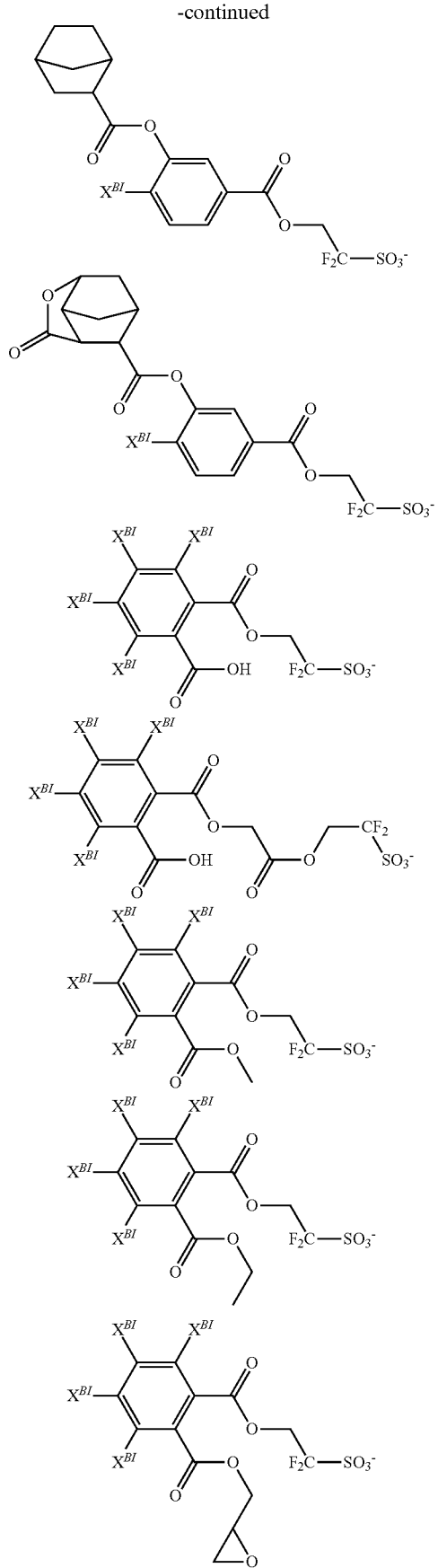
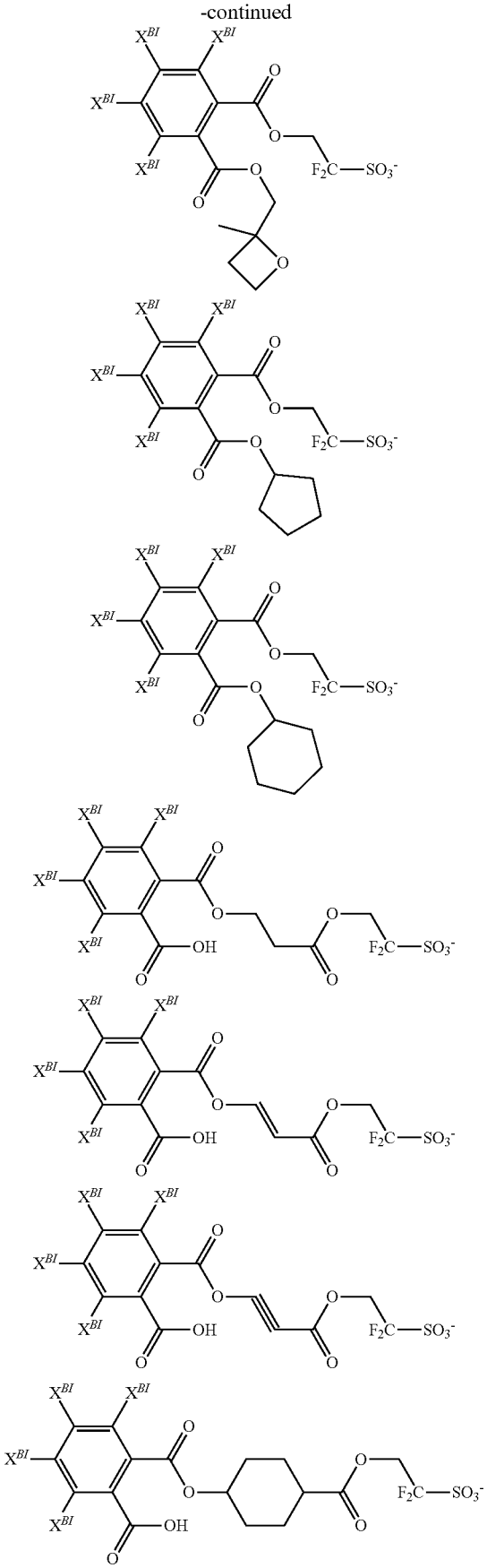

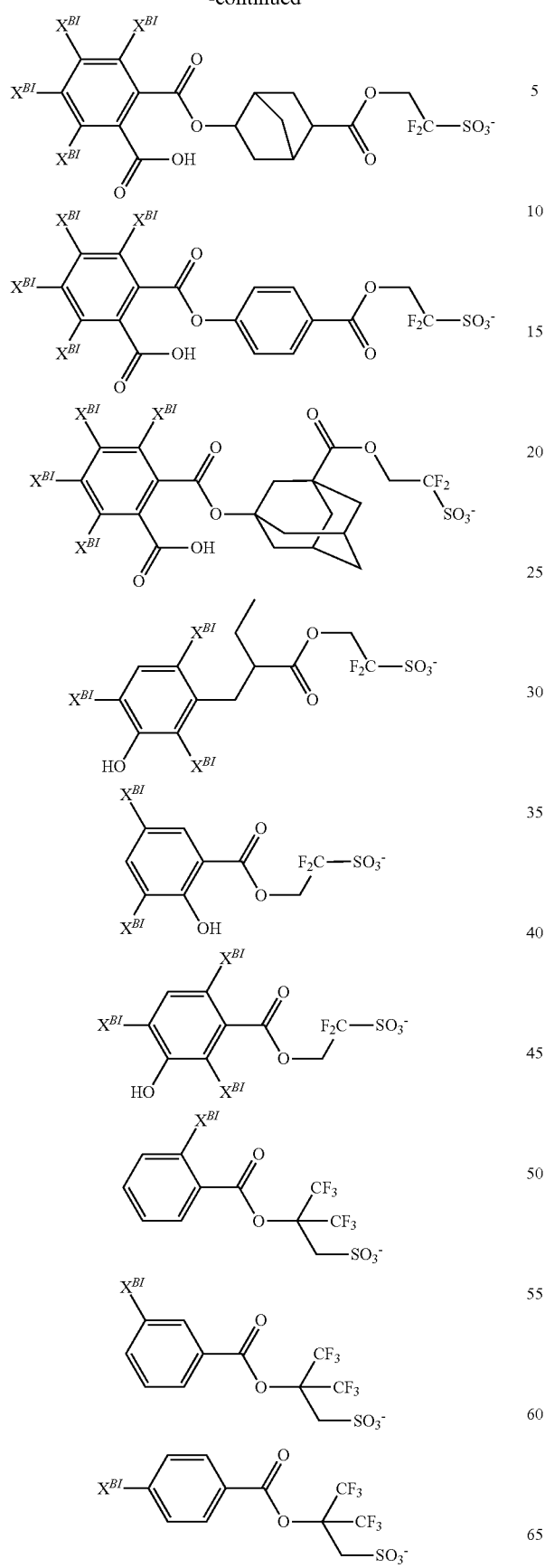
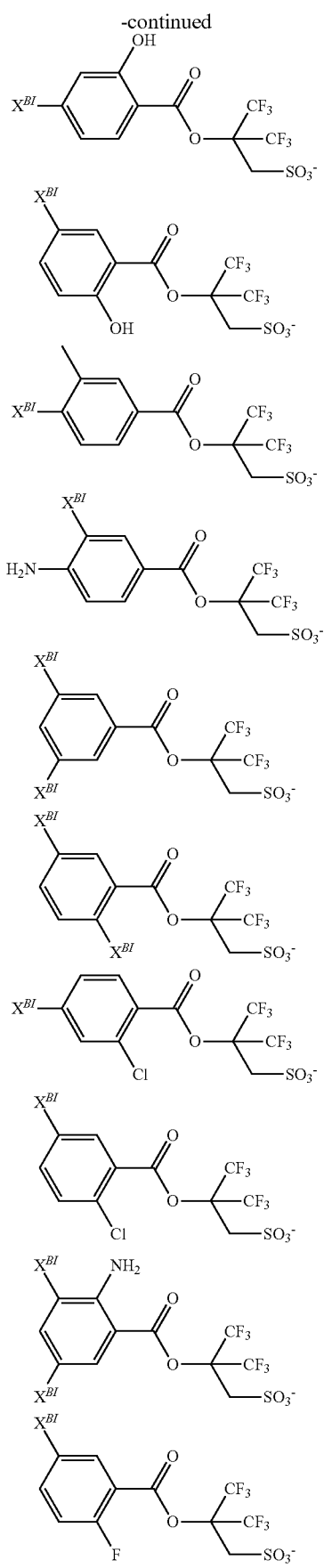

-continued
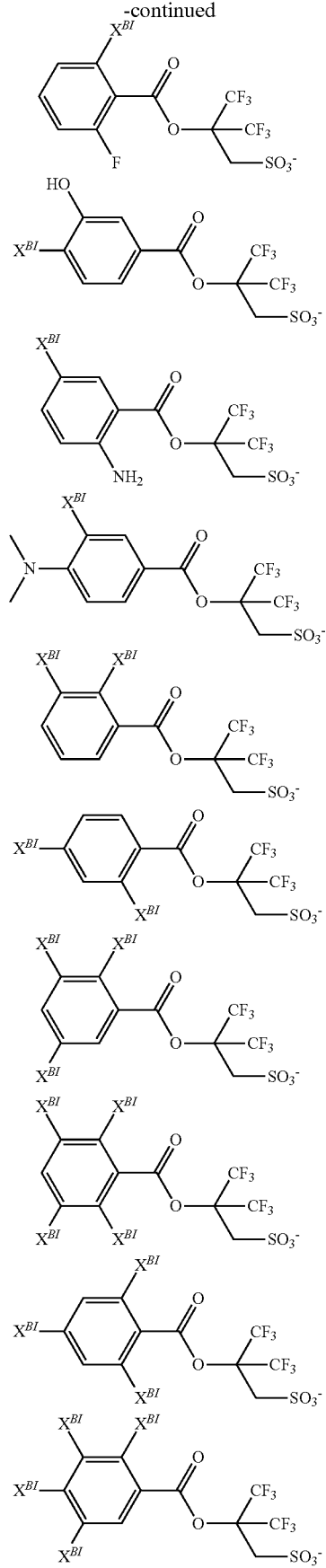
-continued
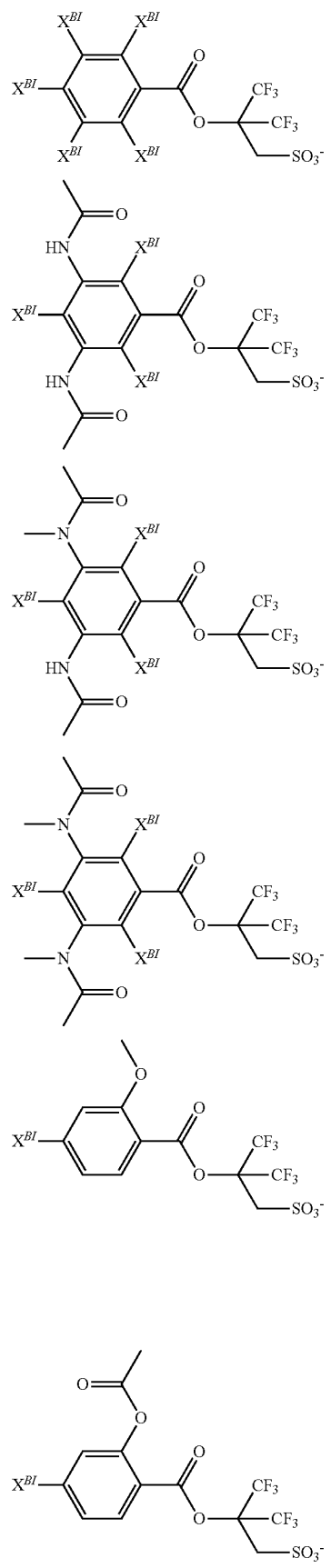

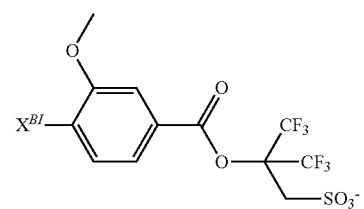
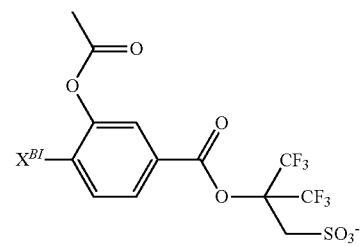
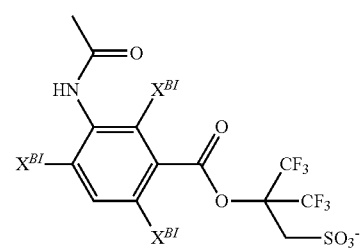
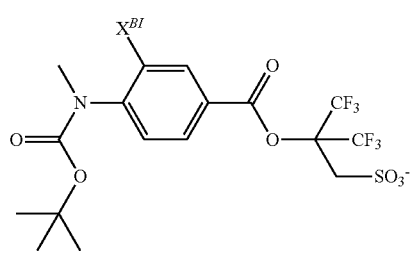
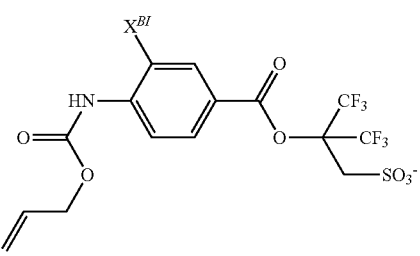
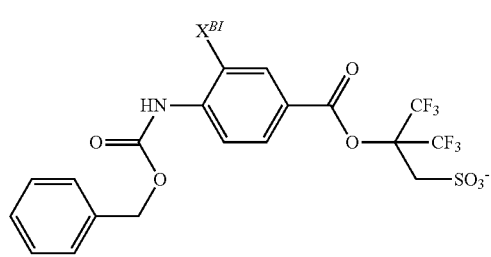
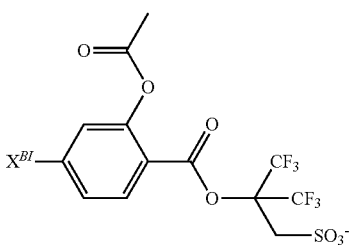
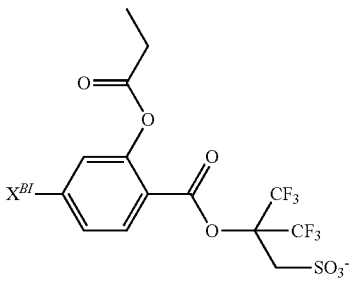
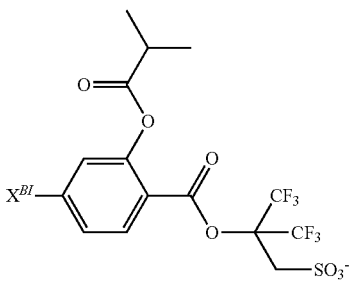
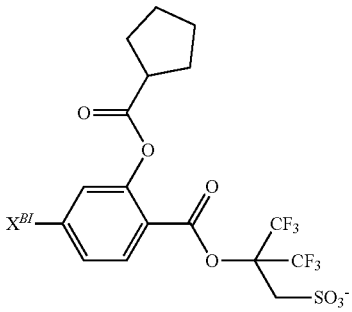
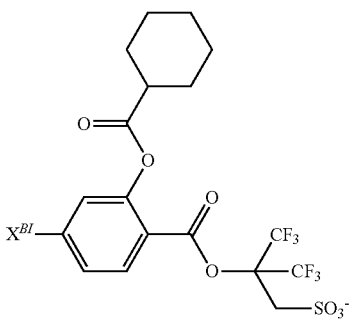

-continued
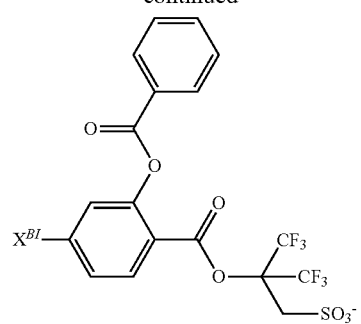
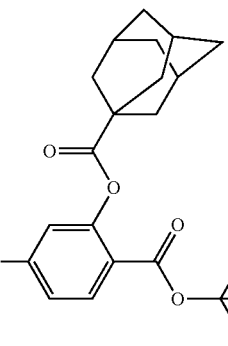
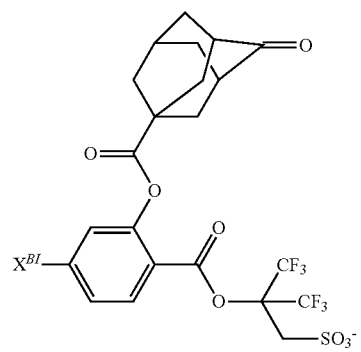
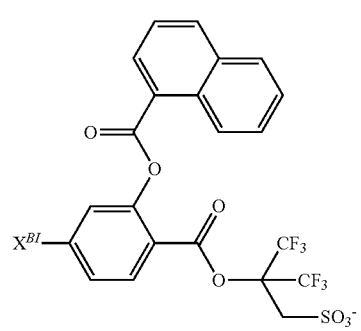
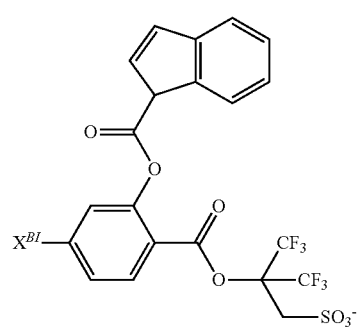
-continued
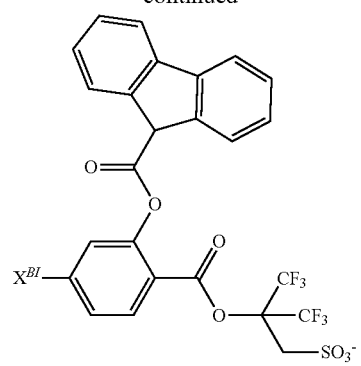
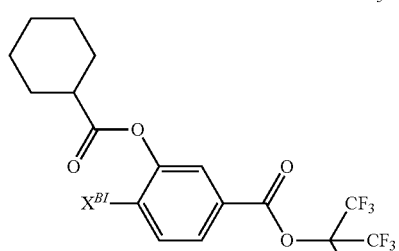
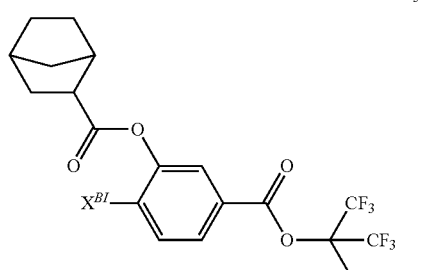
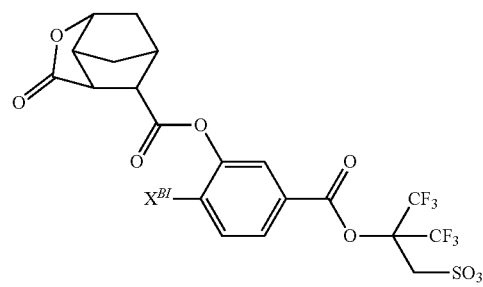
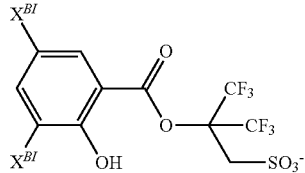
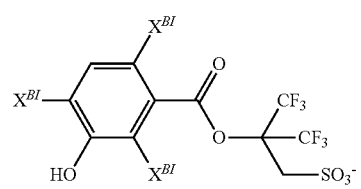

187
-continued
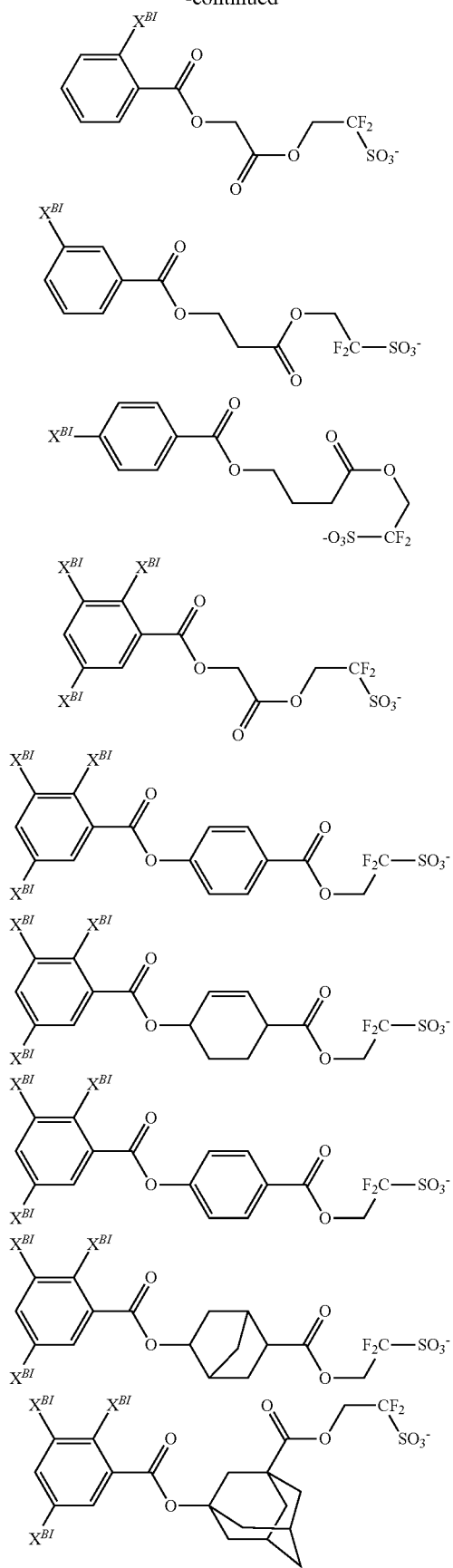
188
-continued
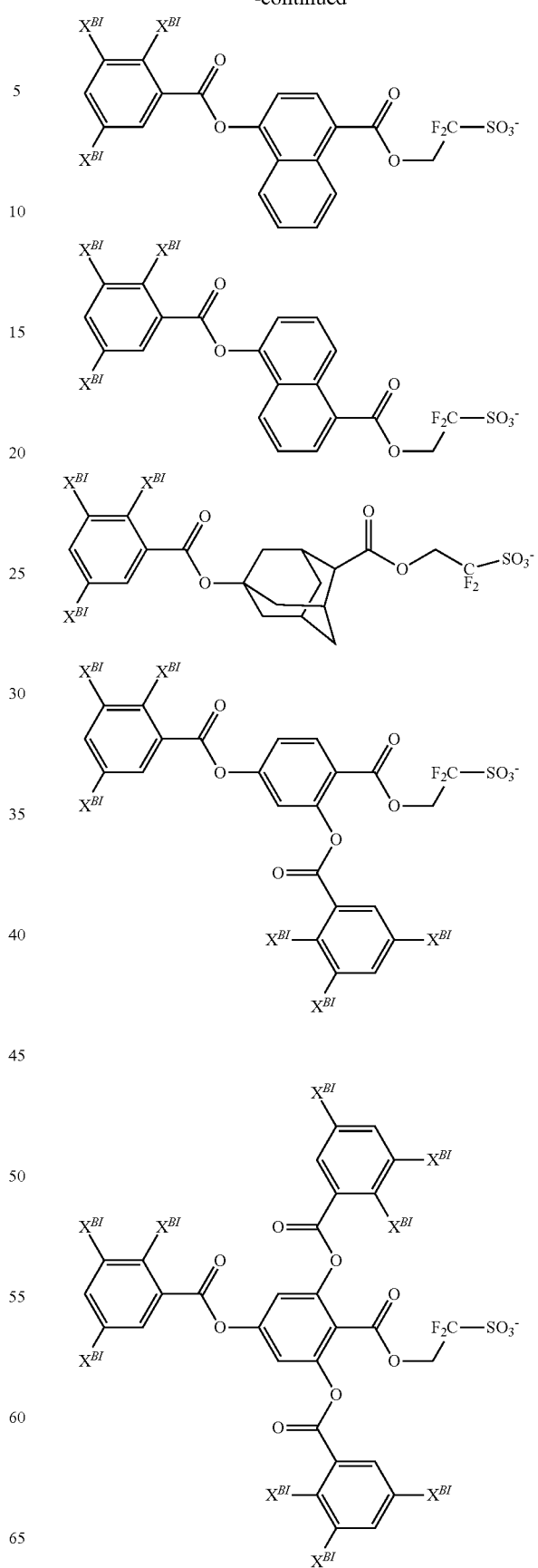

189
-continued
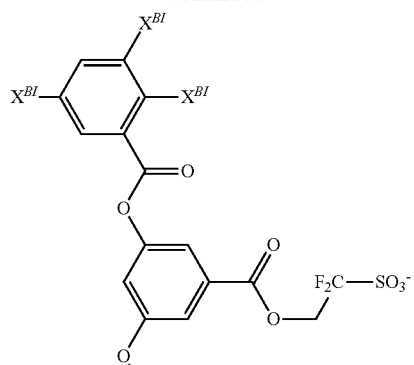
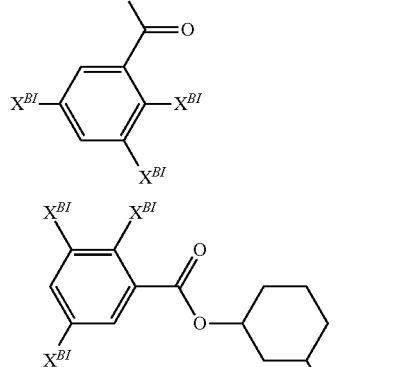
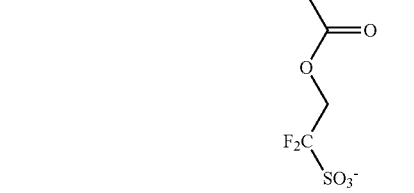
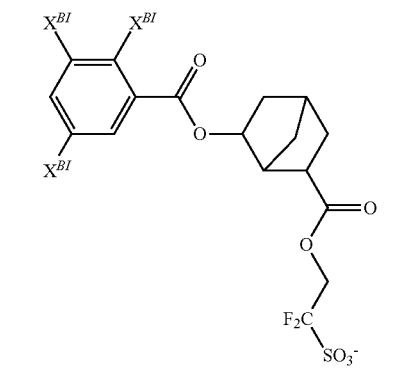
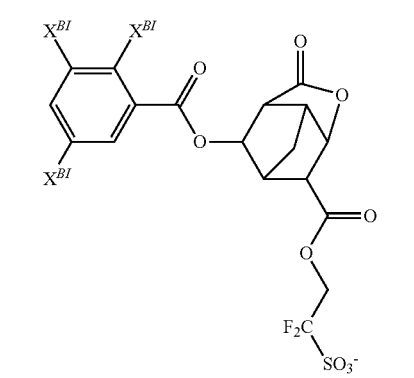
190
-continued
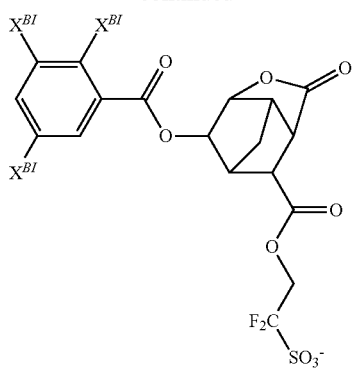
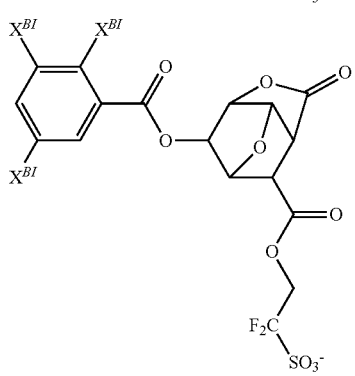
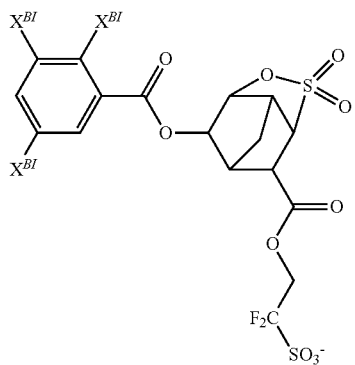
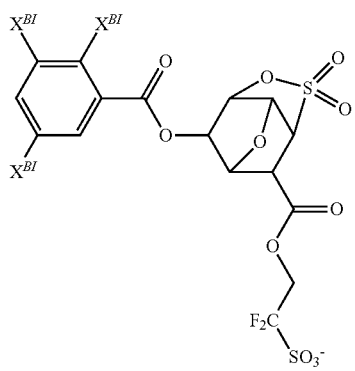

191
-continued
192
-continued
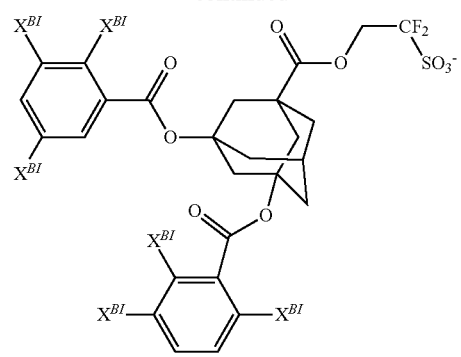
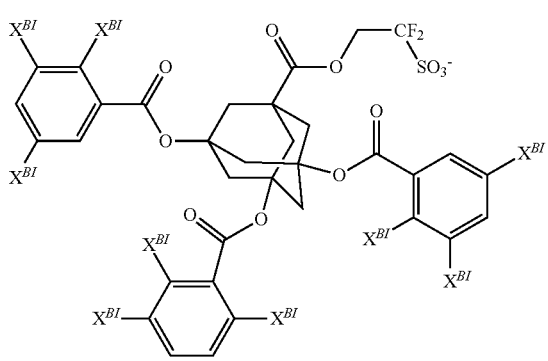
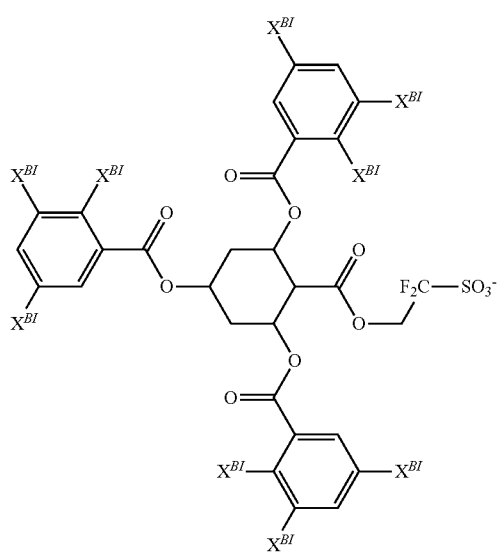
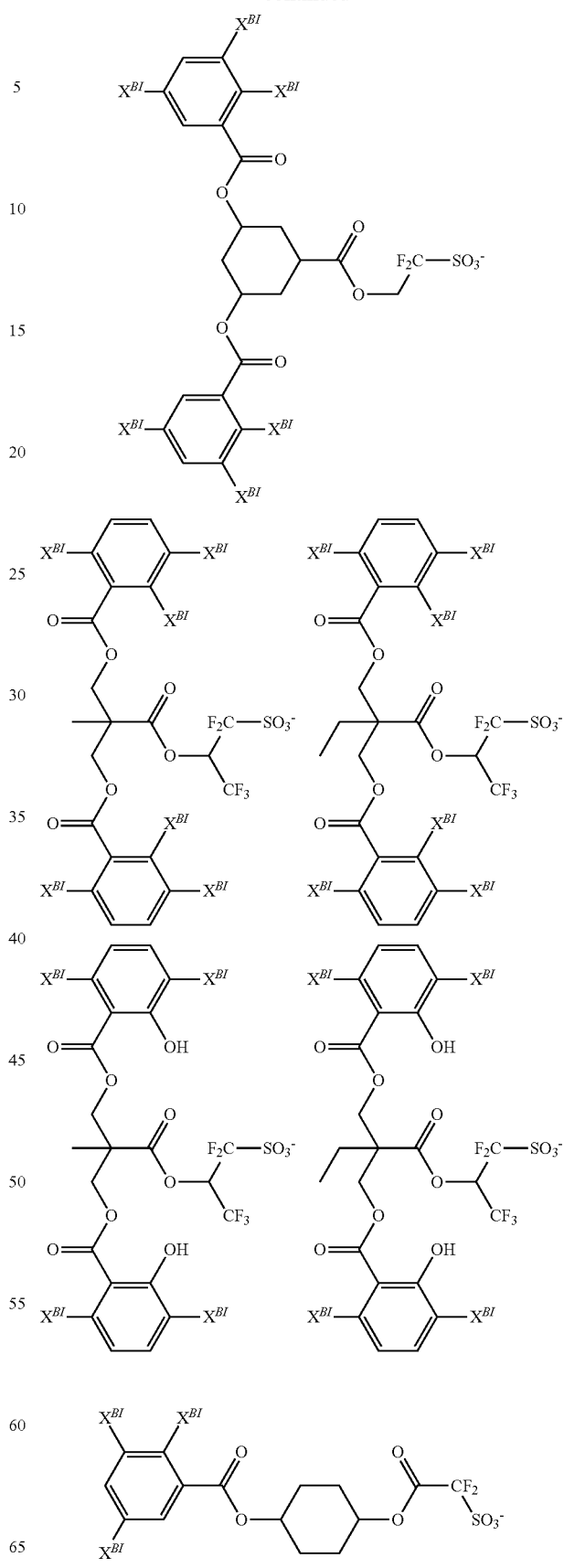

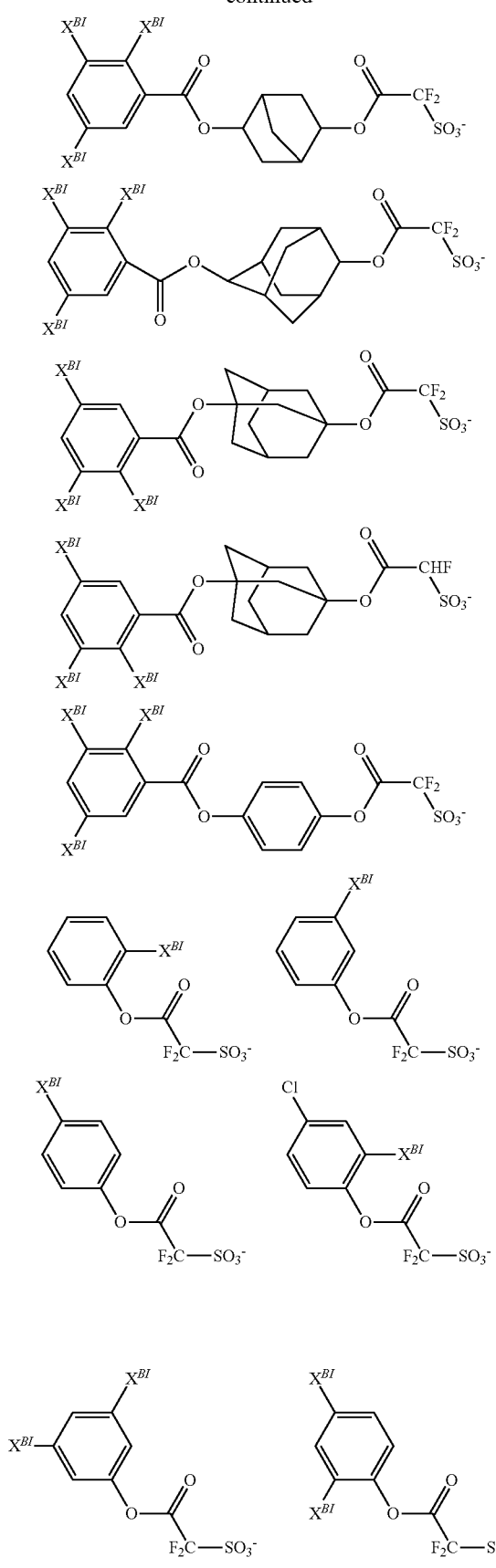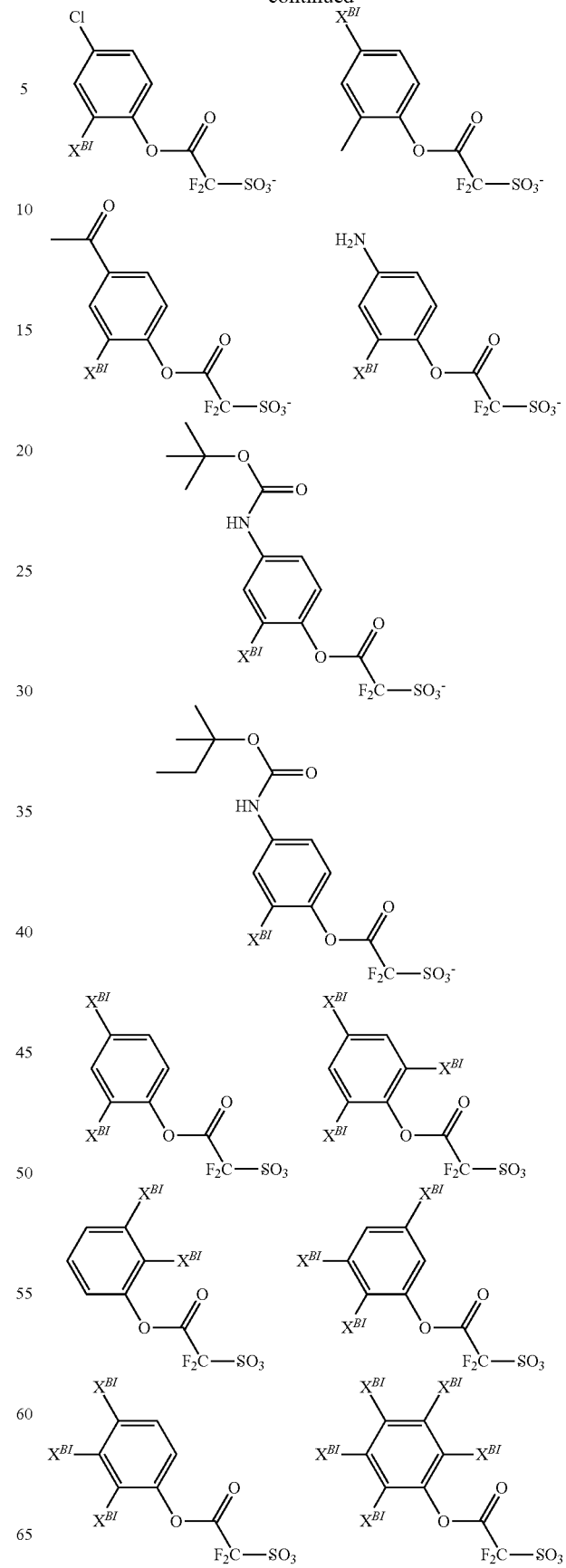

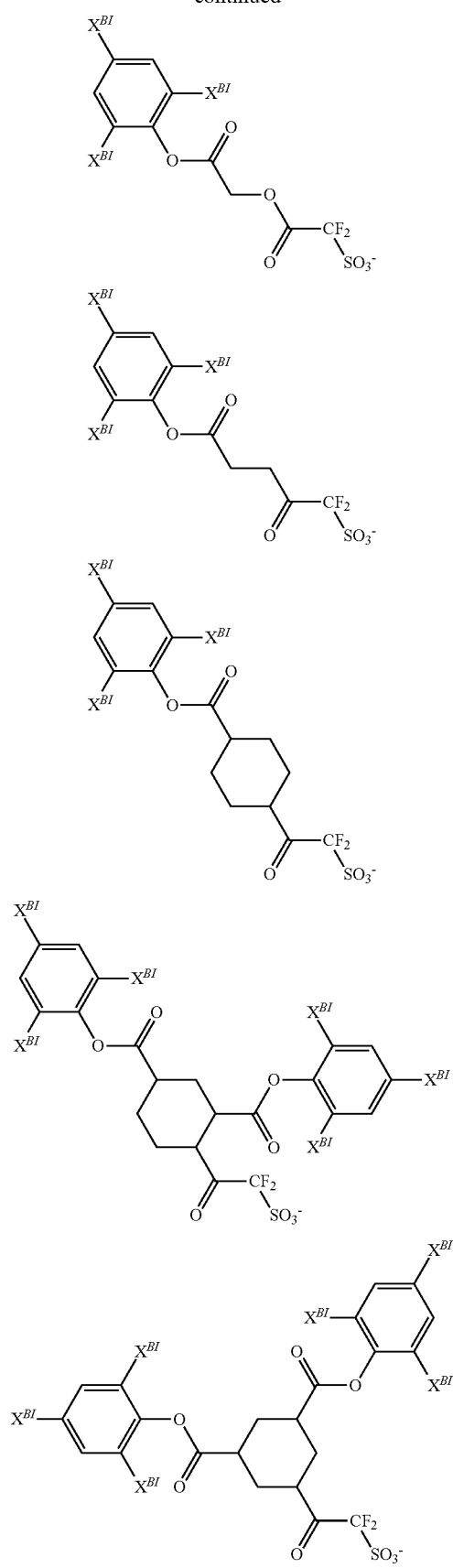
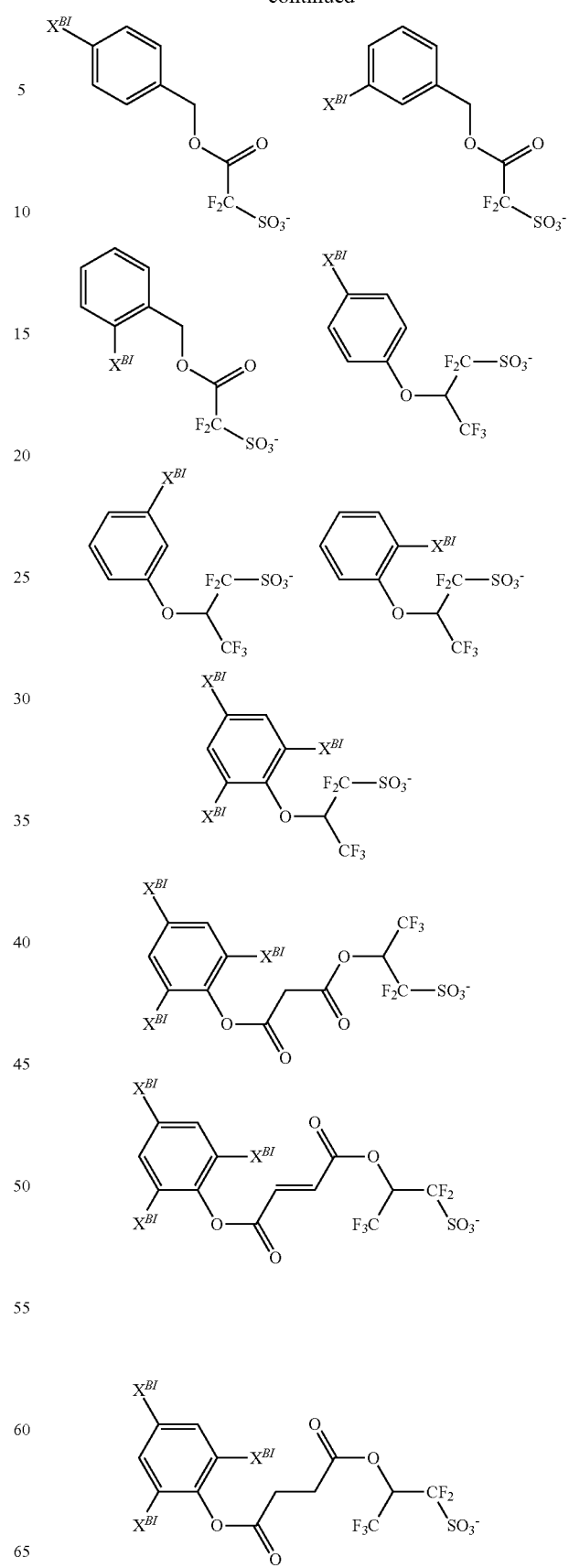

197
-continued
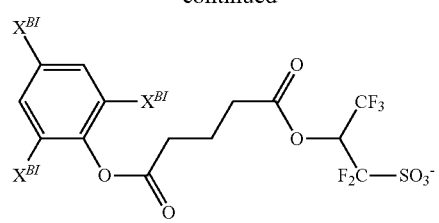
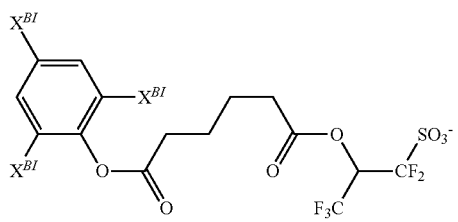
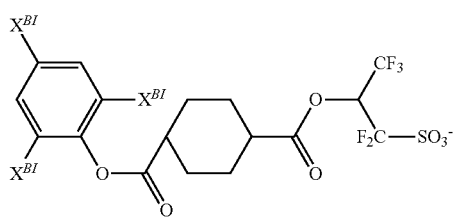
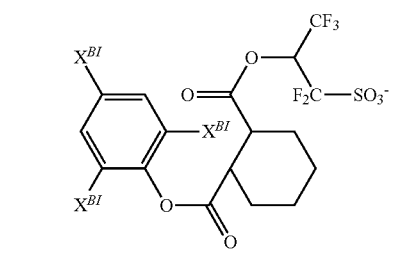
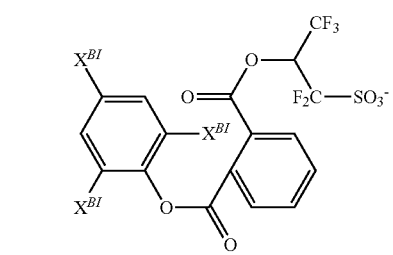
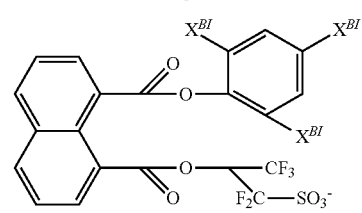
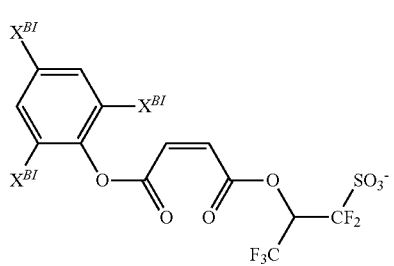
198
-continued
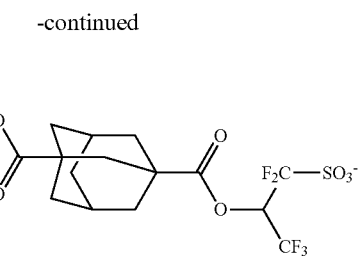
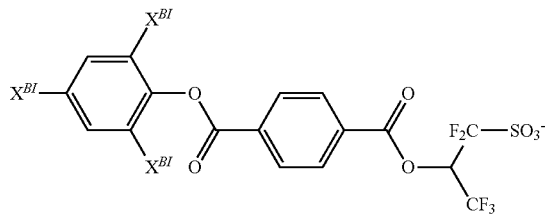
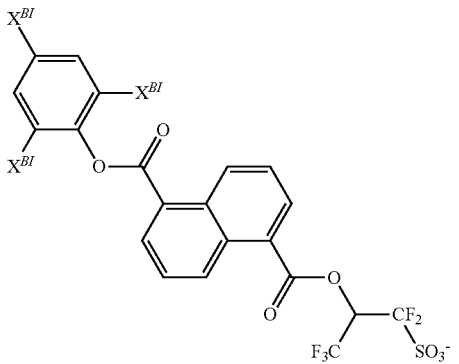
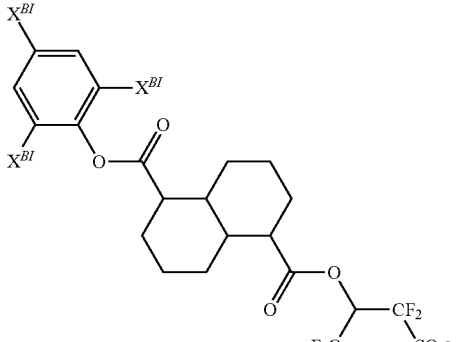
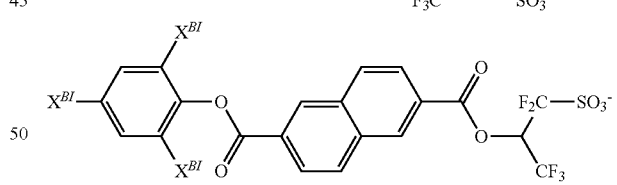
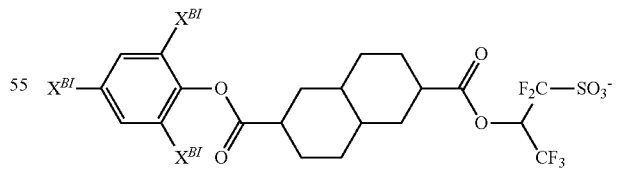
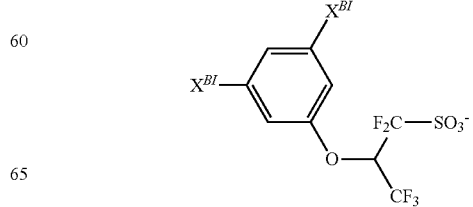

-continued
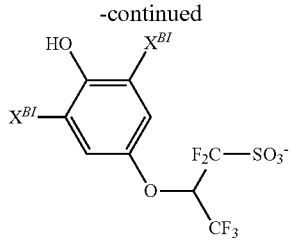
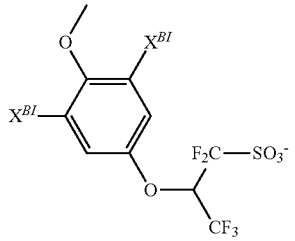
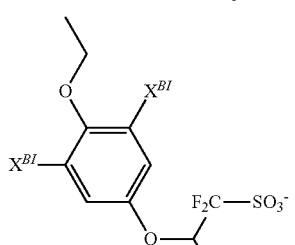
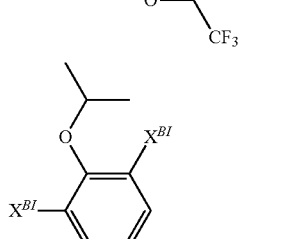
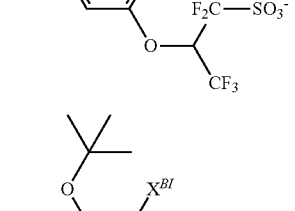
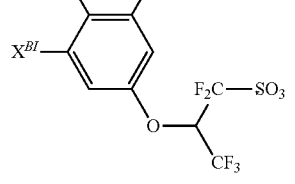
-continued
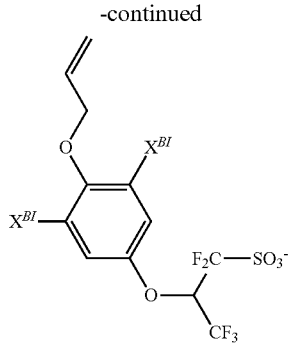
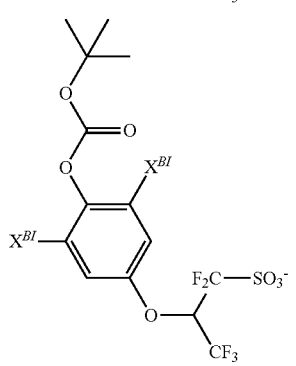
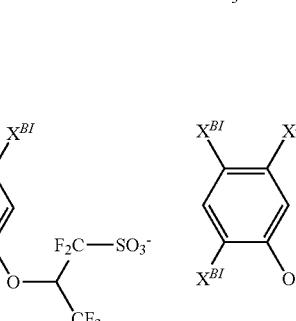
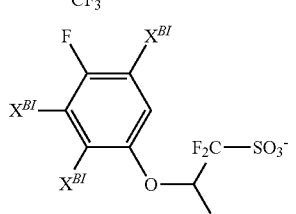
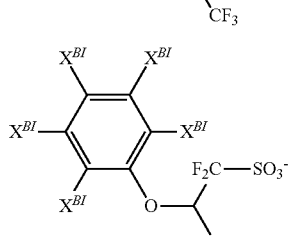
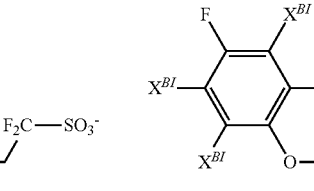

201
-continued
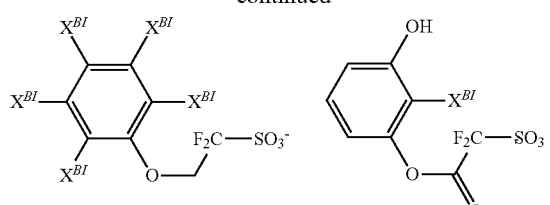
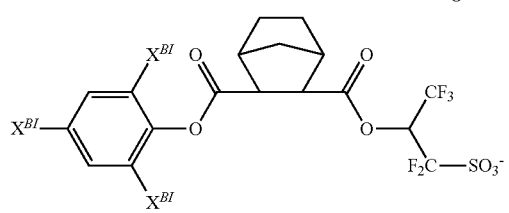
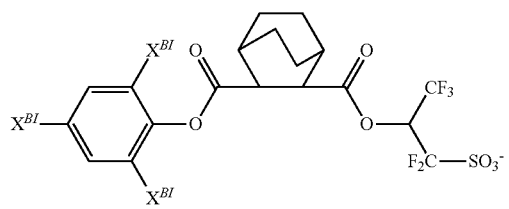
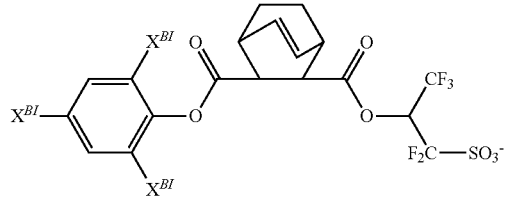
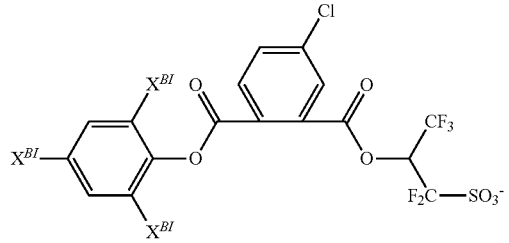
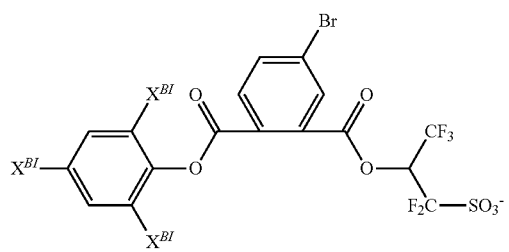
202
-continued
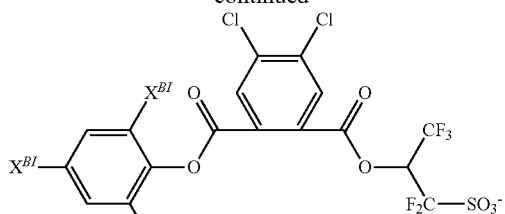
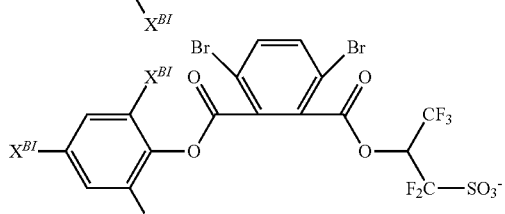
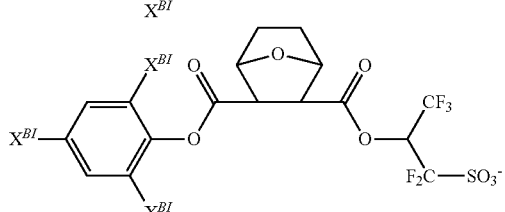
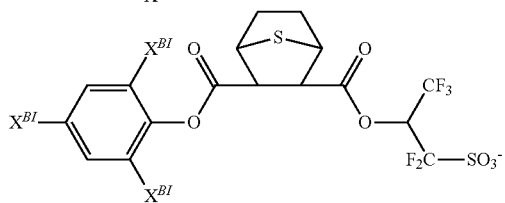
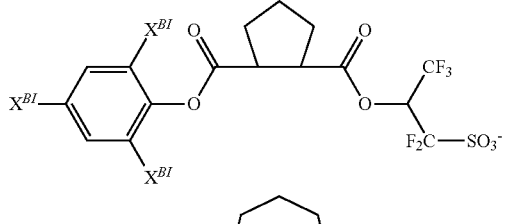
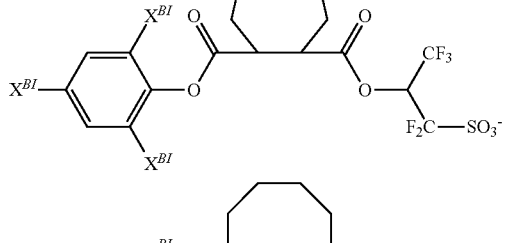

203
-continued
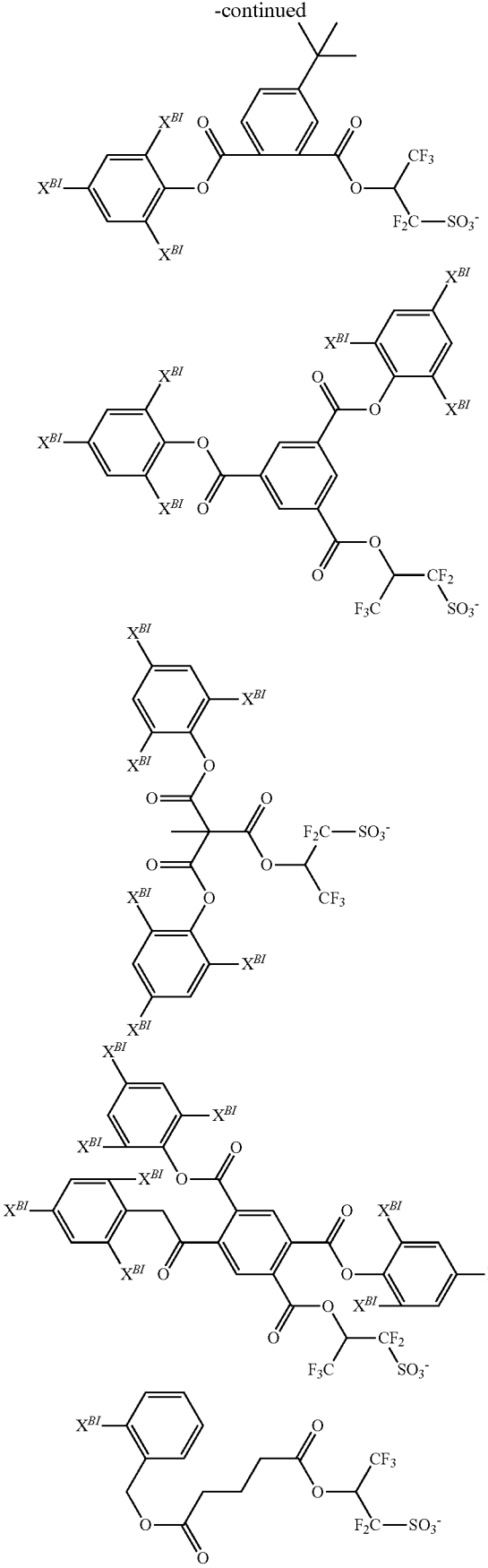
204
-continued
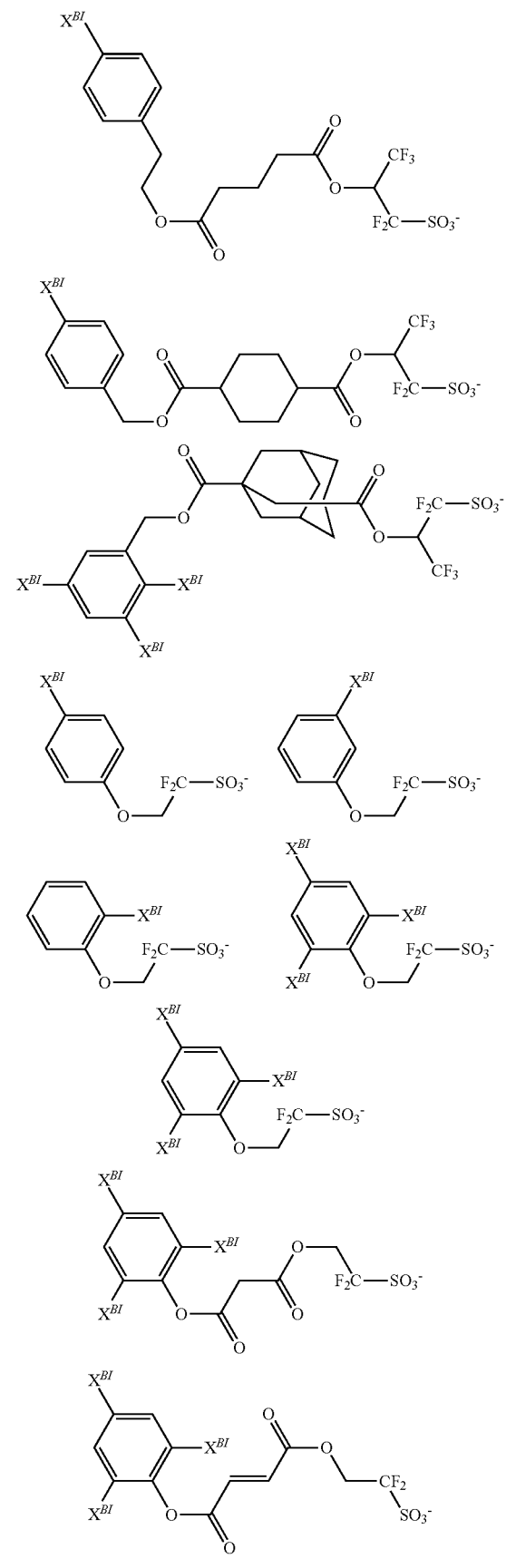

205
-continued
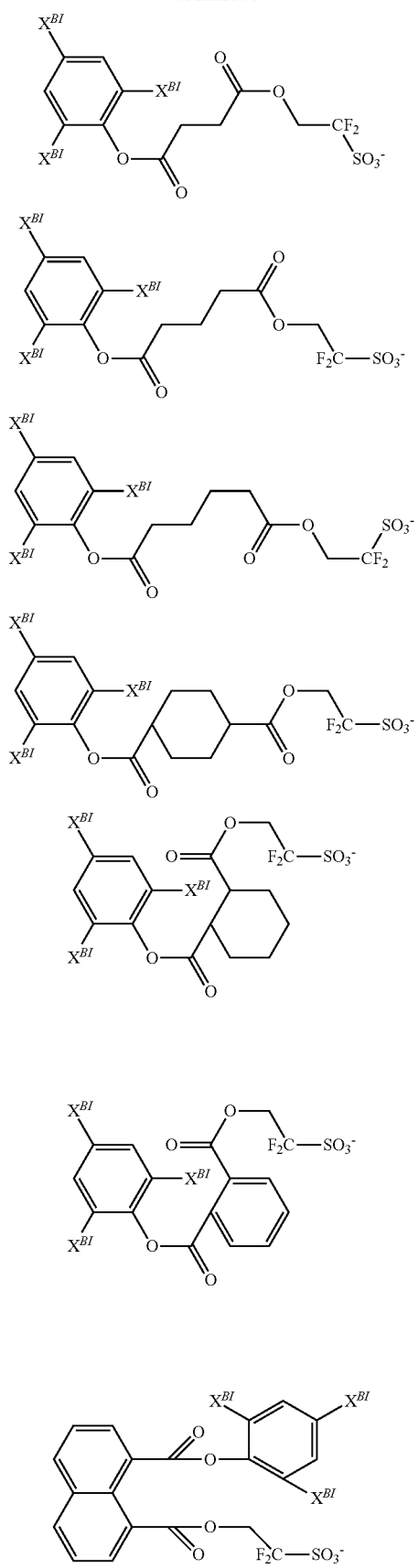
206
-continued
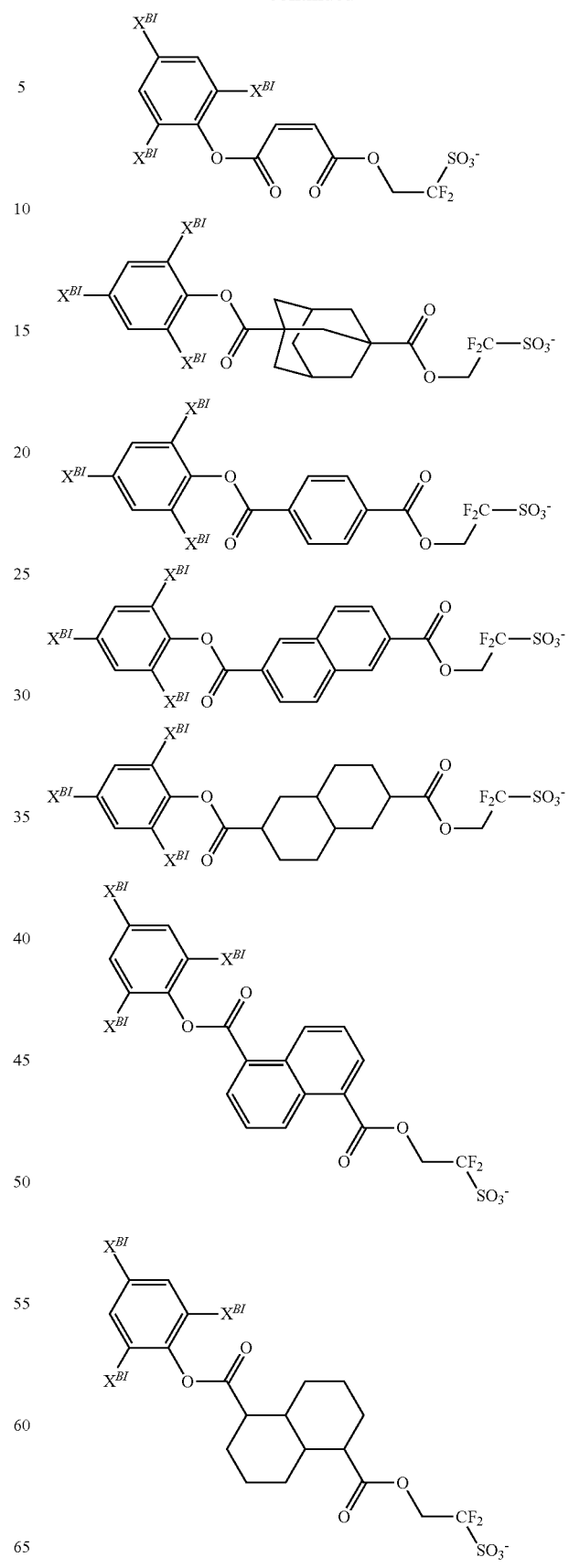

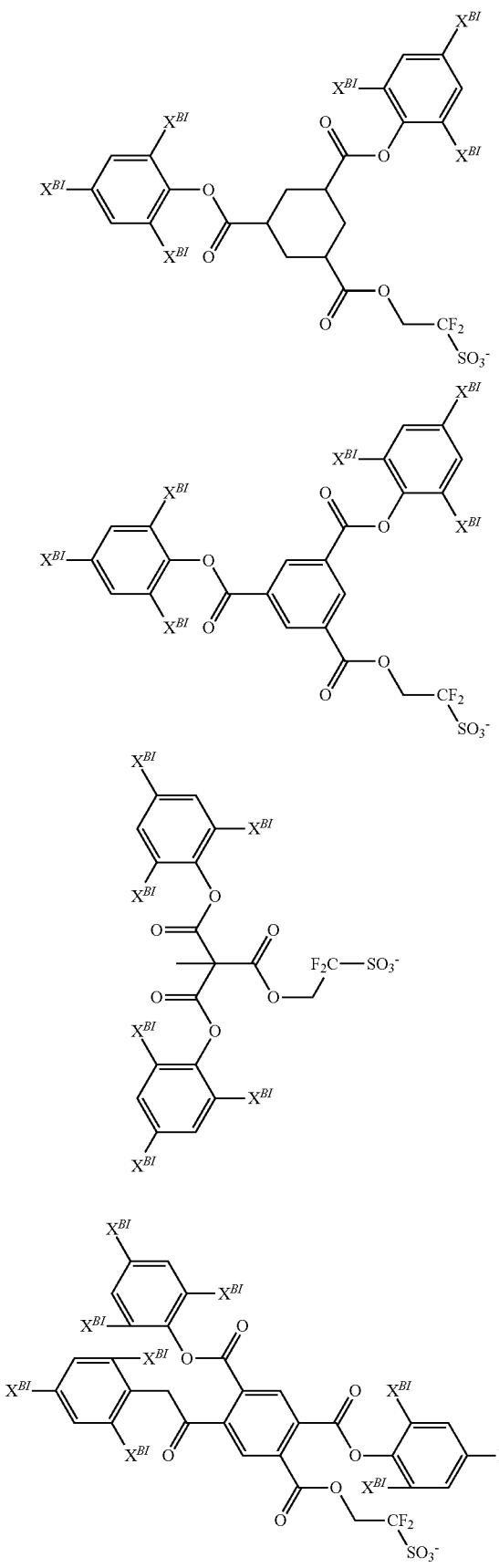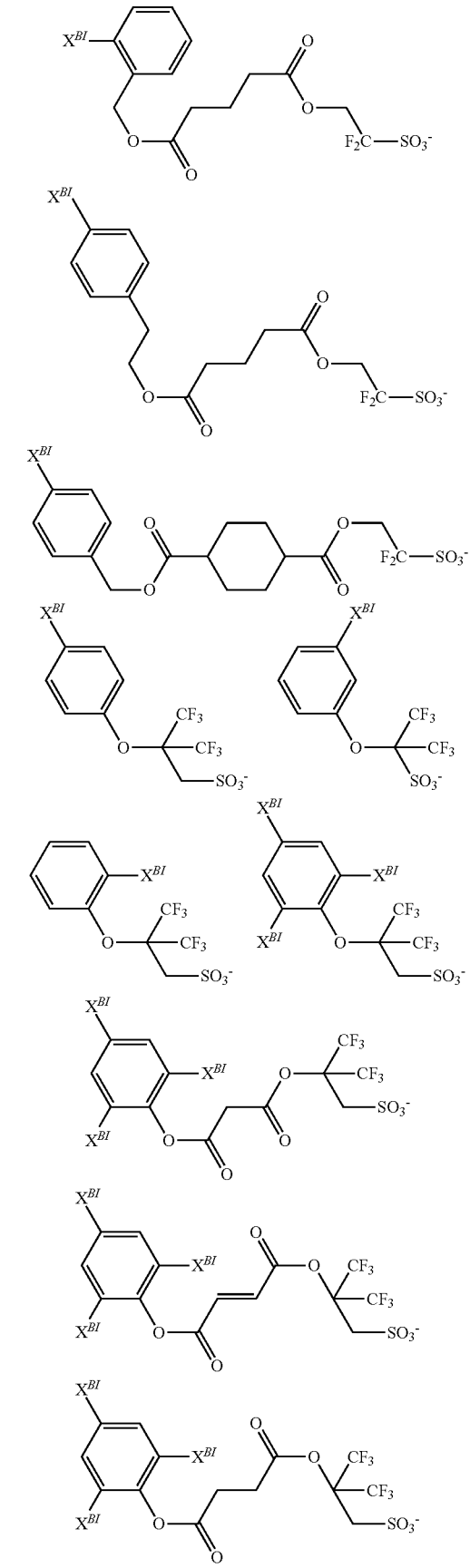

-continued
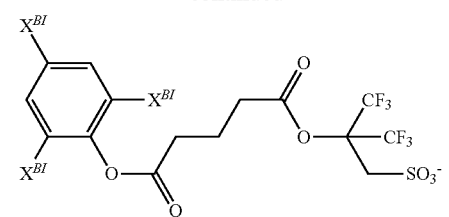
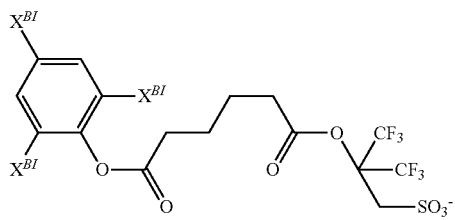
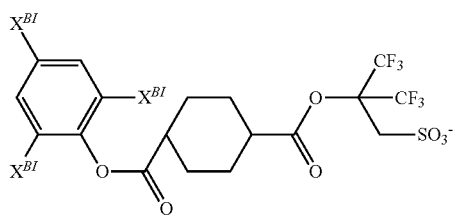
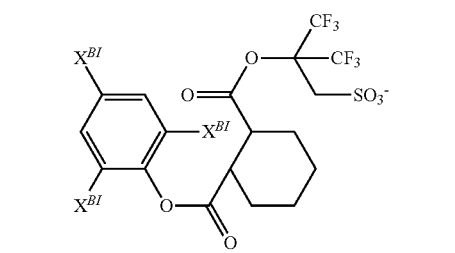
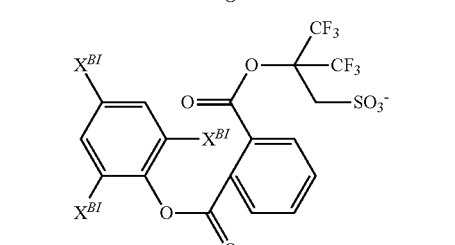
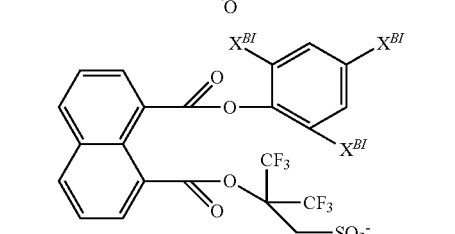
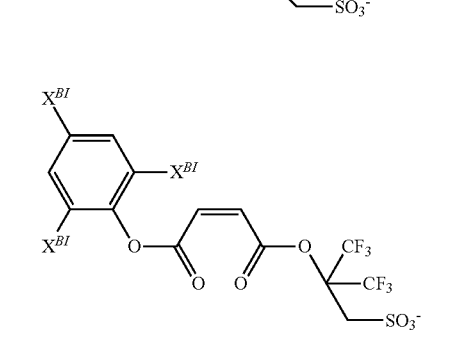
-continued
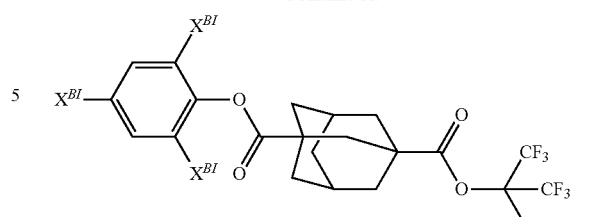
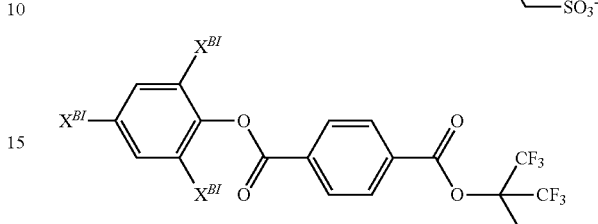
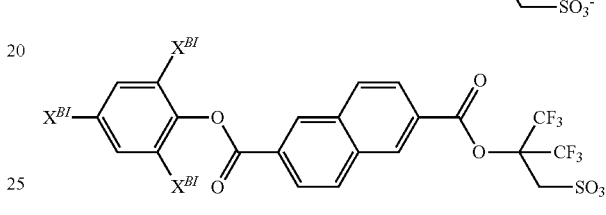
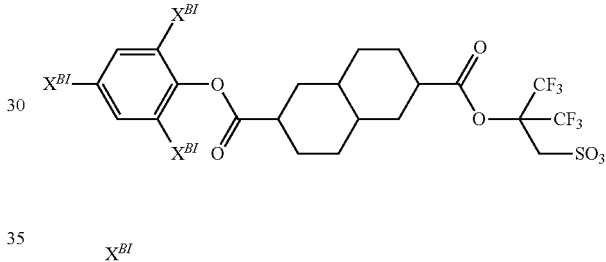
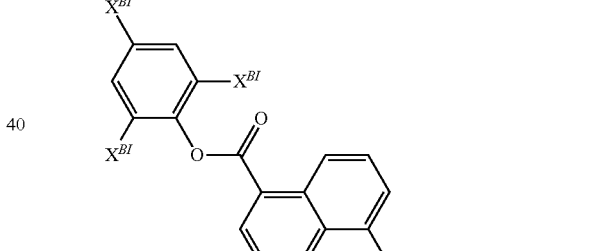
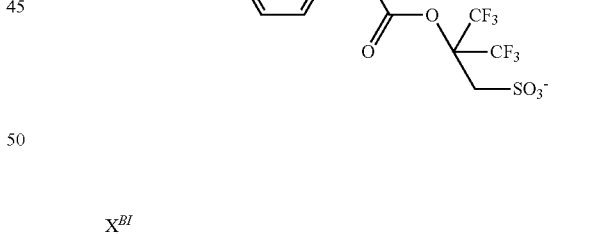
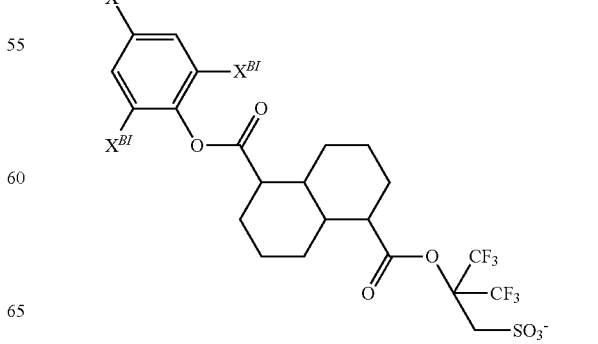

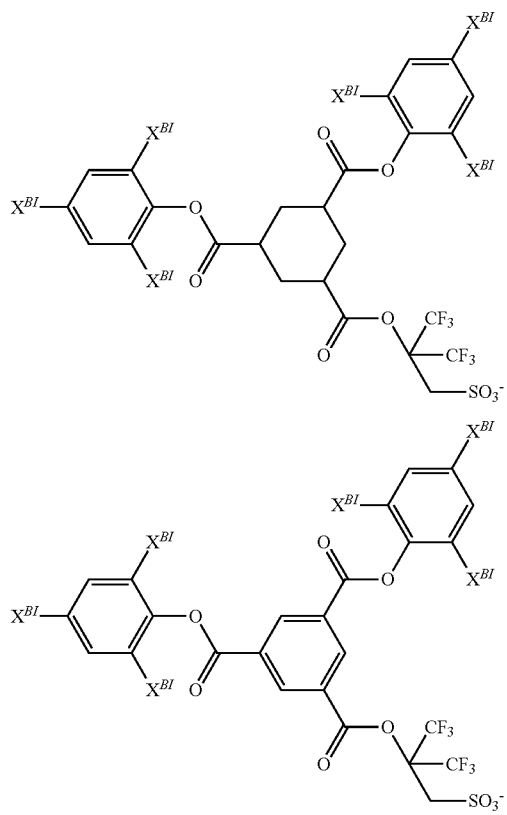

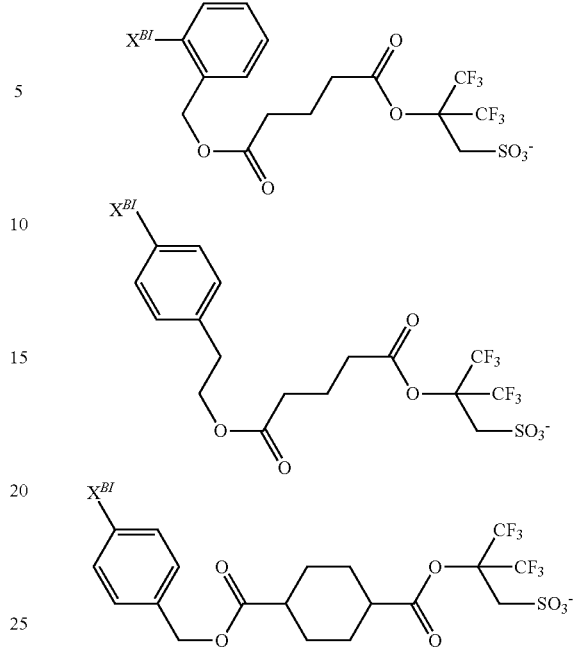

When used, the acid generator of addition type is preferably added in an amount of 0.1 to 50 parts, and more preferably 1 to 40 parts by weight per 100 parts by weight of the base polymer.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

In the case of negative resist compositions, a negative pattern may be formed by adding a crosslinker to reduce the dissolution rate of a resist film in exposed area. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer. The crosslinker may be used alone or in admixture.

In the resist composition of the invention, a quencher other than the onium salt compound having formula (A) may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. The water repellency improver may be used alone or in admixture. An appropriate amount of the water repellency improver is 0 to 20 parts, more preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Pattern Forming Process

The resist composition is used in the fabrication of various integrated circuits. Pattern formation using the resist composition may be performed by well-known lithography processes. The process generally involves the steps of applying the resist composition onto a substrate to form a resist film thereon, exposing the resist film to high-energy radiation, and developing the exposed resist film in a developer. If necessary, any additional steps may be added.

The resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 µm thick.

The resist film is then exposed to a desired pattern of high-energy radiation such as UV, deep-UV, EB, EUV, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto through a mask having a desired pattern in a dose of preferably about 1 to 200 $mJ/cm^2$, more preferably about 10 to 100 $mJ/cm^2$. When EB is used as the high-energy radiation, the resist film is exposed thereto through a mask having a desired pattern or directly in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hotplate or in an oven at 50 to 150° C. for 10 seconds to 30 minutes, preferably at 60 to 120° C. for 30 seconds to 20 minutes.

The PEB may or may not be involved. In the embodiment wherein the polymer is an anion-bound PAG polymer comprising recurring units (f2) or (f3), a sulfonic acid is generated upon exposure whereby alkaline solubility is improved. Then the exposed region of the resist film is dissolvable in alkaline solution without PEB. When PEB is omitted, the image blur by acid diffusion is eliminated, and so, the formation of a pattern of finer size than the pattern formation via PEB is expected.

When PEB is omitted, the resist material is a non-chemically amplified resist material because deprotection reaction with the aid of acid does not take place. In this case, the dissolution contrast is so low that after development, a pattern film thickness loss can occur or some residual film be left in the space region. For the non-chemically amplified resist material, the key is how to improve dissolution contrast.

In the embodiment wherein the polymer is an anion-bound PAG polymer comprising recurring units (f2) or (f3), an α-fluorosulfonic acid is generated upon exposure whereby the solubility in alkaline developer is improved. When an onium salt of α-non-fluorinated sulfonic acid or carboxylic acid is added, the generation of an α-fluorosulfonic acid is controlled by a salt exchange therewith. Further, as the exposure dose is increased, the onium salt of α-non-fluorinated sulfonic acid or carboxylic acid is decomposed, whereby alkaline solubility is improved. Namely, contrast is enhanced by the mechanism that dissolution inhibition is improved in the under-exposure dose region whereas dissolution promotion is improved in the over-exposure dose region. Since the ion exchange reaction proceeds rapidly at room temperature, the PEB may be omitted. Since the onium salt having formula (A) is also a salt of weaker acid than α-fluorosulfonic acid, a similar ion exchange takes place. This ensures a contrast improvement even when PEB is omitted.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In the case of positive resist, the resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

[1] Synthesis of Quenchers

Sulfonium salts SQ-1 to SQ-9, iodonium salts IQ-1 to IQ-3, and ammonium salts NQ-1 to NQ-5 of iodized benzene ring-containing fluorosulfonamide were used in resist compositions within the scope of the invention. The salts have the structure shown below.

SQ-1

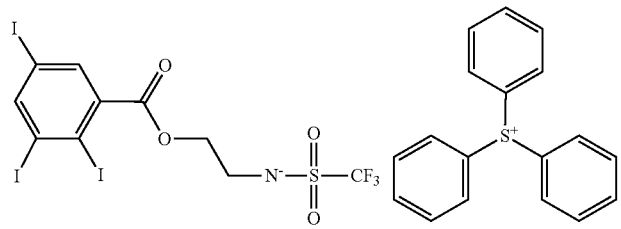

SQ-2

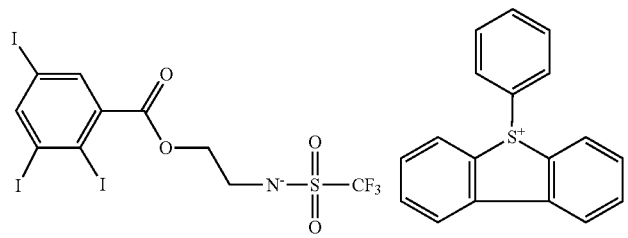

SQ-3
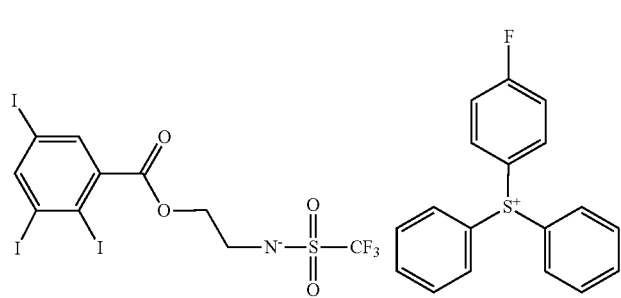
SQ-4
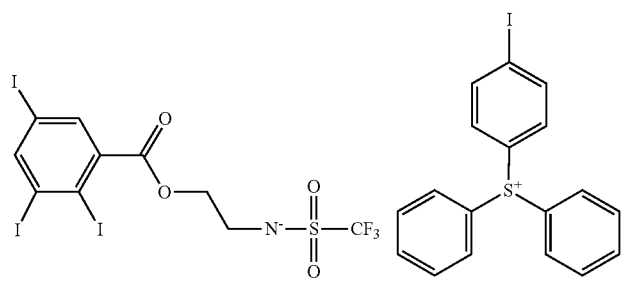
SQ-5
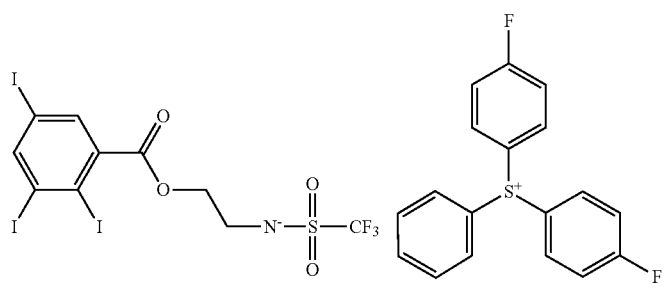
SQ-6
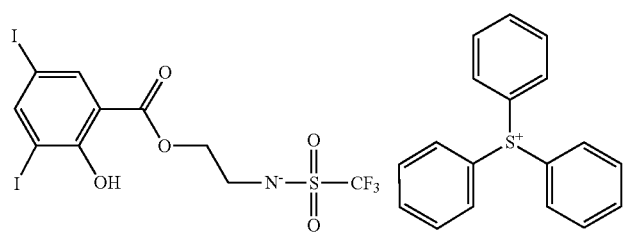
SQ-7
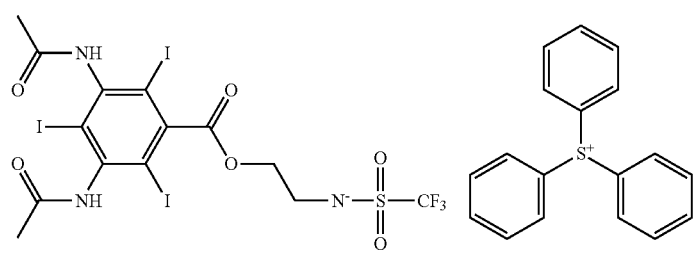
SQ-8
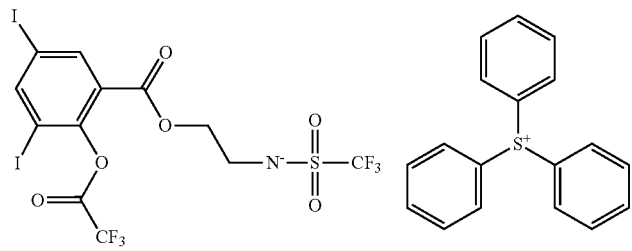

-continued
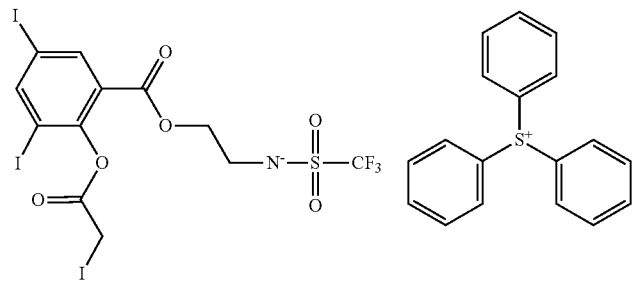
SQ-9
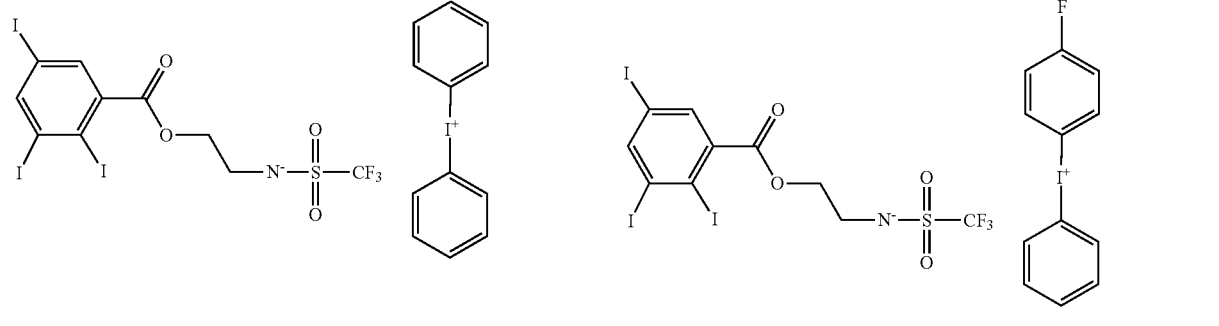
IQ-1
IQ-2
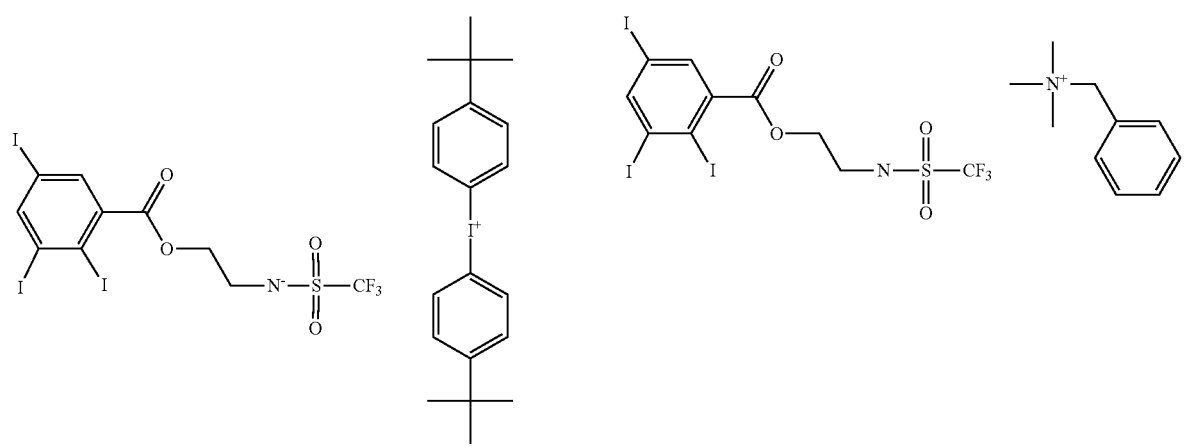
IQ-3
NQ-1
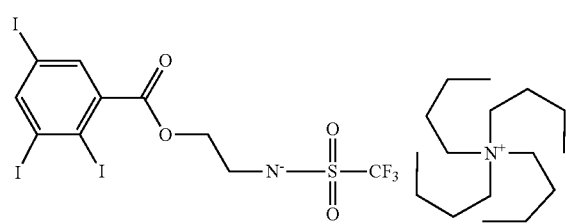
NQ-2
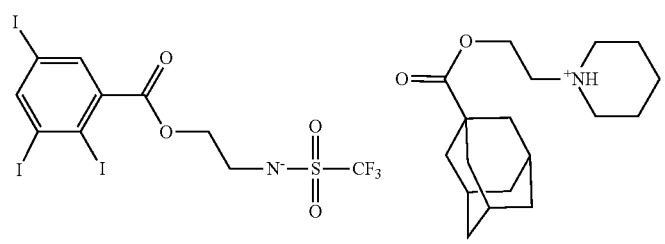
NQ-3

-continued

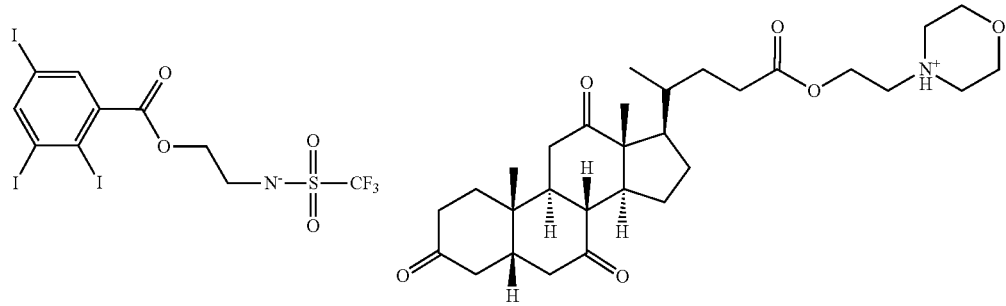

NQ-4

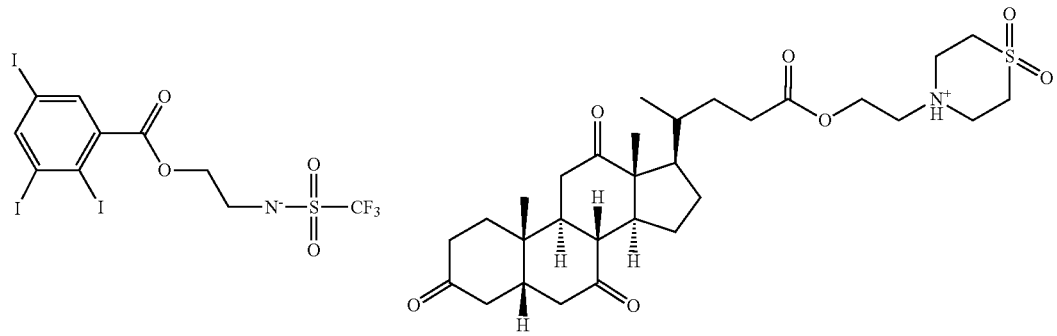

NQ-5

Synthesis Examples 1-1 to 1-13

Sulfonium salt SQ-1 was synthesized by reacting trifluoromethanesulfonic acid amide ethanol with 2,3,5-triiodobenzoic chloride to form N-[2-(2,3,5-triiodophenyl-1-ylcarbonyloxy)ethyl]trifluoromethanesulfonamide and effecting ion exchange thereof with triphenylsulfonium chloride. Sulfonium salts SQ-2 to SQ-5 were similarly synthesized by ion exchange of N-[2-(2,3,5-triiodophenyl-1-ylcarbonyloxy)ethyl]trifluoromethanesulfonamide with a sulfonium chloride providing the desired cation. Sulfonium salts SQ-6 to SQ-9 were similarly synthesized by ion exchange of an iodized benzene ring-containing fluorosulfonamide providing the desired anion with a sulfonium chloride providing the desired cation.

Iodonium salts IQ-1 to IQ-3 were synthesized by ion exchange of N-[2-(2,3,5-triiodophenyl-1-ylcarbonyloxy)ethyl]trifluoromethanesulfonamide with an iodonium chloride providing the desired cation.

Ammonium salts NQ-1 and NQ-2 were synthesized by neutralization reaction of N-[2-(2,3,5-triiodophenyl-1-ylcarbonyloxy)ethyl]trifluoromethanesulfonamide with a quaternary ammonium hydroxide providing the desired cation. Ammonium salts NQ-3 to NQ-5 were synthesized by neutralization reaction of N-[2-(2,3,5-triiodophenyl-1-ylcarbonyloxy)ethyl]trifluoromethanesulfonamide with a tertiary ammine providing the desired cation.

[2] Synthesis of Base Polymers

Synthesis Examples 2-1 to 2-5

Base polymers (Polymers 1 to 5) were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers were analyzed for composition by $^1$H-NMR spectroscopy, and for Mw and Mw/Mn by GPC versus polystyrene standards using THF solvent.

Polymer 1

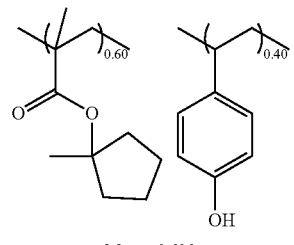

Mw = 6,600
Mw/Mn = 1.55

Polymer 2

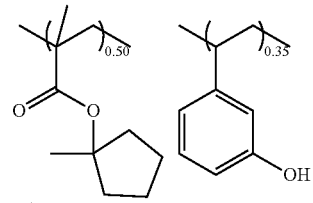

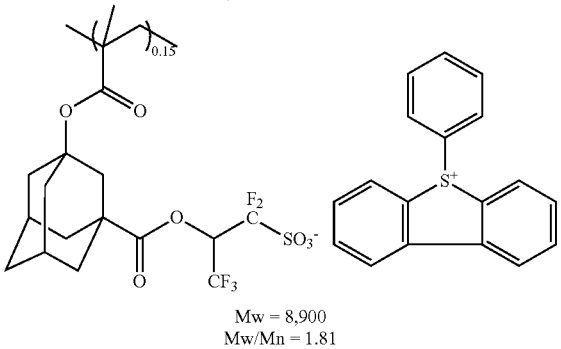

Mw = 8,900
Mw/Mn = 1.81

-continued

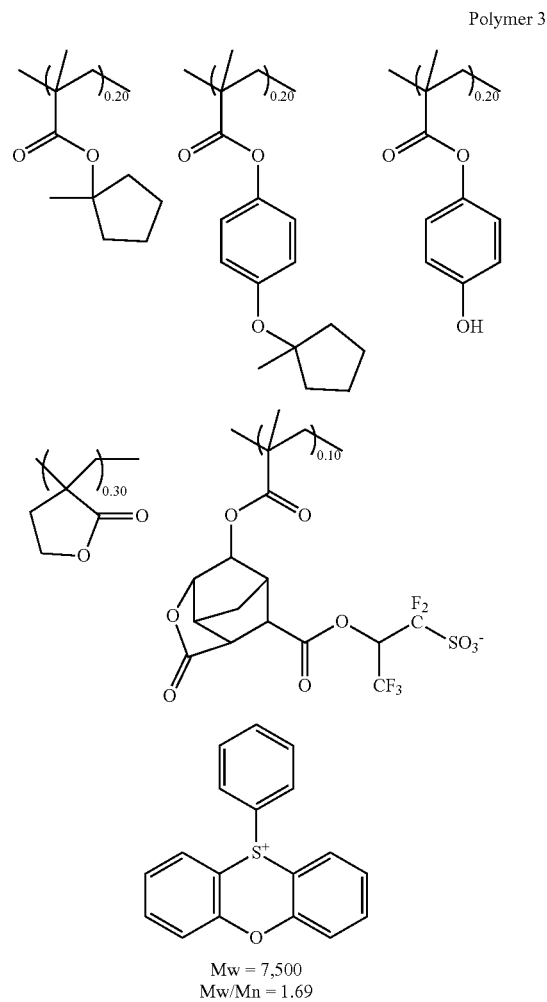

Polymer 3

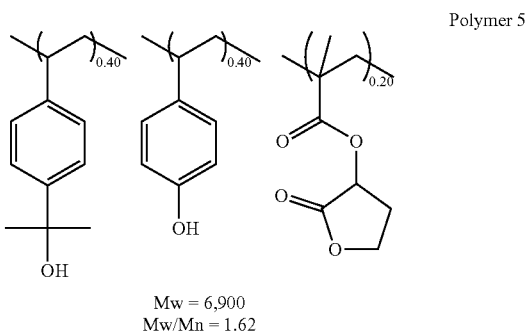

Polymer 5

[3] Preparation and Evaluation of Resist Compositions

Examples 1 to 22 and Comparative Examples 1 to 4

(1) Preparation of resist compositions

Resist compositions were prepared by dissolving the polymer and selected components in a solvent in accordance with the recipe shown in Tables 1 and 2, and filtering through a filter having a pore size of 0.2 μm. The solvent contained 50 ppm of surfactant PolyFox PF-636 (Omnova Solutions Inc.). The resist compositions of Examples 1 to 21 and Comparative Examples 1 to 3 were of positive tone while the resist compositions of Example 22 and Comparative Example 4 were of negative tone. The components in Tables 1 and 2 are as identified below.

Organic Solvents:
PGMEA (propylene glycol monomethyl ether acetate)
DAA (diacetone alcohol)
Acid generators: PAG 1 and PAG 2 of the following structural formulae

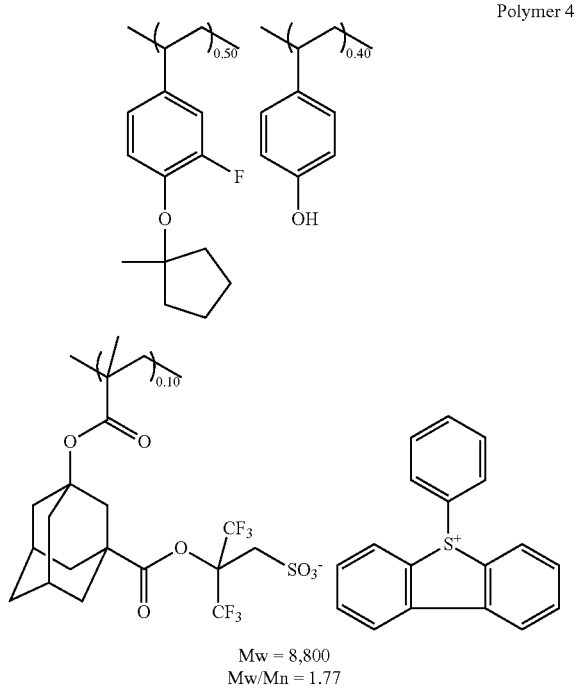

Polymer 4

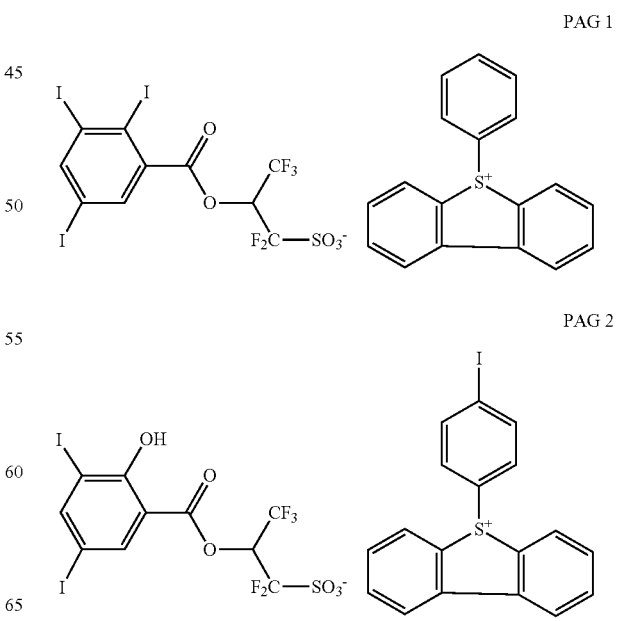

PAG 1

PAG 2

Comparative Quenchers: cQ-1 to cQ-3 of the following structural formulae

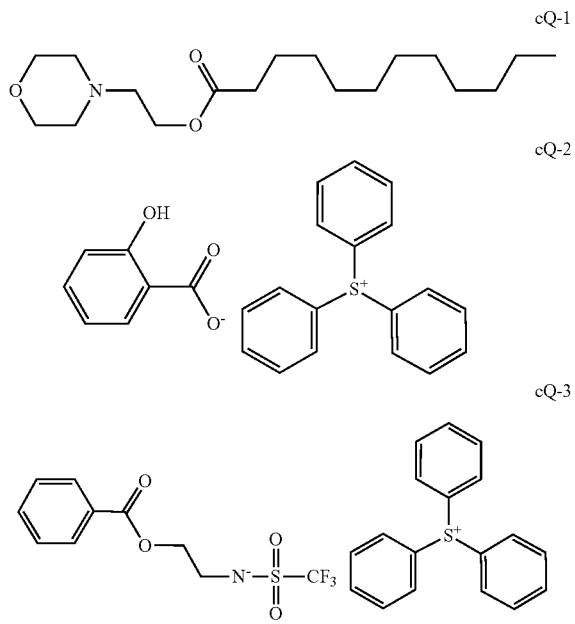

(2) EUV Lithography Test

Each of the resist compositions in Tables 1 and 2 was spin coated on a silicon substrate having a 20-nm coating of silicon-containing spin-on hard mask SHB-A940 (Shin-Etsu Chemical Co., Ltd., silicon content 43 wt %) and prebaked on a hotplate at 105° C. for 60 seconds to form a resist film of 50 nm thick. Using an EUV scanner NXE3300 (ASML, NA 0.33, σ0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 and 2 for 60 seconds and developed in a 2.38 wt % TMAH aqueous solution for 30 seconds to form a hole pattern having a size of 23 nm in Examples 1 to 21 and Comparative Examples 1 to 3 or a dot pattern having a size of 23 nm in Example 22 and Comparative Example 4.

The resist pattern was observed under CD-SEM (CG-5000, Hitachi High-Technologies Corp.). The exposure dose that provides a hole or dot pattern having a size of 23 nm is reported as sensitivity. The size of 50 holes or dots in that dose was measured, from which a 3-fold value (3σ) of standard deviation (σ) was computed and reported as CDU.

The resist composition is shown in Tables 1 and 2 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG 1 (37.0) | SQ-1 (4.69) | PGMEA (2,500) DAA (500) | 75 | 30 | 3.1 |
| | 2 | Polymer 1 (100) | PAG 2 (37.0) | SQ-1 (4.69) | PGMEA (2,500) DAA (500) | 75 | 32 | 2.9 |
| | 3 | Polymer 1 (100) | PAG 1 (37.0) | SQ-2 (4.68) | PGMEA (2,500) DAA (500) | 75 | 30 | 3.0 |
| | 4 | Polymer 1 (100) | PAG 1 (37.0) | SQ-3 (4.77) | PGMEA (2,500) DAA (500) | 75 | 31 | 3.0 |
| | 5 | Polymer 1 (100) | PAG 1 (37.0) | SQ-4 (5.32) | PGMEA (2,500) DAA (500) | 75 | 30 | 3.0 |
| | 6 | Polymer 1 (100) | PAG 1 (37.0) | SQ-5 (4.96) | PGMEA (2,500) DAA (500) | 75 | 27 | 3.1 |
| | 7 | Polymer 1 (100) | PAG 1 (37.0) | IQ-1 (4.77) | PGMEA (2,500) DAA (500) | 75 | 30 | 3.0 |
| | 8 | Polymer 1 (100) | PAG 1 (37.0) | IQ-2 (4.86) | PGMEA (2,500) DAA (500) | 75 | 30 | 3.0 |
| | 9 | Polymer 1 (100) | PAG 1 (37.0) | IQ-3 (5.33) | PGMEA (2,500) DAA (500) | 75 | 34 | 2.7 |
| | 10 | Polymer 1 (100) | PAG 1 (37.0) | NQ-1 (4.44) | PGMEA (2,500) DAA (500) | 75 | 30 | 3.0 |
| | 11 | Polymer 1 (100) | PAG 1 (37.0) | NQ-2 (4.58) | PGMEA (2,500) DAA (500) | 75 | 32 | 3.1 |
| | 12 | Polymer 1 (100) | PAG 1 (37.0) | NQ-3 (4.84) | PGMEA (2,500) DAA (500) | 75 | 32 | 3.2 |
| | 13 | Polymer 1 (100) | PAG 1 (37.0) | NQ-4 (5.95) | PGMEA (2,500) DAA (500) | 75 | 31 | 3.2 |
| | 14 | Polymer 1 (100) | PAG 1 (37.0) | NQ-5 (6.19) | PGMEA (2,500) DAA (500) | 75 | 32 | 3.2 |
| | 15 | Polymer 1 (100) | PAG 1 (37.0) | SQ-6 (4.13) | PGMEA (2,500) DAA (500) | 75 | 32 | 3.0 |
| | 16 | Polymer 1 (100) | PAG 1 (37.0) | SQ-7 (5.25) | PGMEA (2,500) DAA (500) | 75 | 33 | 3.0 |
| | 17 | Polymer 1 (100) | PAG 1 (37.0) | SQ-8 (4.61) | PGMEA (2,500) DAA (500) | 75 | 31 | 3.0 |
| | 18 | Polymer 1 (100) | PAG 1 (37.0) | SQ-9 (4.98) | PGMEA (2,500) DAA (500) | 75 | 31 | 3.1 |
| | 19 | Polymer 2 (100) | — | SQ-5 (4.96) | PGMEA (2,500) DAA (500) | 85 | 26 | 2.6 |
| | 20 | Polymer 3 (100) | — | SQ-5 (4.96) | PGMEA (2,500) DAA (500) | 80 | 28 | 2.6 |

TABLE 1-continued

| | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 21 | Polymer 4 (100) | — | SQ-5 (4.96) | PGMEA (2,500) DAA (500) | 80 | 33 | 2.3 |
| 22 | Polymer 5 (100) | PAG 1 (18.0) | SQ-1 (4.69) | PGMEA (2,500) DAA (500) | 110 | 38 | 4.0 |

TABLE 2

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Comparative Example | 1 | Polymer 1 (100) | PAG 1 (37.0) | cQ-1 (1.57) | PGMEA (2,500) DAA (500) | 75 | 38 | 4.6 |
| | 2 | Polymer 1 (100) | PAG 1 (37.0) | cQ-2 (2.00) | PGMEA (2,500) DAA (500) | 75 | 41 | 3.9 |
| | 3 | Polymer 1 (100) | PAG 1 (37.0) | cQ-3 (2.80) | PGMEA (2,500) DAA (500) | 75 | 38 | 3.6 |
| | 4 | Polymer 5 (100) | PAG 1 (18.0) | cQ-3 (2.80) | PGMEA (2,500) DAA (500) | 110 | 47 | 4.8 |

It is demonstrated in Tables 1 and 2 that resist compositions comprising an onium salt having formula (A) offer a high sensitivity and a reduced value of CDU.

Japanese Patent Application No. 2020-023079 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, the quencher containing an onium salt having the formula (A):

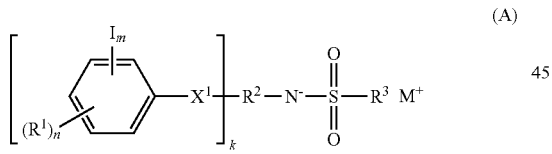

(A)

wherein m is an integer of 1 to 5, n is an integer of 0 to 4, m+n is from 1 to 5, k is 1 or 2, $R^1$ is hydrogen, hydroxyl, optionally halogen-substituted $C_1$-$C_6$ saturated hydrocarbyl group, optionally halogen-substituted $C_1$-$C_6$ saturated hydrocarbyloxy group, optionally halogen-substituted $C_2$-$C_7$ saturated hydrocarbylcarbonyloxy group, optionally halogen-substituted $C_2$-$C_7$ saturated hydrocarbyloxycarbonyl group, optionally halogen-substituted $C_1$-$C_4$ saturated hydrocarbylsulfonyloxy group, fluorine, chlorine, bromine, amino, nitro, cyano, —NR$^{1A}$—C(=O)—R$^{1B}$, or —NR$^{1A}$—C(=O)—O—R$^{1B}$, some or all of the hydrogen atoms in the saturated hydrocarbyl, saturated hydrocarbyloxy, saturated hydrocarbylcarbonyloxy, saturated hydrocarbyloxycarbonyl and saturated hydrocarbylsulfonyloxy groups may be substituted by halogen, $R^{1A}$ is hydrogen or a $C_1$-$C_6$ saturated hydrocarbyl group, $R^{1B}$ is a $C_1$-$C_6$ saturated hydrocarbyl, $C_2$-$C_8$ unsaturated aliphatic hydrocarbyl, $C_6$-$C_{14}$ aryl or $C_7$-$C_{15}$ aralkyl group, $R^2$ is a $C_1$-$C_{10}$ (k+1)-valent hydrocarbon group, $R^3$ is a $C_1$-$C_6$ fluorinated saturated hydrocarbyl group or $C_6$-$C_{10}$ fluorinated aryl group, $X^1$ is a single bond, ether bond, carbonyl group, ester bond, amide bond, carbonate bond or $C_1$-$C_{20}$ hydrocarbylene group, the hydrocarbylene group may contain an ether bond, carbonyl moiety, ester bond, amide bond, sultone ring, lactam ring, carbonate bond, halogen, hydroxyl moiety or carboxyl moiety, $M^+$ is a sulfonium cation having the formula (Aa), iodonium cation having the formula (Ab), or ammonium cation having the formula (Ac):

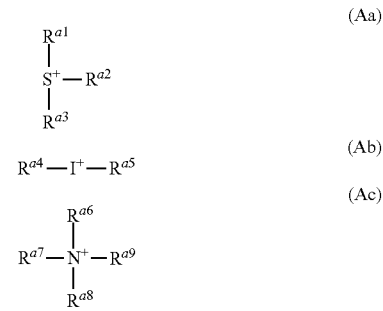

wherein $R^{a1}$ to $R^{a3}$ are each independently halogen or a $C_1$-$C_{20}$ hydrocarbyl group which may contain a heteroatom, $R^{a1}$ and $R^{a2}$ may bond together to form a ring with the sulfur atom to which they are attached, $R^{a4}$ and $R^{a5}$ are each independently halogen or a $C_1$-$C_{20}$ hydrocarbyl group which may contain a heteroatom, $R^{a6}$ to $R^{a9}$ are each independently hydrogen or a $C_1$-$C_{24}$ hydrocarbyl group which may contain at least one moiety selected from halogen, hydroxyl moiety, carboxyl moiety, ether bond, ester bond, thiol moiety, thioester bond, thionoester bond, dithioester bond, amino moiety, nitro moiety, sulfone moiety, and ferrocenyl moiety, $R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ each may bond together to form a spiro-ring with the nitrogen atom to which they are attached, $R^{a8}$ and $R^{a9}$, taken together, may form $=C(R^{a10})(R^{a11})$, $R^{a10}$ and $R^{a11}$ are each independently hydrogen or a $C_1$-$C_{16}$ hydrocarbyl group, $R^{a6}$ and $R^{a10}$ may bond together to form a ring with the carbon and nitrogen atoms to which they are attached, the ring may contain a double bond, oxygen, sulfur or nitrogen.

2. The resist composition of claim 1 wherein m is an integer of 2 to 4.

3. The resist composition of claim 1, further comprising an acid generator capable of generating a sulfonic acid, imide acid or methide acid.

4. The resist composition of claim 1, further comprising an organic solvent.

5. The resist composition of claim 1 wherein the base polymer comprises recurring units having the formula (a1) or recurring units having the formula (a2):

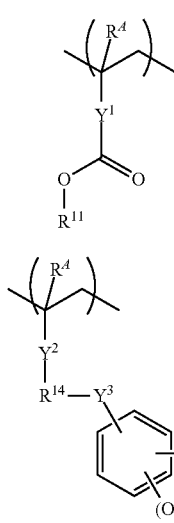

wherein $R^A$ is each independently hydrogen or methyl, $Y^1$ is a single bond, phenylene group, naphthylene group, or $C_1$-$C_{12}$ linking group containing at least one moiety selected from ester bond and lactone ring, $Y^2$ is a single bond or ester bond, $Y^3$ is a single bond, ether bond or ester bond, $R^{11}$ and $R^{12}$ each are an acid labile group, $R^{13}$ is fluorine, trifluoromethyl, cyano or $C_1$-$C_6$ saturated hydrocarbyl group, $R^{14}$ is a single bond or $C_1$-$C_6$ alkanediyl group in which some carbon may be replaced by an ether bond or ester bond, a is 1 or 2, b is an integer of 0 to 4, and a+b is from 1 to 5.

6. The resist composition of claim 5 which is a chemically amplified positive resist composition.

7. The resist composition of claim 1 wherein the base polymer is free of an acid labile group.

8. The resist composition of claim 7 which is a chemically amplified negative resist composition.

9. The resist composition of claim 1 wherein the base polymer comprises recurring units of at least one type selected from recurring units having the formulae (f1) to (f3):

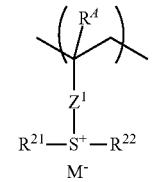

(f1)

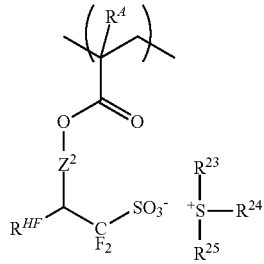

(f2)

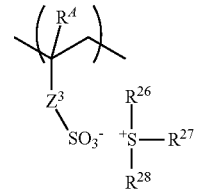

(f3)

wherein $R^A$ is each independently hydrogen or methyl,
$Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl, ester bond, ether bond or hydroxyl moiety,
$Z^2$ is a single bond, —$Z^{21}$—C(=O)—O—, —$Z^{21}$—O— or —$Z^{21}$—O—C(=O)—, $Z^{21}$ is a $C_1$-$C_{12}$ saturated hydrocarbylene group which may contain a carbonyl moiety, ester bond or ether bond,
$Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety,
$R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached,
$R^{HF}$ is hydrogen or trifluoromethyl, and
$M^-$ is a non-nucleophilic counter ion.

10. The resist composition of claim 1, further comprising a surfactant.

11. The resist composition of claim 1 wherein $X^1$ is an ether bond, carbonyl group, ester bond, amide bond, or carbonate bond.

12. A process for forming a pattern comprising the steps of applying the resist composition of claim 1 onto a substrate to form a resist film thereon, exposing the resist film to high-energy radiation, and developing the exposed resist film in a developer.

13. The process of claim 12 wherein the high-energy radiation is ArF excimer laser radiation of wavelength 193 nm or KrF excimer laser radiation of wavelength 248 nm.

14. The process of claim 12 wherein the high-energy radiation is EB or EUV of wavelength 3 to 15 nm.

* * * * *